United States Patent
Xu et al.

(10) Patent No.: US 11,186,606 B2
(45) Date of Patent: *Nov. 30, 2021

(54) COMPOSITIONS AND METHODS OF MODULATING THE IMMUNE RESPONSE BY ACTIVATING ALPHA PROTEIN KINASE 1

(71) Applicant: Shanghai Yao Yuan Biotechnology Co., Ltd., Shanghai (CN)

(72) Inventors: Tian Xu, Shanghai (CN); Cong Xu, Shanghai (CN); Danyang Liu, Shanghai (CN); Jieqing Fan, Shanghai (CN); Yanfang Pan, Shanghai (CN); Tongruei Raymond Li, Shanghai (CN); Xiaodong Chen, Shanghai (CN)

(73) Assignee: Shanghai Yao Yuan Biotechnology Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/759,426

(22) PCT Filed: Oct. 25, 2018

(86) PCT No.: PCT/CN2018/111885
§ 371 (c)(1),
(2) Date: Apr. 27, 2020

(87) PCT Pub. No.: WO2019/080898
PCT Pub. Date: May 2, 2019

(65) Prior Publication Data
US 2020/0283468 A1    Sep. 10, 2020

(30) Foreign Application Priority Data

Oct. 27, 2017 (WO) ............... PCT/CN2017/107962
Apr. 16, 2018 (WO) ............... PCT/CN2018/083153
Aug. 16, 2018 (WO) ............... PCT/CN2018/100871

(51) Int. Cl.
| | |
|---|---|
| *C07H 19/20* | (2006.01) |
| *A61P 11/06* | (2006.01) |
| *A61P 11/00* | (2006.01) |
| *A61P 35/00* | (2006.01) |
| *A61K 31/7076* | (2006.01) |
| *A61K 39/00* | (2006.01) |

(52) U.S. Cl.
CPC ......... *C07H 19/20* (2013.01); *A61K 31/7076* (2013.01); *A61P 11/00* (2018.01); *A61P 11/06* (2018.01); *A61P 35/00* (2018.01); *A61K 39/00* (2013.01)

(58) Field of Classification Search
None
See application file for complete search history.

(56) References Cited

U.S. PATENT DOCUMENTS

| | | |
|---|---|---|
| 10,238,738 B2 | 3/2019 | Gray-Owen et al. |
| 2009/0098056 A1 | 4/2009 | Ko et al. |
| 2010/0016250 A1 | 1/2010 | Nagata et al. |
| 2019/0367553 A1 | 12/2019 | Xu et al. |

FOREIGN PATENT DOCUMENTS

| | | |
|---|---|---|
| CN | 1906190 A | 1/2007 |
| CN | 102099032 A | 6/2011 |
| CN | 104540831 A | 4/2015 |
| CN | 107075569 A | 8/2017 |
| WO | 2013023084 A2 | 2/2013 |
| WO | 2015170108 A1 | 11/2015 |

OTHER PUBLICATIONS

Kodama, Tetrahedron Letters, vol. 34, No. 40, pp. 6419-6422, 1993. (Year: 1993).*
Burkart, Bioorg. Med. Chem. 8 (2000) 1937-1946. (Year: 2000).*
CAS Registry No. 375367-54-7, which entered STN on Dec. 14, 2001. (Year: 2001).*
International Search Report and Written Opinion dated Jan. 30, 2019 for International Application No. PCT/CN2018/111885, filed Oct. 25, 2018 (14 pages).
Milivojevic, M. et al., ALPK1 controls TIFA/TRAF6-dependent innate immunity against heptose-1, 7-bisphosphate of gram-negative bacteria. PLOS Pathogens. Feb. 21, 2017 (Feb. 21, 2017) No. 2 vol. 13 ISSN:1553-7366 e1006244.
Liao, H.F. et al. Down-regulated and Commonly mutated ALPK1 in Lung and Colorectal Cancers. Scientific Reports. Jun. 10, 2016 (Jun. 10, 2016) vol. 6 ISSN:2045-2322 27350.
Adekoye, I. et al. (Prepublished Sep. 17, 2018). "d-Glycero-B-d-manno-heptose 1-Phosphate and d-glycero-B-d-Manno-phosphate 1,7-Biphosphate are both innate immune agonists." The Journal of Immunology 201:2385-2391.
Bendele, A. (2001). "Animal models of rheumatoid arthritis." Journal of Musculoskeletal Neuron Interaction 1(4):377-385.
Didonato, J. et al. (Dec. 31, 2012). "NF-κB And The Link Between Inflammation and Cancer." Immunological Reviews, 246(1): 379-400.

(Continued)

*Primary Examiner* — Layla D Berry
(74) *Attorney, Agent, or Firm* — Muriel Liberto; Mintz Levin Cohn Ferris Glovsky and Popeo, P.C.

(57) ABSTRACT

The disclosure provides compositions and methods related to activating alpha-kinase 1 (ALPK1) for modulating an immune response and treating or preventing cancer, infection, inflammation and related diseases and disorders as well as potentiating an immune response to a target antigen. The disclosure also provides heterocyclic compounds of formula (I) as agonists of alpha protein kinase 1 (ALPK1) and their use in activating ALPK1, modulating an immune response and treating diseases such as cancer, wherein $A^1$, $A^2$, $L^1$, $L^2$, $L^3$, $Z^1$, $Z^2$, $W^1$, $W^2$, $R^1$, $R^2$, $R^3$, $R^4$, $R^5$, $R^6$ and $R^7$ are defined herein.

57 Claims, 27 Drawing Sheets

Specification includes a Sequence Listing.

(56) References Cited

OTHER PUBLICATIONS

Gall, A. et al. (Jul./Aug. 2017). "TIFA signaling in gastric epithelial cells initiates the cag type 4 secretion system-dependent innate immune response to Helicobactor pylori infection." mBio 8:e01168-17. https://doi.org/10.1128/mBio.01168-17. 16 pages.

Gaudet, R. et al. (Jun. 12, 2015). "Cytosolic detection of the bacterial metabolite HBP activates TIFA-dependent innate immunity." Science 348(6240):1251-1255.

Gaudet, R. et al. (2016). "Heptose sounds the alarm: Innate sensing of alpha-bacterial sugar stimulates immunity." PloS Pathog (2016) 12(9):e1005807. doi:10.1371/journal.ppat 1005807. 6 pages.

Gaudet, R. et al. (May 16, 2017). "Innate recognition of intracellular bacterial growth is driven by the TIFA-dependent cytosolic surveillance pathway." Cell Reports 19:1418-1430.

Hariri, N. et al. (2010). "High-fat diet-induced obesity in animal models." Nutrition Research Reviews 23:270-299.

International Search Report and Written Opinion dated Apr. 11, 2018 issued in International Application No. PCT/CN2017/091995, filed Jul. 6, 2017. 13 pages.

International Search Report and Written Opinion dated Oct. 10, 2018 issued in International Application No. PCT/CN2018/094477, filed Jul. 4, 2018. 12 pages.

Jones-Hall, Y. et al. (2014). Immunopathological characterization of selected mouse models of inflammatory bowel disease: Comparison to human disease.

Kneidinger, B. et al. (Mar. 28, 2001). "Biosynthesis of Nucleotide-Activated D-Glycero-D-Manno-Heptose." The Journal of Biological Chemistry, 276(24): 20935-20944.

Ko, A. et al. (Dec. 31, 2013). "ALPK1 Genetic Regulation and Risk in Relation to Gout." International Journal of Epidemiology, 42:466-474.

Kuo, T-M. et al. (Nov. 2015). "ALPK1 Affects Testosterone Mediated Regulation of Proinflammatory Cytokines Production." The Journal of Steroid Biochemistry and Molecular Biology, 154:150-158.

Malott, R. et al. (Jun. 18, 2013). "Neisseria gonorrhoeae-derived heptose elicits an innate immune response and drives HIV-1 expression." Proceedings of the National Academy of Sciences 110(25): 10234-10239.

Sato-Kaneko, F. et al. (2017). "Combination immunotherapy with TLR agonists and checkpoint inhibitors suppresses head and neck cancer." JCI Insight 27(18):e9337. https://doi.org/10.1172/jci.insight.93397. 18 pages.

Strietz, J. et al. (Nov. 4, 2016). "ERN1 and ALPK1 Inhibit Differentiation of Bi-Potential Tumor-Initiating Cells in Human Breast Cancer." Oncotarget, 7(50):83278-83293.

Wang, L. et al. (Feb. 16, 2010). "Divergence of Biochemical Function in the HAD Superfamily: DGlycero-D-Manno-Heptose 1,7-Bisphosphate Phosphatase, GmhB." Biochemistry 49(6):1072-1081.

Zimmermann, S. et al. (Sep. 5, 2017). "ALPK1- and TIFA-Dependent Innate Immune Response Triggered by the Helicobacter pylori Type IV Secretion System." Cell Reports 20(10):2384-2395.

\* cited by examiner

FIG. 1A

ALPK1 isoform 1

```
MNNQKVVAVL LQECKQVLDQ LLLEAPDVSE EDKSEDQRCR ALLPSELRTL IQEAKEMKWP      60
FVPEKWQYKQ AVGPEDKTNL KDVIGAGLQQ LLASLRASIL ARDCAAAAAI VFLVDRFLYG     120
LDVSGKLLQV AKGLHKLQPA TPIAPQVVIR QARISVNSGK LLKAEYILSS LISNNGATGT     180
WLYRNESDKV LVQSVCIQIR GQILQKLGMW YEAAELIWAS IVGYLALPQP DKKGLSTSLG     240
ILADIFVSMS KNDYEKFKNN PQINLSLLKE FDHHLLSAAE ACKLAAAFSA YTPLFVLTAV     300
NIRGTCLLSY SSSNDCPPEL KNLHLCEAKE AFEIGLLTKR DDEPVTGKQE LHSFVKAAFG     360
LTTVHRRLHG ETGTVHAASQ LCKEAMGKLY NFSTSSRSQD REALSQEVMS VIAQVKEHLQ     420
VQSFSNVDDR SYVPESFECR LDKLILHGQG DFQKILDTYS QHHTSVCEVF ESDCGNNKNE     480
QKDAKTGVCI TALKTEIKNI DTVSTTQEKP HCQRDTGISS SLMGKNVQRE LRRGGRRNWT     540
HSDAFRVSLD QDVETETEPS DYSNGEGAVF NKSLSGSQTS SAWSNLSGFS SSASWEEVNY     600
HVDDRSARKE PGKEHLVDTQ CSTALSEELE NDREGRAMHS LHSQLHDLSL QEPNNDNLEP     660
SQNQPQQQMP LTPFSPHNTP GIFLAPGAGL LEGAPEGIQE VRNMGPRNTS AHSRPSYRSA     720
SWSSDSGRPK NMGTHPSVQK EEAFEIIVEF PETNCDVKDR QGKEQGEEIS ERGAGPTFKA     780
SPSWVDPEGE TAESTEDAPL DFHRVLHNSL GNISMLPCSS FTPNWPVQNP DSRKSGGPVA     840
EQGIDPDAST VDEEGQLLDS MDVPCTNGHG SHRLCILRQP PGQRAETPNS SVSGNILFPV     900
LSEDCTTTEE GNQPGNMLNC SQNSSSSSVW WLKSPAFSSG SSEGDSPWSY LNSSGSSWVS     960
LPGKMRKEIL EARTLQPDDF EKLLAGVRHD WLFQRLENTG VFKPSQLHRA HSALLLKYSK    1020
KSELWTAQET IVYLGDYLTV KKKGRQRNAF WVHHLHQEEI LGRYVGKDYK EQKGLWHHFT    1080
DVERQMTAQH YVTEFNKRLY EQNIPTQIFY IPSTILLILE DKTIKGCISV EPYILGEFVK    1140
LSNNTKVVKT EYKATEYGLA YGHFSYEFSN HRDVVVDLQG WVTGNGKGLI YLTDPQIHSV    1200
DQKVFTTNFG KRGIFYFFNN QHVECNEICH RLSLTRPSME KPCT
```

FIG. 1B

ALPK1 isoform 2

```
MCRKRTRART SAAEASLRAS ILARDCAAAA AIVFLVDRFL YGLDVSGKLL QVAKGLHKLQ      60
PATPIAPQVV IRQARISVNS GKLLKAEYIL SSLISNNGAT GTWLYRNESD KVLVQSVCIQ    120
IRGQILQKLG MWYEAAELIW ASIVGYLALP QPDKKGLSTS LGILADIFVS MSKNDYEKFK    180
NNPQINLSLL KEFDHHLLSA AEACKLAAAF SAYTPLFVLT AVNIRGTCLL SYSSSNDCPP    240
ELKNLHLCEA KEAFEIGLLT KRDDEPVTGK QELHSFVKAA FGLTTVHRRL HGETGTVHAA    300
SQLCKEAMGK LYNFSTSSRS QDREALSQEV MSVIAQVKEH LQVQSFSNVD DRSYVPESFE    360
CRLDKLILHG QGDFQKILDT YSQHHTSVCE VFESDCGNNK NEQKDAKTGV CITALKTEIK    420
NIDTVSTTQE KPHCQRDTGI SSSLMGKNVQ RELRRGGRRN WTHSDAFRVS LDQDVETETE    480
PSDYSNGEGA VFNKSLSGSQ TSSAWSNLSG FSSSASWEEV NYHVDDRSAR KEPGKEHLVD    540
TQCSTALSEE LENDREGRAM HSLHSQLHDL SLQEPNNDNL EPSQNQPQQQ MPLTPFSPHN    600
TPGIFLAPGA GLLEGAPEGI QEVRNMGPRN TSAHSRPSYR SASWSSDSGR PKNMGTHPSV    660
QKEEAFEIIV EFPETNCDVK DRQGKEQGEE ISERGAGPTF KASPSWVDPE GETAESTEDA    720
PLDFHRVLHN SLGNISMLPC SSFTPNWPVQ NPDSRKSGGP VAEQGIDPDA STVDEEGQLL    780
DSMDVPCTNG HGSHRLCILR QPPGQRAETP NSSVSGNILF PVLSEDCTTT EEGNQPGNML    840
NCSQNSSSSS VWWLKSPAFS SGSSEGDSPW SYLNSSGSSW VSLPGKMRKE ILEARTLQPD    900
DFEKLLAGVR HDWLFQRLEN TGVFKPSQLH RAHSALLLKY SKKSELWTAQ ETIVYLGDYL    960
TVKKKGRQRN AFWVHHLHQE EILGRYVGKD YKEQKGLWHH FTDVERQMTA QHYVTEFNKR   1020
LYEQNIPTQI FYIPSTILLI LEDKTIKGCI SVEPYILGEF VKLSNNTKVV KTEYKATEYG   1080
LAYGHFSYEF SNHRDVVVDL QGWVTGNGKG LIYLTDPQIH SVDQKVFTTN FGKRGIFYFF   1140
NNQHVECNEI CHRLSLTRPS MEKPCT
```

COMPOSITIONS AND METHODS OF MODULATING THE IMMUNE RESPONSE BY ACTIVATING ALPHA PROTEIN KINASE 1

CROSS-REFERENCE TO RELATED APPLICATIONS

This application is a national stage entry, filed under 35 U.S.C. § 371, of International Application No. PCT/CN2018/111885, filed on Oct. 25, 2018, which claims the benefit of and priority to International Application No. PCT/CN2017/107962, filed on Oct. 27, 2017, International Application No. PCT/CN2018/083153, filed on Apr. 16, 2018, and International Application No. PCT/CN2018/100871, filed on Aug. 16, 2018, the entire contents of which are hereby incorporated herein by reference in their entirety and for all purposes.

The present application contains a sequence listing in ASCII format. The ASCII copy, created on Mar. 26, 2020, is named 052772-502F03WO_ST25.txt and is 21,417 bytes in size, the content of which is hereby incorporated by reference in its entirety.

FIELD OF THE INVENTION

The present invention relates to compositions and methods for therapy by activating alpha protein kinase 1 (ALPK1).

BACKGROUND OF THE INVENTION

The studies on mechanism of inflammatory response have identified various protein kinases that act as essential signaling components. Defects in protein kinase are frequently associated with the pathogenesis of human inflammatory diseases, cancer and diabetes.

Alpha-kinases are a unique protein kinase superfamily, displaying little sequence similarity to typical protein kinases. A total of six alpha kinase members including alpha-protein kinase 1 (ALPK1), ALPK2, ALPK3, elongated factor-2 kinase (eEF2K), and transient receptor potential cation channel M6 and M7 (TRPM6 and TRPM7) have been identified (Ryazanov A G et al., *Curr Biol* 1999 9(2):R43-45; Ryazanov A G et al., *Proc Natl Acad Sci USA* 1997 94(10):4884-4889).

ALPK1 was identified as a new component of raft-containing sucrose-isomerase (SI) vesicles in epithelial cells (Heinet M et al., *J. Biol. Chem.* 2005 280(27): 25637-43). It was shown that ALPK1 phosphorylates myosin 1 and plays an essential role in the exocytic transport to the apical plasma membrane. A transposon-inserted homozygous inactivating mutation of ALPK1 in mice resulted in motor coordination deficits which could be rescued by overexpressing full-length ALPK1 (Chen M et al., *BMC Neurosci.* 2011 12:1).

Several genetic association studies implicated ALPK1 in risk for gout, although not all of the identified polymorphisms replicated in all populations (Wang S J et al., *J. Mol. Med.* 2011 89:1241-51; Ko A M et al., *J. Intl. Epidemiol.* 2013 42: 466-474; Chiba T et al., *Human Cell* 2015 28:1-4). Other genetic association studies linked ALPK1 as a risk factor for chronic kidney disease, myocardial infarction, and diabetes (Yamada Y et al. *J Med Genet* 2013 50:410-418; Fujimaki T et al., *Biomed Report* 2014 2:127-131; Shimotaka S et al., *Biomed Report* 1 2013 940-44; Yamada Y et al., *Biomed. Report* 2015 DOI: 10.3892/br.2015.439).

Overexpression of ALPK1 in mice resulted in lower levels of testosterone and increased production of the pro-inflammatory cytokines IL-1β and TGF-β, suggesting that the balance between ALPK1 and testosterone might play a role in testosterone-mediated inhibition of pro-inflammatory cytokines (Kuo T M et al., *J Steroid Biochem Mol Biol* 2015 154: 150-158).

ALPK1 activation has also been implicated as playing a role in cancer, including lung, colorectal, and breast cancers (Liao H F et al. *Scientific Reports* 2016 6:27350; Strietz J et al., *Oncotarget* 2016 1-16).

Recent studies have implicated ALPK1 as an important regulator of the innate immune response activated by certain bacteria. For example, APLK1 was suggested to be a key regulator of innate immunity against bacteria through its promotion of TIFA oligomerization and interleukin 8 (IL-8) expression in response to infection with *S. flexneri, S. typhimurium*, and *Neisseria meningitides* (Milivojevic M et al., *PLoS Pathog* 2017 13(2): e1006224). Zimmerman et al. describe an ALPK1 and TIFA dependent innate immune response triggered by the *Helicobacter pylori* Type IV Secretion System. (Zimmermann S et al., *Cell Reports* 2017 20(10): 2384-95). Both of these studies suggest that the bacterial metabolite, heptose-1,7-bisphosphate (HBP) activates TIFA-dependent innate immunity.

There are many diseases, disorders, and conditions whose clinical manifestations result from inflammation and various infections. There is a need for new methods for modulating inflammation in target tissues for treating such diseases, disorders, and conditions. The present disclosure addresses this need.

SUMMARY OF THE INVENTION

The present invention is based, in part, on the discovery that certain bacterial metabolites, including D-glycero-β-D-manno-heptose 1,7-bisphosphate (heptose 1,7 bisphosphate or "HBP") as well as D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and derivatives thereof represented by formula IA, IB, or IC described herein, induce ALPK1-dependent activation of downstream signaling, including increased expression of proinflammatory cytokines such as IL-8 and TNFα. The biological activity of HMP-1bP, its downstream product H1b-ADP-6L, and particularly H1b-ADP, was unexpected from what is currently known about ALPK1 and its role in activation of innate immunity by bacterial metabolites. The present disclosure also provides evidence of anti-tumor activity by H1b-ADP and H1b-ADP derviatives and demonstrates that co-administration of H1b-ADP with immune checkpoint inhibitors and immune modulators, including anti-PD-L1 and anti-PD-1 antibodies, anti-CTLA4 antibody, and anti-CD4 antibody, has a synergistic anti-tumor effect. The present disclosure also shows that co-administration of H1b-ADP with immune modulators including each of interferon alpha (INFα), a stimulator of interferon genes ("STING") agonist, and a TLR agonist (resquimod) has a synergistic anti-tumor effect.

Accordingly, the present disclosure provides compositions and methods related to modulating an immune response, treating cancer, potentiating an immune response to a target antigen, treating a disease or disorder amendable to treatment by activation of NFkB, p38, and JNK cell signaling pathways, and treating or preventing a disease or disorder caused by an infectious agent through activation of ALPK1. In certain embodiments, ALPK1 activation is achieved via the administration of an ALPK1 agonist selected from HBP, HMP-ibP, H1b-ADP-6L, and H1b-ADP, preferably HMP-1bP, H1b-ADP-6L, and H1b-ADP, and most preferably H1b-ADP-6L and H1b-ADP, or a derivative thereof represented by formula IA, IB, or IC described herein. In some embodiments, the disclosure provides methods of modulating an immune response in a subject, the methods comprising administering to the subject a composition comprising any one of an ALPK1 agonist represented by formula I, IA, IB, or IC described herein.

The present invention discloses novel heterocyclic compounds as agonists of ALPK1. The compounds are represented by formula (I):

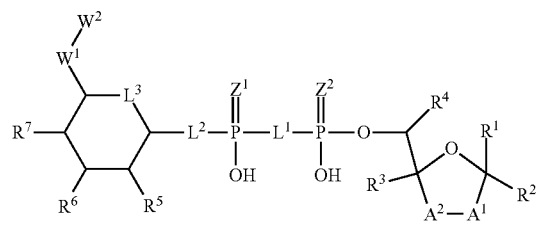

wherein $A^1$, $A^2$, $L^1$, $L^2$, $L^3$, $Z^1$, $Z^2$, $W^1$, $W^2$, $R^1$, $R^2$, $R^3$, $R^4$, $R^5$, $R^6$ and $R^7$ are as defined herein. Also included within the scope of the disclosure are stereoisomers, tautomers, stable isotopes, prodrugs, and pharmaceutically acceptable salts of the compounds of Formula I.

$A^1$ and $A^2$ are independently selected from O, S and —C($R^8R^9$)—, wherein $R^8$ and $R^9$ are independently selected from H, D, —OH, $N_3$, —CN, halogen, C1-C4 alkyl, C1-C4 alkoxyl, C1-C4 haloalkyl, C1-C4 haloalkoxyl, C1-C4 alkanoyloxyl, C1-C4 alkanoyloxyl, and substituted or unsubstituted aralkyloxyl, wherein the optional substituents are 1-3 substituents independently selected from D, halogen, —OH, =O, C1-C4 alkyl and C1-C4 alkoxy; at least one of $A^1$ or $A^2$ is —C($R^8R^9$); wherein $R^8$ or $R^9$ in $A^1$ can cyclize with $R^8$ or $R^9$ in $A^2$ to form C3-C6 cycloalkyl and cycloheteroalkyl containing 3 to 9 ring members and having 1-3 heteroatoms selected from N, O and S as ring members, each optionally substituted by 1-3 substituents independently selected from D, halogen, —OH, =O, C1-C4 alkyl and C1-C4 alkoxyl;

$L^1$ and $L^2$ are independently selected from O, $CH_2$, CHF and $CF_2$;

$L^3$ is O, S, $CH_2$ or CH(OH);

$Z^1$ and $Z^2$ are independently selected from O and S;

$W^1$ is —C($R^{10}R^{11}$)—, wherein $R^{10}$ and $R^{11}$ are independently selected from H, D, —OH, halogen, and optionally substituted groups selected from C1-C4 alkyl, C1-C4 alkoxyl, C1-C4 haloalkyl, C1-C4-haloalkoxyl, C1-C4 alkenyloxyl, aralkyloxyl and $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein the optional substituents for $R^{10}$ and $R^{11}$ are 1-3 substituents independently selected from D, halogen, —OH, =O, C1-C4 alkyl and C1-C4 alkoxy;

$W^2$ is H or C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein $R^{12}$ is C1-C4 alkyl, C1-C4 alkoxy, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members.

$R^1$ is C6-C10 aryl or heteroaryl containing 5 to 10 ring atoms and having 1-4 heteroatoms selected from N, O and S as ring members, wherein $R^1$ is optionally substituted with 1-3 substituents selected from D, halogen, —OH, =O, CN, $NH_2$, C1-C4 alkyl, C1-C4 alkoxy, C1-C4 alkylamine, C1-C4 dialkylamine and ($R^{13}R^{14}$)NCO—, wherein $R^{13}$ and $R^{14}$ are independently selected from H, C1-C4 alkyl, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^2$, $R^3$ and $R^4$ are independently selected from H, D, halogen, C1-C4 alkyl and C1-C4 haloalkyl;

$R^5$, $R^6$ and $R^7$ are selected from H, D, halogen and —OH, $R^{12}CO_2$—, wherein $R^{12}$ is selected from C1-C4 alkyl, C1-C4 alkoxyl, C1-C4 alkanoyloxyl, C1-C4 alkenyloxyl, C1-C4 alkylamino, C3-C6 cycloalkyl, cycloheteroalkyl containing 4 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein any two of the adjacent groups of $R^5$, $R^6$ and $R^7$ can cyclize to form cycloheteroalkyl containing 5 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy.

In embodiments, the disclosure provides a method for modulating an immune response in a subject in need of such treatment, the method comprising administering to the subject a composition comprising any one of an ALPK1 agonist, including an ALPK1 agonist represented by formula I, IA, IB, or IC described herein, a polynucleotide encoding ALPK1 or a constitutively active mutant thereof, or an ALPK1 protein or constitutively active mutant of said protein. In embodiments, the method for modulating an immune response is selected from activation of innate immunity and activation of adaptive immunity.

In embodiments, the disclosure provides a method for treating cancer in a subject in need of such treatment, the method comprising administering to the subject a composition comprising any one of an agonist of ALPK1, including an ALPK1 agonist represented by formula I, IA, IB, or IC described herein, a polynucleotide encoding ALPK1 or a constitutively active mutant thereof, or an ALPK1 protein or constitutively active mutant of said protein. In embodiments, the composition comprises an an ALPK1 agonist selected from a compound represented by formula I, IA, IB, or IC described herein, or selected from HBP, HMP-1bP, H1b-ADP-6L, and H1b-ADP, preferably HMP-1bP, H1b-ADP-6L, and H1b-ADP, and most preferably H1b-ADP-6L and H1b-ADP. In embodiments, the ALPK1 agonist is H1b-ADP. In embodiments, the ALPK1 agonist is selected from any one of Compounds 1-3, 9-17, 19, 20-22, and 26-32. In embodiments, the ALPK1 agonist is Compound 15. In embodiments, the cancer is selected from soft tissue sarcoma, breast cancer, head and neck cancer, melanoma, cervical cancer, bladder cancer, hematologic malignancy, glioblastoma, pancreatic cancer, prostate cancer, colon cancer, breast cancer, renal cancer, lung cancer, merkel cell carcinoma, small intestine cancer, thyroid cancer, acute myelogenous leukemia (AML), acute lymphocytic leukemia (ALL), chronic lymphocytic leukemia (CLL), chronic myelogenous leukemia (CML), gastric cancer, gastrointestinal stromal tumors, non-Hodgkins lymphoma, Hodgkins lymphoma, liver cancer, leukemia, lymphoma, T-cell lymphoma, brain cancer, and multiple myeloma. In embodiments, the cancer is selected from breast cancer, head and neck cancer, melanoma, renal cancer, lung cancer, merkel cell carcinoma, and lymphoma.

In embodiments, the disclosure provides a method for potentiating an immune response to a target antigen in a subject, the method comprising administering to the subject a composition comprising any one of an agonist of ALPK1, including an ALPK1 agonist represented by formula I, IA, IB, or IC described herein, a polynucleotide encoding ALPK1 or a constitutively active mutant thereof, or an ALPK1 protein or constitutively active mutant of said protein, as a vaccine or immunologic adjuvant that acts to potentiate an immune response to the target antigen. In embodiments, the target antigen is an antigen of an infectious agent selected from the group consisting of adenovirus, Coxsackie B virus, cytomegalovirus, eastern equine encephalitis virus, ebola virus, enterovirus 71, Epstein-Barr virus, *Haemophilus influenzae* type b (Hib), hepatitis C virus (HCV), herpes virus, human immunodeficiency virus (HIV), human papillomavirus (HPV), hookworm, Marburg virus, norovirus, respiratory syncytial virus (RSV), rotavirus, *Salmonella typhi, Staphylococcus aureus, Streptococcus pyogenes*, varicella, West Nile virus, *Yersinia pestis*, and Zika virus. In embodiments, the agonist of ALPK1, including an ALPK1 agonist represented by formula I, IA, IB, or IC described herein, the polynucleotide encoding ALPK1 or a constitutively active mutant thereof, or the ALPK1 protein or constitutively active mutant of said protein, acts as a vaccine adjuvant for a vaccine in the treatment or prevention of anthrax, caries, Chagas disease, dengue, diphtheria, ehrlichiosis, hepatits A or B, herpes, seasonal influenza, Japanese encephalitis, leprosy, lyme disease, malaria, measles, mumps, meningococcal disease, including meningitis and septicemia, Onchocerciasis river blindness, pertussis (whooping cough), pneumococcal disease, polio, rabies, rubella, schistosomiasis, severe acute respiratory syndrome (SARS), shingles, smallpox, syphilis, tetanus, tuberculosis, tularemia, tick-borne encephalitis virus, typhoid fever, trypanosomiasis, yellow fever, or visceral leishmaniasis.

In embodiments, the disclosure provides a method for treating a disease or disorder amendable to treatment by activation of NFkB, p38, and JNK cell signaling pathways in cells of a subject, the method comprising administering to the subject a composition comprising any one of an agonist of ALPK1, a polynucleotide encoding ALPK1 or constitutively active mutant thereof, or an ALPK1 protein or constitutively active mutant of said protein. In embodiments, the disease or disorder is selected from tuberculosis, meningitis, pneumonia, ulcer, sepsis, rhinitis, asthma, allergy, COPD, inflammatory bowel disease, arthritis, obesity, radiation-induced inflammation, psoriasis, atopic dermatitis, non-alcoholic steatohepatitis (NASH), Alzheimer's disease, systemic lupus, erythematosus (SLE), autoimmune thyroiditis (Grave's disease), multiple sclerosis, ankylosing spondylitis bullous diseases, and diseases and disorders caused by the hepatitis C virus (HCV), the hepatitis B virus (HBV), or the human immunodeficiency virus (HIV).

In embodiments, the disclosure provides a method for treating or preventing a disease or disorder caused by an infectious agent selected from a bacteria, virus, or parasite in a subject in need thereof, the methods comprising administering to the subject a composition comprising any one of an agonist of ALPK1, including an ALPK1 agonist represented by formula I, IA, IB, or IC described herein, a polynucleotide encoding ALPK1 or constitutively active mutant thereof, or an ALPK1 protein or constitutively active mutant of said protein. In embodiments, the infectious agent is a bacteria. In embodiments, the infectious agent is a virus. In embodiments, the infectious agent is a parasite. In embodiments, the bacteria is a Gram-negative or a Gram-positive bacteria. In embodiments, the Gram-negative bacteria is selected from the group consisting of *Acinetobacter baumanii, Aggregatobacter actinomycetemcomitans, Bartonella bacilliformis, Bartonella henselae, Bartonella quintana, Bifidobacterium, Borrelia, Bortadella pertussis, Brucella* sp, *Burkholderia cepacis, Burkholderia psedomallei, Campylobacterjejuni, Cardiobacterium hominis, Campylobacter fetus, Chlamydia pneumonia, Chlymydia trachomatis, Clostridium difficile, Cyanobacteria, Eikenella corrodens, Enterobacter, Enterococcus faccium, Escherichia coli, Escherichia* coli 0157, *Franceilla tularensis, Fusobacterium nucleatum, Haemophilus influenza, Haemophilus aphrophilus, Haemophilus ducreyi, Haemophilus parainfluenzae, Helicobacter pylori, Kingella kingae, Klebsiella pneumonia, Legionella bacteria, Legionella pneumophila* serogroup 1, *Leptospria, Morganella morganii, Neisseria gonorrhoeae, Neisseria meningitidis, Proteus mirabilis, Proteus vulgaris, Proteus myxofaciens, Providencia rettgeri, Providencia alcalifaciens, Providencia stuartii, Pseudomonas aeruginosa, Pseudomonas paucimobilis, Pseudomonas putida, Pseudomonas fluorescens, Pseudomonas acidovorans, Rickettsiae, Salmonella enterica, Salmonella typhi, Salmonella paratyphi* types A, B typhus, *Salmonella. dublin, Salmonella arizonae, Salmonella choleraesuis, Serratia marcescens, Schigella dysenteriae, Schigella flexneri, Schigella boydii, Schigella sonnei, Treponema, Stenotrophomonas maltophilia, Vibrio cholerae, Vibrio mimicus, Vibrio alginolyticus, Vibrio hollisae, Vibrio parahaemolyticus, Vibrio vulnificus* and *Yersinia pestis*. In embodiments, the Gram-positive bacteria selected from the group consisting of Actinomycetes, *Bacillus anthracis, Bacillus subtilis, Clostridium tetani, Clostridium perfingens, Clostridium botulinum, Clostridium tetani. Corynebacterium diphtheriae, Enterococcus faecalis, Enterococcus faecium, Erysipelothrix ruhsiopathiae, Listeria monocytogenes, Mycobacterium leprae, Mycobacterium tuberculosis, Mycoplasma, Nocardia, Propionibacerium, Pseudomonas aeruginosa, Pneumococci, Staphylococcus aureus, Staphylococcus epidermidis*, methicillin-resistant *Staphylococcus aureus* (MRSA), vancomycin resistant *Staphylococcus aureus* (VRSA), *Staphylococcus lugdunensis, Staphylococcus saprophyticus, Streptococcus pneumonia, Streptococcus pyogenes*, and *Streptococcus* mutants. In embodiments, the virus is selected from the group consisting of ebolavirus, hepatitis B virus, hepatitis C virus, herpes simplex virus, human immunodeficiency virus (HIV), human papillomavirus (HPV-6, HPV-11), human SARS coronavirus, influenza A virus, influenza B virus, influenza C virus, measles virus, rabies virus, poliovirus, SARS corona virus, and yellow fever virus. In embodiments, the parasite is selected from the group consisting of *Acanthamoeba* spp, American trypanosomiasis, *Balamuthia mandnillanis, Babesia divergenes, Babesia bigemina, Babesia equi, Babesia microfti, Babesia duncani, Balantidium coli, Blastocystis* spp *Cryptosporidium* spp, *Cyclospora cayetanensis, Dientamoeba fragilis, Diphyllobothrium latum, Leishmania amazonesis, Naegleria fowderi, Plasmodium falciparum, Plasmodium vivax, Plasmodium ovale curtisi, Plasmodium malariae, Rhinosporidium seeberi, Sarcocystis bovihominis, Sarcocystiss suihominis, Toxoplasma gondii, Trichmonas vaginalis, Trypanosoma brucei, Trypanosoma cruzi*, and *Taenia multiceps*.

In embodiments of any of the foregoing methods, the method may further comprise administering to the subject one or more additional therapeutic agents or immune modulators, and combinations thereof. In embodiments, the one or more additional therapeutic agents is selected from an anti-microbial agent, such as an anti-bacterial agent, an anti-viral agent, or an anti-parasitic agent, an anti-cancer agent, or a therapeutic agent for the treatment of tuberculosis, meningitis, pneumonia, ulcer, sepsis, rhinitis, asthma, allergy, COPD, inflammatory bowel disease, arthritis, obesity, radiation-induced inflammation, psoriasis, atopic dermatitis, non-alcoholic steatohepatitis (NASH), Alzheimer's disease, systemic lupus, erythematosus (SLE), autoimmune thyroiditis (Grave's disease), multiple sclerosis, and ankylosing spondylitis bullous diseases.

In embodiments of the methods for treating cancer, the one or more additional therapeutic agents is an immune modulator. In embodiments, the immune modulator is selected from one or more of an inhibitor or antagonist of an immune checkpoint regulator, an immune stimulatory molecule, and an agonist of an immune co-stimulatory molecule. In embodiments, the inhibitor or antagonist of an immune checkpoint regulator is a PD-1/PD-L1 inhibitor. In embodiments, the PD-1/PD-L1 inhibitor is selected from the group consisting of nivolumab, pembrolizumab, pidilizumab, BMS-936559, atezolizumab, durvalumab, and avelumab. In embodiments, the immune modulator is selected from interferon alpha (INFα), a stimulator of interferon genes ("STING") agonist, a TLR agonist (e.g., resquimod), and an anti-OX40 (CD134) agonist antibody. In embodiments, the agonist of an immune co-stimulatory molecule is an anti-OX40 (CD134) agonist antibody. In embodiments, the cancer is selected from advanced melanoma, non-small cell lung cancer, renal cell carcinoma, bladder cancer, Hodgkin's lymphoma, liver cancer, gastric cancer, colon cancer, breast cancer, non-Hodgkin's lymphoma, prostate cancer, head and neck cancer, thyroid cancer, brain cancer, acute myeloid leukemia (AML), merkel cell carcinoma, multiple myeloma, cervical cancer, and sarcoma.

In embodiments, the one or more additional immune modulators is an inhibitor or antagonist of an immune checkpoint regulator, or a vaccine against an immune checkpoint regulator. In embodiments, the one or more additional immune modulators is an agonist of an immune an immune checkpoint regulator, such as a co-stimulatory molecule, for example an agonist of OX40 (CD134). In embodiments, the immune checkpoint regulator is selected from the pro-gramed cell death 1 (PD-1) receptor (CD279), a ligand of PD-1 (e.g., PD-L1), cytotoxic T-lymphocyte associated protein 4 (CTLA4), tumor necrosis factor receptor superfamily member 9 (alternatively TNFRSF9, 4-1BB) and 4-1BB ligands, tumor necrosis factor receptor superfamily member 4 (alternatively TNFRSF4, OX40) and OX40 ligands, glucocorticoid-induced TNFR-related protein (GITR), Tumor Necrosis Factor Receptor Superfamily Member 7 (alternatively TNFRSF7, cluster of differentiation 27, CD27), TNFRSF25 and TNF-like ligand 1A (TL1A), TNF Receptor Superfamily Member 5 (alternatively TNFRSF5, CD40) and CD40 ligand, Herpesvirus entry mediator (HVEM)-tumor necrosis factor ligand superfamily member 14 (alternatively TNFSF4, LIGHT)-lymphotoxin alpha (LTA), herpesvirus entry mediator-(HVEM)-B- and T-lymphocyte attenuator (BTLA)-CD160 (alternatively TNFSF14), lymphocyte activating gene 3 (LAG3), T-cell immunoglobulin and mucin-domain containing-3 (TIM3), sialic-acid-binding immunoglobulin-like lectins (SIGLECs), inducible T-cell costimulator (ICOS) and ICOS ligand, B7-H3 (B7 family, alternatively CD276), V-set domain-containing T-cell activation inhibitor 1 (VTCN1, alternatively B7-H4), V-Type immunoglobulin domain-containing suppressor of T-cell activation (VISTA), human endogenous retrovirus-H long terminal repeat-associating protein 2 (HHLA2)-transmembrane and Immunoglobulin domain containing 2 (TMIGD2), butyrophilins, natural killer cell receptor 2B4 (alternatively NKR2B4, CD244) and B-Cell Membrane Protein (CD48), T-Cell Immunoreceptor with Immunoglobulin (Ig) and immunoreceptor tyrosine-based inhibition motif domains (TIGIT) and Poliovirus receptor (PVR) family members, killer-cell immunoglobulin-like receptors (KIRs), Immunoglobulin-like transcripts (ILTs) and leukocyte immunoglobulin-like receptor (LIRs), natural killer group protein 2 member D (NKG2D) and natural killer group protein 2 member A (NKG2A), major histocompatibility complex (MHC) class I polypeptide-related sequence A (MICA) and MHC class I polypeptide-related sequence B (MICB), natural killer cell receptor 2B4 (CD244), colony stimulating factor 1 receptor (CSF1R), indoleamine 2,3-dioxygenase (IDO), transforming growth factor beta (TGFβ), Adenosine-ecto-nucleotidase triphosphate diphosphohydrolase 1 (CD39)-5'-nucleotidase (CD73), C-X-C motif chemokine receptor 4 (CXCR4) and C-X-C motif chemokine ligand 12 (CXCL12), phosphatidylserine, signal regulatory protein alpha (SIRPA) and integrin associated protein (CD47), vascular endothelial growth factor (VEGF), and neuropilin.

In embodiments, the one or more additional immune modulators is a vaccine.

In embodiments of a method for treating cancer, the vaccine is a vaccine against a tumor antigen. In embodiments, the tumor antigen is selected from glycoprotein 100 (gp100), mucin 1 (MUC1), and melanoma-associated antigen 3 (MAGEA3).

In embodiments, the one or more additional immune modulators is a T cell, preferably a chimeric antigen receptor T cell. In embodiments, the one or more additional immune modulators is a recombinant protein, preferably selected from granulocyte-macrophage colony-stimulating factor (GM-CSF), interleukin 7 (IL-7), IL-12, IL-15, IL-18, and IL-21.

In embodiments of any of the foregoing methods, the composition may comprise an ALPK1 agonist represented by formula I, IA, IB, or IC described herein, or an ALPK1 agonist selected from D-glycero-β-D-manno-heptose 1,7-bisphosphate (HBP), and prodrugs, analogues and derivatives thereof. In embodiments, the ALPK1 agonist is HBP. In embodiments, the ALPK1 agonist is selected from any one of Compounds 1-3, 9-17, 19, 20-22, and 26-32. In embodiments, the ALPK1 agonist is Compound 15.

In embodiments, the ALPK1 agonist is a prodrug of HBP. In embodiments, the prodrug comprises a protecting group selected from the group consisting of a carbonyloxymethyl, a cyclosaligenyl, a cyclic 1-aryl-1,3-propanyl ester, an aryloxy phosphoramidate or phosphonamidate, and a methylaryl haloalkylamdiate. In embodiments, the prodrug is a compound of Formula 3a, 3b, 3c, 3d, or 3e. In embodiments, the prodrug is selected from a compound of Table 1.

In embodiments of any of the foregoing methods, the composition may comprise a polynucleotide encoding ALPK1, or a constitutively active mutant thereof, or an ALPK1 protein or constitutively active mutant of said protein. In embodiments, the composition comprises a polynucleotide encoding ALPK1, or a constitutively active mutant thereof. In embodiments, the composition is adapted for administration to the subject using a viral or non-viral gene delivery system. In embodiments, the composition is adapted for administration to the subject using a viral gene delivery system. In embodiments, the composition further comprises viral particles. In embodiments, the composition is adapted for administration to the subject using a non-viral gene delivery system. In embodiments, the composition further comprises one or more of liposomal particles, nanoparticles, minicircles, minivectors, and polymeric carriers. In embodiments, the non-viral gene delivery system comprises a gene editing technique. In embodiments, the gene editing technique utilizes a meganuclease, zinc finger nucleases (ZFNs), transcription activator-like effector nucleases (TALENs), or CRISPR/Cas-9.

In embodiments, the disclosure provides a method for treating a liver disease or disorder in a subject in need of such treatment, the method comprising administering a low dose of H1b-ADP, or a derivative thereof, to the subject. In embodiments, the low dose is in the range of from 1 nanogram to 1 milligram per kilogram body weight (1 ng/kg to 1 mg/kg), preferably 1 microgram to 100 micrograms per kilogram body weight (1 ug/kg to 100 ug/kg). In embodiments, the liver disease or disorder is selected from liver cancer, non-alcoholic steatohepatitis (NASH), and a disease or disorder caused by infection with the hepatitis C virus (HCV) or the hepatitis B virus (HBV).

In embodiments, the disclosure provides a method for treating cancer, the method comprising administering to the subject in need of such treatment a composition comprising bacteria producing H1b-ADP or H1b-ADP-6L. In embodiments, the composition is administered via intratumoral injection.

In embodiments of any of the foregoing methods, the subject may be a vertebrate. In embodiments, the subject is a human.

The disclosure also provides a vaccine composition or vaccine adjuvant composition comprising an agonist of ALPK1 and a pharmaceutical composition comprising an agonist of ALPK1, and a carrier. In embodiments of these compositions, the agonist of ALPK1 is a compound represented by formula I, IA, IB, or IC described herein, HBP, or a prodrug, analogue, or derivative thereof. In embodiments, the ALPK1 agonist is selected from any one of Compounds 1-3, 9-17, 19, 20-22, and 26-32. In embodiments, the ALPK1 agonist is Compound 15. In embodiments, the ALPK1 agonist is a prodrug of HBP. In embodiments, the prodrug comprises a protecting group selected from the group consisting of a carbonyloxymethyl, a cyclosaligenyl, a cyclic 1-aryl-1, 3-propanyl ester, an aryloxy phosphoramidate or phosphonamidate, and a methylaryl haloalkylamdiate. In embodiments, the prodrug is a compound of Formula 3a, 3b, 3c, 3d, or 3e. In embodiments, the prodrug is selected from a compound of Table 1.

The disclosure also provides methods of selecting a compound capable of modulating an immune response in a mammalian subject, the method comprising contacting ALPK1 with the test compound in the presence of ATP and, separately but concurrently, in the absence of ATP, followed by performing an assay to detect ALPK1 phosphorylation and/or activation of one or more downstream targets of ALPK1 signaling. In embodiments, the contacting of ALPK1 with the test compound is performed in a cell-free system or in a cellular system. In embodiments, the assay to detect ALPK1 phosphorylation and/or activation of one or more downstream targets of ALPK1 signaling comprises a radiometric based kinase assay, a fluorescence-based kinase assay, a time-resolved fluorescence energy transfer (TR-FRET) based assay, an alpha-technology based assay, an enzyme-linked immunosorbent assay, luminescence detection, a mobility shift based kinase assay, a Western based kinase assay, and a ligand-kinase binding assay.

In accordance with any of the methods described herein, the ALPK1 agonist may be selected from a compound represented by formula I, IA, IB, or IC described herein, D-glycero-b-D-manno-heptose 1,7-bisphosphate (HBP), D-glycero-b-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives of any of the foregoing molecules. In embodiments, the ALPK1 agonist is selected from HMP-1bP, H1b-ADP, and H1b-ADP-6L. In embodiments, the ALPK1 agonist is H1b-ADP or H1b-ADP-6L, and derivatives thereof as described herein. In embodiments, the ALPK1 agonist is H1b-ADP. In embodiments, the ALPK1 agonist is selected from any one of Compounds 1-3, 9-17, 19, 20-22, and 26-32. In embodiments, the ALPK1 agonist is Compound 15.

In embodiments, the disclosure provides a vaccine composition or vaccine adjuvant composition comprising an agonist of ALPK1 selected from a compound represented by formula I, IA, IB, or IC described herein, HBP, HMP-1bP, H1b-ADP, and H1b-ADP-6L. In embodiments, the ALPK1 agonist is selected from HMP-1bP, H1b-ADP, and H1b-ADP-6L. In embodiments, the ALPK1 agonist is H1b-ADP or H1b-ADP-6L, and derivatives thereof as described herein. In embodiments, the ALPK1 agonist is H1b-ADP. In embodiments, the ALPK1 agonist is a compound represented by formula I, IA, IB, or IC described herein. In embodiments, the ALPK1 agonist is selected from any one of Compounds 1-3, 9-17, 19, 20-22, and 26-32. In embodiments, the ALPK1 agonist is Compound 15.

In embodiments, the disclosure provides a pharmaceutical composition comprising an agonist of ALPK1 selected from a compound represented by formula I, IA, IB, or IC described herein, HBP, HMP-1bP, H1b-ADP, and H1b-ADP-6L. In embodiments, the ALPK1 agonist is selected from HMP-1bP, H1b-ADP, and H1b-ADP-6L. In embodiments, the ALPK1 agonist is H1b-ADP or H1b-ADP-6L, and derivatives thereof as described herein. In embodiments, the ALPK1 agonist is H1b-ADP. In embodiments, the ALPK1 agonist is a compound represented by formula I, IA, IB, or IC described herein. In embodiments, the ALPK1 agonist is selected from any one of Compounds 1-3, 9-17, 19, 20-22, and 26-32. In embodiments, the ALPK1 agonist is Compound 15.

In embodiments, the disclosure provides a method of treating cancer in a subject in need of such treatment, comprising administering to the subject a composition comprising an agonist of ALPK1 selected from the group consisting of a compound represented by formula I, IA, IB, or IC described herein, HBP, HMP-1bP, H1b-ADP and H1b-ADP-6L. In embodiments, the ALPK1 agonist is selected from HMP-1bP, H1b-ADP, and H1b-ADP-6L. In embodiments, the ALPK1 agonist is H1b-ADP or H1b-

ADP-6L, and derivatives thereof as described herein. In embodiments, the ALPK1 agonist is H1b-ADP. In embodiments, the ALPK1 agonist is selected from any one of Compounds 1-3, 9-17, 19, 20-22, and 26-32. In embodiments, the ALPK1 agonist is Compound 15. In embodiments, the method further comprises administering to the subject a PD-1/PD-L1 inhibitor or an agonist of an immune co-stimulatory molecule. In embodiments, the ALPK1 agonist is H1b-ADP and the PD-1/PD-L1 inhibitor is selected from the group consisting of nivolumab, pembrolizumab, pidilizumab, BMS-936559, atezolizumab, durvalumab, and avelumab. In embodiments, the ALPK1 agonist is H1b-ADP and the agonist of an immune co-stimulatory molecule is an anti-OX40 (CD134) agonist antibody. In accordance with the foregoing methods, the subject may be a human subject and the cancer may be a cancer as described hereinabove. In embodiments, the cancer is a solid tumor. In embodiments, the cancer is refractory.

The disclosure further provides a composition for use in therapy, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in a method for modulating an immune response in a subject in need of such treatment, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in a method for treating cancer in a subject in need of such treatment, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in a method for potentiating an immune response in a subject in need of such treatment, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in a method for treating a disease or disorder amendable to treatment by activation of NFkB, p38, and JNK cell signaling pathways in cells of a subject in a subject in need of such treatment, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in treating or preventing a disease or disorder caused by an infectious agent selected from a bacteria, virus, or parasite in a subject in need thereof, the composition comprising an ALPK1 agonist selected from D-glycero-β-D-manno-heptose 1,7-bisphosphate (HBP), D-glycero-β-D-manno-heptose-1-phosphate (HMP-1bP), L-glycero-D-manno-heptose-1β-ADP (H1b-ADP-6L) and D-glycero-D-manno-heptose-1β-ADP (H1b-ADP), and prodrugs, analogues and derivatives thereof; or the composition comprising an ALPK1 agonist selected from H1b-ADP-6L, H1b-ADP, or a derivative thereof selected from a compound of any one of claims 1 to 22 and any one of Compounds 1-33 of Table 1.

The disclosure also provides a composition for use in a method for treating cancer in a subject in need of such treatment, the composition comprising an agonist of ALPK1 selected from the group consisting of H1b-ADP-6L, H1b-ADP, or a derivative thereof selected from a compound of any one of claims 1 to 22 and any one of Compounds 1-33 of Table 1, and the method comprising combination therapy of the ALPK1 agonist with an immune modulator selected from one or more of an inhibitor or antagonist of an immune checkpoint regulator, an immune stimulatory molecule, and an agonist of an immune co-stimulatory molecule.

The disclosure also provides a composition for use in a method for treating a liver disease or disorder in a subject in need of such treatment, the composition comprising a low dose of H1b-ADP, or a derivative thereof, wherein the liver disease or disorder is optionally selected from liver cancer, non-alcoholic steatohepatitis (NASH), and a disease or disorder caused by infection with the hepatitis C virus (HCV) or the hepatitis B virus (HBV).

The disclosure also provides a composition for use in a method for treating cancer, the composition comprising bacteria producing H1b-ADP or H1b-ADP-6L, wherein the composition is optionally adapted for intratumoral injection.

BRIEF DESCRIPTION OF THE FIGURES

FIG. 1A-B: Protein sequences for ALPK1 isoform 1 (A) and isoform 2 (B).

DETAILED DESCRIPTION

Figure 2A:
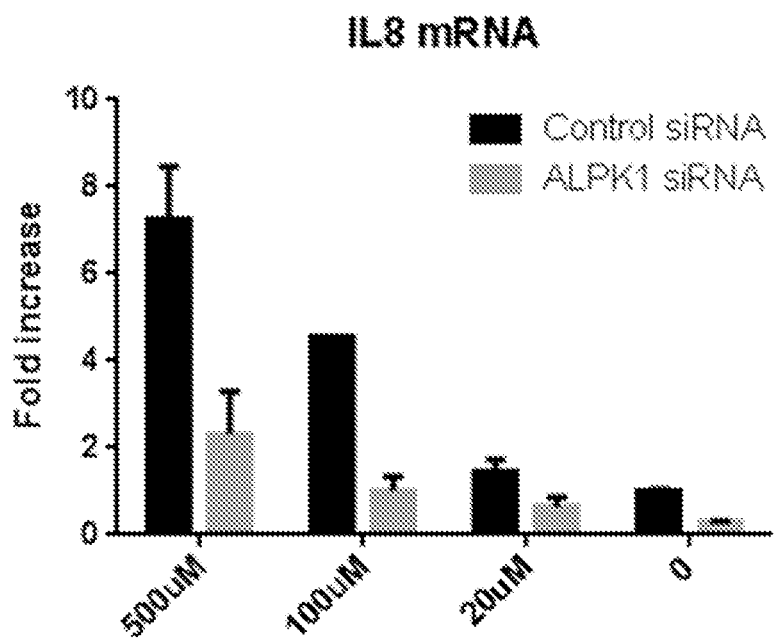
FIG. 2A-B: IL-8 (A) and TNFα (B) mRNA expression were both increased by HBP (chemically-synthesized) in an ALPK1-dependent manner.

The disclosure provides compositions and methods related to the therapeutic activation of ALPK1 with a suitable agonist, a polynucleotide encoding ALPK1 or a constitutively active mutant thereof, or an ALPK1 protein or constitutively active mutant of said protein.

Definitions

As used herein, the term "ALPK1" may refer to either one of two splice variants, isoform 1 or isoform 2, of the human ALPK1 gene. Each isoform shares the same kinase domain. For reference, the human ALPK1 gene is identified by Entrez Gene ID 80216.

As used herein, the term "activation of ALPK1" refers to the activation of ALPK1 kinase activity. In embodiments, the disclosure provides methods of activating ALPK1 by providing an ALPK1 agonist which may be, for example, an ALPK1 activating ligand, such as HBP, or a prodrug, analog or derivative thereof. Methods for making synthetic HBP are known, for example, as described in Inuki S et al. *Organic Letter* 2017 19(12):3079-82. In embodiments, the ALPK1 agonist is selected from HMP-1bP and H1b-ADP and prodrugs, analogs and derivatives thereof. In embodiments, the ALPK1 agonist is H1b-ADP, or a prodrug, analog or derivative thereof. In some embodiments, the disclosure provides methods of activating ALPK1 by providing an ALPK1 agonist represented by formula I, IA, IB, or IC.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, C1-6 alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. In some embodiments, alkyl groups are substituted with 1-2 substituents. As a non-limiting example, suitable substituents include halogen and hydroxyl.

As used herein, "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Alkenyl groups can be substituted or unsubstituted.

As used herein, the term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted. In some embodiments, alkylene groups are substituted with 1-2 substituents. As a non-limiting example, suitable substituents include halogen and hydroxyl.

As used herein, the term "alkoxy" or "alkoxyl" refers to an alkyl group having an oxygen atom that connects the alkyl group to the point of attachment: alkyl-O—. As for alkyl group, alkoxyl groups can have any suitable number of carbon atoms, such as C1-6. Alkoxyl groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be substituted or unsubstituted.

As used herein, the term "alkenyloxy" or "alkenyloxyl" refers to an alkenyl group, as defined above, having an oxygen atom that connects the alkenyl group to the point of attachment: alkenyl-O—. Alkenyloxyl groups can have any suitable number of carbon atoms, such as C1-6. Alkenyloxyl groups can be further substituted with a variety of substituents described within. Alkenyloxyl groups can be substituted or unsubstituted.

As used herein, the term "alkylamine" or "alkylamino" refers to an alkyl group having a nitrogen atom that connects the alkyl group to the point of attachment: alkyl-N—. As for alkyl group, alkoxyl groups can have any suitable number of carbon atoms, such as C1-6.

As used herein, the term "halogen" refers to fluorine, chlorine, bromine and iodine.

As used herein, the term "haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc.

As used herein, the term "haloalkoxyl" or "haloalkoxy" refers to an alkoxyl group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens.

As used herein, the term "alkanoyl" refers to an alkyl group having a carbonyl group that connects the alkyl group to the point of attachment: alkyl-C(O)—. As for alkyl group, alkanoyloxyl groups can have any suitable number of carbon atoms, such as C1-4. For example, an alkanoyl groups include acetyl, propinoyl, butyryl, etc.

As used herein, the term "alkanoyloxyl" refers to an alkanoyl group having a an oxygen atom that connects the alkanoyl group to the point of attachment: alkyl-C(O)—O—. As for the alkyl group, alkanoyloxyl groups can have any suitable number of carbon atoms, such as C1-4. Exemplary alkanoyloxyl groups include acetoxy, propionyloxy, butryloxy, etc.

As used herein, the term "oxo" refers to an oxygen atom connected to the point of attachment by a double bond (=O).

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. In some embodiments, aryl groups are substituted with 1-2 substituents. As a non-limiting example, suitable substituents include halogen, hydroxyl, —NO2, C1-8 alkyl, C1-8 alkoxy.

As used herein, the term "aralkyloxyl" refers to an aryl group, as defined above, having an alkyl and oxygen atom that connects the aryl group to the point of attachment: aryl-alkyl-O—. As for alkyl group, aralkyloxyl groups can have any suitable number of carbon atoms, such as C1-4.

As used herein, the term "heteroaryl" refers to a monocyclic or fused bicyclic aromatic ring assembly containing 5 to 12 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 9 ring members and from 1 to 4 heteroatoms, or from 5 to 9 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), purine. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

As used herein, "cycloalkyl" refers to a saturated ring assembly containing from 3 to 8 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$. Cycloalkyl rings include, for example, cyclopropyl, cyclobutyl, cyclopentyl, cyclohexyl, and cyclooctyl. Cycloalkyl groups can be substituted or unsubstituted.

As used herein "cycloheteroalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, tetrahydrofuran, oxane (tetrahydropyran), oxepane, thiolane (tetrahydrothiophene), thiane (tetrahydrothiopyran), oxazolidine, isoxazolidine, thiazolidine, isothiazolidine, dioxolane, dithiolane, morpholine, etc. Heterocycloalkyl groups can be unsubstituted or substituted. For example, heterocycloalkyl groups can be substituted with $C_{1-6}$ alkyl or oxo (=O), among many others.

Certain compounds of the present invention possess asymmetric carbon atoms (optical centers) or double bonds; the racemates, diastereomer, geometric isomers, regioisomers and individual isomers (e.g., separate enantiomers) are all intended to be encompassed within the scope of the present invention. In some embodiments, the compounds of the present invention are a particular enantiomer, anomer, or diastereomer substantially free of other forms.

As used herein, the term "substantially free" refers to an amount of 10% or less of another form, preferably 8%, 5%, 4%, 3%, 2%, 1%, 0.5%, or less of another form. In some embodiments, the isomer is a stereoisomer.

Detailed Description of the Embodiments

In some embodiments, the disclosure provides an ALPK1 agonist represented by formula (I)

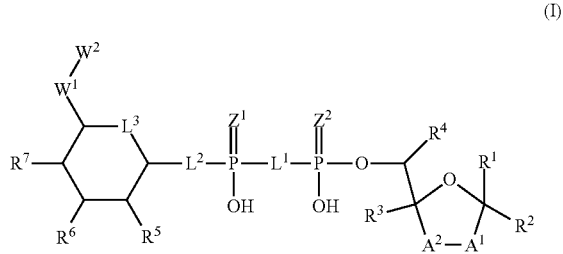

(I)

and/or a stereoisomer, tautomer, stable isotopes, prodrug or pharmaceutically acceptable salt thereof, wherein:

$A^1$ and $A^2$ are independently selected from O, S and —C($R^8R^9$)—, wherein $R^8$ and $R^9$ are independently selected from H, D, —OH, $N_3$, —CN, halogen, C1-C4 alkyl, C1-C4 alkoxyl, C1-C4 haloalkyl, C1-C4 haloalkoxyl, C1-C4 alkanoyloxyl, C1-C4 alkenyloxyl and substituted or unsubstituted aralkyloxyl, wherein the optional substituents are 1-3 substituents independently selected from D, halogen, —OH, =O, C1-C4 alkyl and C1-C4 alkoxy; at least one of $A^1$ or $A^2$ is —C($R^8R^9$); wherein $R^8$ or $R^9$ in $A^1$ can cyclize with $R^8$ or $R^9$ in $A^2$ to form C3-C6 cycloalkyl and cycloheteroalkyl containing 3 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy;

$L^1$ and $L^2$ are independently selected from O, $CH_2$, CHF and $CF_2$;

$L^3$ is O, S, $CH_2$ or CH(OH);

$Z^1$ and $Z^2$ are independently selected from O and S;

$W^1$ is —C($R^{10}R^{11}$)—, wherein $R^{10}$ and $R^{11}$ are independently selected from H, D, —OH, halogen, and optionally substituted groups selected from C1-C4 alkyl, C1-C4 alkoxyl, C1-C4 haloalkyl, C1-C4-haloalkoxyl, C1-C4 alkenyloxyl, aralkyloxyl and $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein the optional substituents for $R^{10}$ and $R^{11}$ are 1-3 substituents independently selected from D, halogen, —OH, =O, C1-C4 alkyl and C1-C4 alkoxy;

$W^2$ is H or C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein R12 is C1-C4 alkyl, C1-C4 alkoxy, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^1$ is C6-C10 aryl or heteroaryl containing 5 to 10 ring atoms and having 1-4 heteroatoms selected from N, O and S as ring members, wherein $R^1$ is optionally substituted with 1-3 substituents selected from of D, halogen, —OH, =O, CN, $NH_2$, C1-C4 alkyl, C1-C4 alkoxy, C1-C4 alkylamine, C1-C4 dialkylamine and ($R^{13}R^{14}$)NCO—, wherein $R^{13}$ and $R^{14}$ are independently selected from H, C1-C4 alkyl, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^2$, $R^3$ and $R^4$ are independently selected from H, D, halogen, C1-C4 alkyl and C1-C4 haloalkyl;

$R^5$, $R^6$ and $R^7$ are selected from H, D, halogen and —OH, $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein any two of the adjacent groups of $R^5$, $R^6$ and $R^7$ can cyclize to form cycloheteroalkyl containing 5 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy.

In some embodiments, the compound of formula I is represented by the compound of formula IA and/or a stereoisomer, a stable isotope, prodrug or a pharmaceutically acceptable salt thereof Formula IA

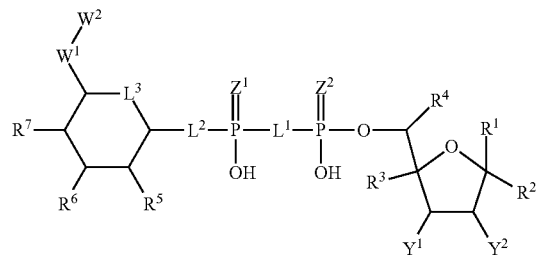

wherein:

$Y^1$ and $Y^2$ are independently selected from H, D, —OH, $N_3$, —CN, halogen and optionally substituted groups selected from C1-C4 alkyl, C1-C4 alkoxyl, C1-C4 haloalkyl, C1-C4 haloalkoxyl, C1-C4 alkanoyloxyl, C1-C4 alkenyloxyl and aralkyloxyl; wherein the optional substituents are 1-3 substituents independently selected from D, halogen, —OH, =O, C1-C4 alkyl and C1-C4 alkoxy; and $R^1$-$R^7$, $L^1$-$L^3$, $Z^1$, $Z^2$, $W^1$ and $W^2$ are defined above.

In some embodiments, $Y^1$ and $Y^2$ in the compound of formula IA are independently selected from H, D, —OH, halogen, C1-C4 alkyl, C1-C4 alkoxyl, C1-C4 haloalkyl, C1-C4 haloalkoxyl, C1-C4 alkanoyloxyl, and C1-C4 alkenyloxyl; and $R^1$-$R^7$, $L^1$-$L^3$, $Z^1$, $Z^2$, $W^1$ and $W^2$ are as defined above.

In some embodiments, $Y^1$ and $Y^2$ in the compound of formula IA are independently selected from —OH, halogen, C1-C4 alkyl, and C1-C4 alkanoyloxyl; and $R^1$-$R^7$, $L^1$-$L^3$, $Z^1$, $Z^2$, $W^1$ and $W^2$ are defined above.

In some embodiments, the compound of formula I or formula IA does not include D-glycero-D-manno-heptose-1β-ADP (also referred to herein as H1b-ADP or H1b-D-ADP), the compound shown below:

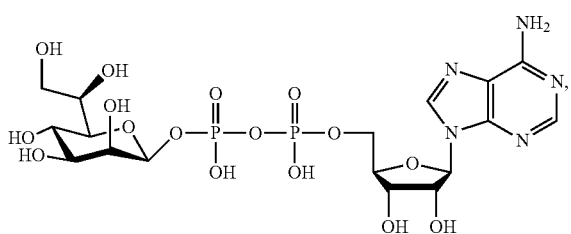

or its diastereomer L-glycero-D-manno-heptose-1β-ADP (also referred to herein as H1b-ADP-6L or H1b-L-ADP).

In some embodiments, the compound of formula I is represented by the compound of formula IB and/or a stereoisomer, a stable isotope, prodrug or a pharmaceutically acceptable salt thereof Formula IB

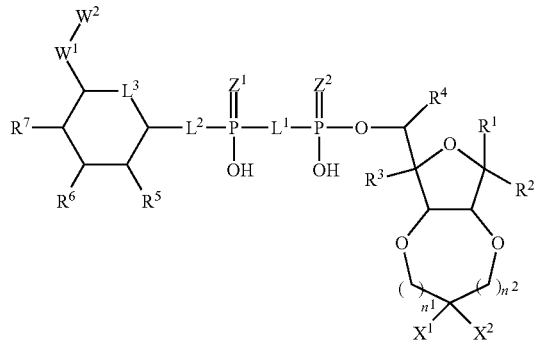

wherein:

$n^1$ and $n^2$ are each an integer independently selected from the group consisting of 0-2;

$X^1$ and $X^2$ are independently selected from H, D, —OH, $N_3$, —CN, halogen and optionally substituted groups selected from C1-C4 alkyl, C1-C4 alkoxyl, C1-C4 haloalkyl, C1-C4 haloalkoxyl, C1-C4 alkanoyloxyl, C1-C4 alkenyloxyl and aralkyloxyl, wherein the optional substituents are 1-3 substituents independently selected from D, halogen, —OH, =O, C1-C4 alkyl and C1-C4 alkoxy; and $R^1$-$R^7$, $L^1$-$L^3$, $Z^1$, $Z^2$, $W^1$ and $W^2$ are defined above.

In some embodiments, $n^1$ and $n^2$ of formula IB are each 0.

In some embodiments, $X^1$ and $X^2$ of formula IB are independently selected from H, D, C1-C4 alkoxyl and C1-C4 alkyl; and $R^1$-$R^7$, $L^1$-$L^3$, $Z^1$, $Z^2$, $W^1$ and $W^2$ are defined above.

In some embodiments, the compound of Formula I is represented by the compound of Formula IC and/or a stereoisomer, a stable isotope, prodrug or a pharmaceutically acceptable salt thereof Formula IC

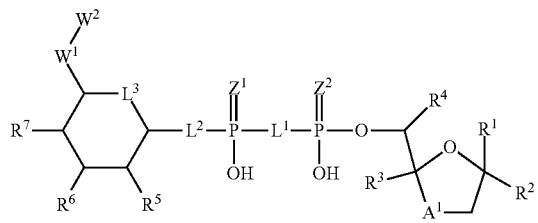

wherein:

$A^1$ is —C($R^8R^9$)—, O or S;

$R^1$-$R^9$, $L^1$-$L^3$, $Z^1$, $Z^2$, $W^1$ and $W^2$ are defined above.

In some embodiments, $R^2$, $R^3$, and $R^4$ in formulas I, IA, IB, and IC are each H.

In some embodiments, $R^5$, $R^6$, and $R^7$ in formulas I, IA, IB, and IC are each independently selected from the group consisting of —OH, and C1-C4 alkanoyloxyl-.

In some embodiments $L^3$ in formulas I, IA, IB, and IC is O.

In some embodiments $L^2$ in formulas I, IA, IB, and IC is O.

In some embodiments, $L^1$ in formulas I, IA, IB, and IC is O or S.

In some embodiments, $W^1$ in formulas I, IA, IB, and IC is —C($R^{10}R^{11}$)—, wherein $R^{10}$ and $R^{11}$ are independently selected from H, D, —OH, halogen, C1-C4 alkyl, C1-C4 alkoxyl, C1-C4 haloalkyl, C1-C4-haloalkoxyl, C1-C4 alkanoyloxyl, C1-C4 alkenyloxyl, $R^{12}CO_2$—, wherein $R^{12}$ is selected from C1-C4 alkyl, C1-C4 alkoxyl, C1-C4 alkanoyloxyl and C1-C4 alkenyloxyl.

In some embodiments, $W^1$ in formulas I, IA, IB, and IC is —C($R^{10}R^{11}$)—, wherein $R^{10}$ and $R^{11}$ are independently selected from H, D, —OH, halogen and C1-C4 alkanoyloxyl.

In some embodiments, $W^2$ in formulas I, IA, IB, and IC is C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein $R^{12}$ is C1-C4 alkyl, C1-C4 alkoxy and C1-C4 alkylamino.

In some embodiments, $W^2$ in formulas I, IA, IB, and IC is C1-C3 alkyl optionally substituted with 1-3 substituents independently selected from D, halogen, —OH and $R^{12}CO_2$—, wherein $R^{12}$ is C1-C3 alkyl.

In some embodiments, $W^2$ in formulas I, IA, IB, and IC is C1 alkyl optionally substituted with 1 substituent selected from —OH and $R^{12}CO_2$—, wherein $R^{12}$ is C1-C3 alkyl.

In some embodiments, $R^1$ in formulas I, IA, IB and IC is

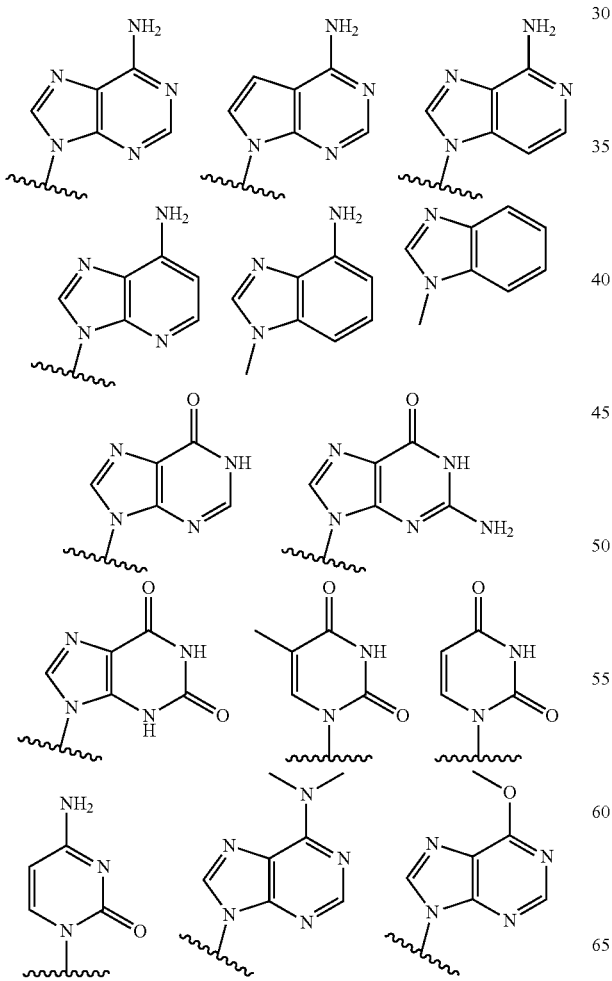

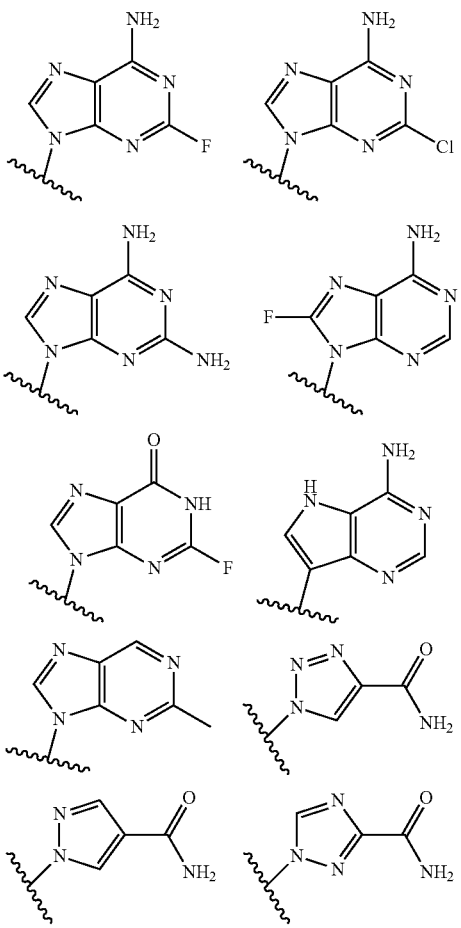

In some embodiments, $R^1$ in formulas I, IA, IB and IC is

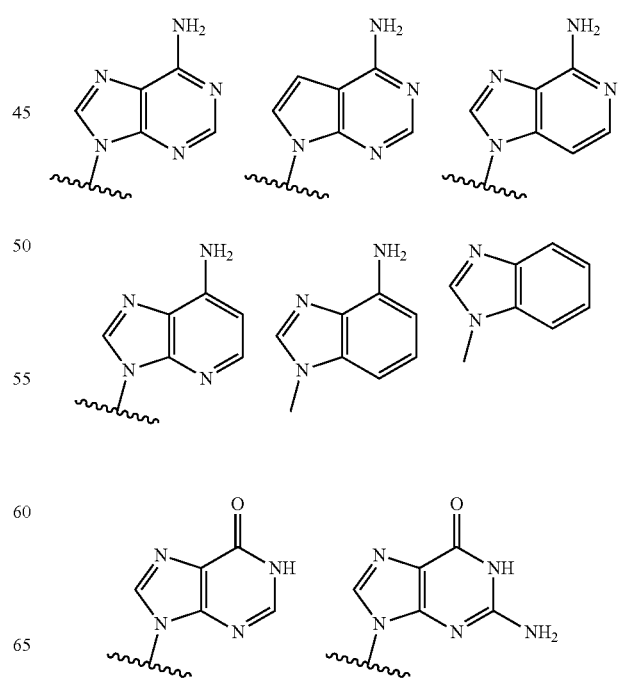

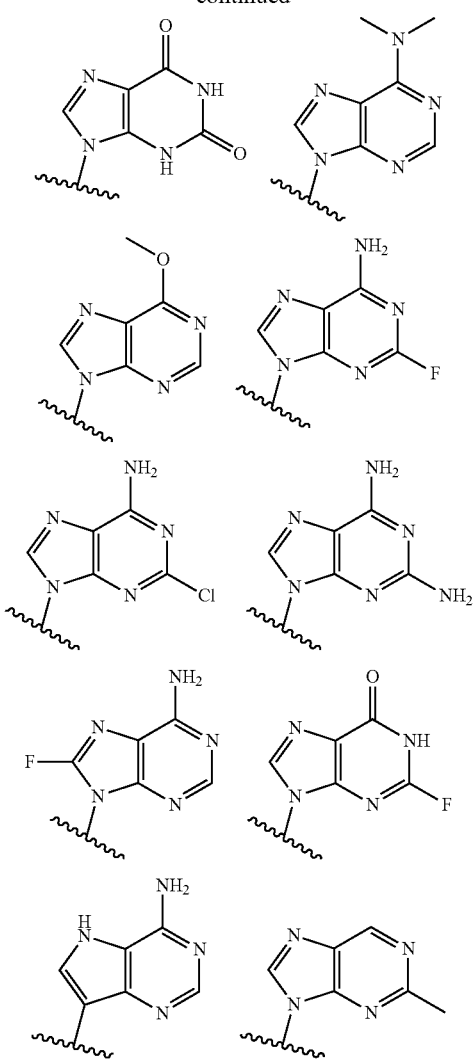
In some embodiments, $R^1$ in formulas I, IA, IB and IC is
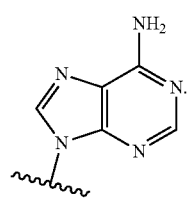
In some embodiments, the compound of Formula I is
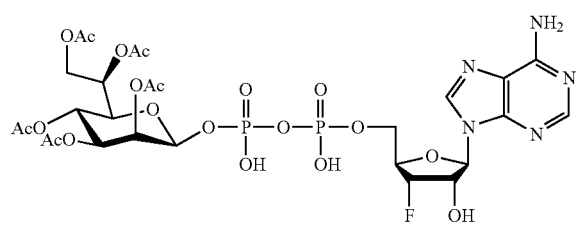
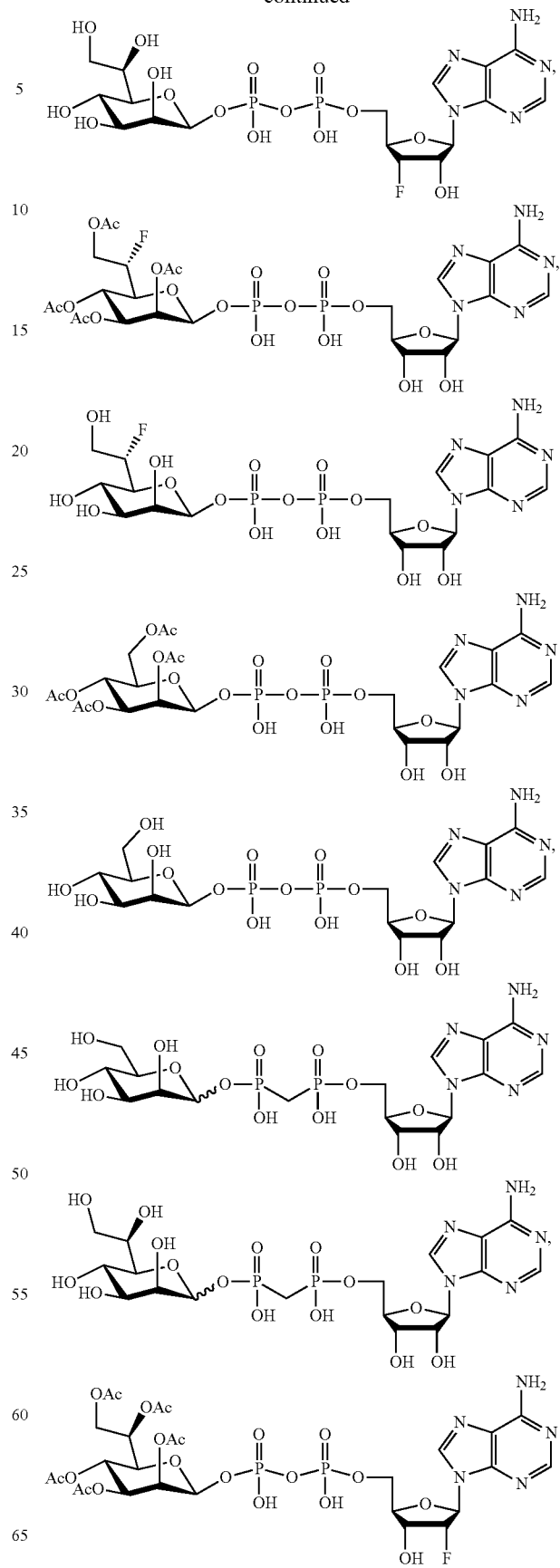

25
-continued
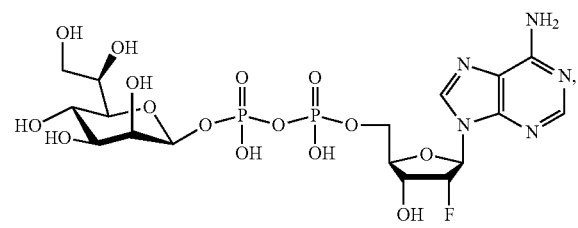
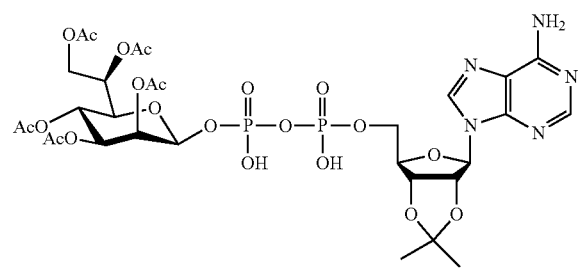
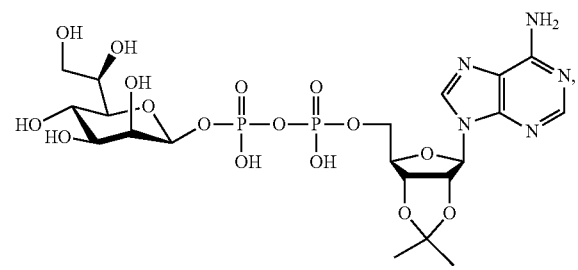
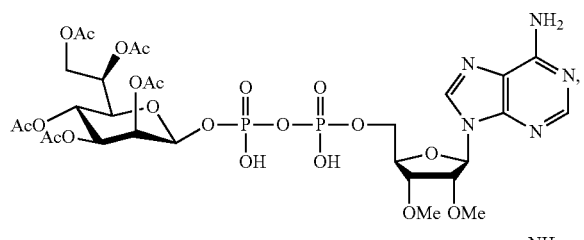
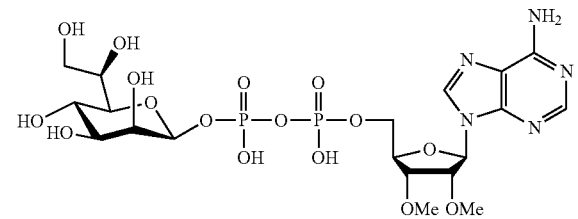
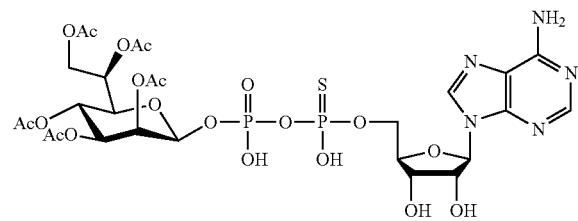
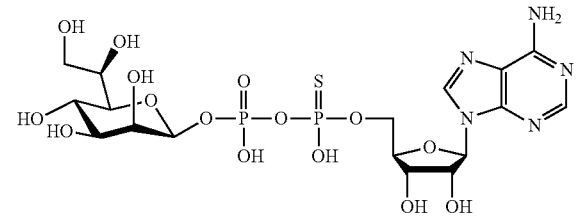
26
-continued
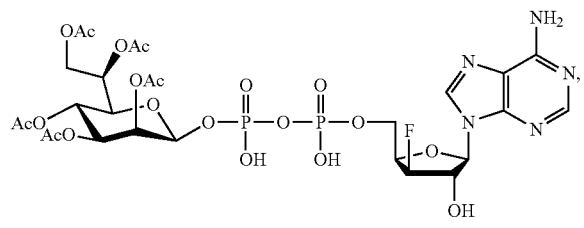
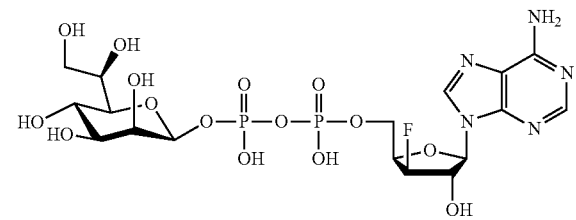
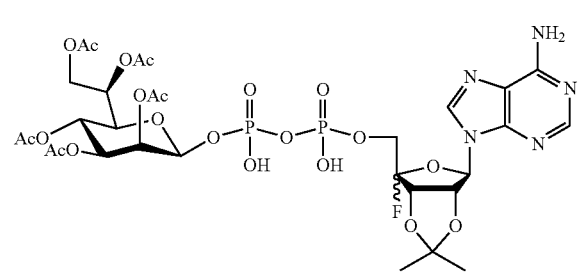
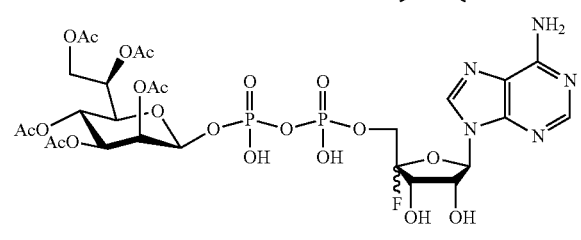
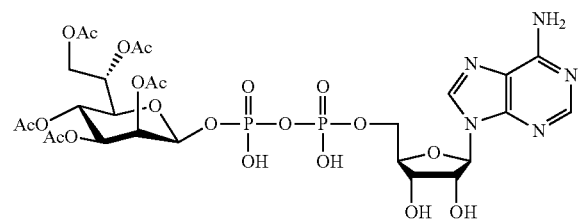
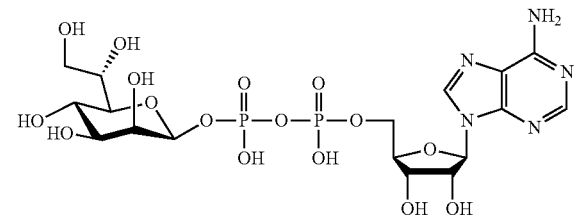
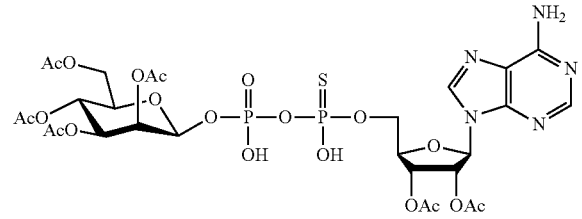

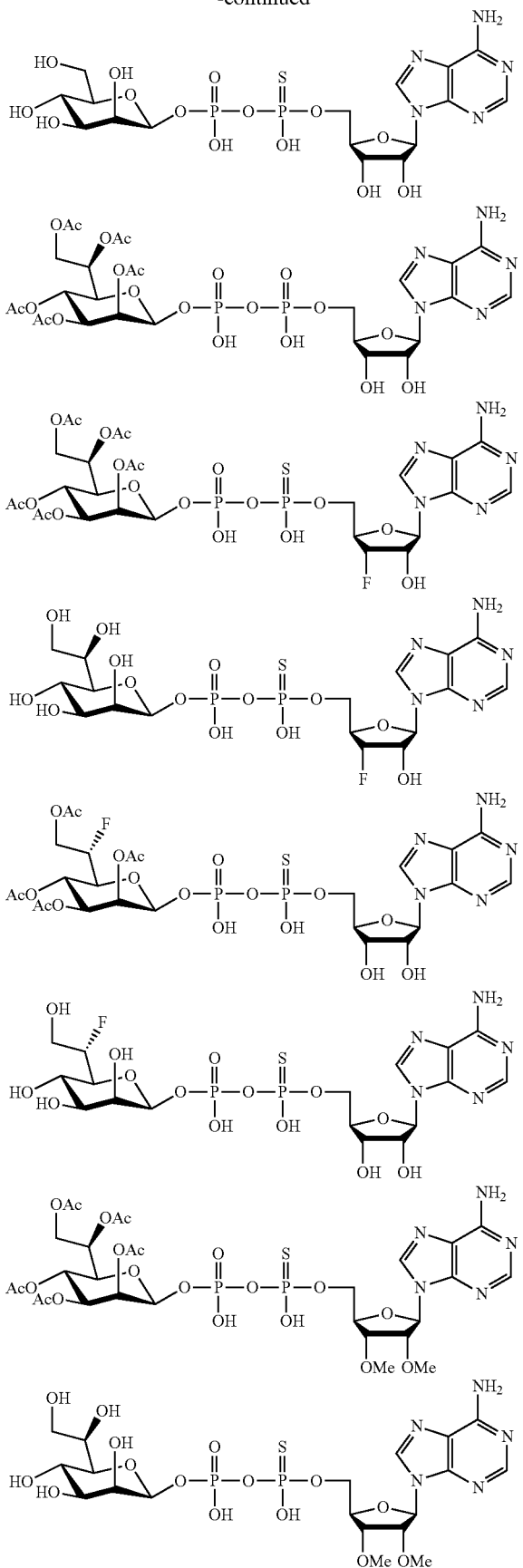

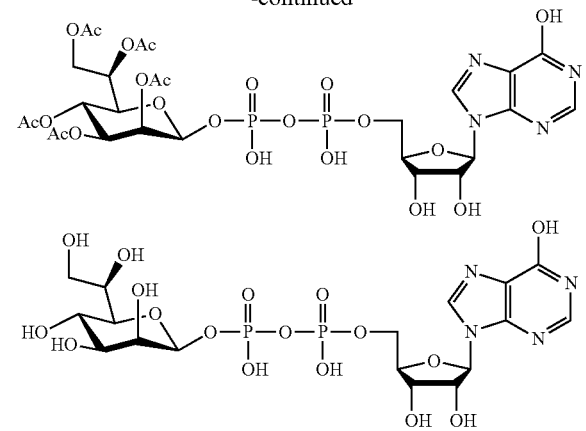

and/or a stereoisomer, a stable isotope, prodrug or a pharmaceutically acceptable salt thereof:

In some embodiments, the compound of formula I is a compound described in the Examples of this application.

The compound of the present disclosure can be prepared using the general processes describes in Schemes I, II, III, and IV as well as the techniques described in the exemplary embodiments.

In embodiments, the disclosure provides an ALPK1 agonist in the form of a small organic molecule, such as D-glycero-β-D-manno-heptose 1,7-bisphosphate (heptose 1,7 bisphosphate or "HBP"), D-glycero-β-D-manno-heptose-1-phosphate (HMP-1bP), D-glycero-D-manno-heptose-1β-ADP (H1b-ADP), and L-glycero-D-manno-heptose-1β-ADP (H1b-ADP-6L) and prodrugs, analogs and derivatives thereof, or in the form of a large biomolecule such as a protein (e.g., ALPK1 itself, or an ALPK1-directed antibody or Fc fragment thereof that activates ALPK1 kinase activity) or a polynucleotide (e.g., a polynucleotide encoding ALPK1).

In embodiments, the disclosure provides methods of treating cancer by administering an ALPK1 agonist selected from HBP, HMP-1bP, H1b-ADP-6L, and H1b-ADP, preferably HMP-1bP, H1b-ADP-6L, and H1b-ADP, and most preferably H1b-ADP-6L and H1b-ADP. In further embodiments of the methods of treating cancer, the disclosure provides a combination therapy comprising administering an ALPK1 agonist selected from H1b-ADP-6L and H1b-ADP and an immune checkpoint modulator selected from a checkpoint inhibitor, such as an anti-PD-1/PD-L1 antibody, and an agonist of an immune co-stimulatory molecule, such as an anti-OX40 (CD134) agonist antibody. Without being bound by any specific theory, the inventors propose that H1b-ADP and similar molecules such as H1b-ADP-6L may promote the antigen-presenting functions of tumor infiltrating antigen presenting cells (APC) and tumor-specific T cell proliferation and differentiation. In addition, these molecules may also heighten the recruitment of tumor-specific $CD8^+$ T cells to tumors by increasing PD-L1 expression in tumor cells.

In other embodiments, the disclosure provides methods of activating ALPK1 by administering ALPK1 to a subject, or introducing ALPK1 into a cell, for example, cells or tissues of a subject, in the form of a recombinant protein or in the form of a polynucleotide encoding ALPK1, or in the form of a composition comprising a recombinant ALPK1 protein or polynucleotide encoding same. A polynucleotide encoding ALPK1 is one which is transcribed and translated into the ALPK1 protein when placed under the control of appropriate regulatory sequences, for example a promoter sequence. Such polynucleotides may include sequences from prokaryotic or eukaryotic DNA, or synthetic DNA sequences, and combinations of any of the foregoing Preferably, the ALPK1 administered or introduced is a constitutively active ALPK1 (or polynucleotide encoding same). The term "constitutively active" refers to an ALPK1 protein whose kinase activity is active in the absence of ligand. In embodiments, a constitutively active ALPK1 carries an activating mutation in its N-terminal domain that promotes ligand-independent oligomerization and kinase activation.

A polynucleotide encoding ALPK1 may in the form of a nucleic acid vector or other vehicle suitable for gene transfer into living cells. A plasmid is a common type of nucleic acid vector that is an extra-chromosomal DNA molecule capable of replicating independently of the chromosomal DNA. Plasmids may be single stranded or double stranded and are often circular. Other useful vehicles may include DNA or RNA minicircles and minivectors. Minicircles are formed by deleting most of the bacterial DNA from the parent plasmid using site-specific recombination. The resulting circular DNA molecules contain the desired gene sequence to be transferred, e.g., an ALPK1 sequence, and only small amounts of bacterial DNA. Minivectors are similar except they include short integration sequences. These and other suitable non-viral DNA vectors for gene transfer are described, for example, in Hardee et al., "Advances in Non-Viral DNA Vectors for Gene Therapy", *Genes* 2017 8:65.

Other suitable nucleic acid vectors for gene transfer of ALPK1 may include, for example, viral vectors such as adenovirus vectors, adeno-associated virus vectors, retrovirus vectors, and lentivirus vectors.

A nucleic acid vector encoding ALPK1 can be introduced into target cells using a suitable technique, for example, a viral delivery system, direct injection such as using a gene gun, or non-viral delivery system including for example, liposomes, nanoparticles, polymers, electroporation, cell squeezing, sonoporation, optical transfection, impalefection, and hydrodynamic delivery. Exemplary non-viral delivery systems and their use are described, for example, in Jones et al., "Contemporary approaches for nonviral gene therapy," *Discov. Med.* 2015; 19: 447-454.

In accordance with any of the embodiments of the methods described here, ALPK1 may be administered in a suitable formulation including, for example, in the form of viral particles, liposomal particles, nanoparticles, as complexes with polymeric carriers, including for example polylysine, polyarginine, polyornithine, protamine, spermine, spermidine, and putrescine. Liposomal particles may be used to deliver ALPK1 in various forms including DNA, RNA, and plasmid forms. In embodiments, the ALPK1 polynucleotide may administered as plasmid DNA in the absence of another particle or carrier.

In embodiments, the polynucleotide encoding ALPK1, or an active mutant thereof, is inserted into cells using a gene editing technique. Gene editing techniques include those based on meganucleases, zinc finger nucleases (ZFNs), transcription activator-like effector nucleases (TALENs), and CRISPR/Cas-9.

In embodiments, the disclosure provides methods of modulating an immune response in a subject, the methods comprising administering to the subject a composition comprising any one of an ALPK1 agonist, a polynucleotide encoding ALPK1 or constitutively active mutant thereof, or an ALPK1 protein or constitutively active mutant of said protein.

In embodiments, the disclosure provides methods of potentiating an immune response to a target antigen in a subject, the methods comprising administering to the subject a composition comprising any one of an ALPK1 agonist, a polynucleotide encoding ALPK1 or constitutively active mutant thereof, or an ALPK1 protein or constitutively active mutant of said protein. In embodiments, the target antigen may be an antigen of an infectious agent, such as a bacterial antigen, a viral antigen, or an antigen of a parasite. In embodiments, the antigen is a tumor antigen. In accordance with any of these embodiments, the ALPK1 agonist, polynucleotide, or protein, as described herein, may serve as an adjuvant to a vaccine composition for the treatment or prevention of a disease or disorder caused by an infectious agent, or for the treatment of cancer, or for the treatment of another disease or disorder that may be treated with a vaccine composition, including, for example, Alzheimer's disease. In embodiments, the antigen is selected from amyloid protein in the treatment of Alzheimer's disease. In embodiments, the antigen is selected from glycoprotein 100 (gp100), mucin 1 (MUC1), and melanoma-associated antigen 3 (MAGEA3) in the treatment of cancer. In embodiments, the cancer is selected from breast, ovarian, or prostate cancer. In embodiments, the cancer is HTLV-1 T-lymphotropic leukemia.

In embodiments, the cancer is melanoma and the ALPK1 agonist, polynucleotide, or protein, as described herein, may serve as an adjuvant to treatment with Talimogene laherparepvec (T-VEC), or may be used in a combination therapy regimen with T-VEC.

In embodiments for the treatment or prevention of an infectious disease, the ALPK1 agonist, polynucleotide, or protein, as described herein, may serve as an adjuvant to a vaccine composition for the treatment or prevention of anthrax, caries, Chagas disease, dengue, diphtheria, ehrlichiosis, hepatitis A or B, herpes, seasonal influenza, Japanese encephalitis, leprosy, lyme disease, malaria, measles, mumps, meningococcal disease, including meningitis and septicemia, Onchocerciasis river blindness, pertussis (whooping cough), pneumococcal disease, polio, rabies, rubella, schistosomiasis, severe acute respiratory syndrome (SARS), shingles, smallpox, syphilis, tetanus, tuberculosis, tularemia, tick-borne encephalitis virus, typhoid fever, trypanosomiasis, yellow fever, and visceral leishmaniasis.

In embodiments for the treatment or prevention of an infectious disease, the ALPK1 agonist, polynucleotide, or protein, as described herein, may serve as an adjuvant to a vaccine composition for the treatment or prevention of a disease or disorder caused by adenovirus, Coxsackie B virus, cytomegalovirus, eastern equine encephalitis virus, ebola virus, enterovirus 71, Epstein-Barr virus, *Haemophilus influenzae* type b (Hib), hepatitis C virus (HCV), herpes virus, human immunodeficiency virus (HIV), human papillomavirus (HPV), hookworm, Marburg virus, norovirus, respiratory syncytial virus (RSV), rotavirus, *Salmonella typhi, Staphylococcus aureus, Streptococcus pyogenes*, varicella, West Nile virus, *Yersinia pestis*, and Zika virus.

In accordance with any of the foregoing embodiments, the method may comprise administering a vaccine composition or adjuvant comprising any one of an ALPK1 agonist, preferably an ALPK1 agonist selected from HBP, HMP-1bP, H1b-ADP-6L and H1b-ADP, or selected from HMP-1bP, H1b-ADP-6L, and H1b-ADP, and most preferably an ALPK1 agonist selected from H1b-ADP-6L and H1b-ADP, a polynucleotide encoding ALPK1 or constitutively active mutant thereof, or an ALPK1 protein or constitutively active mutant of said protein.

In embodiments, the disclosure provides methods of treating a disease or disorder amendable to treatment by activation of NFkB, p38, and JNK cell signaling pathways in cells of a subject, the method comprising administering to the subject a composition comprising any one of an agonist of ALPK1, a polynucleotide encoding ALPK1 or constitutively active mutant thereof, or an ALPK1 protein or constitutively active mutant of said protein. In embodiments, the disease or disorder is caused by a bacterial, viral, or parasitic infection, as described in more detail below, and including for example diseases and disorders caused by the hepatitis C virus (HCV), the hepatitis B virus (HBV), and the human immunodeficiency virus (HIV). In embodiments, the disease or disorder is selected from tuberculosis, meningitis, pneumonia, ulcer, and sepsis. In embodiments, the disease or disorder is selected from rhinitis, asthma, allergy, COPD, inflammatory bowel disease, arthritis, obesity, radiation-induced inflammation, psoriasis, atopic dermatitis, non-alcoholic steatohepatitis (NASH), Alzheimer's disease, systemic lupus, erythematosus (SLE), autoimmune thyroiditis (Grave's disease), multiple sclerosis, ankylosing spondylitis and bullous diseases. In embodiments, the disease or disorder is selected from actinic keratoses, ulcerative colitis, Crohn's disease, and alopecia areata.

In embodiments, the disclosure provides methods of treating or preventing a bacterial, viral, or parasitic infection in a subject in need thereof, the methods comprising administering to the subject a composition comprising any one of an ALPK1 agonist, a polynucleotide encoding ALPK1 or constitutively active mutant thereof, or an ALPK1 protein or constitutively active mutant of said protein.

In embodiments, the method is a method of treating or preventing a bacterial infection. In embodiments, the bacterial infection is caused by a Gram-negative or a Gram-positive bacteria. In embodiments, the bacteria is a Gram-negative bacteria selected from the group consisting of *Acinetobacter baumanii, Aggregatobacter actinomycetemconmitans, Bartonella bacilliformis, Bartonella henselae, Bartonella quintana, Bifidobacterium Borrelia, Bortadella pertussis, Brucella sp, Burkholderia cepacis, Burkholderia pseudomallei, Campylobacter jejuni, Cardiobacterium hominis, Campylobacter fetus, Chlamydia pneumonia, Chlymydia trachomatis, Clostridium difficile, Cyanobacteria, Eikennella corrodens, Enterobacter, Enterococcus faccium, Escherichia coli, Escherichia coli* 0157, *Franceilla tularensis, Fusobacterium nucleatum, Haemophilus influenza, Haemophilus aphrophilus, Haemophilus ducreyi, Haemophilus parainfluenzae, Helicobacter pylori, Kingella kingae, Klebsiella pneumonia, Legionella bacteria, Legionella pneunoplhila* serogroup 1, *Leptospria, Morganella morganii, Neisseria gonorrhoeae, Neisseria meningitidis, Proteus mirabilis, Proteus vulgaris, Proteus myxofaciens, Providencia rettgeri, Providencia alcalifaciens, Providencia stuartii, Pseudomonas aeruginosa, Pseudomonas paucimnobilis, Pseudomonas putida, Pseudomonas fluorescens, Pseudomonas acidovorans, Rickettsiae, Salmonella emerica, Salmonella typhi, Salmonella paratyphi* types A, B typhus, *Salmonella dublin, Salmonella arizonae, Salmonella chloleraesuis, Serratia marcescens, Schigella dysenteriae, Schigella flexneri, Schigella boydii, Schigella sonnei, Treponema, Stenostrophonmonas maltophilia, Vibrio cholerae, Vibrio mimicus, Vibrio alginolyticus, Vibrio hollisae, Vibrio parahaemolyticus, Vibrio vulnificus* and *Yersinia pestitis*.

In embodiments, the bacteria is a Gram-positive bacteria selected from the group consisting of Actinomycetes, *Bacillus anthracis, Bacillus subtilis, Clostridium tetani, Clostridium perfingens, Clostridium botulinum, Clostridium tetani. Corynebacterium diphtheriae, Enterococcus faecalis, Enterococcus faecium, Erysipelothrix ruhsiopathiae, Listeria monocytogenes, Mycobacterium leprae, Mycobacterium tuberculosis, Mycoplasma, Nocardia, Propionibacerium, Pseudomonas aeruginosa, Pneumococci, Staphylococcus aureus, Staphylococcus epidermidis,* methicillin resistant *Staphylococcus aureus* (MRSA), vancomycin resistant *Staphylococcus aureus* (VRSA), *Staphylococcus lugdunensis, Staphylococcus saprophyticus, Streptococcus pneumonia, Streptococcus pyogenes*, and *Streptococcus mutants*.

In embodiments, the method is a method of treating or preventing a viral infection. In embodiments, the viral infection is caused by a virus selected from the group consisting of Adeno-associated virus, Aichi virus, Alpha virus, Arena virus, Arobovirus, Australian bat lyssavirus, BKpolyomavirus, Banna virus, Birnavirus, Bornavirus, bunyamwera virus, Bunyavirus La Crosse, Bunyavirus snowshoe hare, Valicivirus, Cercopithecine herpesvirus, Chandipura virus, Chikugunya virus, Cosavirus A, Coxpox virus, Coxsakievirus, Crimean-Congo hemorrhagic fever virus, Dengue virus, Dhori virus, Dugbe virus, Devenhage virus, Eastern equine encephalitis virus, Ebolavirus, Echovirus, Encephalomyocarditis virus, Epstein-Barr virus, European bat lyssavirus, Flavivirus, GB virus/Hepatitis G virus, Hantaan virus, Hendra virus, hepadnavirus, Hepatitis A virus, Hepatitis B virus, Hepatitis C virus, Hepatitis E virus, Hepatitis delta virus, Herpes simplex virus, horsepox virus, human adenovirus, human astrovirus, human coronavirus, human cytomegalovirus, human enterovirus 68,70, human herpesvirus 1, human herpesvirus 2, human herpesvirus 6, human herpesvirus 7, human herpesvirus 8, human immunodeficiency virus (HIV), human papillomavirus (HPV-6, HPV-11), human spumaretrovirus, human T-lymphotropic virus, human torovirus, Infleunza A virus, Infleunza B virus, Infleunza C virus, Isfaha virus, JC polyomavirus, Japanese encephalitis virus, Junin arenavirus, Kaposi's sarcoma (HHV-8), KI polyomavirus, Kunjin virus, Lagos bat virus, Lake Vitoria marbugvirus, Langat virus, Lassa virus, LMC virus, Lordsdale virus, Louping ill virus, Lymphocytic choriomeningitis virus, Machupovirus, Marmath forest virus, Mayaro virus, MERS coronavirus, Measles virus, Mengo encephalomycarditis virus, Merkel cell polyomavirus, mlluscum contagiosum, parvovirus B19, Mokola virus, Mumps virus, Murray valley encephalitis virus, New York virus, Nipha virus, Norwalk virus, O'nyong-hyong virus, Orf virus, Oropouche virus, Orthomyxovirus, parainfluenza virus, paramyxovaris, parvovirus, Phchinde virus, picomavirus, poliovirus, polyomavirus, poxvirus, Punta toro phleboviris, Puumala virus, rabdovirus, Rabies virus, reovirus, rhinovirus, respiratory syncytial virus, Rift valley fever virus, Rosavirus A, Ross river virus, Rotavirus A, Rotavirus B, Rotavirus C, Rubella virus, Sagiyama virus, Salivirus A, Sandfly fever sicillian virus, Sapporo virus, Semliki forest virus, Seoul virus, Simian foamy virus, Simian virus 5, Sindbis virus, Southampton virus, St. louis encephalitis virus, Tick-borne powassan virus, togavirus, Torque virus, Toscana virus, Uukuniemi virus, Vaccina virus, Varicella-zoster virus, Variola virus, Venezuelan equine encephalitis virus, Vesicular stomatitis virus, Western equine encephalitis virus, UU polyomavirus, West Nile virus, Yaba monkey tumor virus, Yaba-like disease virus, Yellow fever virus, and Zika virus.

In embodiments, the method is a method of treating or preventing a parasitic infection. In embodiments, the parasitic infection is caused by parasite selected from the group consisting of *Acanthamoeba* spp, American trypanosomiasis, *Balamuthia mandnillanis, Babesia divergenes, Babesia bigemina, Babesia equi, Babesia microfti, Babesia duncani, Balantidium coli, Blastocystis* spp *Cryptosporidium* spp, *Cyclospora cayetanensis, Dientamoeba fragilis, Diphyllobothrium latum, Leishmania amazonesis, Naegleria fowderi, Plasmodium falciparum, Plasmodium vivax, Plasmodium ovale curtisi, Plasmodium malariae, Rhinosporidium seeberi, Sarcocystis bovihominis, Sarcocystiss suihominis, Toxoplasma gondii, Trichmonas vaginalis, Trypanosoma brucei, Trypanosoma cruzi*, and *Taenia multiceps*.

In embodiments, the disclosure provides methods of treating cancer in a subject, the methods comprising administering to the subject a composition comprising any one of an ALPK1 agonist, a polynucleotide encoding ALPK1 or constitutively active mutant thereof, or an ALPK1 protein or constitutively active mutant of said protein. In embodiments of the methods for treating cancer, the ALPK1 agonist is selected from HBP, HMP-1bP, H1b-ADP-6L and H1b-ADP, preferably selected from HMP-1bP, H1b-ADP-6L, and H1b-ADP, and most preferably an ALPK1 agonist selected from H1b-ADP-6L and H1b-ADP, and prodrugs, analogs and derivatives thereof. In certain embodiments of the methods for treating cancer, the ALPK1 agonist is HMP-1bP, H1b-ADP-6L or H1b-ADP, or a prodrug, analog or derivative thereof. In further embodiments of the methods for treating cancer, the ALPK1 agonist is H1b-ADP-6L or H1b-ADP, or a prodrug, analog or derivative thereof. In embodiments, the cancer is selected from soft tissue sarcoma, breast cancer, head and neck cancer, melanoma, cervical cancer, bladder cancer, hematologic malignancy, glioblastoma, pancreatic cancer, prostate cancer, colon cancer, breast cancer, renal cancer, lung cancer, merkel cell carcinoma, small intestine cancer, thyroid cancer, acute myelogenous leukemia (AML), acute lymphocytic leukemia (ALL), chronic lymphocytic leukemia (CLL), chronic myelogenous leukemia (CML), gastric cancer, gastrointestinal stromal tumors, non-Hodgkins lymphoma, Hodgkins lymphoma, liver cancer, leukemia, lymphoma, T-cell lymphoma.

In embodiments of any of the methods described here the ALPK1 agonist, preferably selected from H1b-ADP-6L and H1b-ADP, may be administered in combination with one or more additional therapeutic agents or immune modulators, including for example in combination with a vaccine or vaccine adjuvant. In embodiments, the one or more additional therapeutic agents is an inhibitor or antagonist of, or a vaccine against, an immune checkpoint molecule including, for example, the programed cell death 1 (PD-1) receptor (CD279), a ligand of PD-1 (e.g., PD-L1), cytotoxic T-lymphocyte associated protein 4 (CTLA4), tumor necrosis factor receptor superfamily member 9 (alternatively TNFRSF9, 4-1BB) and 4-1BB ligands, tumor necrosis factor receptor superfamily member 4 (alternatively TNFRSF4, OX40) and OX40 ligands, glucocorticoid-induced TNFR-related protein (GITR). Tumor Necrosis Factor Receptor Superfamily Member 7 (alternatively TNFRSF7, cluster of differentiation 27, CD27). TNFRSF25 and TNF-like ligand 1A (TL1A). TNF Receptor Superfamily Member 5 (alternatively TNFRSF5, CD40) and CD40 ligand, Herpesvirus entry mediator (HVEM)-tumor necrosis factor receptor ligand superfamily member 14 (alternatively TNFSF14. LIGHT)-lymphotoxin alpha (LTA), herpesvirus entry mediator-(HVEM)-B- and T-lymphocyte attenuator (BTLA)-CD160 (alternatively TNFSF14), lymphocyte activating gene 3 (LAG3). T-cell immunoglobulin and mucin-domain containing-3 (TIM3), sialic-acid-binding immunoglobulin-like lectins (SIGLECs), inducible T-cell costimulator (ICOS) and ICOS ligand, B7-H3 (B7 family, alternatively CD276), V-set domain-containing T-cell activation inhibitor 1 (VTCN1, alternatively B7-H4), V-Type immunoglobulin domain-containing suppressor of T-cell activation (VISTA), human endogenous retrovirus-H long terminal repeat-associating protein 2 (HHLA2)-transmembrane and Immunoglobulin domain containing 2 (TMIGD2), butyrophilins, natural killer cell receptor 2B4 (alternatively NKR2B4, CD244) and B-Cell Membrane Protein (CD48), T-Cell Immunoreceptor with Immunoglobulin (Ig) and immunoreceptor tyrosine-based inhibition motif domains (TIGIT) and Poliovirus receptor (PVR) family members, killer-cell immunoglobulin-like receptors (KIRs), Immunoglobulin-like transcripts (ILTs) and leukocyte immunoglobulin-like receptor (LIRs), natural killer group protein 2 member D (NKG2D) and natural killer group protein 2 member A (NKG2A), major histocompatibility complex (MHC) class I polypeptide-related sequence A (MICA) and MHC class I polypeptide-related sequence B (MICB), natural killer cell receptor 2B4 (CD244), colony stimulating factor 1 receptor (CSFIR), indoleamine 2,3-dioxygenase (IDO), transforming growth factor beta (TGFβ), Adenosine-ecto-nucleotidase triphosphate diphosphohydrolase 1 (CD39)-5'-nucleotidase (CD73), C-X-C motif chemokine receptor 4 (CXCR4) and C-X-C motif chemokine ligand 12 (CXCL12), phosphatidylserine, signal regulatory protein alpha (SIRPA) and integrin associated protein (CD47), vascular endothelial growth factor (VEGF), and neuropilin.

In embodiments of any of the methods described here the ALPK1 agonist may be administered in combination with checkpoint inhibitor or an agonist of an immune co-stimulatory molecule, such as an anti-OX40 (CD134) agonist antibody. In embodiments, the checkpoint inhibitor is a PD-1/PD-L1 inhibitor, such as an anti-PD1 antibody or an anti-PD-L1 antibody, and the ALPK1 agonist is selected from H1b-ADP-6L and H1b-ADP, and prodrugs, analogs and derivatives thereof.

In embodiments, the ALPK1 agonist may be administered in combination with one or more immune modulators. In embodiments, the immune modulator may be a vaccine. In embodiments, the vaccine is a vaccine against an infectious agent, as described above. In embodiments, the vaccine is a cancer vaccine. In embodiments, the cancer vaccine targets a tumor antigen selected from glycoprotein 100 (gp100), mucin 1 (MUC1), and melanoma-associated antigen 3 (MAGEA3).

In embodiments, the one or more immune modulators may be a recombinant protein, for example, granulocyte-macrophage colony-stimulating factor (GM-CSF), interleukin 7 (IL-7), IL-12, IL-15, IL-18, or IL-21.

In embodiments of the treatment of cancer, the ALPK1 agonist may be administered in combination with a T cell therapy, such as chimeric antigen receptor (CAR) T cell therapy.

In embodiments of the methods for treating cancer the ALPK1 agonist may be administered in combination with a PD-1/PD-L1 inhibitor or an agonist of an immune co-stimulatory molecule, such as an anti-OX40 (CD134) agonist antibody. In embodiments, the ALPK1 agonist administered in combination with a PD-1/PD-L1 inhibitor or an agonist of an immune co-stimulatory molecule is selected from H1b-ADP-6L and H1b-ADP. In embodiments, the ALPK1 agonist is H1b-ADP, or a prodrug, analog or derivative thereof. In embodiments, the cancer is selected from advanced melanoma, non-small cell lung cancer, renal cell carcinoma, bladder cancer, liver cancer, gastric cancer, colon cancer, breast cancer, non-Hodgkin's lymphoma, prostate cancer, head and neck cancer, thyroid cancer, brain cancer, acute myeloid leukemia (AML), merkel cell carcinoma, multiple myeloma, cervical cancer, and sarcoma and the method further comprises administering a PD-1/PD-L1 inhibitor or an agonist of an immune co-stimulatory molecule to the subject.

In embodiments of the methods for modulating an immune response or for treating or preventing a bacterial, viral, or parasitic infection, the one or more additional therapeutic agents may be an immune modulator, for example, an inhibitor or antagonist of immune checkpoint molecule. Such molecules generally act as key regulators of the immune system, for example, as co-stimulators of the immune response.

In embodiments, the disclosure also provides a vaccine composition or vaccine adjuvant comprising an ALPK1 agonist. A vaccine composition described here may further comprise one or more adjuvants.

In embodiments, the disclosure also provides a pharmaceutical composition comprising an ALPK1 agonist. In embodiments, the ALPK1 agonist may be in the form of a small organic molecule, such as HBP, or in the form of a large biomolecule such as a protein (e.g., ALPK1 itself, or an ALPK1-directed antibody or Fc fragment thereof that activates ALPK1 kinase activity) or a polynucleotide (e.g., a polynucleotide encoding ALPK), as discussed above. In embodiments, the ALPK1 agonist is selected from HMP-1bP and H1b-ADP and prodrugs, analogs and derivatives thereof. In embodiments, the ALPK1 agonist is H1b-ADP, or a prodrug, analog or derivative thereof.

In embodiments, the disclosure also provides methods of selecting a compound capable of modulating an immune response by measuring the effect of a test compound on ALPK1 autophosphorylation and/or the activation of downstream targets of ALPK1 signaling, the method comprising contacting ALPK1 with the test compound in the presence of ATP and, separately, in the absence of ATP, followed by performing an assay to detect ALPK1 autophosphorylation and/or activation of one or more downstream targets of ALPK1 signaling. In embodiments, the contacting of ALPK1 with the test compound is performed in a cell-free system or in a cell-based system.

In the context of the methods described here, the term "treating" may refer to the amelioration or stabilization of one or more symptoms associated with the disease, disorder or condition being treated. The term "treating" may also encompass the management of disease, disorder or condition, referring to the beneficial effects that a subject derives from a therapy but which does not result in a cure of the underlying disease, disorder, or condition. In the context of the present disclosure, the term "prevention" refers to preventing the recurrence, development, progression or onset of one or more symptoms of the disease, disorder, or condition.

In embodiments where a therapeutically effective amount of a compound or composition is administered to a subject, the therapeutically effective amount is the amount sufficient to achieve a desired therapeutic outcome, for example the amelioration or stabilization of one or more symptoms of the disease, disorder or condition being treated, or in the context of prevention, the amount sufficient to achieve prevention of the recurrence, development, progression or onset of one or more symptoms of the disease, disorder, or condition.

In embodiments, a therapeutically effective amount is the amount required to achieve at least an equivalent therapeutic effect compared to a standard therapy. An example of a standard therapy is an FDA-approved drug indicated for treating the same disease, disorder or condition.

In the context of any of the methods described here, the subject is preferably a human but may be a non-human vertebrate. In other embodiments, the non-human vertebrate may be, for example, a dog, cat, a rodent (e.g., a mouse, a rat, a rabbit), a horse, a cow, a sheep, a goat, a chicken, a duck, or any other non-human vertebrate.

In embodiments, the human subject is selected from an adult human, a pediatric human, or a geriatric human, as those terms are understood by the medical practitioner, for example as defined by the U.S. Food and Drug Administration.

In embodiments, the disclosure provides a composition comprising an ALPK1 agonist, or a composition comprising a polynucleotide encoding ALPK1, or a composition comprising ALPK1 protein, and one or more excipients or carriers, preferably pharmaceutically acceptable excipients or carriers. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Excipients for preparing a pharmaceutical composition are generally those that are known to be safe and non-toxic when administered to a human or animal body. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures of any of the foregoing. The particular excipients utilized in a composition will depend upon various factors, including chemical stability and solubility of the compound being formulated and the intended route of administration.

A pharmaceutical composition can be provided in bulk or unit dosage form. It is especially advantageous to formulate pharmaceutical compositions in unit dosage form for ease of administration and uniformity of dosage. The term "unit dosage form" refers to physically discrete units suited as unitary dosages for the subject to be treated; each unit containing a predetermined quantity of an active compound calculated to produce the desired therapeutic effect in association with the required pharmaceutical carrier. A unit dosage form can be an ampoule, a vial, a suppository, a dragee, a tablet, a capsule, an IV bag, or a single pump on an aerosol inhaler.

In therapeutic applications, dose may vary depending on the chemical and physical properties of the active compound as well as clinical characteristics of the subject, including e.g., age, weight, and co-morbidities. Generally, the dose should be a therapeutically effective amount. An effective amount of a pharmaceutical composition is that which provides an objectively identifiable improvement as noted by the clinician or other qualified observer. For example, alleviating a symptom of a disorder, disease or condition.

A pharmaceutical compositions may take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). In embodiments, the pharmaceutical composition is in the form of an orally acceptable dosage form including, but not limited to, capsules, tablets, buccal forms, troches, lozenges, and oral liquids in the form of emulsions, aqueous suspensions, dispersions or solutions. Capsules may contain excipients such as inert fillers and/or diluents including starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added.

In embodiments, the pharmaceutical composition is in the form of a tablet. The tablet can comprise a unit dose of a compound described here together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. butylated hydroxytoluene), buffering agents (e.g. phosphate or citrate buffers), and effervescent agents such as citrate/bicarbonate mixtures. The tablet may be a coated tablet. The coating can be a protective film coating (e.g. a wax or varnish) or a coating designed to control the release of the active compound, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecyl sulfate, magnesium aluminum silicate, and triethanolamine.

In embodiments, the pharmaceutical composition is in the form of a hard or soft gelatin capsule. In accordance with this formulation, the compound of the present invention may be in a solid, semi-solid, or liquid form.

In embodiments, the pharmaceutical composition is in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions can be prepared in water with the aid of co-solvent or a surfactant. Examples of suitable surfactants include polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides. Dispersions can also be prepared, for example, in glycerol, liquid polyethylene glycols and mixtures of the same in oils.

In embodiments, a compound or composition described here may be administered as monotherapy or adjunctive therapy. In embodiments, a compound or composition described here may be administered alone or in combination with one or more additional therapeutic agents (i.e., additional APIs) or therapies, for example as part of a therapeutic regimen that includes, e.g., aspects of diet and exercise). In embodiments, the methods described here include administration of an ALPK1 agonist as the primary therapy. In other embodiments, the administration of an ALPK1 agonist is an adjuvant therapy. In either case, the methods of the invention contemplate the administration of an ALPK1 agonist in combination with one or more additional therapeutic agents and/or therapies for the treatment or prevention of a disease, disorder, or condition as described here. The terms "therapy" and "therapies" refer to any method, protocol and/or agent that can be used in the prevention, treatment, management or amelioration of a disease, disorder, or condition, one or more symptoms thereof.

The present disclosure also provides packaging and kits comprising pharmaceutical compositions for use in the methods described here. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting a compound or composition described here.

Preparation of Compounds of Formula I and Exemplary Compounds

The compounds of formula I in which $L^1$ is O (compound VI) can be made by general synthetic method as illustrated in Scheme 1. Compound II ("PG" refers to a protection group) can be obtained by compound I (when M is OH) with protected phosphorochloridate under basic condition or appropriate protected phosphate under Mitsunobu reaction condition. Compound II can be obtained as a mixture of alpha and beta isomers which can be separated on silica gel chromatography. The beta isomer of compound II is deprotected under 1-4 atm of $H_2$ catalyzed by Pd/C or $PtO_2$ to give compound III. Coupling of compound IV with morpholine, or another suitable base, by DCC in an appropriate solution such as t-BuOH/$H_2$O to give compound V. Coupling of compound III and compound V in an appropriate solvent such as pyridine with an appropriate catalyst such as tetrazole under room temperature for 24-72 h provides compound VI.

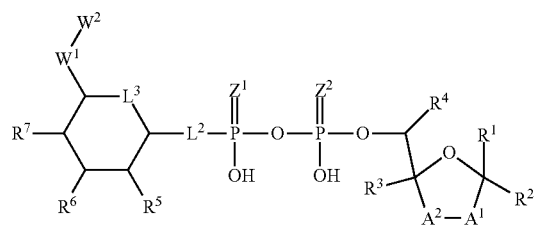

VI

The compounds of formula I in which $Z^2$ is S ($L^1$ is O, compound XI), can be synthesized as illustrated in Scheme II. Compound VIII ("PG" refers to a protection group) can be obtained by reaction of compound VII and protected dialkylphosphoramidite in a suitable solvent like dichloromethane and at temperature ranging from −10 to 25° C. Coupling of VIII and III can be accomplished in a suitable solvent like DMF under inert gas system at temperature below 25° C. to give compound IX, which is oxidized by sulfur in situ to provide compound X. De-preotection of compound X gives the final compound XI.

Scheme I

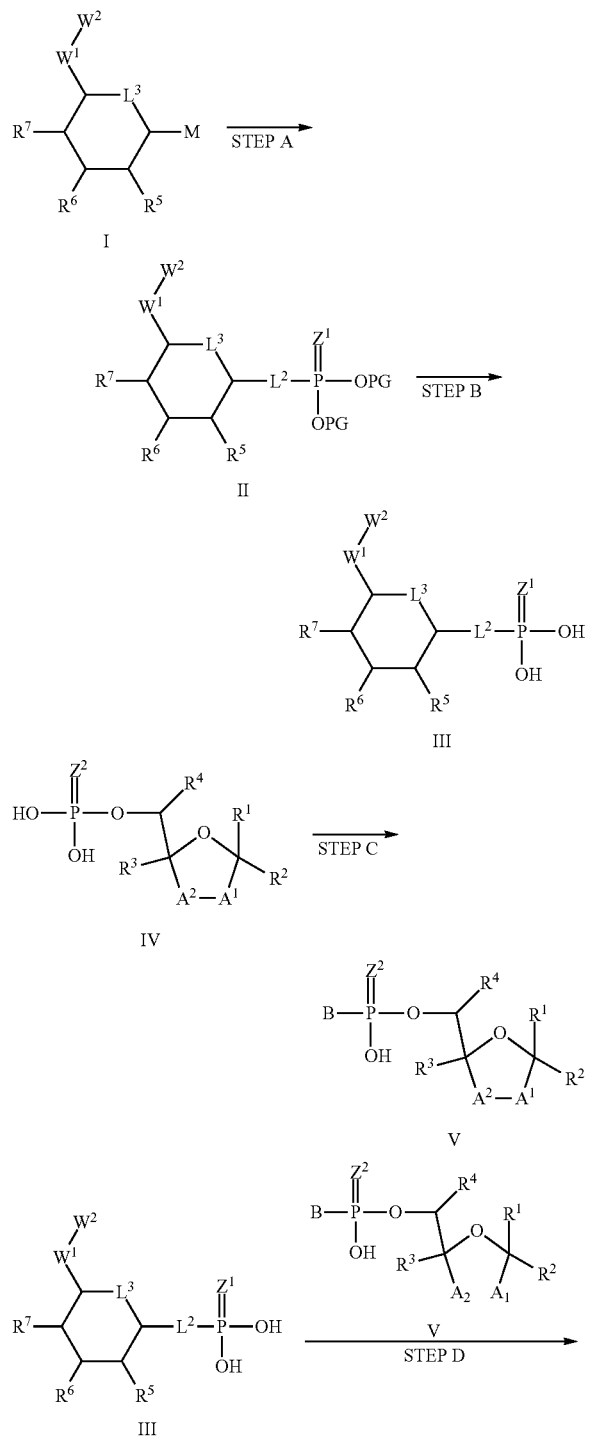

Scheme II

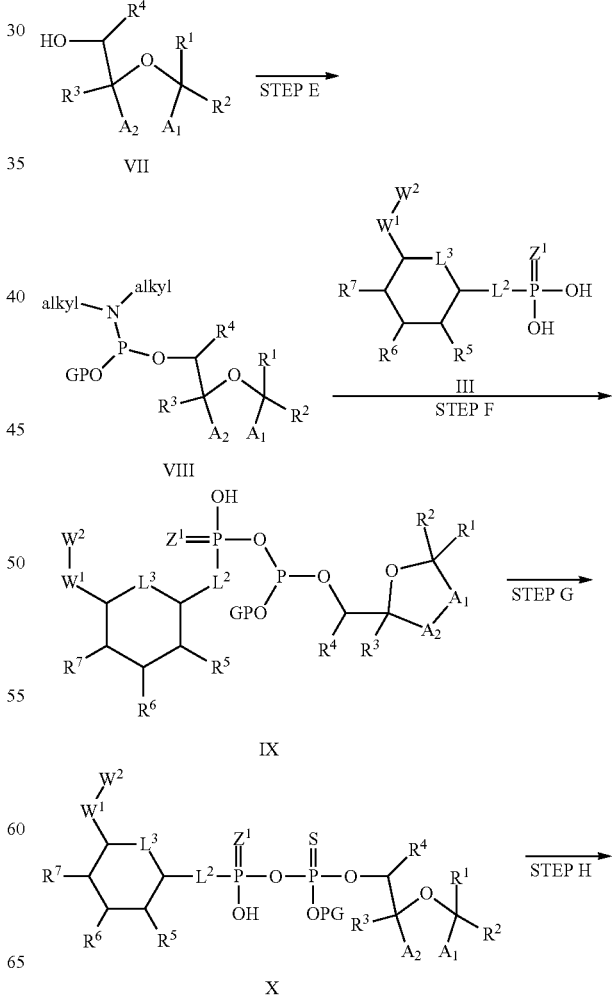

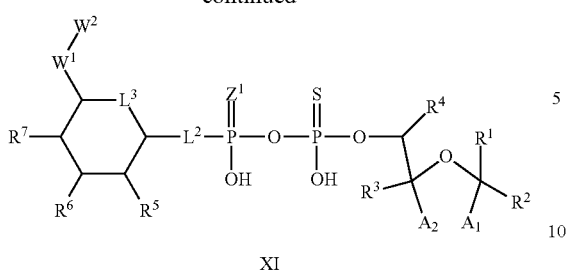

XI

The compounds of formula I in which $Z^2$ is S ($L^1$ is O, compound XV) can be synthesized by the alternatively method as illustrated in Scheme III. The compound III can be activated by forming imidazole salt under 10 to 40° C. in a suitable solvent like DMF under inert gas system. Compound VII is introduced phosphate by reaction with phenoxyphosphonoyloxybenzene. Following the oxidation with sulfur under 0-10° C., compound XIV can be obtained. The coupling of compound XII and XIV under mild condition, like 0-40° C. in a suitable solvent like DMF inert gas system with the catalyst of Lewis acid provides the final compound XV.

Scheme III

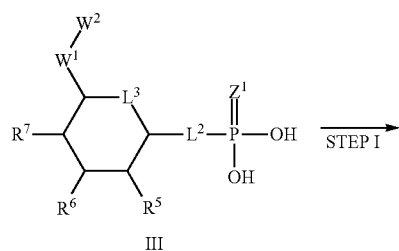

III

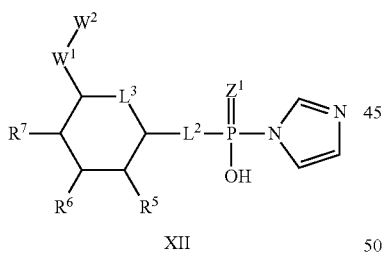

XII

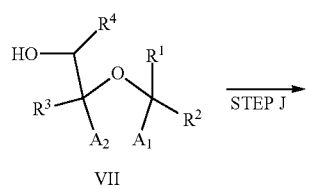

VII

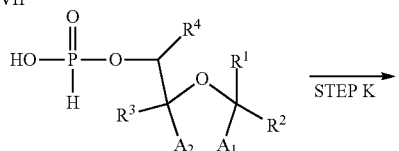

XIII

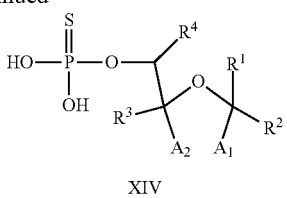

XIV

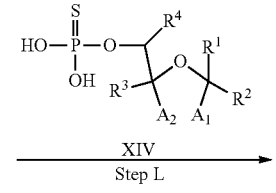

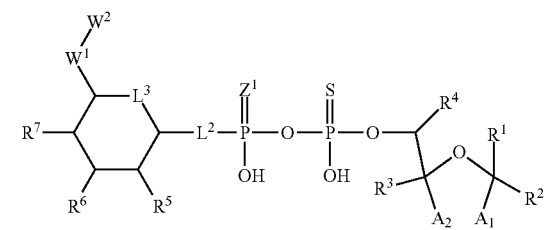

XV

The compounds of formula I in which $L^1$ is $CH_2$ (compound XVIII) can be made by the general synthetic method as illustrated in Scheme IV. Mitsunobu reaction of compound I (when M is OH) and the protected methyl diphosphate at 30-50° C. for 2-4 h provides compound XVI ("PG" refers to a protection group). Compound XVI undergoes a second Mitsunobu reaction with compound VI under the similar condition gives compound XVII. Deprotection reaction of compound XVII provides the final compound XVIII.

Scheme IV

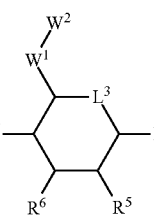

I

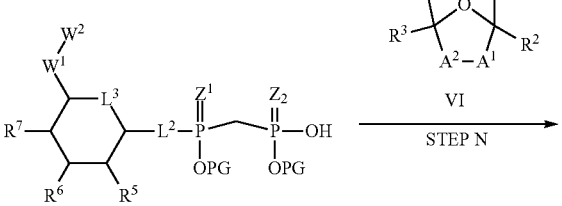

XVI

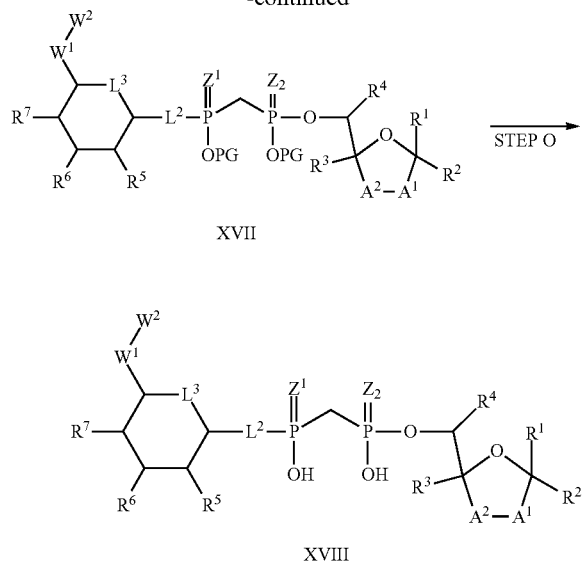

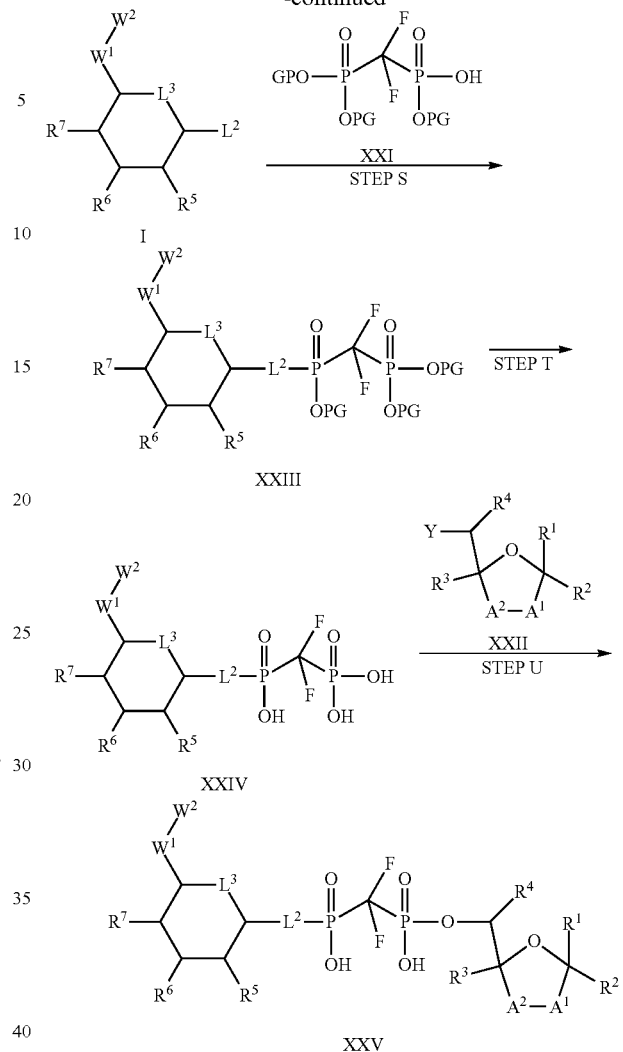

The compounds of formula I in which $L^1$ is $CF_2$ (compound XXV) can be made by general synthetic method as illustrated in Scheme V. Compound XIX ("PG" refers to a protection group) is converted to the protected di-fluoromethyl diphosphate compound XX by using N-fluorobenzenesulfonimide (NFSI) under basic NaH conditions in a suitable solvent starting from a low reaction temperature of −20° C. to 0° C. Selective removal of one of the protection groups in compound XX yields compound XXI. Compound VII is converted to compound XXII by converting the hydroxyl group into a leaving group, such as OTs, OMs or halogen. The Mitsunobu reaction of compound I (when M is OH) and compound XXI at 30-50° C. for 2-4 h yields compound XXIII. Deprotection of compound XXIII yields compound XXIV. The coupling of compound XXIV with compound XXII in a suitable solvent such as $CH_3CN$ with the base $Bu_4N$ yields the final compound XXV.

Scheme V

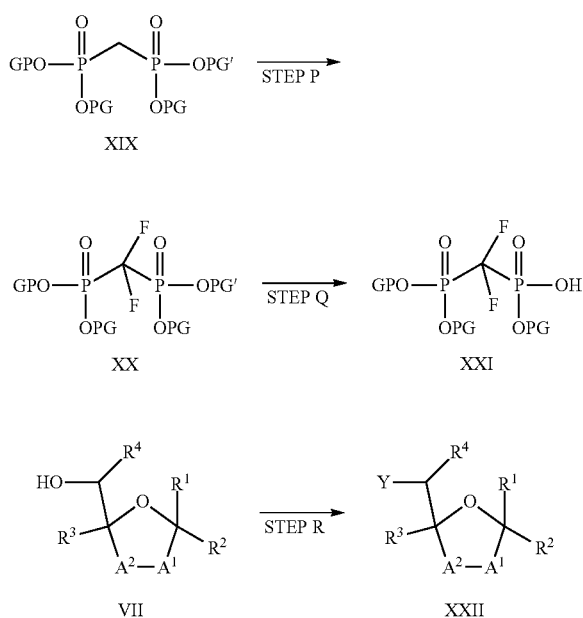

The compounds of formula IC in which $A^1$ is S (compound XXXII) can be made by a general synthetic method as illustrated in Scheme VI. Reaction of compound XXVI with protected 2-hydroxyacetaldehyde similar to 2-oxoethyl benzoate in a suitable solvent yields compound XXVII ("PG" refers to a protection group) as a mixture of two isomers. Alternatively, the reaction of compound XXVI with 2-oxoethyl benzoate in the presence of an organic base (e.g., triethylamine), phenyl acetate, surfactant-treated subtilisin (STS), and Carlsberg in a suitable solvent such as THF yields compound XXVII in the R configuration. Using CAL B instead of STS could yield compound XXVII in the S configuration (Reference: Hu, L et al. *Chem. Commun.*, 2013, 49, 10376-10378). Compound XXVII reacted with $SnCl_4$ in a suitable solvent solution yields compound XXVIII. Deprotection of compound XXVIII yields compound XXIX. Phosphorination of compound XXIX can be accomplished by reacting it with $POCl_3$ and pyridine in a suitable solvent to yield compound XXX. The remaining reactions of converting compound XXX to the final compound XXXII can be done by the same reaction procedures as described in Scheme I.

Scheme VI
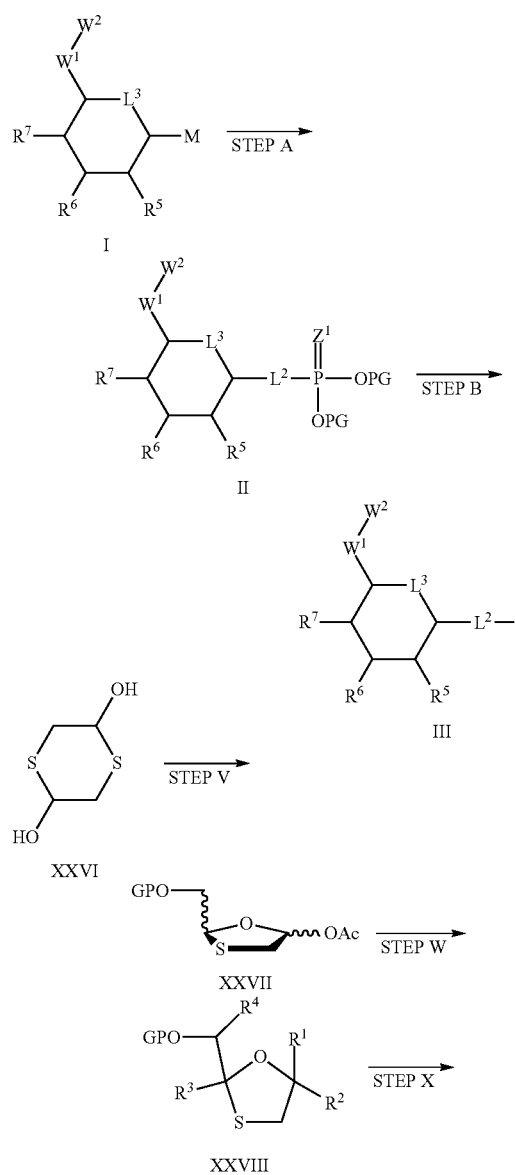
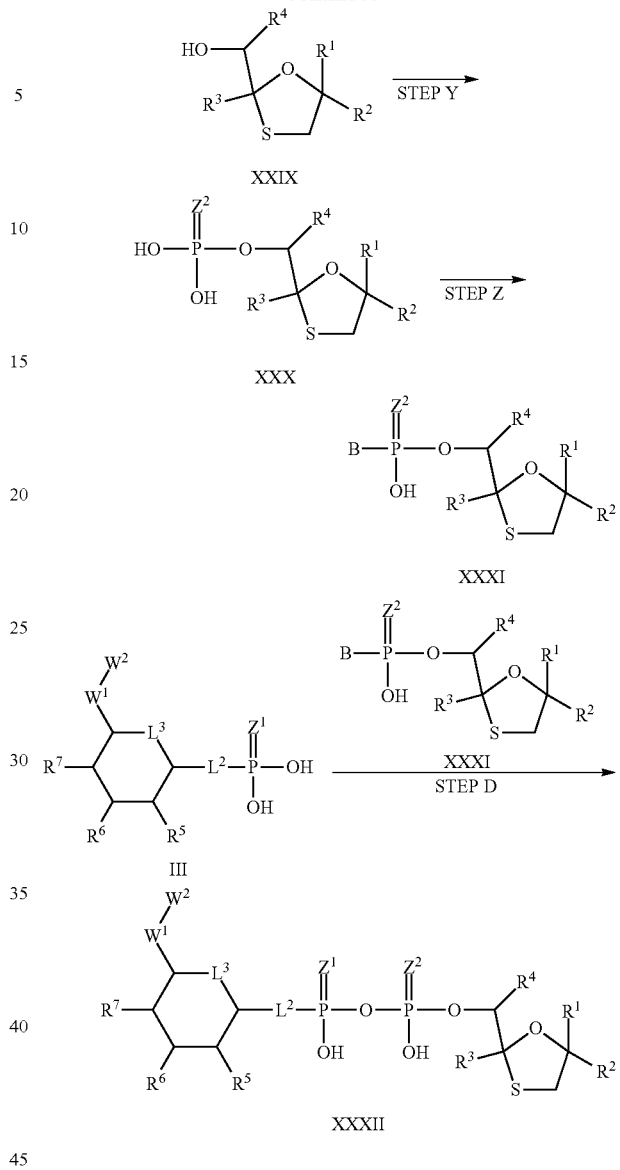
Table 1 lists exemplary compounds prepared according to the procedures as described herein.
TABLE 1
Exemplary Compounds of Formula I
| Structure | Compound Name |
|---|---|
| Compound 1 | ((2S,3S,4S,5R,6R)-2-(((((((2R,3S,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |

TABLE 1-continued

Exemplary Compounds of Formula I

| Structure | Compound Name |
|---|---|
| Compound 2 | Adenosine-3'-fluoro-5'-(D-glycero-β-D-mannoheptopyranosyl)diphosphate |
| Compound 3 | (2S,3S,4S,5S,6S)-2-((S)-2-acetoxy-1-fluoroethyl)-6-(((((((2R,3S,4R,5R)-5-(6-amino-9H-purin-9-yl)-3,4-dihdroxytetrahydrofuran-2-yl)methoxy)(hydroxy)phosphoryl)oxy)(hydroxy)phosphoryl)oxy)tetrahydro-2H-pyran-3,4,5-triyl triacetate |
| Compound 4 | Adenosine-5'-(L-glycero-β-D-manno-6-fluoro-heptopyranosyl)diphosphate |
| Compound 5 | (2R,3R,4S,5S,6S)-2-(acetoxymethyl)-6-(((((((2R,3S,4R,5R)-6-(6-amino-9H-purin-9-yl)-3,4-dihydroxytetrahydrofuran-2-yl)methoxy)(hydroxy)phosphoryl)oxy)(hydroxy)phosphoryl)oxy)tetrahydro-2H-pyran-3,4,5-triyl triacetate |
| Compound 6 | Adenosine-5'-(β-D-manno-heptopyranosyl)diphosphate |

TABLE 1-continued

Exemplary Compounds of Formula I

| Structure | Compound Name |
|---|---|
| 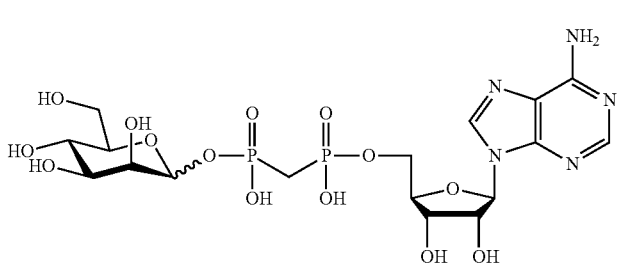<br>Compound 7 | (3S,4S,5S,6R)-3,4,5-trihydroxy-6-(hydroxymethyl)tetrahydro-2H-pyran-2-yl hydrogen(((((2R,3S,4R,5R)-5-(6-amino-9H-purin-9-yl)-3,4-dihydroxytetrahydrofuran-2-yl)methoxy)(hydroxy)phosphoryl)methyl)phosphonate |
| 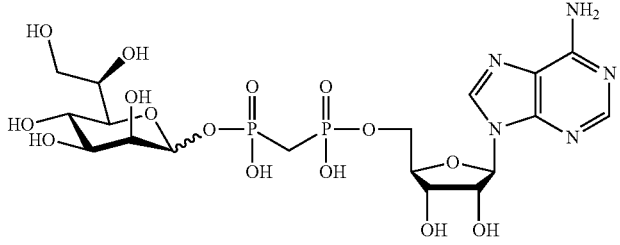<br>Compound 8 | (3S,4S,5S,6R)-6-((R)-1,2-dihydroxyethyl)-3,4,5-trihydroxytetrahydro-2H-pyran-2-yl hydrogen(((((2R,3S,4R,5R)-5-(6-amino-9H-purin-9-yl)-3,4-dihydroxytetrahydrofuran-2-yl)methoxy)(hydroxy)phosphoryl)methyl)phosphonate |
| 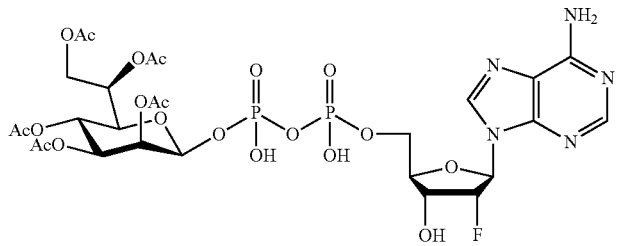<br>Compound 9 | 2-(((((((2R,3R,4R,5R)-5-(6-amino-9H-purin-9-yl)-4-fluoro-3-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 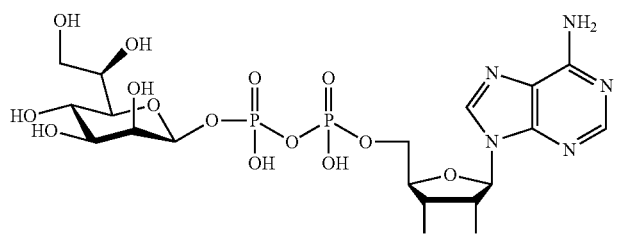<br>Compound 10 | Adenosine-2'-fluoro-5'-(D-glycero-β-D-mannoheptopyranosyl)diphosphate |

TABLE 1-continued

Exemplary Compounds of Formula I

| Structure | Compound Name |
|---|---|
| 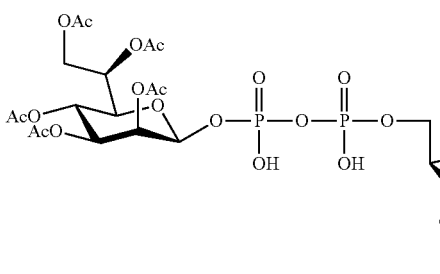<br>Compound 11 | (2S,3S,4S,5R,6R)-2-((((((3aR,4R,6R,6aR)-6-(6-amino-9H-purin-9-yl)-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 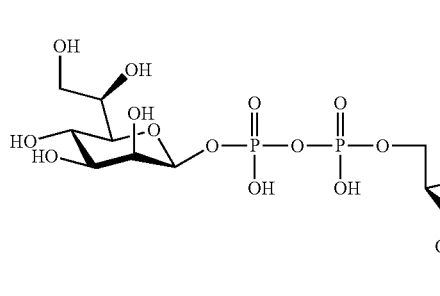<br>Compound 12 | ((3aR,4R,6R,6aR)-6-(6-amino-9H-purin-9-yl)-2,2-dimethyltetrahydrofuro[3,4-d][1,3]dioxol-5-yl)methanol(D-glycero-β-D-mannoheptopyranosyl) diphosphate |
| 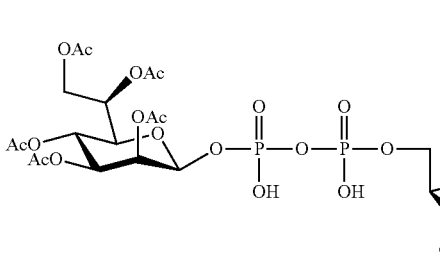<br>Compound 13 | (2S,3S,4S,5R,6R)-2-((((((2R,3R,4R,5R)-5-(6-amino-9H-purin-9-yl)-3,4-dimethoxytetrahydrofuran-2-yl)methoxy)(hydroxy)phosporyl)oxy)(hydroxy)phosphoryl)oxy)-6-((R)-1,2-diacetoxyethyl)tetrahydro-2H-pyran-3,4,5-triyl triacetate |
| 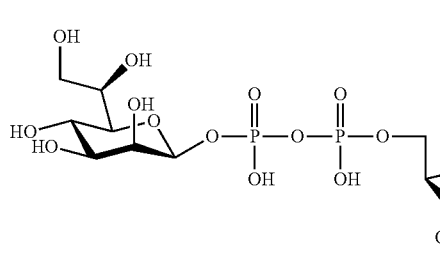<br>Compound 14 | Adenosine-2'3'-dimethoxy-5'-(D-glycero-β-D-mannoheptopyranosyl) diphosphate |

TABLE 1-continued

Exemplary Compounds of Formula I

| Structure | Compound Name |
|---|---|
| 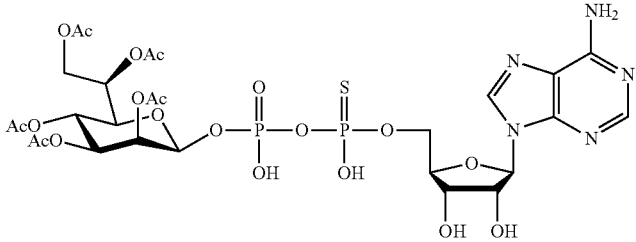<br>Compound 15 | (2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate |
| 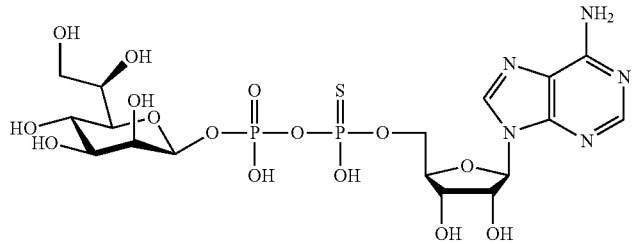<br>Compound 16 | Adenosine-5'-(D-glycero-β-D-manno-6-fluoro-heptopyranosyl)(hydroxy)phosphorothioyloxyphosphate |
| 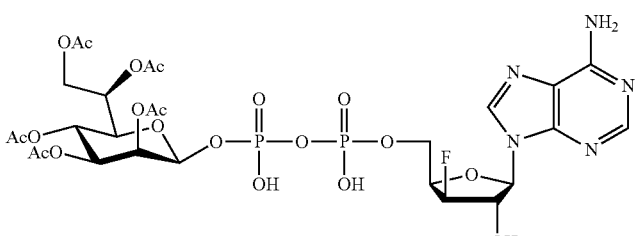<br>Compound 17 | (2S,3S,4S,5R,6R)-2-(((((((2R,3R,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 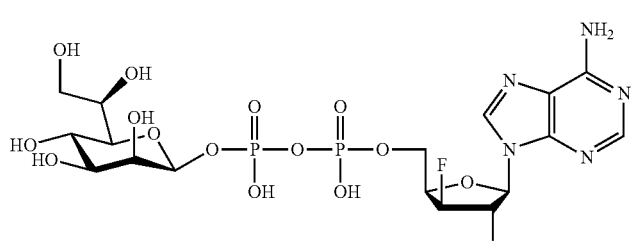<br>Compound 18 | 3'-(s)-fluoro-adenosine-5'-(D-glycero-β-D-manno-heptopyranosyl)di-phosphate |

TABLE 1-continued

Exemplary Compounds of Formula I

| Structure | Compound Name |
|---|---|
| 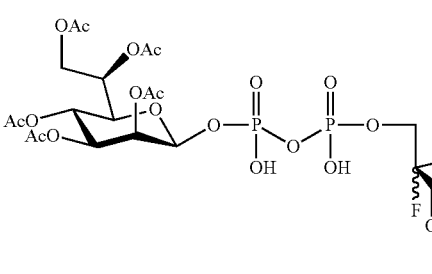<br>Compound 19 | (2S,3S,4S,5R,6R)-2-((((((3aS,4S,6R,6aR)-6-(6-amino-9H-purin-9-yl)-4-fluoro-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 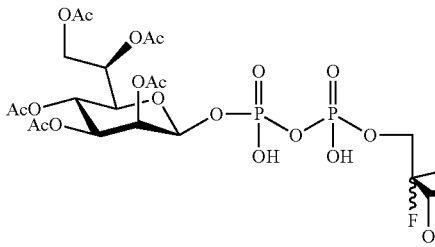<br>Compound 20 | (2S,3S,4S,5R,6R)-2-(((((((2S,3S,4R,5R)-5-(6-amino-9H-purin-9-yl)-2-fluoro-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 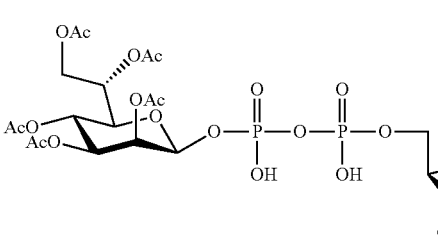<br>Compound 21 | (2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((S)-1,2-diacetoxyethyl)tetrahydro-2H-pyran-3,4,5-triyl triacetate |
| 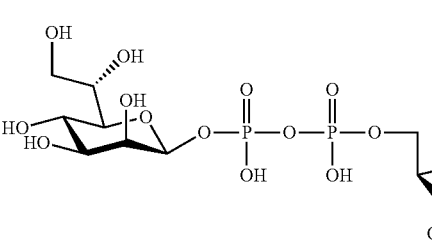<br>Compound 22 | Adenosine-5'-(L-glycero-β-D-mannoheptopyranosyl)diphosphate |

TABLE 1-continued

Exemplary Compounds of Formula I

| Structure | Compound Name |
| --- | --- |
| 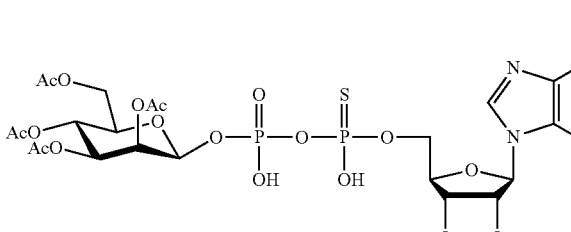<br>Compound 23 | (2R,3R,4S,5S,6S)-2-(acetoxymethyl)-6-((((((2R,3R,4R,5R)-3,4-diacetoxy-5-(6-amino-9H-purin-9-yl)tetrahydrofuran-2-yl)methoxy)(hydroxy)phosphorothioyl)oxy)(hydroxy)phosphoryl)oxy)tetrahydro-2H-pyran-3,4,5-triyl triacetate |
| 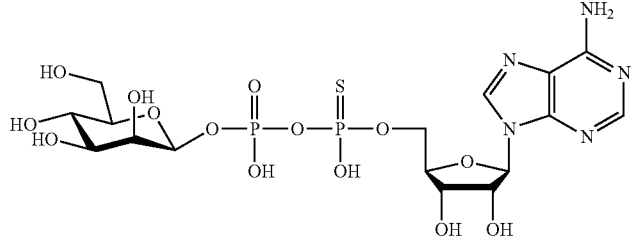<br>Compound 24 | Adenosine-(5'-Mannose-pyranosyl)(hydroxy)phosphorothioyloxyphosphate |
| 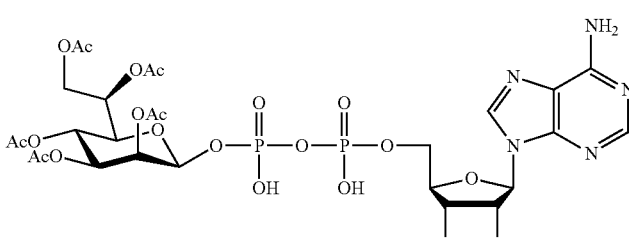<br>Compound 25 | (2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate |
| 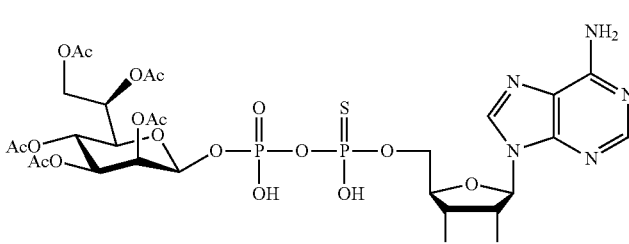<br>Compound 26 | 2S,3S,4S,5R,6R)-2-(((((((2R,3S,4S,5R)-5-(6-amino-9H-purin-9-yl)-3-fluoro-4-hydroxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate |

TABLE 1-continued

Exemplary Compounds of Formula I

| Structure | Compound Name |
|---|---|
| Compound 27 | Adenosine-3'-fluoro-5'-(D-glycero-β-D-manno-heptopyranosyl) (hydroxy)phosphorothioyloxyphosphate |
| Compound 28 | (2S,3S,4S,5S,6S)-2-((S)-2-acetoxy-1-fluoroethyl)-6-(((((((2R,3S,4R,5R)-5-(6-amino-9H-purin-9-yl)-3,4-dihydroxytetrahydrofuran-2-yl)methoxy)(hydroxy)phosphorothioyl)oxy)(hydroxy)phosphoryl)oxy)tetrahydro-2H-pyran-3,4,5-triyl triacetate |
| Compound 29 | Adenosine-5'-(L-glycero-β-D-manno-6-fluoro-heptopyranosyl) (hydroxy)phosphorothioyloxyphosphate |
| Compound 30 | (2S,3S,4S,5R,6R)-2-(((((((2R,3R,4R,5R)-5-(6-amino-9H-purin-9-yl)-3,4-dimethoxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate |
| Compound 31 | Adenosine-2'3'-dimethoxy-5'-(D-glycero-β-D-mannoheptopyranosyl) (hydroxy)phosphorothioyloxyphosphate |

TABLE 1-continued

Exemplary Compounds of Formula I

| Structure | Compound Name |
|---|---|
| 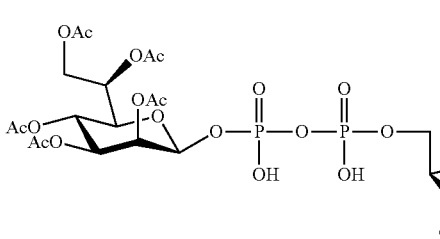 | (2R,3R,4S,5S,6S)-2-((R)-1,2-diacetoxyethyl)-6-(((((((2R,3S,4R,5R)-3,4-dihydroxy-5-(6-hydroxy-9H-purin-9-yl)tetrahydrofuran-2-yl)methoxy)(hydroxy)phosphoryl)oxy)(hydroxy)phosphoryl)oxy)tetrahydro-2H-pyran-3,4,5-triyl triacetate |
| Compound 32 | |
| 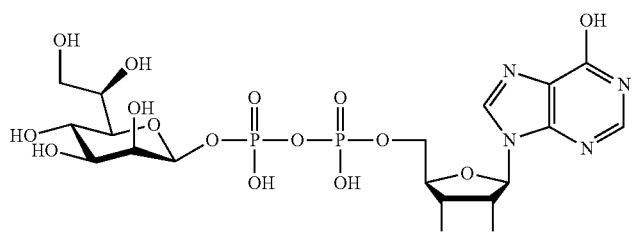 | Inosine-5'-(D-glycero-β-D-mannoheptopyranosyl)diphosphate |
| Compound 33 | |

Synthesis of Representative Compounds of Formula (I):

All moisture-sensitive reactions were performed using syringe-septum cap techniques under Ar. Analytical thin layer chromatography (TLC) was performed on Silica gel 60 F 254 Plates (Qindao, 0.25 mm thickness). $^1$H-NMR spectra were recorded with a Varian-400 spectrometer, and chemical shifts were reported as (ppm) values relative to internal tetramethylsilane or the residual proton of the deuterated solvent. $^{13}$C-NMR spectra were recorded with a Varian-400 spectrometer, and chemical shifts were reported as δ (ppm) values relative to internal tetramethylsilane or the residual proton of the deuterated solvent. $^{31}$P-NMR spectra were recorded with a Varian-400 spectrometer, and chemical shifts were reported as δ (ppm) values relative to external 85% phosphoric acid. $^1$H-NMR spectra are tabulated as follows: chemical shift, multiplicity (br=broad, s=singlet, d=doublet, t=triplet, q=quartet, m=multiplet), number of protons, and coupling constant(s).

Compound 1

(2S,3S,4S,5R,6R)-2-(((((((2R,3S,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

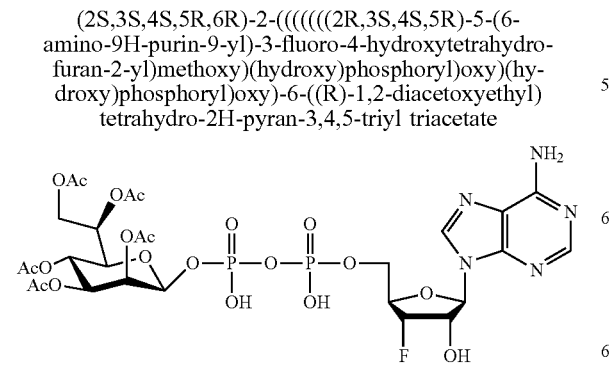

Step 1. Preparation of Compound (2R,3R,4R,5R)-5-(6-amino-9H-purin-9-yl)-2-(hydroxymethyl)-4-((4-methoxybenzyl)oxy)tetrahydrofuran-3-ol

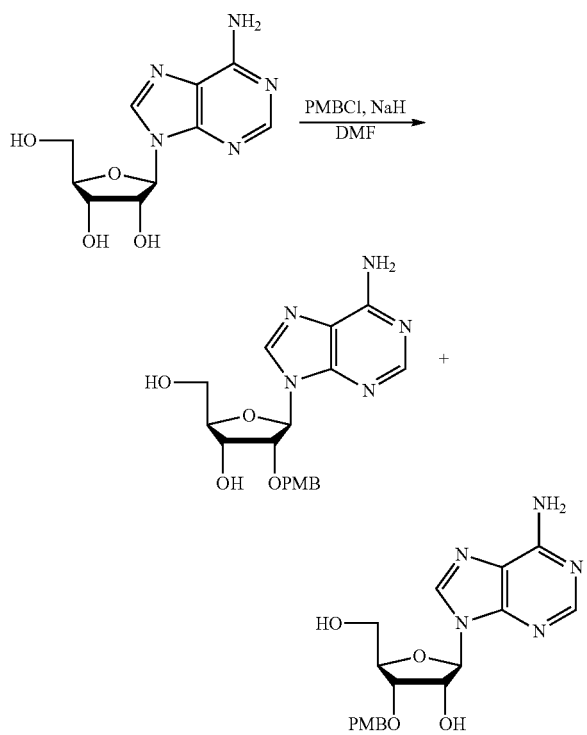

The suspension of adenosine (40 g, 149.6 mmol) in DMF (500 mL) was cooled to −5° C. NaH (8.0 g, 200.0 mmol, 60% purity) was added to the mixture and the mixture was stirred for 1 h at −5° C. Then PMB-Cl (23.0 mL, 168.8 mmol) was added dropwise to the mixture during 1 h under such temperature. After addition, the reaction was stirred at 15° C. for 12 h. The reaction was concentrated under reduced pressure to remove the solvent. $H_2O$ (50 mL) and EA (100 mL) were added to the residue and the organic layer was separated. The organic layer was washed with brine (50 mL), dried over anhydrous $Na_2SO_4$, filtered and concentrated under reduced pressure. The crude product was purified by silica gel chromatography (DCM/MeOH: 20/1 to 10/1) to afford the mixture of desired compound and the isomer (27 g, yield: 46.1%) as white solid which was used in the next step without further separation. $^1$H NMR (400 MHz, DMSO-d6) δ 8.38-8.29 (m, 1H), 8.15-8.06 (m, 1H), 7.39-7.30 (m, 2H), 7.11-6.91 (m, 2H), 6.88-6.69 (m, 2H), 6.08-5.90 (m, 1H), 5.58-5.44 (m, 1H), 5.29 (d, J=5.3 Hz, 1H), 4.71-4.50 (m, 2H), 4.40-3.99 (m, 3H), 3.76-3.68 (m, 3H), 3.68-3.63 (m, 1H), 3.60-3.47 (m, 1H).

Step 2. Preparation of Compound (2R,3R,4R,5R)-4-((4-methoxybenzyl)oxy)-5-(6-(tritylamino)-9H-purin-9-yl)-2-((trityloxy)methyl)tetrahydrofuran-3-ol To a solution of the mixture of product of Step 1 and its isomer above (10 g, 25.8 mmol) in pyridine (20 mL) was added DMAP (2.5 g, 20.7 mmol) and TrtCl (16.4 g, 59.0 mmol). Then the reaction was stirred at 80° C. for 4 h. HCl (1N, 20 mL) and EA (50 mL) were added to the mixture and the organic layer was separated. The organic layer was washed with HCl (1N, 20 mL x 3), brine (100 mL), dried over anhydrous $Na_2SO_4$, filtered and concentrated under reduced pressure. The crude product was purified by silica gel chromatography (PE/EA: 20/1 to 1/1) to afford the mixture of desired product and its the isomer (total 18 g, yield: 77.2%) as white solid which was used for the next step without further separation $^1$H NMR (400 MHz, DMSO-d6) δ 8.40-8.27 (m, 1H), 7.86-7.77 (m, 1H), 7.57-7.46 (m, 1H), 7.37-7.31 (m, 11H), 7.30-7.16 (m, 22H), 6.88-6.74 (m, 2H), 6.16-5.91 (m, 1H), 5.70-5.30 (m, 1H), 5.01-4.44 (m, 1H), 4.53-4.23 (m, 1H), 4.19-4.08 (m, 1H), 3.72-3.66 (m, 3H), 3.30-3.07 (m, 2H).

Step 3. Preparation of Compound (2R,4S,5R)-4-((4-methoxybenzyl)oxy)-5-(6-(tritylamino)-9H-purin-9-yl)-2-((trityloxy)methyl)dihydrofuran-3 (2H)-one

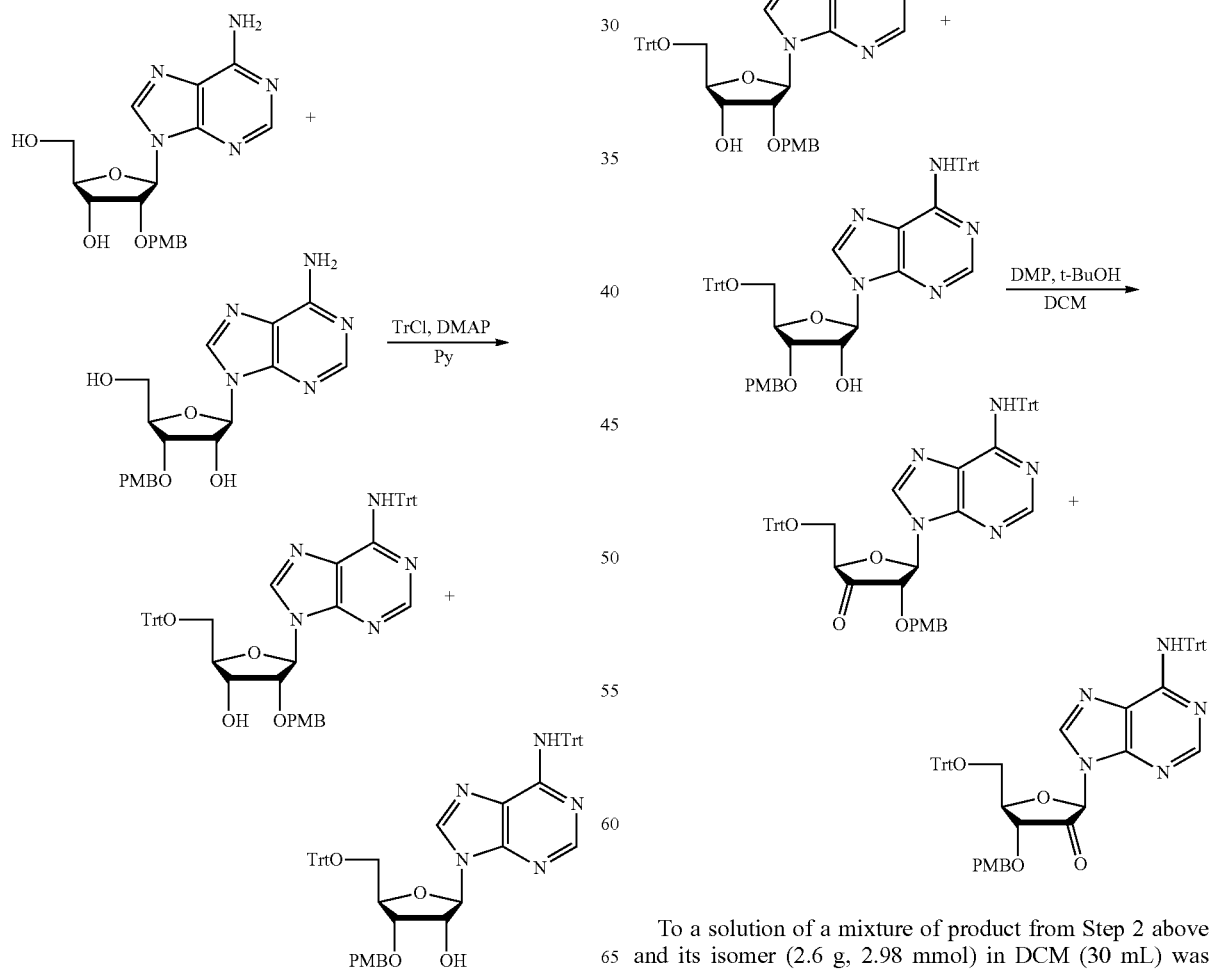

To a solution of a mixture of product from Step 2 above and its isomer (2.6 g, 2.98 mmol) in DCM (30 mL) was added DMP (2.54 g, 5.99 mmol) and t-BuOH (503.9 mg, 6.80 mmol, 650.17 μL). The mixture was stirred at 25° C. for 4 h. The reaction mixture was diluted with DCM (100 mL), quenched with sat. $Na_2S_2O_3$/sat. $NaHCO_3$ (1/1, 700 mL). The organic layer was separated and the aqueous layer was extracted with DCM (100 mL×3). The combined organic layers were washed with brine (300 mL), dried over anhydrous $Na_2SO_4$, filtered and concentrated to give a residue. The desired product and the isomer (2.79 g, crude) were obtained as a pale-yellow solid which was used into the next step without further purification. MS (ESI) m/z (M+H)$^+$: 870.4.

Step 4. Preparation of Compound (2R,3S,4R,5R)-4-((4-methoxybenzyl)oxy)-5-(6-(tritylamino)-9H-purin-9-yl)-2-((trityloxy)methyl)tetrahydrofuran-3-ol

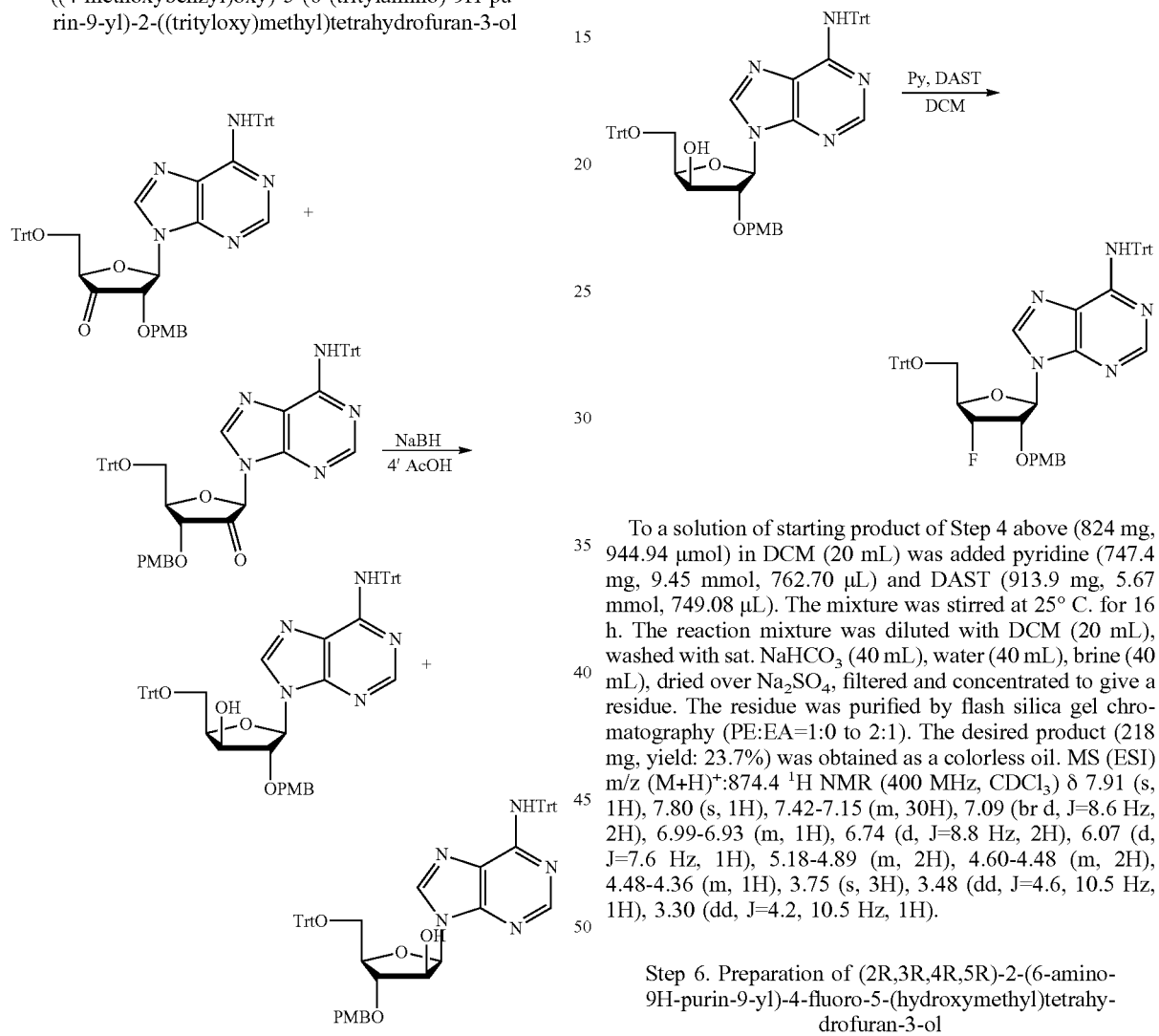

A solution of $NaBH_4$ (565.3 mg, 14.94 mmol) in $CH_3CO_2H$ (25 mL) was stirred at 15° C. for 10 min, and then was added the mixture of product of Step 3 above and its isomer (2 g, 2.30 mmol). The mixture was stirred at 25° C. for 20 h. The reaction mixture was evaporated with EtOH (50 mL×2), and then was partitioned between DCM (40 mL×3) and $H_2O$ (50 mL), the organic layer was washed with sat. $NaHCO_3$ (60 mL), brine (60 mL), dried over $Na_2SO_4$, filtered and concentrated to give a residue. The products of the two isomers were separated by flash silica gel chromatography (PE:EA=1:0 to 2:1). The desired product (824 mg, yield: 40.8%) was obtained as a white solid. And the isomer (203 mg, yield: 10%) was obtained as a white solid. MS (ESI) m/z (M+H)$^+$: 872.4. Desired product: $^1$H NMR (400 MHz, CDCl3) δ 7.85 (s, 1H), 7.69 (s, 1H), 7.44-7.09 (m, 32H), 7.03 (s, 1H), 6.85 (d, J=8.6 Hz, 2H), 5.73 (s, 1H), 4.63 (d, J=11.2 Hz, 1H), 4.44 (d, J=11.2 Hz, 1H), 4.32 (s, 1H), 4.28-4.16 (m, 2H), 3.78 (s, 3H), 3.56-3.44 (m, 2H).

Step 5. Preparation of 9-((2R,3S,4R,5R)-4-fluoro-3-((4-methoxybenzyl)oxy)-5-((trityloxy)methyl)tetrahydrofuran-2-yl)-N-trityl-9H-purin-6-amine

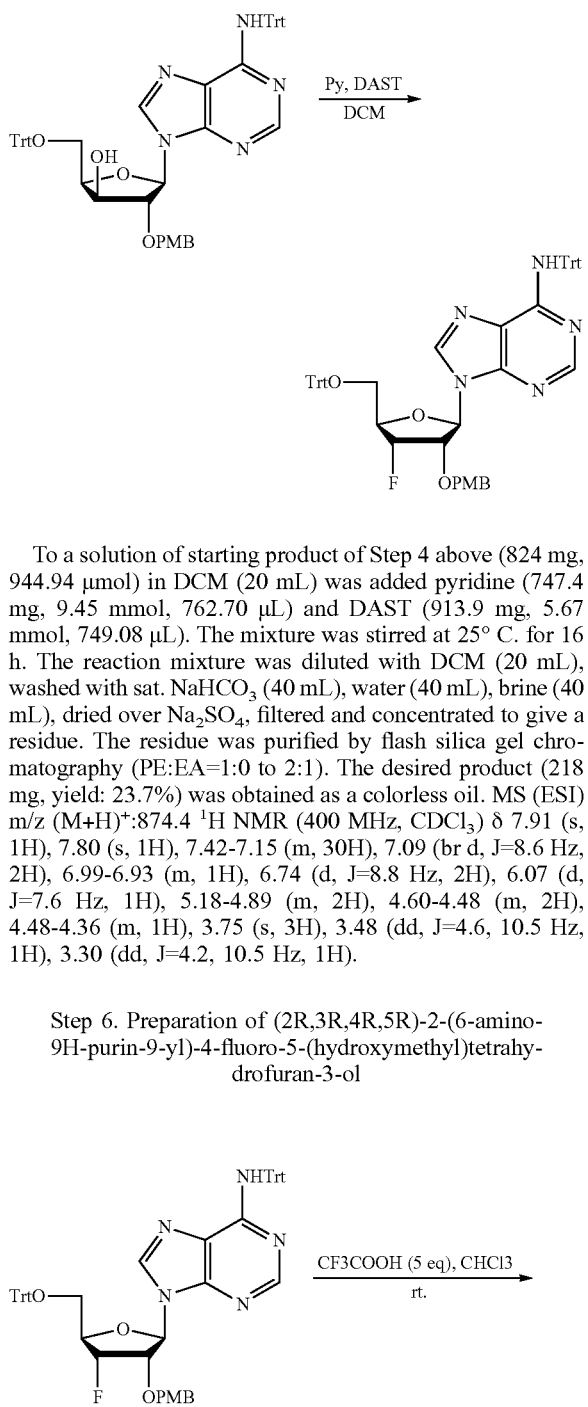

To a solution of starting product of Step 4 above (824 mg, 944.94 μmol) in DCM (20 mL) was added pyridine (747.4 mg, 9.45 mmol, 762.70 μL) and DAST (913.9 mg, 5.67 mmol, 749.08 μL). The mixture was stirred at 25° C. for 16 h. The reaction mixture was diluted with DCM (20 mL), washed with sat. $NaHCO_3$ (40 mL), water (40 mL), brine (40 mL), dried over $Na_2SO_4$, filtered and concentrated to give a residue. The residue was purified by flash silica gel chromatography (PE:EA=1:0 to 2:1). The desired product (218 mg, yield: 23.7%) was obtained as a colorless oil. MS (ESI) m/z (M+H)$^+$:874.4 $^1$H NMR (400 MHz, CDCl$_3$) δ 7.91 (s, 1H), 7.80 (s, 1H), 7.42-7.15 (m, 30H), 7.09 (br d, J=8.6 Hz, 2H), 6.99-6.93 (m, 1H), 6.74 (d, J=8.8 Hz, 2H), 6.07 (d, J=7.6 Hz, 1H), 5.18-4.89 (m, 2H), 4.60-4.48 (m, 2H), 4.48-4.36 (m, 1H), 3.75 (s, 3H), 3.48 (dd, J=4.6, 10.5 Hz, 1H), 3.30 (dd, J=4.2, 10.5 Hz, 1H).

Step 6. Preparation of (2R,3R,4R,5R)-2-(6-amino-9H-purin-9-yl)-4-fluoro-5-(hydroxymethyl)tetrahydrofuran-3-ol

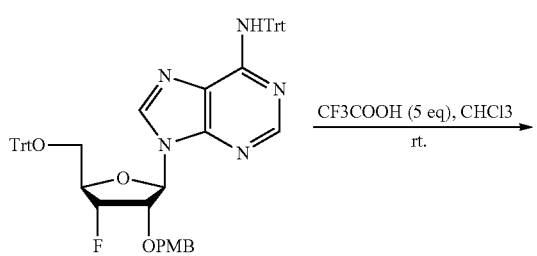

-continued

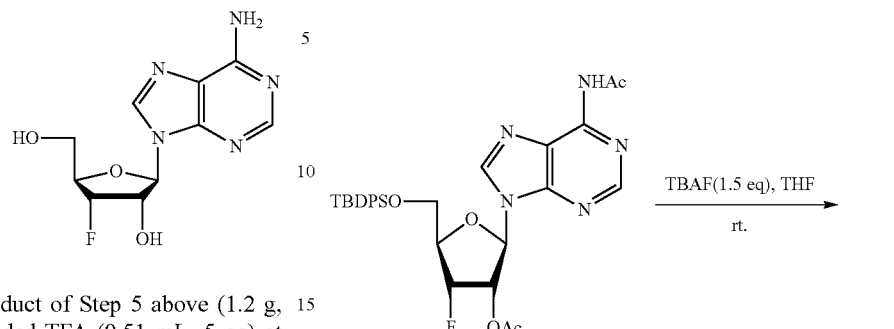

To a stirred solution of product of Step 5 above (1.2 g, 1.37 mmol) in CHCl₃ was added TFA (0.51 mL, 5 eq) at room temperature. The solution was stirred at this temperature for 2 h. The solution was concentrated under reduced pressure to give the desired product as an oily residue (360 mg, 1.34 mmol) which was used for the next step without further purification.

Step 7. Preparation of (2R,3R,4S,5R)-2-(6-acetamido-9H-purin-9-yl)-5-(((tert-butyldiphenylsilyl)oxy)methyl)-4-fluorotetrahydrofuran-3-yl acetate

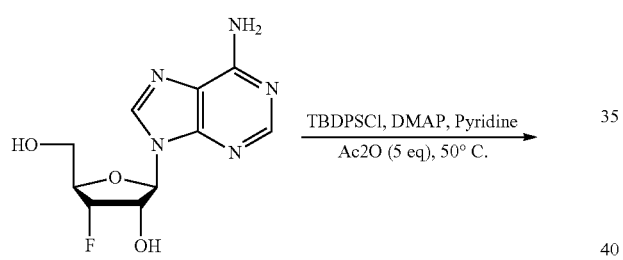

To a stirred solution of product of Step 6 above (360 mg, 1.34 mmol) in pyridine (10 mL) was added DMAP (16 mg, 0.134 mmol) at room temperature. The solution was heated to 50° C. At this temperature TBDPSCl (734 mg, 2.68 mmol) was added and the reaction was stirred at this temperature overnight. LC-MS showed no SM left. The solution was added Ac₂O (633 µL, 6.7 mmol) dropwise. After stirring for 5 h at this temperature, LC-MS showed the desired compound was formed. The reaction was partitioned between DCM and water. The combined extract was washed with H₂O and brine, and dried over Na₂SO₄. The filtrate was concentrated under reduced pressure to give the desired product as an oily residue (792 mg, 1.34 mmol) which was used for the next step without further purification.

Step 8. Preparation of (2R,3R,4S,5R)-2-(6-acetamido-9H-purin-9-yl)-4-fluoro-5-(hydroxymethyl)tetrahydrofuran-3-yl acetate

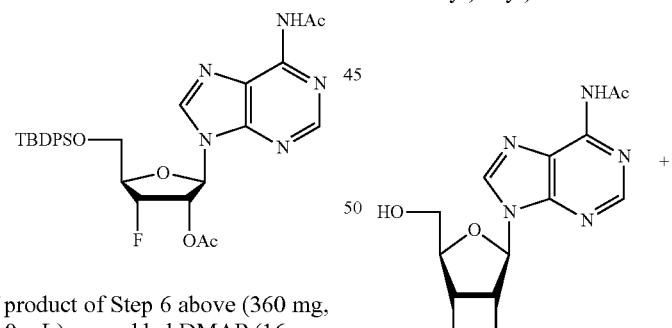

To a stirred solution of product of Step 7 above (792 mg, 1.34 mmol) in THF (10 mL) was added TBAF (1 M in THF, 2.00 mL, 2.00 mmol) at room temperature. After stirring overnight, the reaction was quenched with saturated NH₄Cl. The reaction was partitioned between DCM and water. The combined extract was washed with brine and dried over Na₂SO₄. The filtrate was concentrated under reduced pressure to give an oily residue, which was purified by flash chromatography on silica gel eluting with DCM/MeOH (20:1) to give the desired product as a colorless oil (254 mg, 0.72 mmol).

Step 9. Preparation of (2R,3R,4S,5R)-2-(6-acetamido-9H-purin-9-yl)-5-(2-(bis(benzyloxy)phosphoryl)ethyl)-4-fluorotetrahydrofuran-3-yl acetate

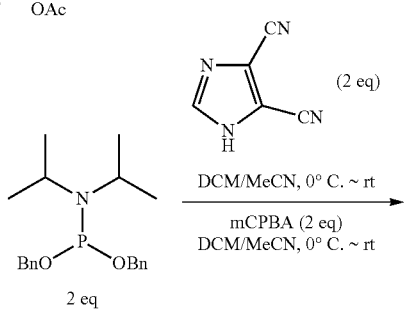

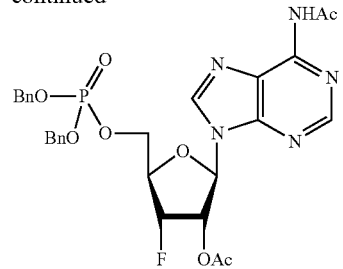

To a 25 mL round flask was charged with the product of Step 8 above (254 mg, 0.72 mmol) and 1H-imidazole-4,5-dicarbonitrile (170 mg, 1.44 mmol) under nitrogen atmosphere. Dry DCM and MeCN were added (DCM:MeCN=5:1, v/v). The resultant solution was cooled in ice-water bath and dibenzyl diisopropylphosphoramidite (497 mg, 1.44 mmol) was added. After the reaction was warmed to RT, it was stirred for another 1-2 h. The reaction was cooled in ice-water bath again and mCPBA (291 mg, 1.44 mmol) was added directly. After it was warmed to RT, Sat. NaHCO$_3$ (aq) was added to quench the reaction and the organic phase was separated. The water phase was extracted with DCM twice. The combined extract was washed with H$_2$O and brine, and dried over Na$_2$SO$_4$. The filtrate was concentrated under reduced pressure to give an oily residue, which was purified on Silica gel flash chromatography eluting with DCM/MeOH (30:1) to give the desired product (441 mg, 0.72 mmol).

Step 10. Preparation of (2R,3R,4S,5R)-2-(6-acetamido-9H-purin-9-yl)-4-fluoro-5-((phosphonooxy)methyl)tetrahydrofuran-3-yl acetate

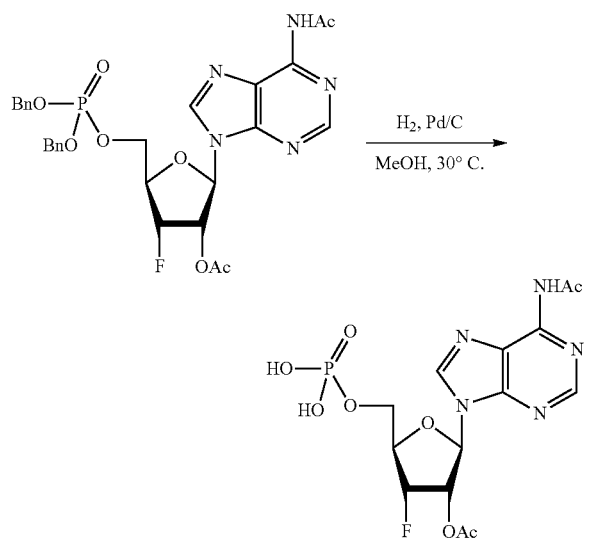

A mixture of product of Step 9 above (441 mg, 0.72 mmol) and Pd/C (132 mg) in MeOH (4 mL) was stirred at room temperature under H$_2$. After stirring overnight, the mixture was filtrated through an Advantec PTFE membrane filter with a pore size of 0.45 μm with MeOH. The filtrate was concentrated under reduced pressure to get the desired product (233 mg, 0.54 mmol), which was used for the next step without further purification.

Step 11. Preparation of Morphine DCC Salt of ((2R,3R,4R,5R)-5-(6-amino-9H-purin-9-yl)-3-fluoro-4-hydroxytetrahydrofuran-2-yl)methyl hydrogen morpholinophosphonate

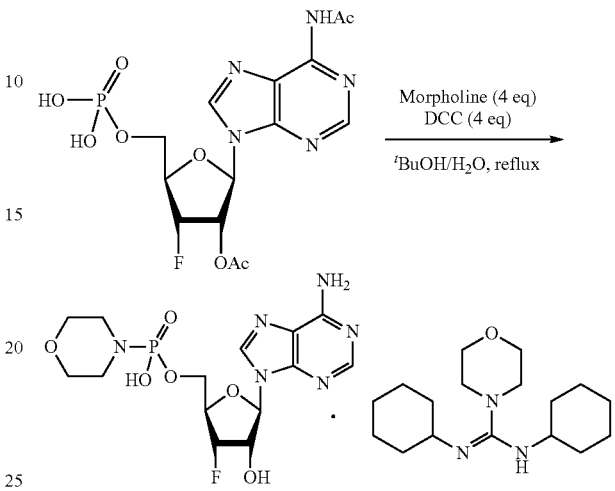

To a solution of DCC (445 mg, 2.16 mmol) in t-butyl alcohol (5 mL) was added dropwise to a refluxing solution of product of Step 10 above (233 mg, 0.54 mmol) in a mixture of t-BuOH/H$_2$O (1:1, 10 mL), and purified morpholine (188 mg, 2.16 mmol). The addition was completed in about 3 h, and the mixture was refluxed overnight until TLC showed completion of the reaction. The mixture was cooled to room temperature. The filtrate was evaporated until t-BuOH was largely removed, and the remaining aqueous phase was extracted three times with ether. The clear aqueous solution was then evaporated to dryness with freeze drying to give the desired product, which was used for the next step without further purification.

Step 12. Preparation of (2R,3R,4S,5S,6S)-2-((R)-1,2-diacetoxyethyl)-6-((diphenoxyphosphoryl)oxy)tetrahydro-2H-pyran-3,4,5-triyl triacetate

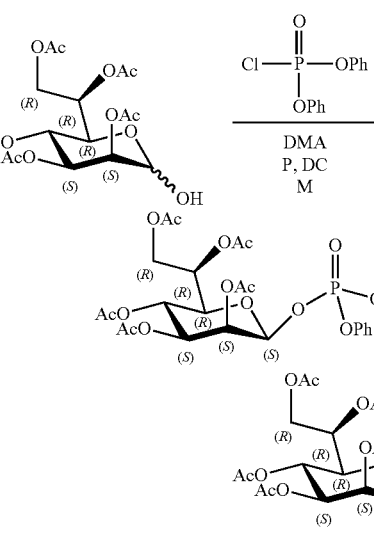

To the solution of (2R,3R,4S,5S)-2-((R)-1,2-diacetoxyethyl)-6-hydroxytetrahydro-2H-pyran-3,4,5-triyl triacetate (400 mg, 1 eq.; Shinsuke Inuki et al. *Org. Lett.* 2017, 19: 3079-3082; Alla Zamyatina et al., *Carbohydrate Research*, 2003, 338: 2571-2589) and DMAP (265.1 mg, 2.17 mmol, 2.28 eq) in DCM (10 mL), the solution of diphenyl phosphorochloridate (600.7 mg, 2.35 eq.) in DCM (10 mL) was added by syringe during 1 h. Then the reaction was stirred at 25° C. for 2 h. The starting material was remained partly detected by TLC (PE:EA=2:1, 3 times). DMAP (1.2 g) was added and then the solution of diphenyl phosphorochloridate (0.6 g) in DCM (15 mL) was added dropwise to the system and then stirred at 25° C. for 2 h. The reaction was diluted with DCM (20 mL), washed with sat. NaHCO$_3$ (30 mL) and brine (30 mL). The organic phase was concentrated to give a residue. The residue was purified by silica gel column chromatography (PE:EA=10:1 to 1:1) to give the isomer (alfa conformation 70 mg, yield: 11.3%) and the desired product (beta conformation, 400 mg, yield: 64.4%), both as colorless oil. Beta conformation: $^1$H NMR (400 MHz, CDCl$_3$) δ 7.42-7.12 (m, 10H), 5.70-5.61 (m, 1H), 5.44 (br d, J=1.2 Hz, 1H), 5.32-5.21 (m, 2H), 5.12-5.03 (m, 1H), 4.44-4.35 (m, 1H), 4.24-4.15 (m, 1H), 3.92-3.83 (m, 1H), 2.15-1.94 (m, 15H). Alfa conformation: $^1$H NMR (400 MHz, CDCl$_3$) δ 7.42-7.30 (m, 4H), 7.29-7.15 (m, 6H), 5.85 (br d, J=6.4 Hz, 1H), 5.41-5.26 (m, 3H), 5.19-5.11 (m, 1H), 4.37 (dd, J=3.7, 12.0 Hz, 1H), 4.29-4.17 (m, 2H), 2.23-1.96 (m, 15H).

Step 13. Preparation of 2R,3R,4S,5S,6S)-2-((R)-1,2-diacetoxyethyl)-6-(phosphonooxy)tetrahydro-2H-pyran-3,4,5-triyl triacetate

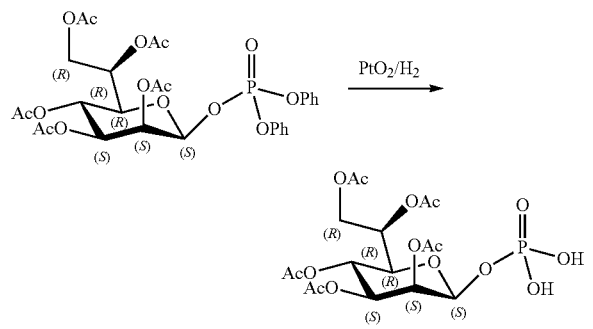

The solution consist of product of Step 12 above (400 mg, 1 eq.) in EtOAc (4 mL) and EtOH (4 mL) was mixed with PtO$_2$ (69.60 mg, 0.5 eq) and stirred at 25° C. for 16 h under 1 atm H$_2$ atmosphere. Filtered and the filtrate was concentrated to give a residue. The desired product (300 mg, 97.81% yield) was obtained as colorless oil. The product was pure enough to use directly in next step. $^1$H NMR (400 MHz, methanol-d4) δ 5.52-5.44 (m, 2H), 5.25-5.18 (m, 3H), 4.44 (dd, J=3.4, 12.0 Hz, 1H), 4.27 (dd, J=7.2, 12.1 Hz, 1H), 4.01-3.95 (m, 1H), 2.15 (s, 3H), 2.10-2.02 (m, 9H), 1.98-1.94 (m, 3H).

Step 14. Preparation of 2R,3R,4S,5S,6S)-2-((R)-1,2-diacetoxyethyl)-6-(phosphonooxy)tetrahydro-2H-pyran-3,4,5-triyl triacetate triethylammonium salt

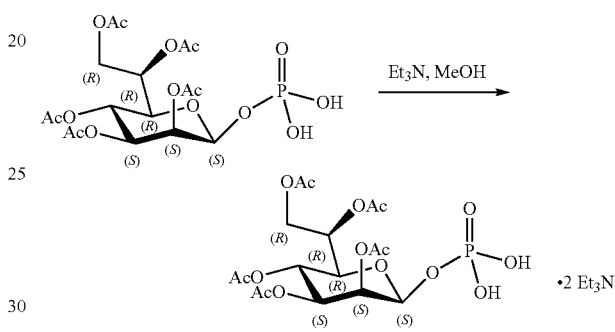

The solution of product of Step 13 above (300 mg, 1 eq) and Et$_3$N (0.2 mL, 2.40 eq.) in MeOH (5 mL) was stirred at 25° C. for 1.5 h. The solvent was removed under reduced pressure to give the triethylammonium salt of the desired product as white solid (340 mg, yield: 80.69%, with 2 Et$_3$N). The product was used directly in the next step.

Step 15. Preparation of (2S,3S,4S,5R,6R)-2-((((((2R,3S,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

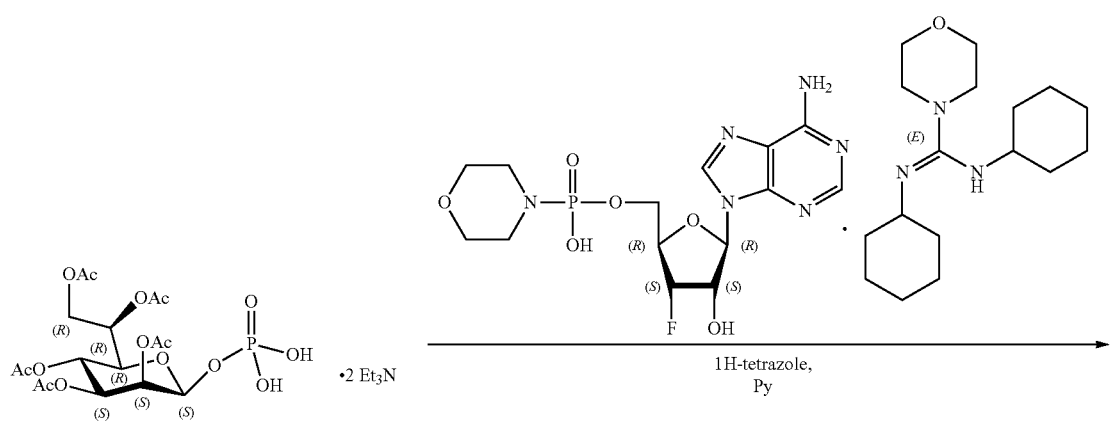

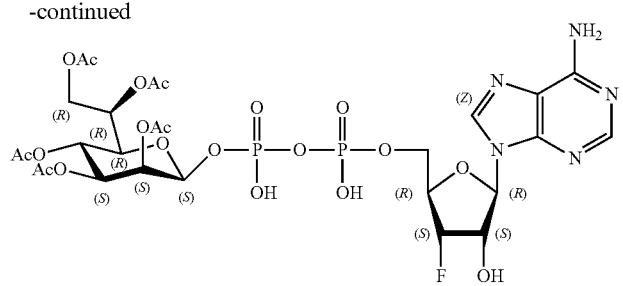

The mixture of product of Step 14 above (200 mg, 1 eq.) and morphine DCC salt of compound of product of Step 9 above (357.17 mg, 3 eq, DCC-morpholine) was dried with dry pyridine (5 mL×3). Then the residue was dissolved in pyridine (3 mL), 1H-tetrazole (99.68 mg, 5 eq.) was added and stirred at 25° C. for 32 h. The reaction was concentrated to give a residue which was purified by silica gel column chromatography (CHCl$_3$:MeOH:NH$_3$.H$_2$O:H$_2$O=1:0:0:0 to 50:50:1:1) to give the crude product (300 mg), which was purified by pre-HPLC (Column: Waters Xbridge 150*25 5t, Condition: water (10 mM NH$_4$HCO$_3$)-ACN, 3% to 33%) to give part of the less pure of the desired product (15 mg, yield: 3.9%, 61.6% purity) as white solid and the pure desired product (18 mg, yield: 7.16%, 94.1% purity) as a white solid. MS (ESI) m/z (M+H)$^+$: 832.4. $^1$H NMR (400 MHz, methanol-d4) δ 8.71 (s, 1H), 8.27 (s, 1H), 6.11 (d, J=7.6 Hz, 1H), 5.61-5.56 (br. s, 2H), 5.34 (br d, J=4.2 Hz, 0.5H), 5.25-5.15 (m, 3.5H), 4.61-4.50 (m, 1H), 4.45-4.41 (m, 1H), 4.31-4.21 (m, 3H), 3.95-3.90 (m, 1H), 2.13 (s, 3H), 2.08-2.02 (m, 6H), 1.99 (s, 3H), 1.91 (s, 3H).

Compound 2

Adenosine-3'-fluoro-5'-(D-glycero-β-D-mannoheptopyranosyl) diphosphate

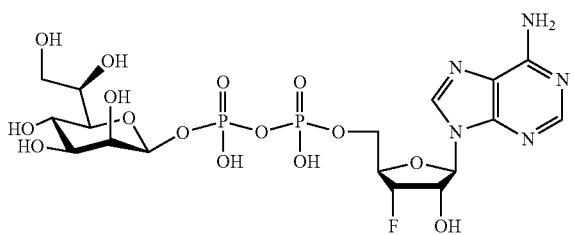

Step 1. Preparation of Adenosine-3'-fluoro-5'-(D-glycero-β-D-mannoheptopyranosyl) diphosphate

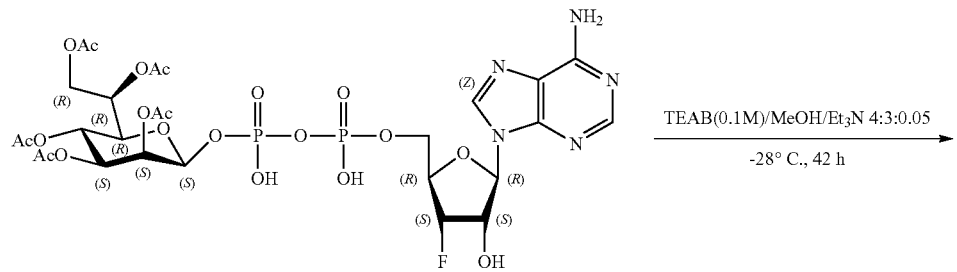

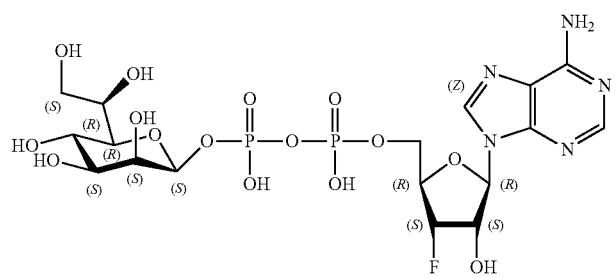

The compound of the product of Step 15 in the preparation of Compound 1 above (15.0 mg, 1 eq) was dissolved in 3 mL solvent consist of (TEAB (0.1 M):MeOH:Et₃N=4:3:0.05) and stirred at −28° C. for 42 h. Then the reaction was lyophilized by freeze dryer to give a white solid. The resulting solid was purified sequentially by preparative HPLC (RP-C18, isocratic eluting with triethylammonium acetate buffer (pH 6.8)/2% acetonitrile) and G25 Sephadex chromatography eluting with distilled H₂O to give the desired compound (6.1 mg, yield: 54.4%). MS (ESI) m/z (M−H)⁻: 619.8.

Compound 3

(2S,3S,4S,5S,6S)-2-((S)-2-acetoxy-1-fluoroethyl)-6-((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)tetrahydro-2H-pyran-3,4,5-triyl triacetate

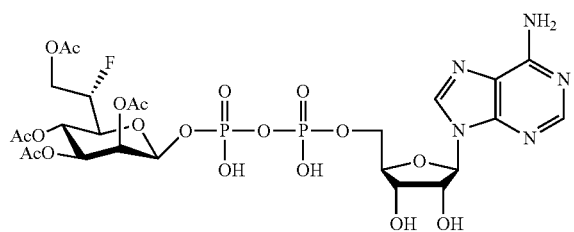

Step 1. Preparation of Compound 1-((2R,3S,4S,5S,6S)-3,4,5-tris(benzyloxy)-6-methoxytetrahydro-2H-pyran-2-yl)-2-(trityloxy)ethan-1-ol

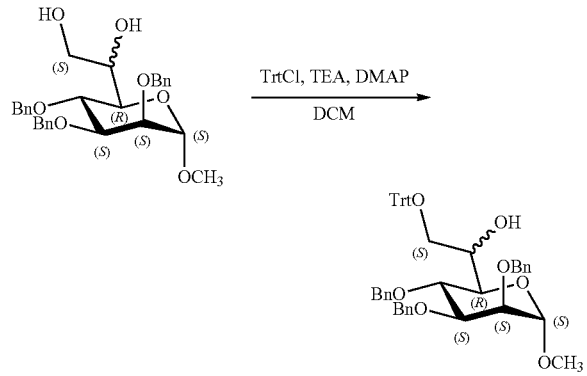

To a solution of compound 1-((2R,3S,4S,5S,6S)-3,4,5-tris (benzyloxy)-6-methoxytetrahydro-2H-pyran-2-yl)ethane-1,2-diol (17.4 g, 35.2 mmol; Tiehai Li et al., (2014) *Bioorg. Med. Chem.* 22:1139-1147; Shinsuke Inuki et al., *Org. Lett.* (2017), 19: 3079-3082), TEA (7.1 g, 70.4 mmol, 9.8 mL) and DMAP (2.2 g, 17.6 mmol) in DCM (200 mL) was added TrtCl (19.6 g, 70.4 mmol). The mixture was stirred at 50° C. for 20 h. The reaction mixture was quenched with H₂O (100 mL) and then separated. The aq. layer was extracted with DCM (60 mL×2). The combined organic layer was washed with brine (150 mL), dried over Na₂SO₄, filtered and concentrated to give a residue. The residue was purified by flash silica gel chromatography (PE:EA=1:0 to 1:1). The desired compound (24.6 g, yield: 95%, 93% purity) was obtained as a pale yellow oil. MS (ESI) m/z (M+H)⁺:782.4.

Step 2. Preparation of Compound 1-((2S,3S,4S,5S,6S)-3,4,5-tris(benzyloxy)-6-methoxytetrahydro-2H-pyran-2-yl)-2-(trityloxy)ethan-1-one

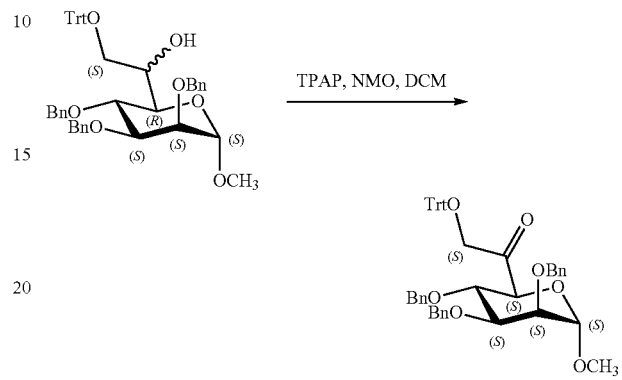

The mixture of product obtained from step 1 above (24.6 g, 33.4 mmol), NMO (19.6 g, 166.9 mmol, 17.6 mL) and 4 Å molecular sieve (24 g, 33.4 mmol) in DCM (250 mL) was stirred at 25° C. for 0.5 h. Then TPAP (1.17 g, 3.34 mmol) was added at 0° C. The mixture was stirred at 25° C. for 4 h. The mixture was filtered and washed with DCM (50 mL×3). The filtrate was concentrated under vacuum. The residue was purified by flash silica gel chromatography (PE:EA=1:0 to 4:1). The desired product (21.7 g, Yield: 85.6%) was obtained as a light yellow oil. MS (ESI) m/z (M+H)⁺: 757.3. ¹H NMR (400 MHz, CDCl₃): δ 7.45-7.25 (m, 30H), 4.72-4.52 (m, 6H), 4.20-4.07 (m, 4H), 3.99 (s, 2H), 3.68-3.67 (m, 1H), 3.22 (s, 3H).

Step 3. Preparation of (R)-1-((2R,3S,4S,5S,6S)-3,4,5-tris(benzyloxy)-6-methoxytetrahydro-2H-pyran-2-yl)-2-(trityloxy)ethan-1-ol

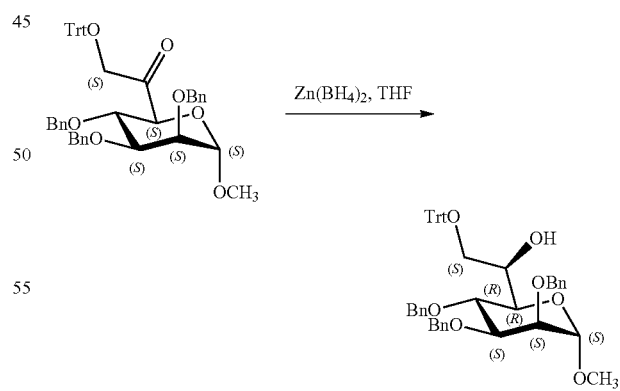

To the solution of the product obtained from step 2 above (21.7 g, 29.5 mmol) in THF (200 mL) was added Zn(BH₄)₂ (0.5 M, 66.7 mL) dropwisely at 0° C. for 0.5 h. The reaction was carefully quenched with H₂O (50 mL). The organic layer was extracted with ethyl acetate (150 mL×3). The organic layer was dried over Na₂SO₄ and concentrated under vacuum. The residue was purified by flash silica gel chromatography (PE:EA=1:0 to 7:1). The desired compound (19.5 g, Yield: 88.27%, 98.5% purity) was obtained as a colorless oil. MS (ESI) m/z (M+H)+: 759.3.

Step 4. Preparation of Compound (2S,3S,4S,5S,6S)-3,4,5-tris(benzyloxy)-2-((S)-1-fluoro-2-(trityloxy)ethyl)-6-methoxytetrahydro-2H-pyran

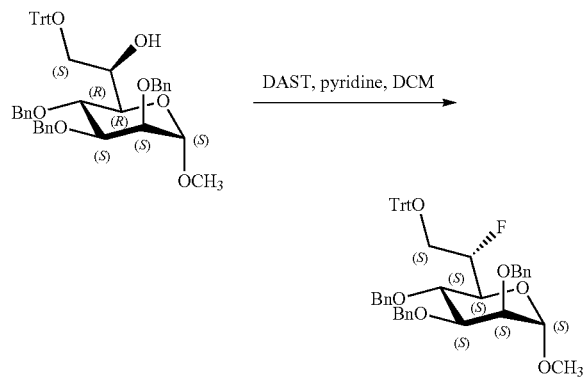

To the mixture of the compound of the product of Step 3 above (9.5 g, 12.9 mmol) in DCM (100 mL) were added DAST (10.4 g, 64.5 mmol, 8.5 mL) and pyridine (10.2 g, 128.9 mmol, 10.4 mL) at 0° C. The mixture was stirred at 25° C. for 16 h. The reaction was quenched with sat. NaHCO₃ (100 mL) carefully. The mixture was extracted with DCM (100 mL×3). The combined organic layers were washed with 2N HCl (150 mL), dried over Na₂SO₄ and concentrated under vacuum. The residue was purified by flash silica gel chromatography (PE:EA=1:0 to 12:1). The desired compound (4.2 g, Yield: 44.1%) was obtained as a light yellow oil. $^1$H NMR (400 MHz, CDCl₃): δ 7.38-7.18 (m, 30H), 4.92-4.61 (m, 2H), 4.53-4.51 (m, 6H), 4.06-4.02 (m, 1H), 3.77-3.75 (m, 1H), 3.65-3.51 (m, 3H), 3.14-3.06 (m, 1H), 2.96 (s, 3H).

Step 5. Preparation of Compound (S)-2-fluoro-2-((2S,3S,4S,5S,6S)-3,4,5-tris(benzyloxy)-6-methoxytetrahydro-2H-pyran-2-yl)ethan-1-ol

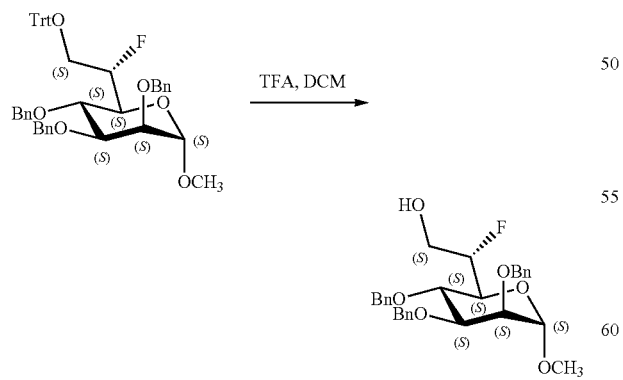

To the solution of the compound of the product of Step 4 above (5.8 g, 7.9 mmol) in DCM (60 mL) was added TFA (13.9 g, 121.6 mmol, 9 mL). The mixture was stirred at 25° C. for 1 h. To the mixture was added sat. NaHCO₃ (150 mL). The mixture was extracted with DCM (100 mL×3). The combined organic layers were dried over Na₂SO₄ and concentrated under vacuum. The residue was purified by flash silica gel chromatography (PE:EA=10:1 to 1:1). The desired compound (3.2 g, Yield: 79.7%, 96.2% purity) was obtained as a colorless oil. MS (ESI) m/z (M+H)+: 519.1. $^1$H NMR (400 MHz, CDCl₃): δ 7.35-7.28 (m, 15H), 4.99-4.96 (m, 2H), 4.73-4.65 (m, 4H), 4.60 (s, 2H), 4.14-4.10 (m, 3H), 3.77-3.76 (m, 1H), 3.70 (m, 1H), 3.60-3.57 (m, 1H), 3.27 (s, 3H). $^{19}$F NMR δ −207.84.

Step 6. Preparation of Compound (3S,4S,5S,6S)-6-((S)-2-acetoxy-1-fluoroethyl)-3,4,5-tris(benzyloxy)tetrahydro-2H-pyran-2-yl acetate

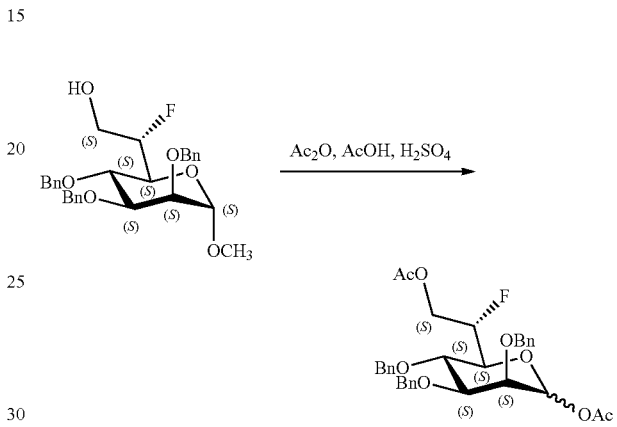

To the solution of the compound of the product of Step 5 above (3.2 g, 6.5 mmol) in HOAc (15 mL) and Ac₂O (15 mL) was added H₂SO₄ (2.8 g, 27.6 mmol, 1.5 mL, 98% purity). The mixture was stirred at 25° C. for 1 h. The reaction was quenched with methanol (15 mL) at 0° C. Most of the solvent was removed under vacuum. 30 mL of sat. NaHCO₃ was added and the mixture was extracted with ethyl acetate (50 mL×3). The combined organic layers were washed with brine (50 mL), dried over Na₂SO₄ and concentrated under vacuum. The desired compound (3.9 g, crude) was obtained as a light yellow oil which was used for next step directly.

Step 7. Preparation of Compound (3S,4S,5S,6S)-6-((S)-2-acetoxy-1-fluoroethyl)-3,4,5-trihydroxytetrahydro-2H-pyran-2-yl acetate

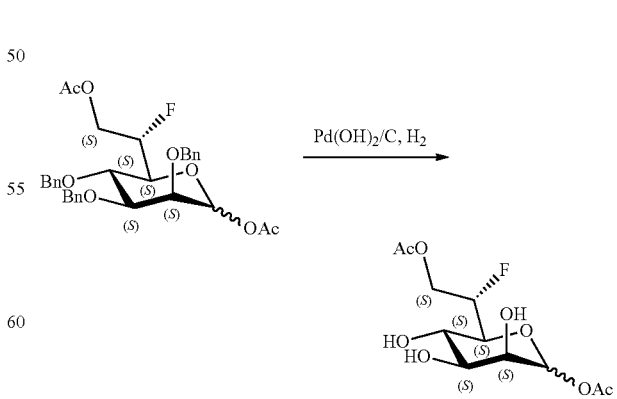

To the mixture of the compound of the product of Step 6 above (3.9 g, 6.9 mmol) in methanol (20 mL), THF (10 mL), H₂O (2 mL) and HOAc (0.5 mL) were added Pd(OH)₂/C (0.6 g, 20% purity) at 25° C. The mixture was stirred at 25° C. under hydrogen (50 psi) for 32 h. The mixture was filtered through celite and washed with methanol (50 mL×3). The filtrate was collected and concentrated under vacuum. The desired compound (2.5 g, crude) was obtained as a light yellow oil which was used for next step directly.

Step 8. Preparation of Compound (3S,4S,5S,6S)-6-((S)-2-acetoxy-1-fluoroethyl)tetrahydro-2H-pyran-2,3,4,5-tetrayl tetraacetate

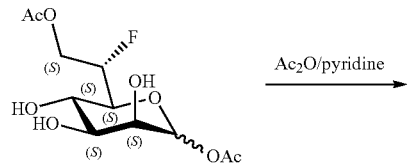

To the solution of the compound of the product of Step 7 above (2.5 g, 8.4 mmol) in pyridine (20 mL) were added Ac$_2$O (4.3 g, 42.2 mmol, 4.0 mL) and DMAP (515.5 mg, 4.2 mmol). The mixture was stirred at 25° C. for 0.5 h. The reaction was quenched with methanol (15 mL). Most of pyridine was removed under vacuum. 1 N HCl (20 mL) was added to the residue. The residue was extracted with ethyl acetate (30 mL×3). The combined organic layers were washed with 2N HCl (30 mL), dried over Na$_2$SO$_4$ and concentrated under vacuum. The residue was purified by flash silica gel chromatography (PE:EA=10:1 to 3:2). The desired compound (1.6 g, Yield: 44.6%) was obtained as a colorless oil. MS (ESI) m/z (M+H)$^+$: 445.0. $^1$H NMR (400 MHz, CDCl$_3$): δ 6.07 (s, 1H), 5.54-5.49 (m, 1H), 5.34-5.31 (m, 1H), 5.24-5.22 (m, 1H), 4.70-4.56 (m, 1H), 4.38-4.24 (m, 2H), 3.98-3.89 (m, 1H), 2.16 (d, J=6.4 Hz, 6H), 2.06 (d, J=6.0 Hz, 6H), 1.99 (s, 3H).

Step 9. Preparation of Compound (2S,3S,4S,5S)-2-((S)-2-acetoxy-1-fluoroethyl)-6-hydroxytetrahydro-2H-pyran-3,4,5-triyl triacetate

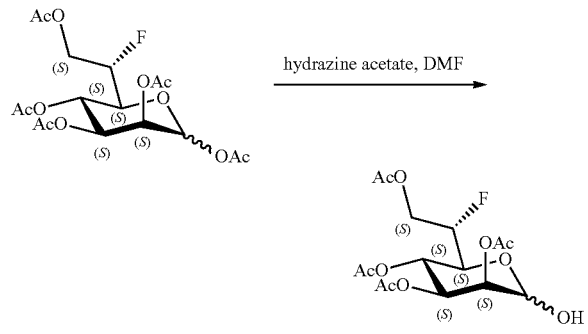

To the solution of the compound of the product of Step 8 (1.6 g, 3.8 mmol) in DMF (15 mL) was added hydrazine acetate (520.1 mg, 5.7 mmol). The mixture was stirred at 25° C. for 20 min. The reaction was quenched with H$_2$O (15 mL). The mixture was extracted with ethyl acetate (20 mL×3). The combined organic layers were washed with H$_2$O (20 mL×3), dried over Na$_2$SO$_4$ and concentrated under vacuum. The residue was purified by flash silica gel chromatography (PE:EA=10:1 to 1:1). The desired compound (860 mg, Yield: 60.1%) was obtained as a colorless oil.

$^1$H NMR (400 MHz, CDCl$_3$): δ 5.52-5.47 (m, 1H), 5.42-5.39 (m, 1H), 5.26-5.25 (m, 2H), 4.75-4.60 (m, 1H), 4.39-4.31 (m, 2H), 4.14-4.05 (m, 1H), 2.15 (s, 3H), 2.10 (s, 3H), 2.06 (s, 3H), 1.99 (s, 3H).

Step 10. Preparation of Compound (2S,3S,4S,5S,6S)-2-((S)-2-acetoxy-1-fluoroethyl)-6-((diphenoxyphosphoryl)oxy)tetrahydro-2H-pyran-3,4,5-triyl triacetate

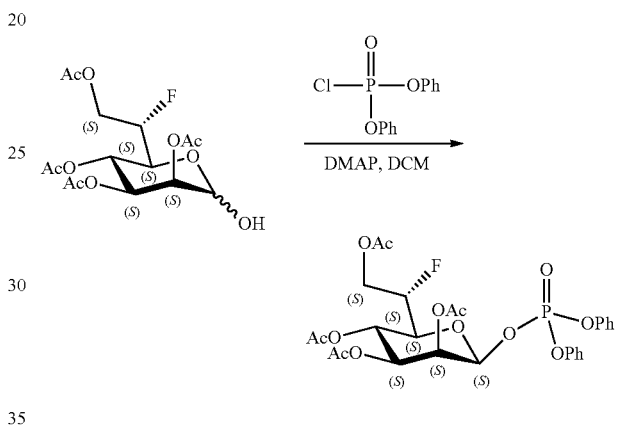

[chloro(phenoxy)phosphoryl]oxybenzene (2.1 g, 7.7 mmol, 1.6 mL) in DCM (50 mL) was added dropwisely to the solution of the compound of the product of Step 9 above (970 mg, 2.6 mmol) and DMAP (1.6 g, 12.8 mmol) in DCM (50 mL) at 25° C. within 3.5 h. The mixture was stirred at 25° C. for 16 h. The reaction was quenched with sat-.NaHCO$_3$ (50 mL). The mixture was extracted with DCM (80 mL×3). The combined organic layers were dried over Na$_2$SO$_4$ and concentrated under vacuum. The residue was purified by flash silica gel chromatography (PE:EA=10:1 to 3:2). The desired compound (1.21 g, Yield: 77.5%, 100% purity) was obtained as a colorless oil. MS (ESI) m/z (M+H)$^+$: 658.1. $^1$H NMR (400 MHz, CDCl$_3$) δ 7.35-7.13 (m, 10H), 5.54 (d, J=6.8 Hz, 1H), 5.50-5.46 (m, 2H), 5.07-5.04 (m, 1H), 4.72-4.57 (m, 1H), 4.30-4.26 (m, 1H), 4.23-4.19 (m, 1H), 3.74-3.65 (m, 1H), 2.10 (s, 3H), 2.07 (s, 3H), 2.05 (s, 3H), 1.98 (s, 3H). $^{19}$F NMR δ -205.5.

Step 11. Preparation of Compound (2S,3S,4S,5S,6S)-2-((S)-2-acetoxy-1-fluoroethyl)-6-(phosphonooxy)tetrahydro-2H-pyran-3,4,5-triyl triacetate

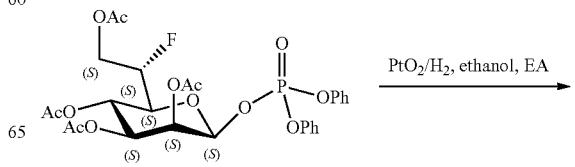

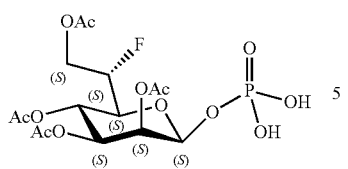

To the mixture of the compound of the product of Step 10 above (600 mg, 979.6 μmol) in ethanol (10 mL) and ethyl acetate (10 mL) was added PtO$_2$ (150 mg). The mixture was stirred at 25° C. under hydrogen (15 psi) for 20 h. The reaction mixture was filtered through celite and washed with methanol (20 mL×4). The filtrate was collected and concentrated under vacuum. The desired compound (450 mg, crude) was obtained as a white solid. The compound was used for next step directly.

Step 12. Preparation of Compound (2S,3S,4S,5S, 6S)-2-((S)-2-acetoxy-1-fluoroethyl)-6-(phosphonooxy)tetrahydro-2H-pyran-3,4,5-triyl triacetate triethyl amine salt

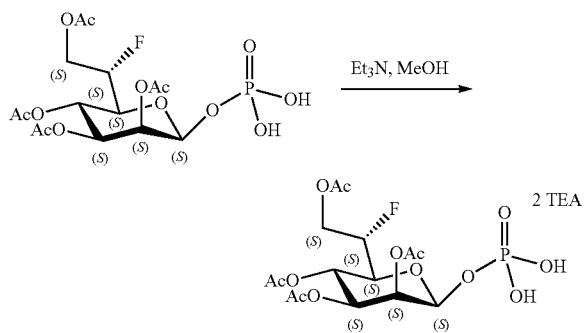

The compound of the product of Step 11 (980 mg, 2.1 mmol) was dissolved in methanol (10 mL). TEA (646.3 mg, 6.4 mmol, 889 μL) was added to the mixture and the mixture was stirred at 25° C. for 0.5 h. The mixture was concentrated under vacuum. The desired salt (950 mg, yield: 96.9%) was obtained as a light yellow foam. The compound was used for next step directly.

Step 13. Preparation of Compound (2S,3S,4S,5S, 6S)-2-((S)-2-acetoxy-1-fluoroethyl)-6-(((((((2R,3S, 4R,5R)-5-(6-amino-9H-purin-9-yl)-3,4-dihydroxytetrahydrofuran-2-yl)methoxy)(hydroxy) phosphoryl)oxy)(hydroxy)phosphoryl)oxy) tetrahydro-2H-pyran-3,4,5-triyl triacetate

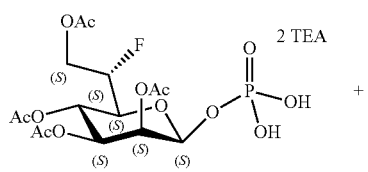

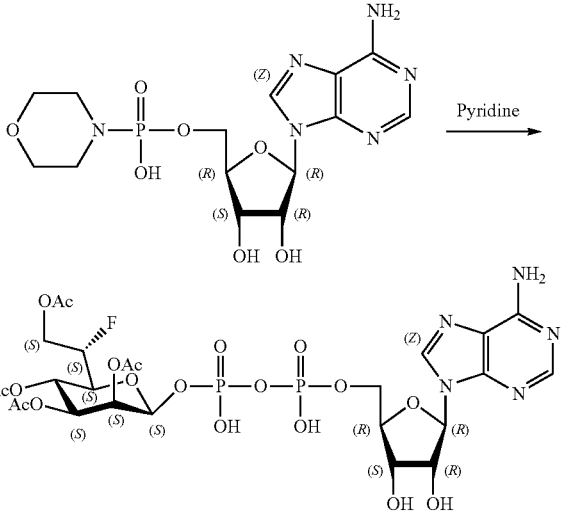

The compound of the product of Step 12 above (300 mg, 651.8 μmol, TEA salt) and compound AMP-morpholidate (4'-morpholine-N'N'-dicyclohexylcarboxamidinium salt) (693.9 mg, 977.6 μmol) were dehydrated twice with pyridine (4 mL). Then 1H-tetrazole (228.3 mg, 3.3 mmol, 289.0 μL) was added and the residue was dissolved in pyridine (5 mL). The mixture was stirred at 25° C. under nitrogen for 40 h. The mixture was concentrated under vacuum. The residue was dissolved in methanol (30 mL). The mixture was filtered and the solid was discarded. The filtrate was concentrated under vacuum. The residue was purified by flash silica gel chromatography (DCM:methanol:NH$_3$.H$_2$O=20:1:0.05 to 1:1:0.05) to afford 240 mg of crude product as a colorless oil. The crude compound was purified by prep-HPLC (neutral condition, column: Waters Xbridge 150*25 5u; mobile phase: [water (10 mM NH$_4$HCO$_3$)-ACN]; B %: 0%-30%, 10 min). The desired compound (75.1 mg, Yield: 14.5%, 99.2% purity) was obtained as a white solid. MS (ESI) m/z (M+H)$^+$: 790.1. $^1$H NMR (400 MHz, CD$_3$OD) δ 8.60 (s, 1H), 8.19 (s, 1H), 6.08 (d, J=6.8 Hz, 1H), 5.57-5.55 (m, 2H), 5.36-5.21 (m, 2H), 4.74-4.72 (m, 1H), 4.64-4.37 (m, 4H), 4.23-4.22 (m, 3H), 3.86-3.78 (m, 1H), 2.12 (s, 3H), 2.02 (s, 3H), 2.01 (s, 3H), 1.91 (s, 3H).

Compound 4

Adenosine-5'-(L-glycero-β-D-manno-6-fluoro-heptopyranosyl) diphosphate

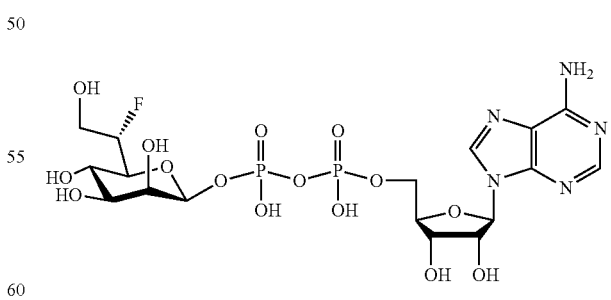

Step 1. Preparation of Compound Adenosine-5'-(L-glycero-β-D-manno-6-fluoro-heptopyranosyl) diphosphate The compound of the product of Step 13 in the preparation of Compound 3 above (24 mg, 30.4 μmol, 1 eq) was dissolved in TEAB/MeOH/TEA (0.3 mL, v/v/v=1/1/1). The mixture was stirred at −28° C. for 48 h. The reaction was diluted with CH₃CN (2 mL) and lyophilized. The desired compound (15.3 mg, yield 61.1%, 2Et₃N) was obtained as a white solid. $^1$H NMR (400 MHz, D₂O) δ 8.34 (s, 1H), 8.08-8.07 (m, 1H), 5.97-5.96 (m, 1H), 5.05 (d, J=9.6 Hz, 1H), 4.61-4.58 (m, 2H), 4.37-4.35 (m, 1H), 4.23-4.22 (m, 1H), 4.07-4.04 (m, 2H), 3.92-3.91 (m, 1H), 3.83-3.60 (m, 3H), 3.53-3.50 (m, 1H), 3.25 (dd, J=10.4 Hz, 26.8 Hz, 1H), 3.05-3.00 (m, 12H), 1.09 (t, J=7.6 Hz, 18H).

Compound 5

(2R,3R,4S,5S,6S)-2-(acetoxymethyl)-6-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)tetrahydro-2H-pyran-3,4,5-triyl triacetate

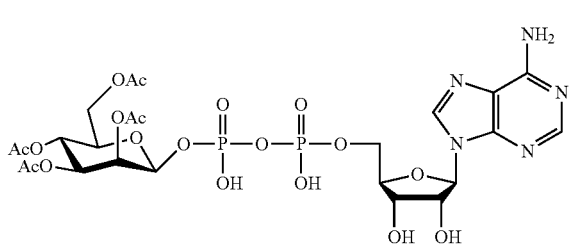

Step 1. Preparation of (2R,3R,4S,5S)-2-(acetoxymethyl)-6-hydroxytetrahydro-2H-pyran-3,4,5-triyl triacetate

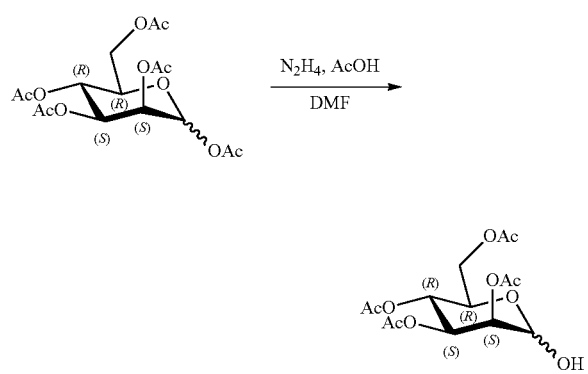

AcOH (6.92 g, 115.28 mmol, 6.59 mL, 1.5 eq) was added to the solution of NH₂NH₂.H₂O (5.60 mL, 115.28 mmol) in DMF (60 mL) at 0° C. and stirred for 0.5 h. (3S,4S,5R,6R)-6-(acetoxymethyl)tetrahydro-2H-pyran-2,3,4,5-tetrayl tetraacetate (30 g, 76.86 mmol) was added to the system and stirred at 25° C. for 1.5 h. The reaction was diluted with H₂O (200 mL) and extracted with EtOAc (150 mL×3). The organic phase was combined and washed with brine (150 mL×3), concentrated to give a residue. The residue was purified by silica gel column chromatography (PE:EA=1:0 to 1:1) to give the desired compound (26 g, yield: 97.1%) as a colorless oil. $^1$H NMR (400 MHz, CDCl₃) δ 5.45-5.20 (m, 3H), 4.30-4.10 (m, 4H), 2.20-2.00 (m, 12H).

Step 2. Preparation of (2R,3R,4S,5S,6S)-2-(acetoxymethyl)-6-((diphenoxyphosphoryl)oxy)tetrahydro-2H-pyran-3,4,5-triyl triacetate

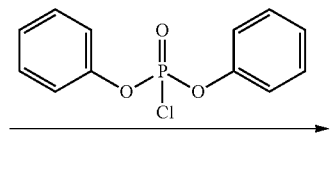

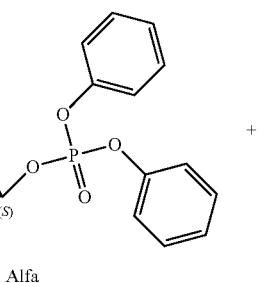

Alfa

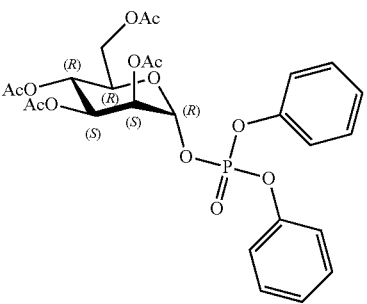

Bata

To the mixture of product of Step 1 above (864.4 mg, 2.48 mmol) and DMAP (3.03 g, 24.82 mmol) in DCM (10 mL), the solution of diphenyl phosphorochloridate (5 g, 18.61 mmol) in DCM (40 mL) was added dropwise and stirred at 25° C. for 16 h. The reaction was diluted with DCM (50 mL), washed with sat. NaHCO₃ (50 mL) and brine (50 mL), concentrated to give a residue. The residue was purified by silica gel column chromatography (PE:EA=1:0 to 1:1) to give the alfa configuration compound (750 mg, yield: 52.1%) and the desired beta configuration compound (380 mg, yield: 26.4%) and both were obtained as yellow oil. Alfa configuration compound: $^1$H NMR (400 MHz, CDCl₃) δ 7.42-7.11 (m, 10H), 5.59 (dd, J=1.1, 7.2 Hz, 1H), 5.48 (d, J=2.9 Hz, 1H), 5.25 (t, J=9.7 Hz, 1H), 5.07 (dd, J=3.4, 9.8 Hz, 1H), 4.27 (dd, J=5.6, 12.2 Hz, 1H), 4.17-4.08 (m, 1H), 3.84-3.74 (m, 1H), 2.16-1.95 (m, 12H). Beta configuration compound: $^1$H NMR (400 MHz, CDCl₃) δ 7.43-7.14 (m, 11H), 5.87 (dd, J=1.6, 6.7 Hz, 1H), 5.42-5.26 (m, 3H), 4.25-4.02 (m, 3H), 3.92 (dd, J=2.1, 12.3 Hz, 1H), 2.16 (s, 3H), 2.08-1.94 (m, 9H).

Step 3. Preparation of Compound (2R,3R,4S,5S, 6S)-2-(acetoxymethyl)-6-(phosphonooxy)tetrahydro-2H-pyran-3,4,5-triyl triacetate

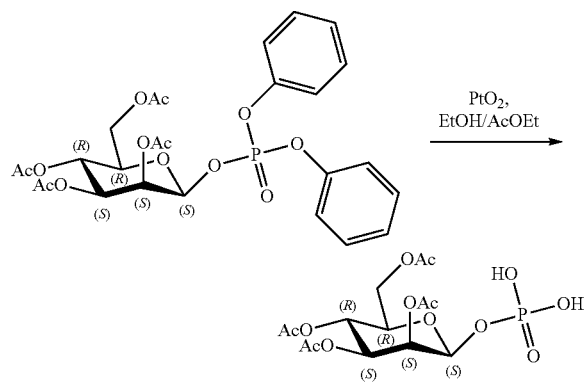

The mixture of compound of product Step 2 above (400 mg, 689.09 μmol) and PtO₂ (15.65 mg, 68.91 μmol) in EtOAc (4 mL) and EtOH (4 mL) was stirred at 25° C. for 16 h under H₂ atmosphere (1 atm). The reaction mixture was filtered and the filter cake was washed with EtOAc/EtOH (5 mL/5 mL). The filtrate was concentrated to give the target compound (300 mg, crude) as a colorless oil. The crude product was used directly in next step. ¹H NMR (400 MHz, methanol-d₄) δ 5.54-5.48 (m, 2H), 5.27-5.22 (m, 2H), 4.38-4.31 (m, 1H), 4.17 (dd, J=2.5, 12.5 Hz, 1H), 3.97-3.90 (m, 1H), 2.19 (s, 3H), 2.08 (s, 3H), 2.07-2.05 (m, 3H), 1.98 (s, 3H).

Step 4. Preparation of (2R,3R,4S,5S,6S)-2-(cetoxymethyl)-6-(phosphonooxy)tetrahydro-2H-pyran-3,4,5-triyl triacetate ditriethylammonium salt

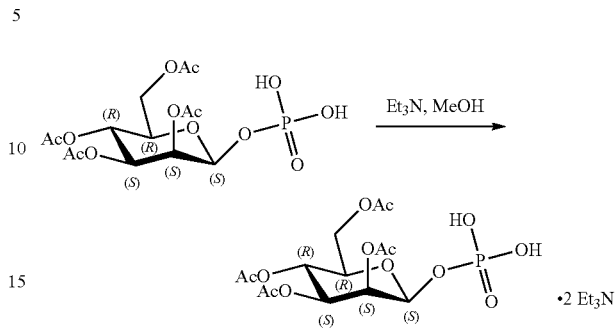

The mixture of compound of product 3 above (300 mg, 700.47 μmol) and Et₃N (0.2 mL, 1.40 mmol) in MeOH (10 mL) was stirred at 25° C. for 2 h. The solvent was removed to give the triethyl ammonium salt (450 mg, crude, with 2 Et₃N) as a colorless oil. The crude product was used directly in next step.

Step 5. Preparation of (2R,3R,4S,5S,6S)-2-(acetoxymethyl)-6-((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)tetrahydro-2H-pyran-3,4,5-triyl triacetate

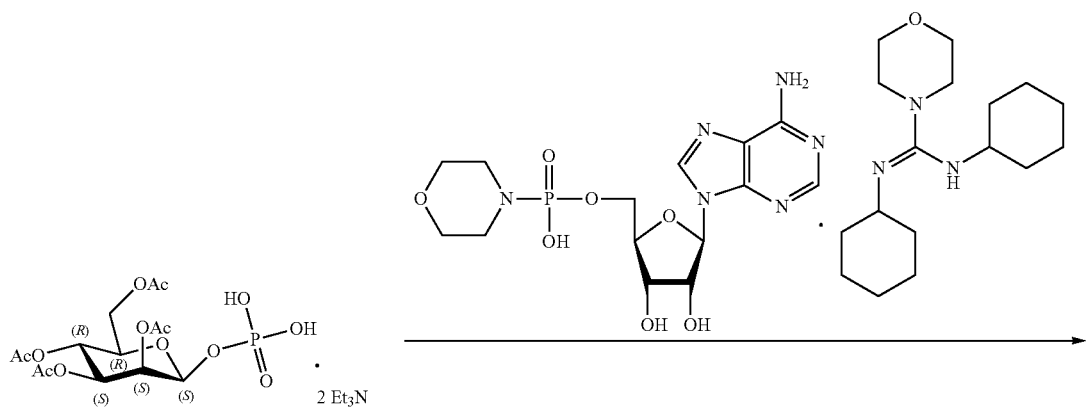

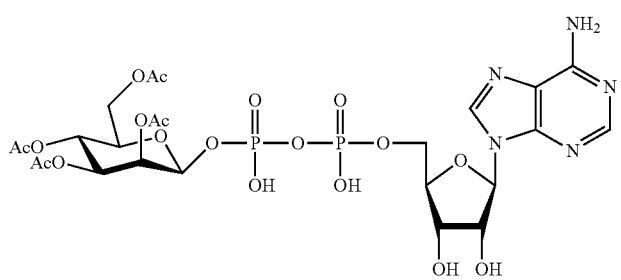

The mixture of product of Step 4 above (56.44 mg, 135.57 µmol) and compound AMP-morpholidate (4'-morpholine-N'N'-dicyclohexylcarboxamidinium salt) (50 mg, 70.4 µmol) was dried with dry pyridine (5 mL×3). Then the mixture was dissolved with pyridine (1 mL), 1H-tetrazole (16.66 mg, 237.84 µmol) was added and stirred at 25° C. for 16 h. The solvent was removed to give a residue, which was purified by Pre-HPLC (Column: Waters Xbridge 150*25 5 u, Mobile phase: water (10 mM NH$_4$HCO$_3$)—CAN, B %: 5% to 25%. Gradient Time (min): 7, 100% B Hold Time (min): 0.5. FlowRate (mL/min): 25) to give the desired compound (5.5 mg, yield: 2.7%) as a white solid. MS (ESI) m/z (M+H)$^+$: 758.2. $^1$H NMR (400 MHz, D$_2$O) δ 8.43 (s, 1H), 8.16 (s, 1H), 6.05 (d, J=5.8 Hz, 1H), 5.43 (d, J=2.5 Hz, 1H), 5.37 (d, J=9.5 Hz, 1H), 5.06-4.96 (m, 2H), 4.64-4.58 (m, 2H), 4.42-4.37 (m, 1H), 4.31-4.25 (m, 1H), 4.19 (dd, J=3.1, 12.7 Hz, 1H), 4.14-4.07 (m, 2H), 3.94 (dd, J=2.0, 12.5 Hz, 1H), 3.58 (br d, J=9.0 Hz, 1H), 2.10 (s, 3H), 1.96 (d, J=10.3 Hz, 6H), 1.88 (s, 3H).

Compound 6

Adenosine 5'-β-D-manno-heptopyranosyl)diphosphate

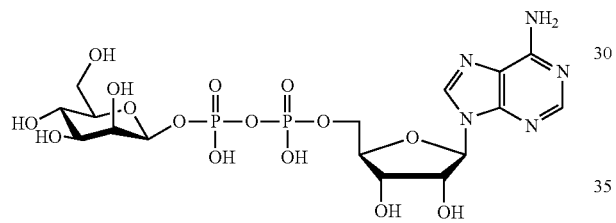

Step 1. Preparation of Adenosine 5'-β-D-manno-heptopyranosyl)diphosphate

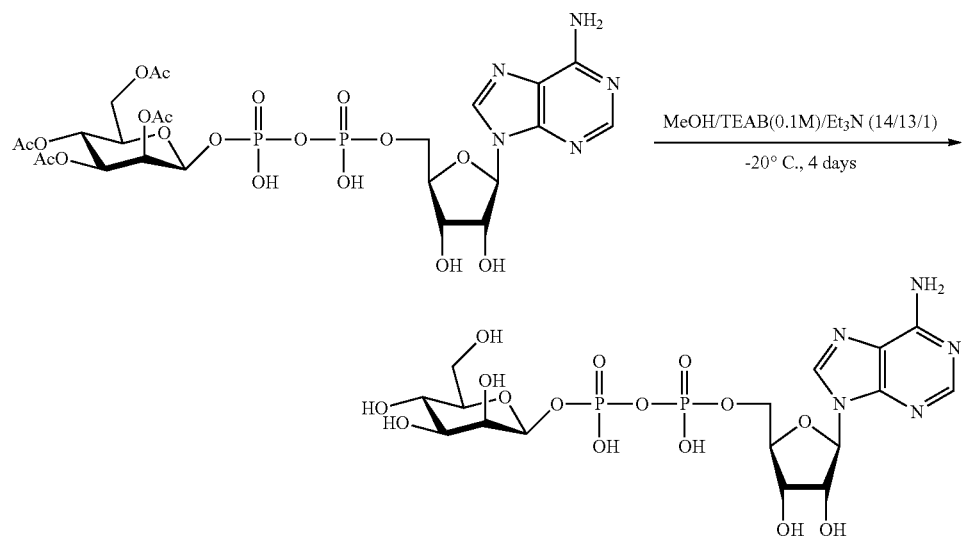

The compound of the product of Step 5 in the preparation of Compound 5 above (2.5 mg, 3.30 µmol) was dissolved in 0.3 mL solution (which consisted of TEAB (0.1 M)/MeOH/ TEA (13/14/1) and stirred at −20° C. for 4 days. The reaction was lyophilized to give the desired compound (0.9 mg, yield: 17.5%, as Et$_3$N salt) as a white solid. MS (ESI) m/z (M−H)$^-$: 587.8.

Compound 7

(3S,4S,5S,6R)-3,4,5-trihydroxy-6-(hydroxymethyl) tetrahydro-2H-pyran-2-yl hydrogen (((((2R,3S,4R, 5R)-5-(6-amino-9H-purin-9-yl)-3,4-dihydroxytetra-hydrofuran-2-yl)methoxy)(hydroxy)phosphoryl) methyl)phosphonate

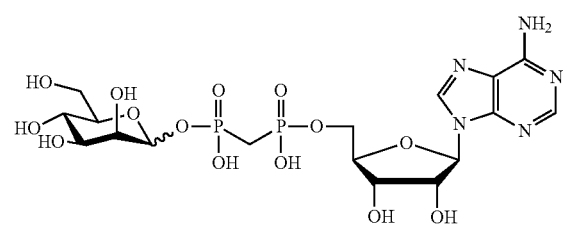

Step 1. Preparation of tetrabenzyl methylenebis(phosphonate)

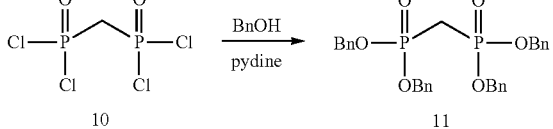

A mixture of dry phenylmethanol (6.2 g, 57.3 mmol, 6.0 mL) and dry pyridine (4.2 g, 52.5 mmol, 4.2 mL) was added over 30 min by syringe pump to a suspension of methylen-ebis(phosphonic dichloride) (3.45 g, 13.8 mmol) in dry toluene (10 mL) at 0° C. After the addition was complete, the reaction was allowed to reach 20° C. and stirred for a further 3 h. After completion of the reaction, the solids were removed by filtration and washed twice with toluene (2×20 mL). The filtrate was washed twice with 2 M NaOH (2×15 mL) and water (15 mL), dried over $Na_2SO_4$, filtered and concentrated under reduced pressure to give a crude product, which was purified by silica gel column (PE:EA=1:0 to 1:1) to give the desired compound (3 g, yield: 40.5%, 99.9% purity) as colorless oil. $^1$H NMR (400 MHz, $CDCl_3$) δ 7.31 (s, 20H), 4.96-5.09 (m, 8H), 2.44-2.59 (m, 2H).

Step 2. Preparation of benzyl hydrogen ((bis(benzyloxy)phosphoryl)methyl)phosphonate

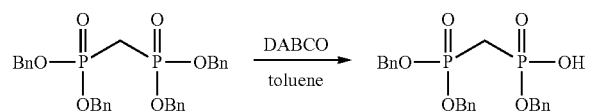 [SMILES: O=P(CP(=O)(OCc1ccccc1)OCc1ccccc1)(OCc1ccccc1)OCc1ccccc1 ; "DABCO" ; O=P(O)(CP(=O)(OCc1ccccc1)OCc1ccccc1)OCc1ccccc1]

DABCO (627 mg, 5.59 mmol, 615 μL) was added to a solution of tetrabenzyl methylenebis(phosphonate) (product of Step 1 above) (3 g, 5.59 mmol) in toluene (50 mL). The resulting mixture was stirred at 110° C. for 3 h. The volatile was removed under vacuum and the residue was treated dropwise with aqueous HCl (37%, 1.2 mL). The mixture was extracted with EtOAc (20 mL) and the organic layer was dried over $Na_2SO_4$ and evaporated under reduced pressure to give the desired compound (2.2 g, crude) as a yellow oil. The product was used directly in next step. $^1$H NMR (400 MHz, $CDCl_3$) δ 7.27-7.36 (m, 15H), 4.99-5.10 (m, 6H), 2.51-2.64 (m, 2H)

Step 3. Preparation of (2R,3R,4S,5S)-2-(acetoxymethyl)-6-(((benzyloxy)(bis(benzyloxy)phosphoryl)methyl)phosphoryl)oxy)tetrahydro-2H-pyran-3,4,5-triyl triacetate

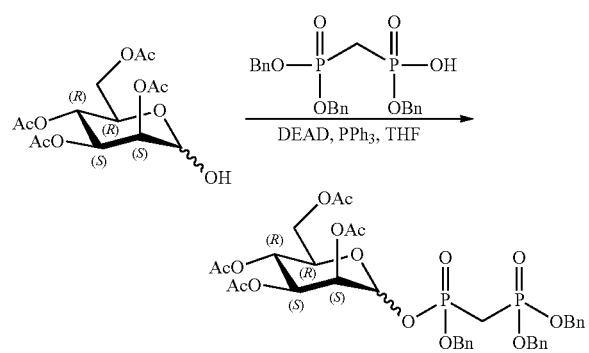

PPh3 (360.0 mg, 1.4 mmol) and DEAD (239.5 mg, 1.4 mmol, 250 μL) were added sequentially to a solution of the product of Step 2 above (200 mg, 448.1 μmol) and (2R,3R,4S,5S)-2-(acetoxymethyl)-6-hydroxytetrahydro-2H-pyran-3,4,5-triyl triacetate (225 mg, 574.9 μmol) in THF (5 mL). The resulting mixture was stirred at 40° C. for 2 h. After completion of the reaction, the mixture was concentrated under reduced pressure to give the crude product, which was purified by pre-HPLC (column: Boston Green ODS 150*30 5 u; mobile phase: [water (0.075% TFA)-ACN]; B %: 55%-75%, 9 min) to give the desired compound (130 mg, yield: 36.6%, 98.0% purity) as a white solid. MS (ESI) m/z (M+Na)$^+$: 799.1. $^1$H NMR (400 MHz, $CDCl_3$) δ 7.20-7.33 (m, 15H), 4.86-5.76 (m, 10H), 3.50-4.29 (m, 3H), 2.40-2.62 (m, 2H), 1.88-2.09 (m, 12H)

Step 4. Preparation of (2R,3R,4S,5S)-2-(acetoxymethyl)-6-(((benzyloxy)(((benzyloxy)(hydroxy)phosphoryl)methyl)phosphoryl)oxy)tetrahydro-2H-pyran-3,4,5-triyl triacetate

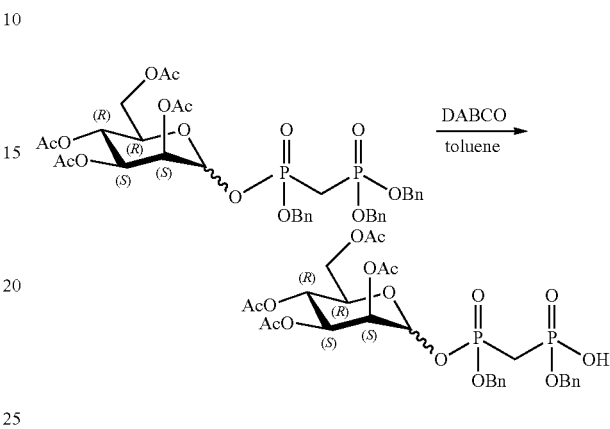

DABCO (40.0 mg, 356.6 μmol, 39.2 μL) was added to a solution of product of Step 3 above (250 mg, 321.9 μmol) in toluene (6 mL). The resulting mixture was stirred at 120° C. for 2 h. After completion of the reaction, the solvent was removed under vacuum and the residue was dissolved in EtOAc (20 mL) and washed with 1N aqueous HCl (10 mL). The aqueous phase was extracted with EtOAc (20 mL) and the combined organic layer were dried over $Na_2SO_4$, filtered, and evaporated under reduced pressure to give desired compound (220 mg, crude) as yellow syrup. The product was used directly in next step. MS (ESI) m/z (M+H)$^+$: 686.9

Step 5. Preparation of (2R,3R,4S,5R)-2-(6-(tritylamino)-9H-purin-9-yl)-5-((trityloxy)methyl)tetrahydrofuran-3,4-diol

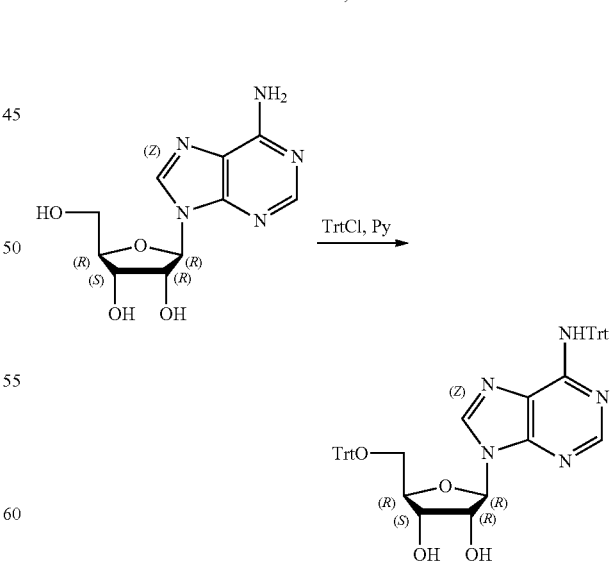

To a solution of adenine in pyridine (100 mL) was added TrtCl (38.5 g, 138.0 mmol) and DMAP (5.9 g, 48.6 mmol). The mixture was stirred at 80° C. for 20 h. The reaction mixture was concentrated to give a residue. The residue was purified by flash silica gel chromatography (PE:EA=1:0 to 0:1, EA:MeOH=1:0 to 20:1) to give the desired compound (25.9 g, yield: 53.5%) as a white solid. MS (ESI) m/z (M+H)⁻: 752.3. ¹H NMR (400 MHz, CDCl₃) δ 8.08 (s, 1H), 8.00 (s, 1H), 7.44-7.03 (m, 30H), 6.67 (br s, 1H), 5.89 (d, J=6.4 Hz, 1H), 4.78 (br t, J=5.7 Hz, 1H), 4.44 (br s, 1H), 4.30 (br d, J=4.4 Hz, 1H), 3.49 (dd, J=3.4, 10.5 Hz, 1H), 3.18 (dd, J=2.9, 10.8 Hz, 1H).

Step 6. Preparation of (2R,3R,4R,5R)-2-(6-(tritylamino)-9H-purin-9-yl)-5-((trityloxy)methyl)tetrahydrofuran-3,4-diyl diacetate

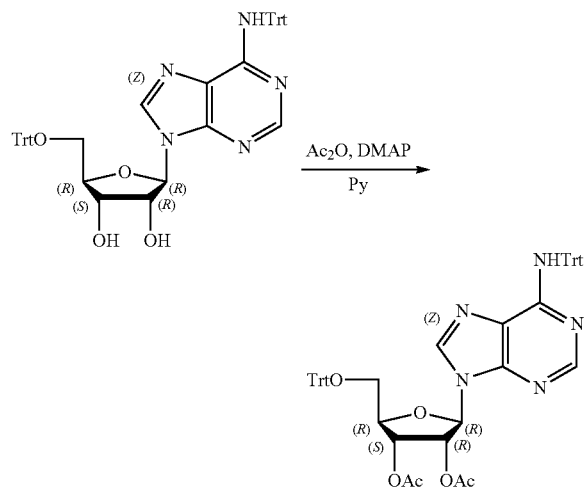

Ac₂O (545.0 mg, 5.34 mmol, 500 µL) and DMAP (52 mg, 425.6 µmol) were added to a solution of product of Step 5 above (1.6 g, 2.13 mmol) in pyridine (5 mL). The resulting mixture was stirred at 15-20° C. for 24 h. After completion of the reaction, the reaction was quenched by adding MeOH (2 mL); the mixture was concentrated under reduced pressure. The residue was dissolved in ethyl acetate (30 mL) and washed with aqueous 1N HCl (20 mL). The organic phase was dried over Na₂SO₄, filtered, and concentrated under reduced pressure to give crude product, which was purified by silica gel column (PE:EA=1:0 to 1:1) to afford the desired compound (1.43 g, yield: 77.0% yield, 95.8% purity) as a white foam. MS (ESI) m/z (M+H)⁺: 836.4. ¹H NMR (400 MHz, DMSO-d6) δ 8.39 (s, 1H), 7.76 (s, 1H), 7.61 (s, 1H), 7.21-7.35 (m, 30H), 6.22 (d, J=5.4 Hz, 1H), 6.12-6.17 (m, 1H), 5.68 (t, J=5.4 Hz, 1H), 4.26 (q, J=4.4 Hz, 1H), 3.28 (d, J=4.2 Hz, 2H), 2.06 (s, 3H), 2.03 (s, 3H).

Step 7. Preparation of (2R,3R,4R,5R)-2-(hydroxymethyl)-5-(6-(tritylamino)-9H-purin-9-yl)tetrahydrofuran-3,4-diyl diacetate

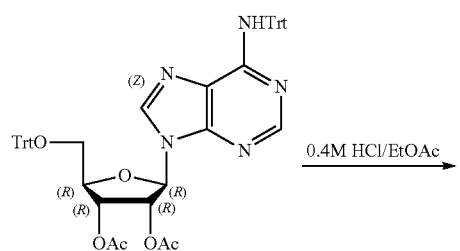

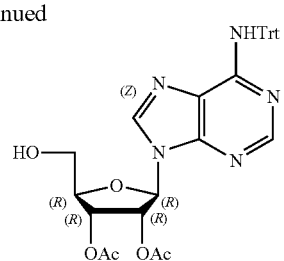

To a solution of product of Step 6 above (1.9 g, 2.3 mmol) in EtOAc (76.5 mL) was added HCl/EtOAc (4 M, 8.50 mL) and the reaction mixture was stirred at 15° C. for 2 h. After completion of the reaction, the pH was adjusted to 7 with Et₃N and the reaction mixture was concentrated under reduced pressure. The residue was dissolved in CH₂Cl₂ (10 mL) and washed with saturated NaHCO₃ (5 mL) and brine (5 mL). The organic layer was dried over Na₂SO₄, filtered, and concentrated under reduced pressure to give crude product, which was purified by silica gel chromatography (PE:EA=1:0 to 1:1) to afford the desired compound (735 mg, yield: 49.6%, 91% purity) as a white solid. MS (ESI) m/z (M+H)⁺: 594.1. ¹H NMR (400 MHz, DMSO-d6): δ 8.50 (s, 1H), 7.93 (s, 1H), 7.66 (s, 1H), 7.39-7.16 (m, 9H), 6.21 (d, J=6.8 Hz, 1H), 6.02-5.88 (m, 1H), 5.65-5.34 (m, 2H), 4.26-4.12 (m, 1H), 3.76-3.50 (m, 2H), 2.12 (s, 3H), 1.99 (s, 3H).

Step 8. Preparation of 2R,3R,4S,5S)-2-(acetoxymethyl)-6-(((benzyloxy)(((benzyloxy)(((2R,3R,4R,5R)-3,4-diacetoxy-5-(6-(tritylamino)-9H-purin-9-yl)tetrahydrofuran-2-yl)methoxy)phosphoryl)methyl)phosphoryl)oxy)tetrahydro-2H-pyran-3,4,5-triyl triacetate

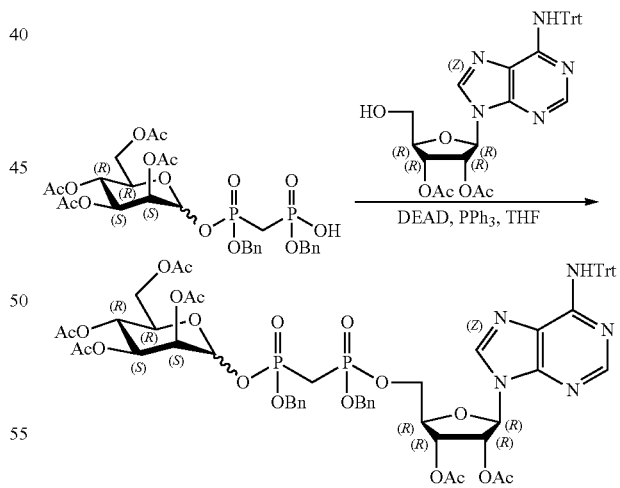

PPh₃ (221.7 mg, 845.1 µmol) and DEAD (145.6 mg, 836.1 µmol, 152.0 uL) were added sequentially to a solution of product of Step 4 above (190 mg, 276.7 mol) and product of Step 7 above (171.0 mg, 288.1 mol) in THF (3 mL). The resulting mixture was stirred at 40° C. for 2 h. After completion of the reaction, the mixture was concentrated under reduced pressure to give the crude product, which was purified pre-HPLC (column: Boston Green ODS 150*30 5 u; mobile phase: [water (0.075% TFA)-ACN]; B %: 70%-

80%, 9 min) to give the desired compound (120 mg, yield: 28.2% yield, 82.0% purity) as a white solid. MS (ESI) m/z (M+H)⁺: 1262.3.

Step 9. Preparation of (2R,3R,4S,5S)-2-(acetoxymethyl)-6-(((benzyloxy)(((benzyloxy)(((2R,3R,4R,5R)-3,4-diacetoxy-5-(6-amino-9H-purin-9-yl)tetrahydrofuran-2-yl)methoxy)phosphoryl)methyl) phosphoryl)oxy)tetrahydro-2H-pyran-3,4,5-triyl triacetate

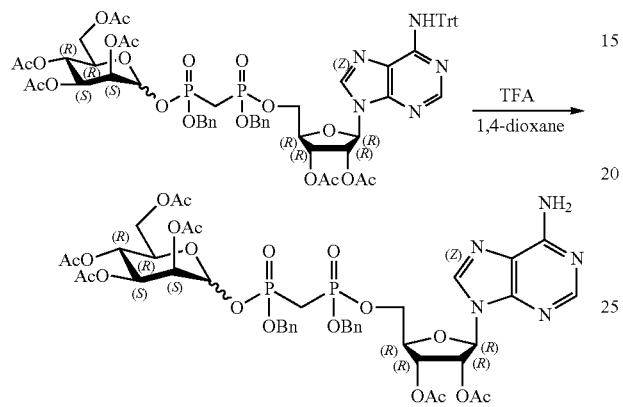

TFA (616.0 mg, 5.4 mmol, 400.0 μL was added to a solution of product of Step 8 above (120 mg, 95.1 μmol) in 1,4-dioxane (1.6 mL). The mixture was stirred at 25° C. for 3 h. After completion of the reaction, the mixture was diluted with EA (30 mL), and washed with saturated NaHCO₃ (20 mL×2), the organic phase was dried over Na₂SO₄, filtered, and concentrated under reduced pressure to afford the desired compound (110 mg, crude) as a yellow syrup, which was used directly in next step. MS (ESI) m/z (M+H)⁺: 1020.5

Step 10. Preparation of benzyl ((3S,4S,5S,6R)-3,4,5-trihydroxy-6-(hydroxymethyl)tetrahydro-2H-pyran-2-yl) (((((2R,3S,4R,5R)-5-(6-amino-9H-purin-9-yl)-3,4-dihydroxytetrahydrofuran-2-yl)methoxy)(benzyloxy)phosphoryl)methyl) phosphonate

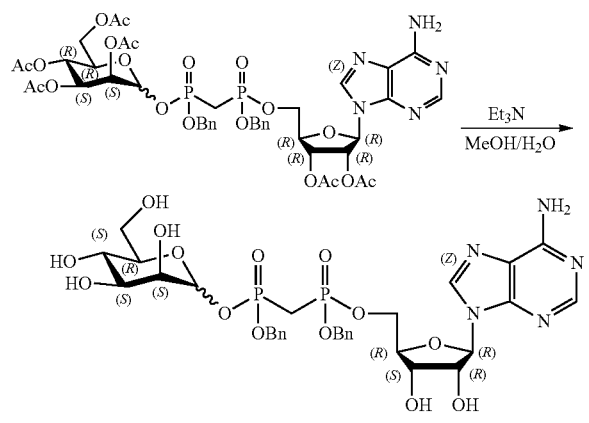

A solution of the product of Step 9 above (30 mg, 29.4 μmol) in MeOH (1.4 mL), Et₃N (0.6 mL) and H₂O (0.2 mL) was stirred at 25° C. for 1 h. After completion of the reaction, the reaction was concentrated under reduced pressure to give crude product, which was purified by pre-HPLC (column: Boston Green ODS 150*30 5 u; mobile phase: [water (0.075% TFA)-ACN]; B %: 24%-44%, 9 min) to afford the desired compound (8 mg, yield: 35.4% yield, 99.9% purity) as a white solid. MS (ESI) m/z (M-H)⁻: 517.1/604.2. ¹H NMR (400 MHz, METHANOL-d₄) δ 8.71 (br s, 1H), 8.24 (br s, 1H), 7.27-7.32 (m, 10H), 6.04 (d, J=4.4 Hz, 1H), 5.26-5.31 (m, 1H), 4.99-5.16 (m, 6H), 4.91-4.92 (m, 1H), 4.49-4.64 (m, 1H), 4.37-4.44 (m, 1H), 4.26-4.36 (m, 1H), 4.16-4.26 (m, 2H), 3.60-3.94 (m, 3H), 2.56-2.76 (m, 2H).

Step 11. Preparation of (3S,4S,5S,6R)-3,4,5-trihydroxy-6-(hydroxymethyl)tetrahydro-2H-pyran-2-yl hydrogen (((((2R,3S,4R,5R)-5-(6-amino-9H-purin-9-yl)-3,4-dihydroxytetrahydrofuran-2-yl)methoxy) (hydroxy)phosphoryl)methyl)phosphonate

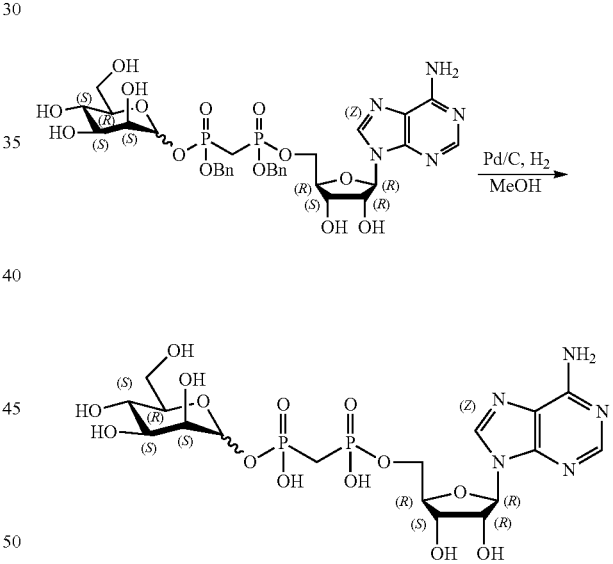

To a solution of benzyl product of Step 10 above (6 mg, 7.8 μmol) in MeOH (2 mL) was added dry Pd/C (10 mg, 10% purity) under N₂. The suspension was degassed under vacuum and purged with H₂ several times. The mixture was stirred under H₂ (15 psi) at 25° C. for 2 h. After completion of the reaction, the mixture was filtered, and the filtrate was concentrated under reduced pressure to give the desired compound (4 mg) as a white solid. MS (ESI) m/z (M-H)⁻: 337.0120/424.0460; MS (ESI) m/z (M+H)⁻: 426.0591. ¹H NMR (400 MHz, D₂O) δ 8.38 (s, 1H), 8.09 (s, 1H), 5.97 (d, J=5.87 Hz, 1H), 5.14 (d, J=1.00 Hz, 1H), 4.79-4.91 (m, 1H), 4.38-4.44 (m, 1H), 4.17-4.28 (m, 2H), 3.97-4.05 (m, 2H), 3.60-3.74 (m, 5H), 1.99-2.04 (m, 2H).

Compound 8

(3S,4S,5S,6R)-6-((R)-1,2-dihydroxyethyl)-3,4,5-trihydroxytetrahydro-2H-pyran-2-yl hydrogen (((((2R,3S,4R,5R)-5-(6-amino-9H-purin-9-yl)-3,4-dihydroxytetrahydrofuran-2-yl)methoxy)(hydroxy)phosphoryl)methyl)phosphonate

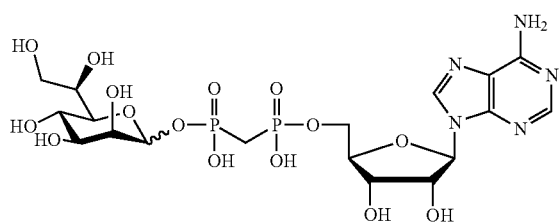

Step 1. Preparation of (3S,4S,5R,6R)-2-(((benzyloxy)((bis(benzyloxy)phosphoryl)methyl)phosphoryl)oxy)-6-((R)-1,2-diacetoxyethyl)tetrahydro-2H-pyran-3,4,5-triyl triacetate

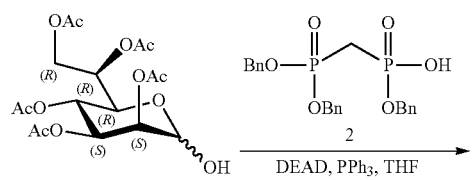

PPh$_3$ (540.0 mg, 2.1 mmol) and DEAD (367.9 mg, 2.1 mmol, 384.0 µL) were added sequentially to a solution of the product of Step 2 in the preparation of Compound 7 above (300 mg, 672.1 µmol) and (2R,3R,4S,5S)-2-((R)-1,2-diacetoxyethyl)-6-hydroxytetrahydro-2H-pyran-3,4,5-triyl triacetate (300.0 mg, 713.7 µmol) in THF (10 mL). The resulting mixture was stirred at 40° C. for 2 h. After completion of the reaction, the mixture was concentrated under reduced pressure to give the crude product, which was purified by pre-HPLC (column: Boston Green ODS 150*30 5 u; mobile phase: [water (0.075% TFA)-ACN]; B %: 58%-74%, 8 min) to afford the desired compound (188 mg, yield: 28.6% yield, 87.0% purity) as a white solid. MS (ESI) m/z (M+Na)$^+$: 871.5

Step 2. Preparation of (3S,4S,5R,6R)-2-(((benzyloxy)(((benzyloxy)(hydroxy)phosphoryl)methyl)phosphoryl)oxy)-6-((R)-1,2-diacetoxyethyl)tetrahydro-2H-pyran-3,4,5-triyl triacetate

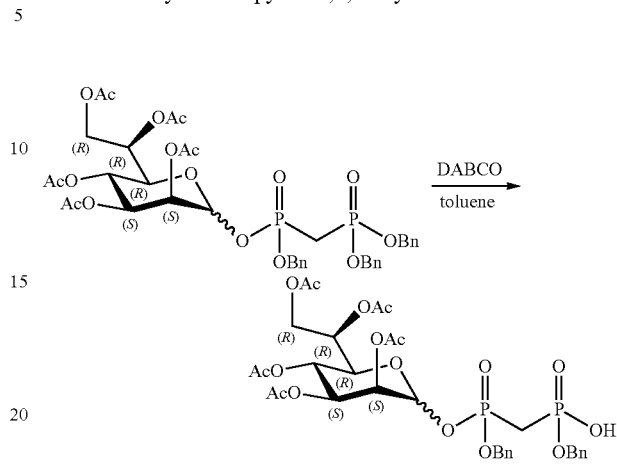

DABCO (36.4 mg, 324.0 µmol) was added to a solution of the product of Step 1 above (250 mg, 294.6 mol) in toluene (6 mL). The resulting mixture was stirred at 120° C. for 2 h. After completion of the reaction, the solvent was removed under vacuum and the residue was dissolved in EtOAc (20 mL) and washed with 1N aqueous HCl (10 mL). The aqueous phase was extracted with EtOAc (20 mL) and the combined organic layer were dried over Na$_2$SO$_4$, filtered, and evaporated under reduced pressure to give the desired compound (220 mg, crude) as yellow syrup. The crude product was used directly in next step. MS (ESI) m/z (M+H)$^+$: 759.5

Step 3. Preparation of 3S,4S,5R,6R)-2-(((benzyloxy)(((benzyloxy)(((2R,3R,4R,5R)-3,4-diacetoxy-5-(6-(tritylamino)-9H-purin-9-yl)tetrahydrofuran-2-yl)methoxy)phosphoryl)methyl)phosphoryl)oxy)-6-((R)-1,2-diacetoxyethyl)tetrahydro-2H-pyran-3,4,5-triyl triacetate

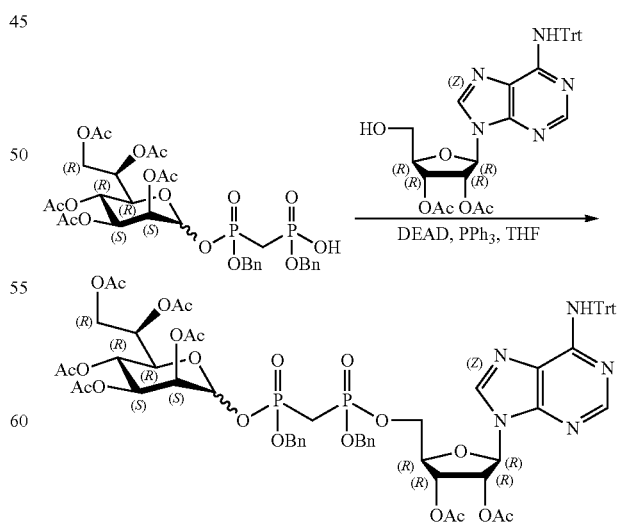

PPh$_3$ (210.0 mg, 800.6 µmol) and DEAD (143.7 mg, 825.1 µmol, 150.0 µL) were added sequentially to a solution of the product of Step 7 in the preparation of Compound 7 above (172.2 mg, 290.0 µmol) and the product of Step 2 above (200 mg, 263.6 µmol) in THF (5 mL). The resulting mixture was stirred at 40° C. for 2 h. After completion of the reaction, the mixture was concentrated under reduced pressure to give crude product, which was purified by pre-HPLC (column: Boston Green ODS 150*30 5 u; mobile phase: [water (0.075% TFA)-ACN]; B %: 71%-85%, 9 min) to afford the desired compound (117 mg, yield: 29.9%, 90.0% purity) as a white solid. MS (ESI) m/z (M+H)⁺: 1334.3

Step 4. Preparation of (3S,4S,5R,6R)-2-(((benzyloxy)(((benzyloxy)(((2R,3R,4R,5R)-3,4-diacetoxy-5-(6-amino-9H-purin-9-yl)tetrahydrofuran-2-yl)methoxy)phosphoryl)methyl)phosphoryl)oxy)-6-((R)-1,2-diacetoxyethyl)tetrahydro-2H-pyran-3,4,5-triyl triacetate

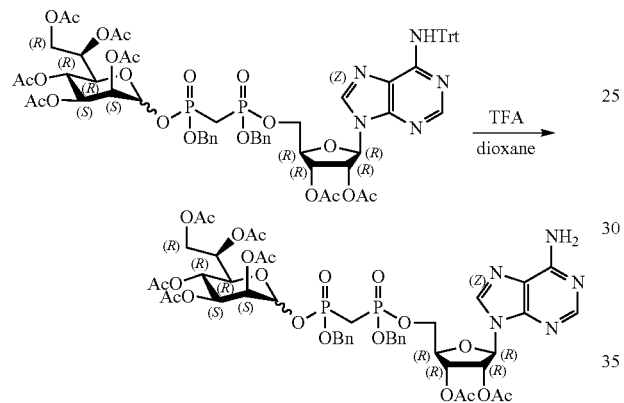

TFA (1.23 g, 10.8 mmol, 800 µL) was added to a solution of the product of Step 3 above (113 mg, 84.7 mol) in dioxane (1.2 mL). The mixture was stirred at 40° C. for 1.5 h. After completion of the reaction, the mixture was diluted with EA (30 mL), and washed with saturated NaHCO₃ (20 mL×2), the organic phase was dried over Na₂SO₄, filtered, and concentrated under reduced pressure to afford the desired compound (110 mg, crude) as a white solid. The crude product was used directly in next step. MS (ESI) m/z (M+H)⁺: 1092.2

Step 5. Preparation of benzyl ((3S,4S,5S,6R)-6-((R)-1,2-dihydroxyethyl)-3,4,5-trihydroxytetrahydro-2H-pyran-2-yl) (((((2R,3S,4R,5R)-5-(6-amino-9H-purin-9-yl)-3,4-dihydroxytetrahydrofuran-2-yl)methoxy)(benzyloxy)phosphoryl)methyl)phosphonate

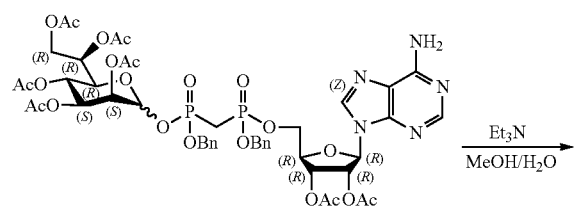

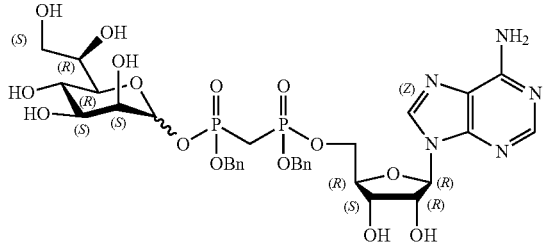

A solution of the product of Step 4 above (105 mg, 96.2 µmol) in MeOH (3.5 mL), Et₃N (0.5 mL) and H₂O (0.5 mL) was stirred at 25° C. for 1 h. After completion of the reaction, the mixture was concentrated under reduced pressure to give crude product, which was purified by pre-HPLC (column: Boston Green ODS 150*30 5 u; mobile phase: [water (0.075% TFA)-ACN]; B %: 30%-50%, 7.5 min) to afford the desired compound (16 mg, 20.0 µmol, yield: 20.7%, 99.4% purity) as a white solid. MS (ESI) m/z (M−H)⁻: 547.1/604.1

Step 6. Preparation of (3S,4S,5S,6R)-6-((R)-1,2-dihydroxyethyl)-3,4,5-trihydroxytetrahydro-2H-pyran-2-yl hydrogen (((((2R,3S,4R,5R)-5-(6-amino-9H-purin-9-yl)-3,4-dihydroxytetrahydrofuran-2-yl)methoxy)(hydroxy)phosphoryl)methyl)phosphonate

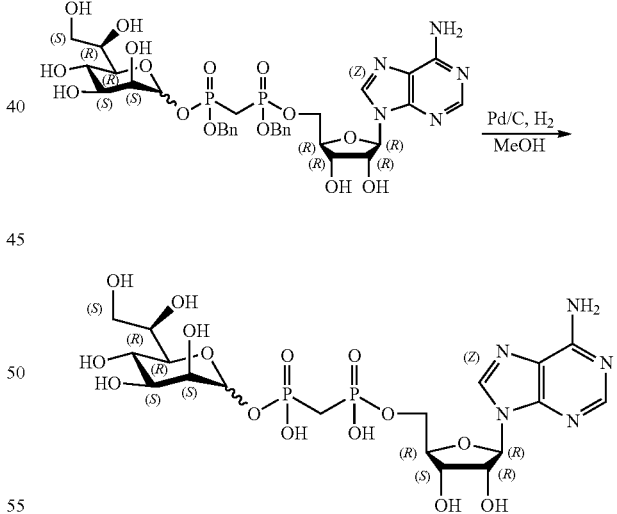

To a solution of of the product of Step 5 above (14 mg, 17.6 µmol) in MeOH (2.5 mL) was added dry Pd/C (20 mg, 10% purity) under N₂. The suspension was degassed under vacuum and purged with H₂ several times. The mixture was stirred under H₂ (15 psi) at 25° C. for 2 h. After completion of the reaction, the mixture was filtered, and the filtrate was concentrated under reduced pressure to give the desired compound (10 mg, 16.2 µmol) as a white solid. MS (ESI) m/z (M−H)⁻: 366.4/423.8

Compound 9

2-(((((((2R,3R,4R,5R)-5-(6-amino-9H-purin-9-yl)-4-fluoro-3-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

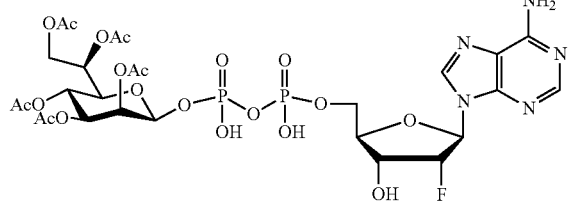

Step 1. Preparation of (2R,3R,4R,5R)-5-(6-acetamido-9H-purin-9-yl)-2-(((tert-butyldiphenylsilyl)oxy)methyl)-4-fluorotetrahydrofuran-3-yl acetate

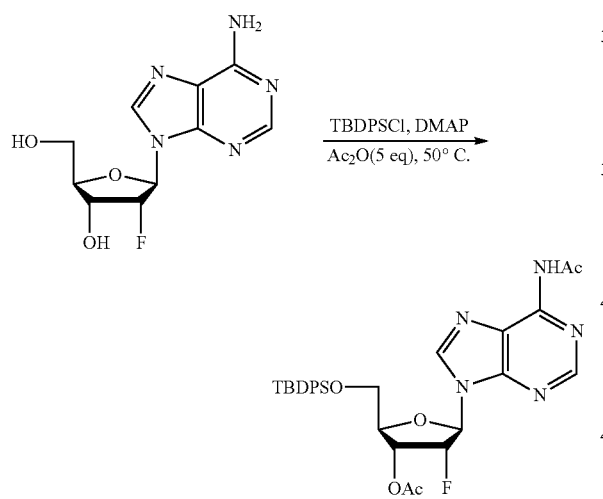

To a stirred solution of (2R,3R,4R,5R(2R,3R,4R,5R)-5-(6-amino-9H-purin-9-yl)-4-fluoro-2-(hydroxymethyl)tetrahydrofuran-3-ol)-5-(6-amino-9H-purin-9-yl)-4-fluoro-2-(hydroxymethyl)tetrahydrofuran-3-ol (389 mg, 1.44 mmol) in pyridine (3 mL) was added DMAP (18 mg, 0.14 mmol) at rt. The solution was heated to 50° C. At this temperature TBDPSCl (594 mg, 2.16 mmol) was added and the reaction was stirred at this temperature overnight. LC-MS showed no SM left. The solution was added Ac₂O (642 µL, 6.85 mmol) dropwise. After stirring for 5 h at this temperature, LC-MS showed the desired compound was formed. The reaction was partitioned between DCM and water. The combined extract was washed with H₂O and brine, and dried over Na₂SO₄. The filtrate was concentrated under reduced pressure to give the desired compound as a white foam (531 mg, 0.90 mmol). MS (ESI) m/z (M+H)⁺: 592.

Step 2. Preparation of (2R,3S,4S,5R)-5-(6-acetamido-9H-purin-9-yl)-4-fluoro-2-(hydroxymethyl)tetrahydrofuran-3-yl acetate

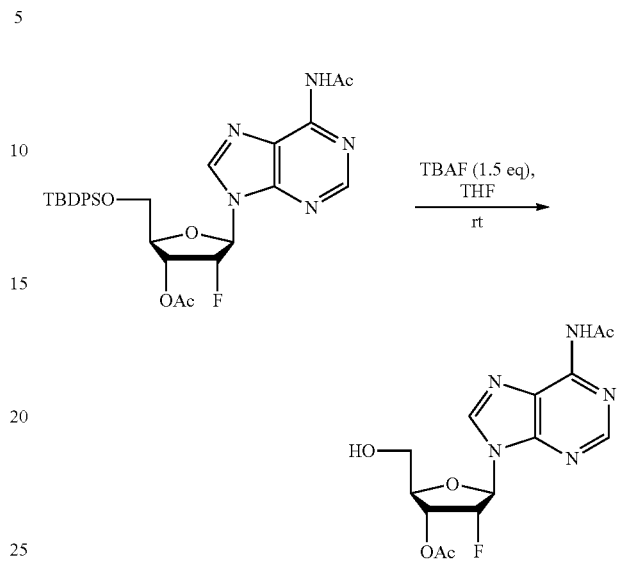

To a stirred solution of compound of product of Step 1 above (531 mg, 0.90 mmol) in THF (4 mL) was added TBAF (1 M in THF, 1.4 mLl, 1.35 mmol) at room temperature. After stirring overnight, the reaction was quenched with saturated NH₄Cl. The reaction was partitioned between DCM and water. The combined extract was washed with brine and dried over Na₂SO₄. The filtrate was concentrated under reduced pressure to give an oily residue, which was purified by flash chromatography on silica gel eluting with DCM/MeOH (20:1) to give the desired compound as an white foam (96 mg, 0.27 mmol). MS (ESI) m/z (M+H)⁺: 354.

Step 3. Preparation of (2R,3R,4R,5R)-5-(6-acetamido-9H-purin-9-yl)-2-(((bis(benzyloxy)phosphoryl)oxy)methyl)-4-fluorotetrahydrofuran-3-yl acetate

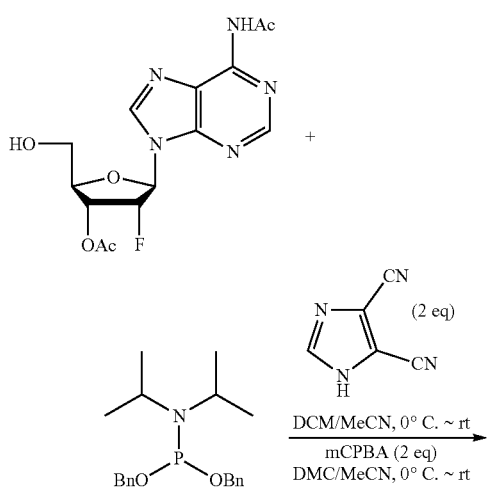

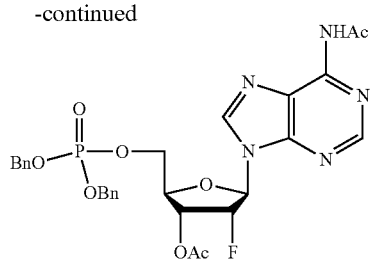

A 25 mL round flask was charged with compound of product from Step 2 above (96 mg, 0.27 mmol) and 1H-imidazole-4,5-dicarbonitrile (64 mg, 0.54 mmol) under nitrogen atmosphere. Dry DCM and MeCN were added (DCM:MeCN=5:1, v/v). The resultant solution was cooled in ice-water bath and dibenzyl diisopropylphosphoramidite (188 mg, 0.54 mmol) was added. After the reaction was warmed to RT, it was stirred for another 2 h. The reaction was cooled in ice-water bath again and mCPBA (110 mg, 0.54 mmol) was added directly. After it was warmed to RT, LC-MS indicated the formation of the desired compound as the major product. Sat. NaHCO₃ (aq) was added to quench the reaction and the organic phase was separated. The water phase was extracted with DCM twice. The combined extract was washed with H₂O and brine, and dried over Na₂SO₄. The filtrate was concentrated under reduced pressure to give an oil, which was purified on Silica gel flash chromatography to give the desired the desired compound (126 mg, 0.21 mmol). MS (ESI) m/z (M+H)⁺: 612.

Step 4. Preparation of (2R,3S,4S,5R)-5-(6-acetamido-9H-purin-9-yl)-4-fluoro-2-((phosphonooxy) methyl)tetrahydrofuran-3-yl acetate

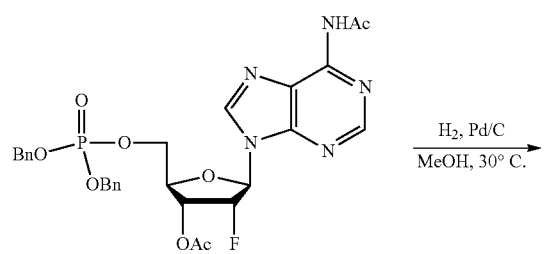

A mixture of compound of product of Step 3 above (126 mg, 0.21 mmol) and Pd/C (132 mg) in MeOH (4 mL) was stirred at room temperature under H₂. After stirring overnight, the mixture was filtrated through an Advantec PTFE membrane filter with a pore size of 0.45 μm with MeOH. The filtrate was concentrated under reduced pressure to get the desired compound (90 mg, 0.21 mmol). MS (ESI) m/z (M+H)⁺: 434.

Step 5. Preparation of morphine DCC salt ((2R,3R, 4R,5R)-5-(6-amino-9H-purin-9-yl)-4-fluoro-3-hydroxytetrahydrofuran-2-yl)methyl hydrogen morpholinophosphonate

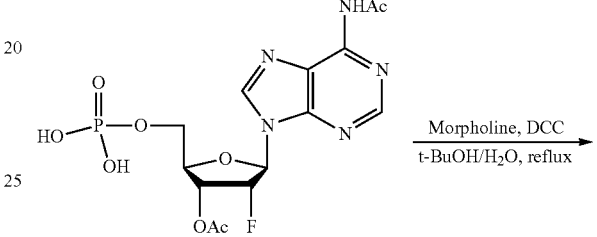

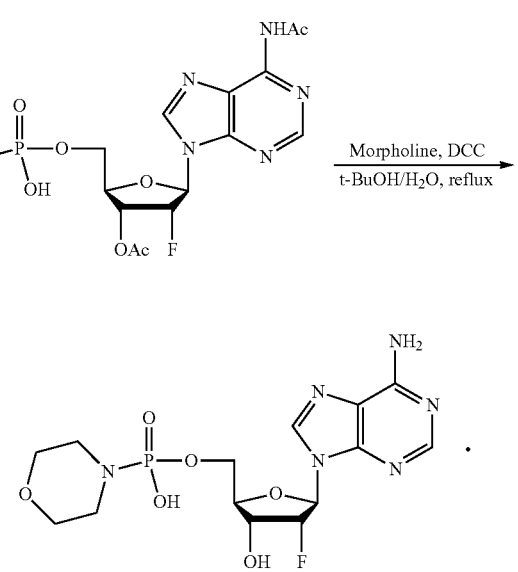

A solution of DCC (173 mg, 0.84 mmol) in t-butyl alcohol (5 mL) was added dropwise to a refluxing solution of the compound of product of Step 4 above (90 mg, 0.21 mmol) in a mixture of t-BuOH/H₂O (1:1) (10 mL), and purified morpholine (113 mg, 1.30 mmol). The addition was completed in 3 h, and the mixture was refluxed overnight until TLC showed completion of the reaction. The mixture was cooled to rt. The filtrate was evaporated until t-BuOH was largely removed, and the remaining aqueous phase was extracted three times with ether. The clear aqueous solution was then evaporated to dryness with freeze drying to give the desired compound as DCC salt (133 mg, 90% yield). MS (ESI) m/z (M+H)⁺: 419.

Step 6. Preparation of (2S,3S,4S,5R,6R)-2-((((((2R,3R,4R,5R)-5-(6-amino-9H-purin-9-yl)-4-fluoro-3-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

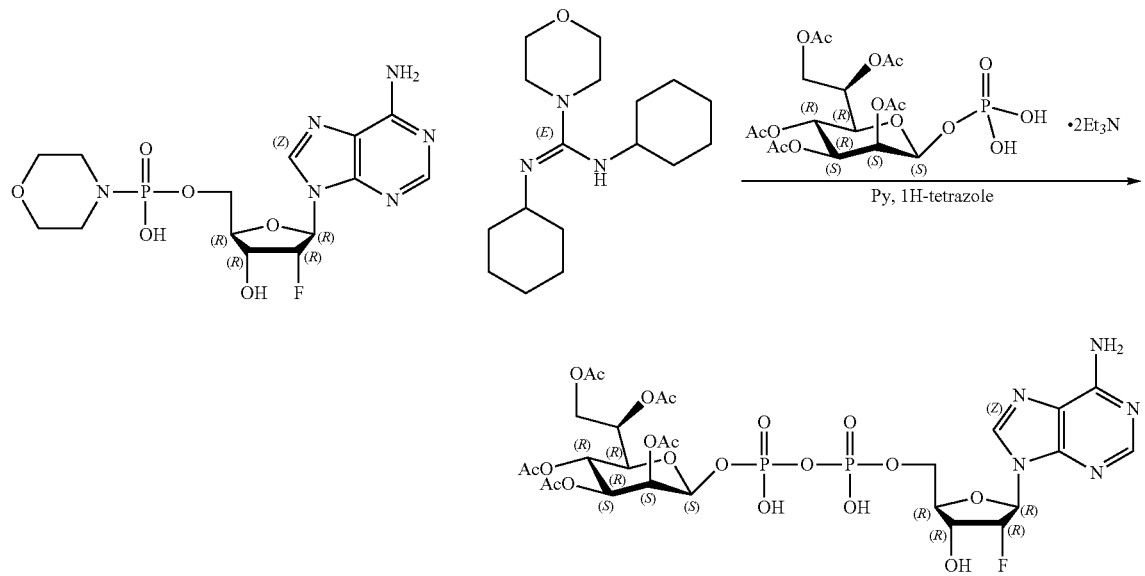

The mixture of compound of product of Step 5 above (152 mg, 213 umol) and compound of product of Step 14 in the preparation of Compound 1 above (100 mg, 142 μmol) was subjected to azeotropic dehydration with anhydrous pyridine (3 mL×3). Then the solvent was dissolved in pyridine (2 mL), and 2H-tetrazole (49.84 mg, 711.52 μmol) was added. The reaction mixture was stirred at 25° C. for 3 days. The solvent was removed under reduced pressure. And the residue was purified by silica gel column chromatography (CHCl$_3$:MeOH:NH$_3$.H$_2$O=1:0:0:0 to 50:50:1) to give a crude product (200 mg), which was purified by Pre-HPLC (column: Waters Xbridge 150*25 5 u, water (10 mM NH$_4$HCO$_3$)-ACN, 0% to 30%) to afford the title compound (35 mg, 28.2% yield, 95.2% purity) as a light yellow solid. MS (ESI) m/z (M+H)$^+$: 832.2. $^1$H NMR (400 MHz, methanol-d4) δ 8.60 (s, 1H), 8.29 (s, 1H), 6.36-6.26 (m, 1H), 5.62-5.52 (m, 2H), 5.38-5.33 (m, 0.5H), 5.24-5.21 (m, 0.5H), 5.20-5.15 (m, 3H), 4.72-4.63 (m, 1H), 4.46-4.38 (m, 2H), 4.32-4.20 (m, 3H), 3.94-3.89 (m, 1H), 2.11 (s, 3H), 2.04 (s, 3H), 2.02 (s, 3H), 1.99 (s, 3H), 1.90 (s, 3H).

Compound 10

Adenosine-2'-fluoro-5'-(D-glycero-β-D-mannoheptopyranosyl) diphosphate

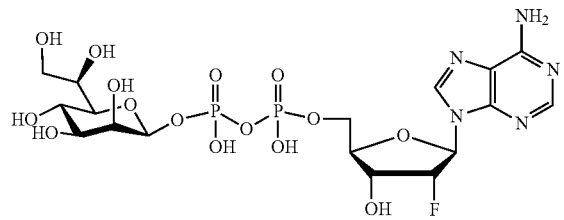

Step 1. Preparation of Adenosine-2'-fluoro-5'-(D-glycero-β-D-mannoheptopyranosyl) diphosphate

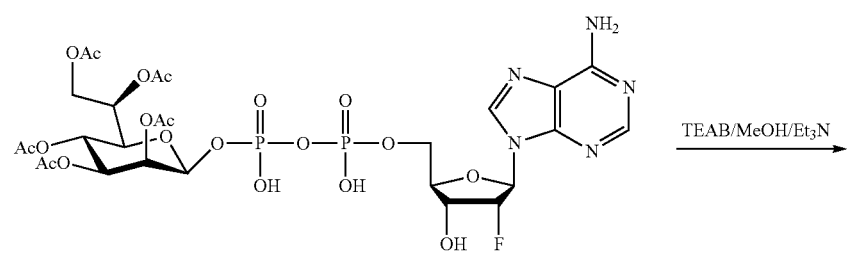

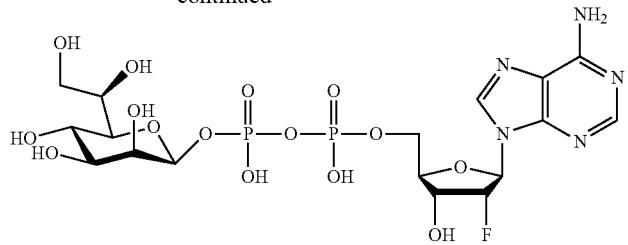

The compound of the product of Step 6 in the preparation of Compound 9 above (10 mg, 12.0 μmol) in 3 mL of solvent (consist of TEAB (0.1 M, 16.00 mL), MeOH (12 mL) and Et$_3$N (145 mg, 1.44 mmol, 200 μL) was stirred at −28° C. for 40 h. After completion of the reaction, the mixture was directly lyophilized on a freeze dryer to afford the desired compound (7 mg, yield: 38.5%, 54.5% purity, as 2 Et$_3$N salt) as a light yellow solid. MS (ESI) m/z (M–H)$^-$: 619.8. $^1$H NMR (400 MHz, D$_2$O) δ 8.28 (s, 1H), 8.10 (s, 1H), 6.30-6.24 (m, 1H), 5.36-5.30 (m, 1H), 5.23-5.17 (m, 1H), 5.06-5.00 (m, 1H), 4.56-4.51 (m, 3H), 4.47-4.42 (m, 1H), 4.2-4.18 (m, 2H), 4.14-4.04 (m, 3H), 3.85-3.80 (m, 1H).

Compound 11

(2S,3S,4S,5R,6R)-2-(((((((3aR,4R,6R,6aR)-6-(6-amino-9H-purin-9-yl)-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

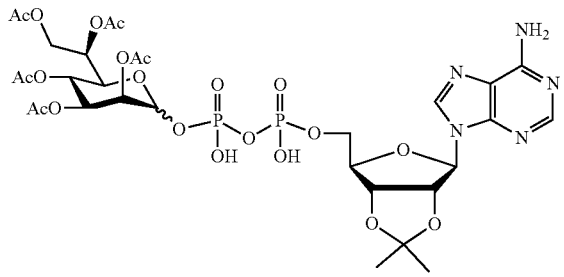

Step 1. Preparation of ((3aS,4R,6R,6aS)-6-(6-amino-9H-purin-9-yl)-2,2-dimethyltetrahydrofuro[3,4-d][1,3]dioxol-4-yl)methanol

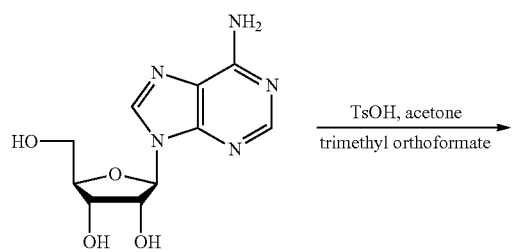

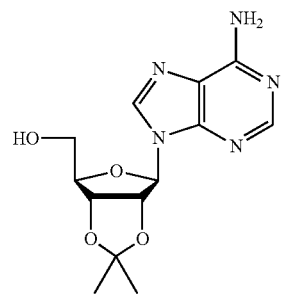

Adenosine (2.5 g, 9.36 mmol) was suspended in dried acetone (100 mL) containing p-toluenesulfonic acid monohydrate (8 g, 42.1 mmol). Trimethyl orthoformate (6.6 mL, 60.8 mmol) was then added over a period of 1 h at ambient temperature with vigorous stirring to give a clear solution and then a white solid formed after a while. The mixture was stirred overnight. The mixture was adjusted pH=8 with saturated aqueous potassium carbonate. The precipitate was filtered off, the filtrate was evaporated and the residue was extracted with EA. The combined organic phase was washed with saturated aqueous potassium carbonate and water, dried and concentrated. The crude was triturated (PE:EA=10:1) to afford the desired compound (2.6 g, 8.47 mmol). MS (ESI) m/z (M+H)$^+$: 308.

Step 2. Preparation of (Z)-N'-(9-((3aS,4R,6R,6aS)-6-(hydroxymethyl)-2,2-dimethyltetrahydrofuro[3,4-d][1,3]dioxol-4-yl)-9H-purin-6-yl)-N,N-dimethylformimidamide

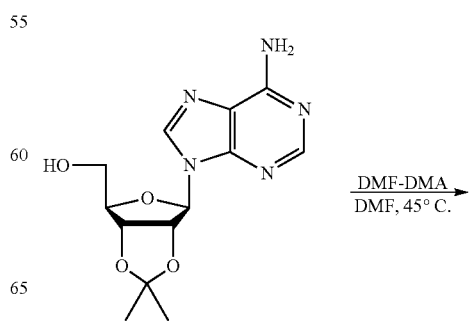

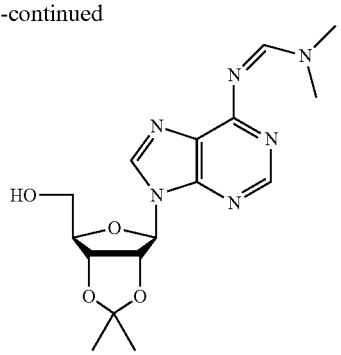

To a stirred solution of compound of product of Step 1 above (1 g, 3.26 mmol) in DMF (2 mL) was added DMF-DMA (1.64 mL, 12.04 mmol) at rt. The solution was heated to 45° C. for 1 h. LC-MS showed the desired compound was formed. The solvent was then removed in vacuo and the residue was taken up with DCM, washed with brine, dried over anhydrous $Na_2SO_4$, filtered, and evaporated to dryness. The dried product was purified on silica gel flash chromatography to give the desired compound (750 mg, 2.07 mmol). MS (ESI) m/z $(M+H)^+$: 363.

Step 3. Preparation of dibenzyl (((3aS,4R,6R,6aS)-6-(6-(((Z)-(dimethylamino)methylene)amino)-9H-purin-9-yl)-2,2-dimethyltetrahydrofuro[3,4-d][1,3]dioxol-4-yl)methyl) phosphate

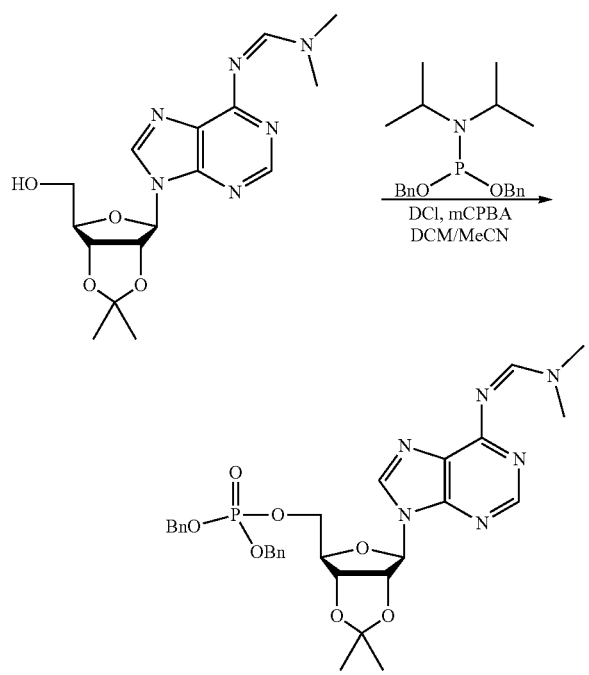

To a stirred solution of compound of product of Step 2 above (400 mg, 1.10 mmol) in DCM/MeCN (6 mL) was added DCI (260 mg, 2.20 mmol), mCPBA (447 mg, 2.20 mmol) and dibenzyl diisopropylphosphoramidite (760 mg, 2.20 mmol) at 0° C. Then the reaction was stirred at room temperature overnight. LC-MS showed the reaction was completed. The reaction mixture was concentrated, the residue was purified by flash chromatography on silica gel eluting with DCM/MeOH (30:1) to give the desired compound as an colorless gum (609 mg, 0.98 mmol). MS (ESI) m/z $(M+H)^+$: 623.

Step 4. Preparation of ((3aS,4R,6R,6aS)-6-(6-amino-9H-purin-9-yl)-2,2-dimethyltetrahydrofuro[3,4-d][1,3]dioxol-4-yl)methyl dihydrogen phosphate

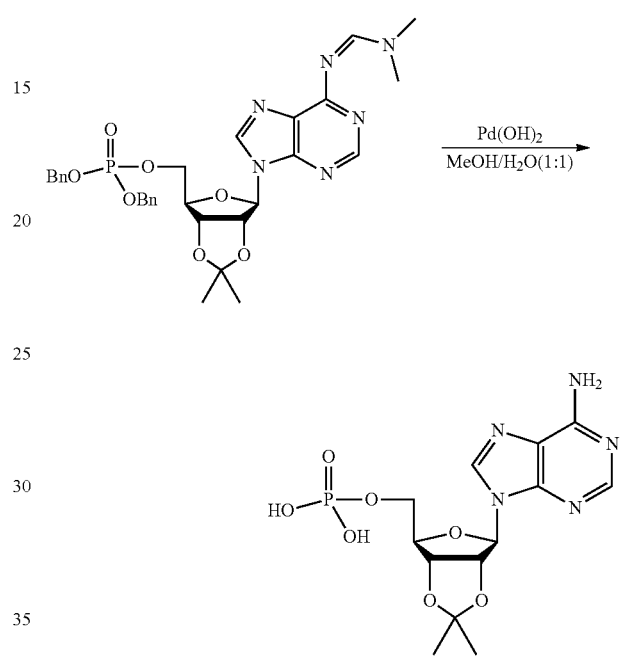

A mixture of compound of product of Step 3 above (609 mg, 0.98 mmol) and $Pd(OH)_2$ (200 mg) in $MeOH/H_2O$ (10 mL) was stirred at room temperature under $H_2$. After stirring overnight, the mixture was filtrated through an Advantec PTFE membrane filter with a pore size of 0.45 m with MeOH. The filtrate was concentrated under reduced pressure to get the desired compound (383 mg, 0.99 mmol). MS (ESI) m/z $(M+H)^+$: 388.

Step 5. Preparation of Morphine DCC Salt of ((3aS,4R,6R,6aS)-6-(6-amino-9H-purin-9-yl)-2,2-dimethyltetrahydrofuro[3,4-d][1,3]dioxol-4-yl)methyl dihydrogen phosphate

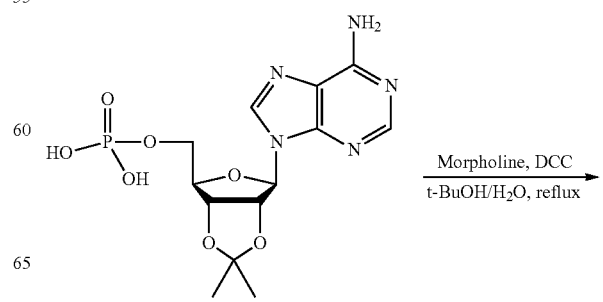

-continued

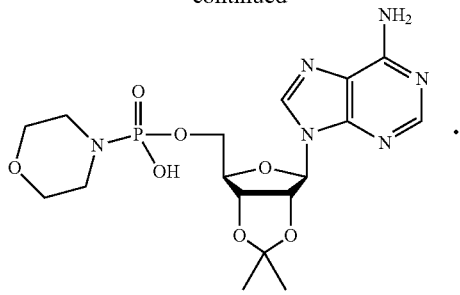

·

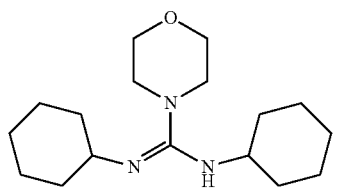

A solution of DCC (825 mg, 4.00 mmol) in t-butyl alcohol (20 mL) was added dropwise to a refluxing solution of compound of product of Step 4 above (383 mg, 0.99 mmol) in a mixture of t-BuOH/H$_2$O (1:1) (20 mL), and purified morpholine (384 mg, 4.00 mmol). The addition was completed in about 3 h, and the mixture was refluxed overnight until TLC showed completion of the reaction. The mixture was cooled to rt. The filtrate was evaporated until t-BuOH was largely removed, and the remaining aqueous phase was extracted three times with ether. The clear aqueous solution was then evaporated to dryness with freeze drying to give the desired product. MS (ESI) m/z (M+H)$^+$: 457.

Step 6. Preparation of (2S,3S,4S,5R,6R)-2-(((((((3aR,4R,6R,6aR)-6-(6-amino-9H-purin-9-yl)-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

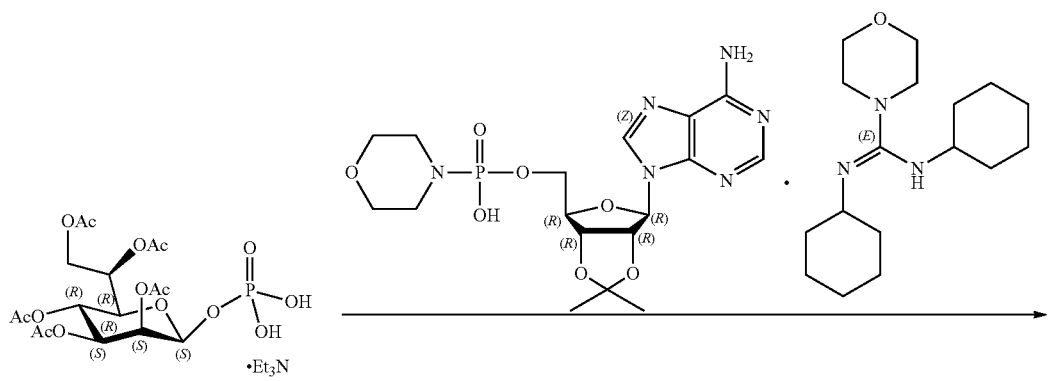

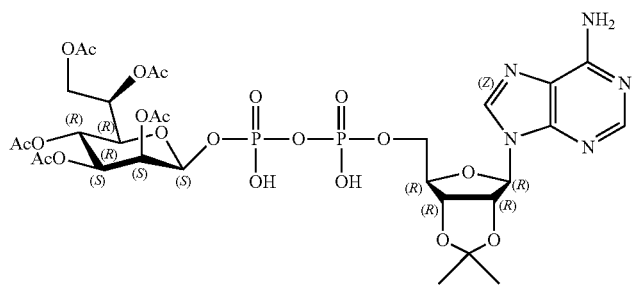

Compound 12

((3aR,4R,6R,6aR)-6-(6-amino-9H-purin-9-yl)-2,2-dimethyltetrahydrofuro[3,4-d][1,3]dioxol-4-yl) methanol (D-glycero-β-D-mannoheptopyranosyl) diphosphate

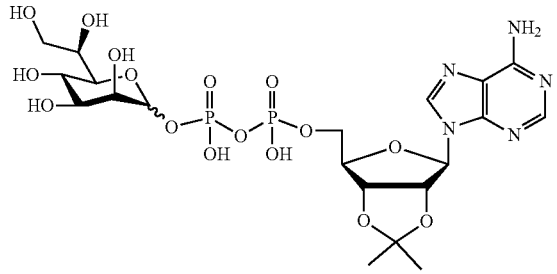

The mixture of compound of product of Step 14 in the preparation of Compound 1 above (200 mg, 284.61 umol, as 2 Et₃N) and compound of product of Step 5 above (389.68 mg, 853.82 umol) was dried with dry pyridine ("Py") (5 mL×3). Then the residue was dissolved in pyridine (5 mL) and mixed with 1H-tetrazole (99.69 mg, 1.42 mmol), stirred at 25° C. for 72 h. The solvent was removed to give a residue, which was purified by silica gel column chromatography (DCM:MeOH:NH₃.H₂O 1:0:0 to 30:50:1) to give impure product (200 mg) which was purified by Pre-HPLC (Column: Waters Xbridge 150*25 5 u, Condition: water (10 mM NH₄HCO₃)-ACN, 3% to 33%) to give the desired compound (50 mg, yield: 19.6%) as a white solid. MS (ESI) m/z (M+H)⁺: 870.3. ¹H NMR (400 MHz, methanol-d4) δ 8.59 (s, 1H), 8.21 (s, 1H), 6.22 (d, J=3.4 Hz, 1H), 5.58-5.52 (m, 2H), 5.27 (dd, J=3.3, 6.0 Hz, 1H), 5.22-5.14 (m, 4H), 4.53 (br s, 1H), 4.41 (dd, J=3.4, 12.0 Hz, 1H), 4.27-4.13 (m, 3H), 3.91 (dd, J=2.9, 9.8 Hz, 1H), 2.11 (s, 3H), 2.03 (d, J=3.7 Hz, 6H), 1.99 (s, 3H), 1.91 (s, 3H), 1.60 (s, 3H), 1.39 (s, 3H).

Step 1. Preparation of ((3aR,4R,6R,6aR)-6-(6-amino-9H-purin-9-yl)-2,2-dimethyltetrahydrofuro[3,4-d][1,3]dioxol-4-yl)methanol (D-glycero-b-D-mannoheptopyranosyl) diphosphate

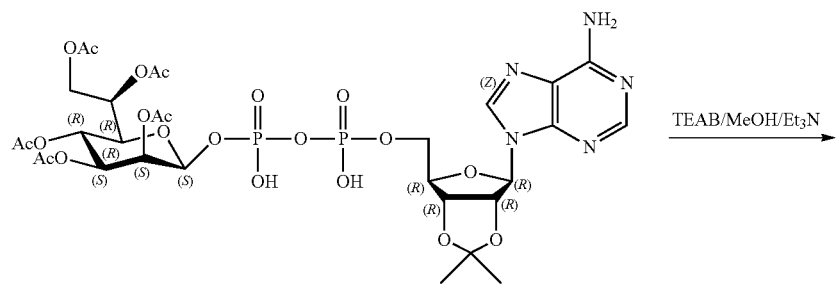

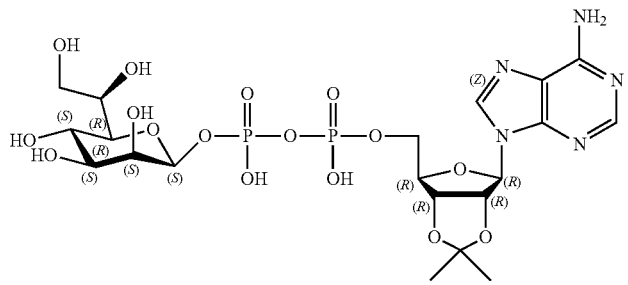

The compound of the product of Step 6 in the preparation of Compound 11 above (10 mg, 11.50 μmol) was dissolved in 2 mL of mixed solvent, which was consist of TEAB (8 mL), MeOH (6 mL) and Et$_3$N (0.1 mL). The obtained solution was stirred at −28° C. for 46 h. The reaction was lyophilized on a freeze drier. The desired compound (9 mg, yield: 70.84%, as 2.6 Et$_3$N salt) was obtained as a white solid. MS (ESI) m/z (M−H)$^-$: 657.9. $^1$H NMR (400 MHz, D$_2$O) δ 8.28 (s, 1H), 8.09 (s, 1H), 6.13 (d, J=3.2 Hz, 1H), 5.23 (br d, J=3.4 Hz, 1H), 5.13-4.97 (m, 2H), 4.01 (br s, 2H), 3.92-3.78 (m, 1H), 3.66-3.42 (m, 4H), 3.33-3.23 (m, 1H), 1.52 (s, 3H), 1.29 (s, 3H).

Compound 13

(2S,3S,4S,5R,6R)-2-(((((((2R,3R,4R,5R)-5-(6-amino-9H-purin-9-yl)-3,4-dimethoxytetrahydro-furan-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

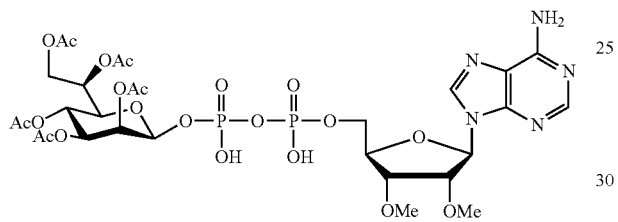

Step 1. Preparation of 9-((2R,3R,4R,5R)-3,4-dimethoxy-5-((trityloxy)methyl)tetrahydrofuran-2-yl)-N-trityl-9H-purin-6-amine

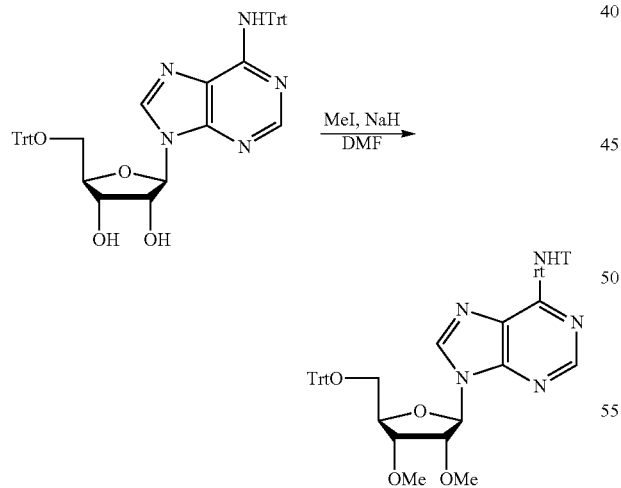

To a solution of product of Step 5 in the preparation of Compound 7 above (20 g, 18.62 mmol) in DMF (100 mL) was added NaH (1.71 g, 42.83 mmol, 60%), after stirring at 0° C. for 30 min, CH$_3$I (7.85 g, 55.31 mmol, 3.44 mL) was added at 0° C. The mixture was stirred at 25° C. for 4 h. The reaction mixture was quenched with H$_2$O (200 mL) at 0° C., extracted with EA (100 mL×3), the combined organic layers were washed with brine (200 mL), dried over Na$_2$SO$_4$, filtered and concentrated to give a residue. The residue was purified by flash silica gel chromatography (PE:EA=1:0 to 2:1). The desired compound (7.3 g, yield: 39.57%) was obtained as a white solid. MS (ESI) m/z (M+H)$^+$: 780.3.

Step 2. Preparation of ((2R,3R,4R,5R)-3,4-dimethoxy-5-(6-(tritylamino)-9H-purin-9-yl)tetrahydrofuran-2-yl)methanol

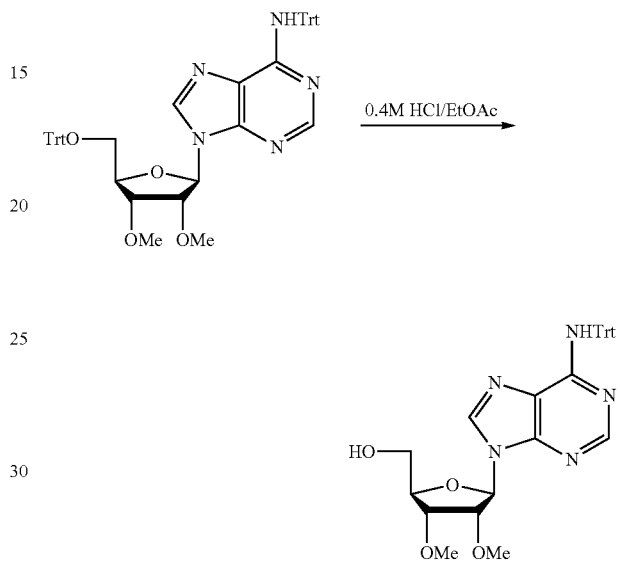

To a solution of product of Step 1 above (3.81 g, 3.85 mmol) in EtOAc (126 mL) was added HCl/EtOAc (4 M, 14 mL). The reaction mixture was stirred at 20° C. for 0.5 h. The pH was adjusted to 7 with Et$_3$N (5 mL) and the reaction mixture was concentrated under reduced pressure. The residue was dissolved in CH$_2$Cl$_2$ (30 mL) and washed with saturated NaHCO$_3$ (20 mL×3) and brine (20 mL×2). The organic layer was dried over Na$_2$SO$_4$, filtered, and concentrated under reduced pressure. The crude product was purified by silica gel column (PE:EA=1:0 to 1:1, then PE:EA=0:1) to give the desired compound (1.23 g, 2.25 mmol, 58.62% yield) as a white solid MS (ESI) m/z (M+H)$^+$: 538.3.

Step 3. Preparation of dibenzyl (((2R,3R,4R,5R)-3,4-dimethoxy-5-(6-(tritylamino)-9H-purin-9-yl)tetrahydrofuran-2-yl)methyl) phosphate

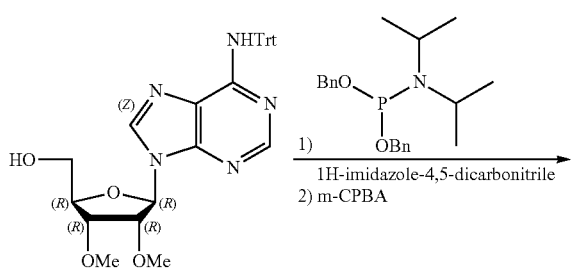

-continued

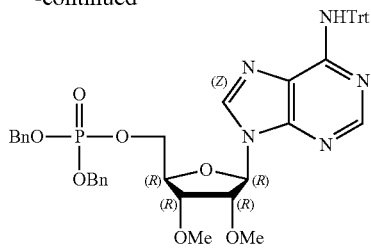

To the mixture of product of Step 2 above (2.03 g, 3.78 mmol) and 1H-imidazole-4,5-dicarbonitrile (892 mg, 7.55 mmol, 2 eq) in DCM (40 mL) and CH$_3$CN (8 mL) was added dibenzyl diisopropylphosphoramidite (2.61 g, 7.55 mmol, 2.53 mL) at 0° C. under nitrogen. The mixture was stirred at 0° C. for 5 min then it was warmed to 25° C. and stirred at 25° C. for 1 h. The mixture was cooled to 0° C. and m-CPBA (1.63 g, 7.55 mmol, 80% purity) was added in portions at 0° C. After addition, the mixture was stirred at 25° C. for 0.25 h. 35 mL of sat. NaHCO$_3$ was added and the mixture was extracted with DCM (40 mL×3). The combined organic layers were dried over Na$_2$SO$_4$ and concentrated under vacuum. The residue was purified by silica gel chromatography (200-300 mesh, Eluent of 20-55% ethyl acetate/petroleum ether gradient). The desired compound (2.54 g, yield: 79.92%) was obtained as a colorless gum. MS (ESI) m/z (M+H)$^+$: 798.2. $^1$H NMR (400 MHz, CDCl$_3$) δ 8.00-7.98 (m, 2H), 7.33-7.25 (m, 25H), 6.97 (s, 1H), 6.03-6.02 (m, 1H), 5.07-5.01 (m, 4H), 4.51 (t, J=4.4 Hz, 1H), 4.31-4.24 (m, 3H), 4.00-3.97 (m, 1H), 3.37 (s, 3H), 3.35 (s, 3H).

Step 4. Preparation of ((2R,3R,4R,5R)-5-(6-amino-9H-purin-9-yl)-3,4-dimethoxytetrahydrofuran-2-yl)methyl dibenzyl phosphate

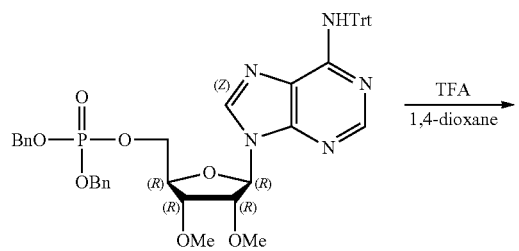

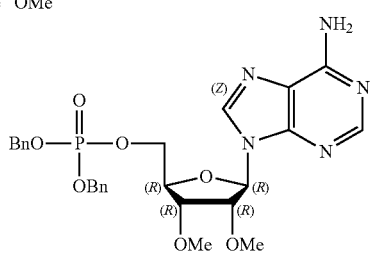

The product of Step 3 above (2.54 g, 3.18 mmol) was dissolved in dioxane (15 mL). TFA (5 mL, 67.53 mmol) was added and the mixture was stirred at 40° C. for 6 h. Sat. NaHCO$_3$ (~50 mL) was added to the mixture until pH=8. The mixture was extracted with ethyl acetate (50 mL×4). The combined organic layers weres dried over Na$_2$SO$_4$ and concentrated under vacuum. The residue was purified by flash silica gel chromatography (ISCO®; 4 g SepaFlash® Silica Flash Column, eluent of 0-10% methanol/ethyl acetate gradient @ 35 mL/min). The desired compound (1.75 g, yield: 98.95%) was obtained as a colorless oil. MS (ESI) m/z (M+H)$^+$: 556.1. $^1$H NMR (400 MHz, CDCl$_3$) δ 8.30 (s, 1H), 8.04 (s, 1H), 7.34-7.31 (m, 10H), 6.08-6.02 (m, 2H), 5.07-5.02 (m, 4H), 4.48-4.20 (m, 5H), 4.00-3.97 (m, 1H), 3.49 (s, 3H), 3.38 (s, 3H).

Step 5. Preparation of ((2R,3R,4R,5R)-5-(6-amino-9H-purin-9-yl)-3,4-dimethoxytetrahydrofuran-2-yl)methyl dihydrogen phosphate

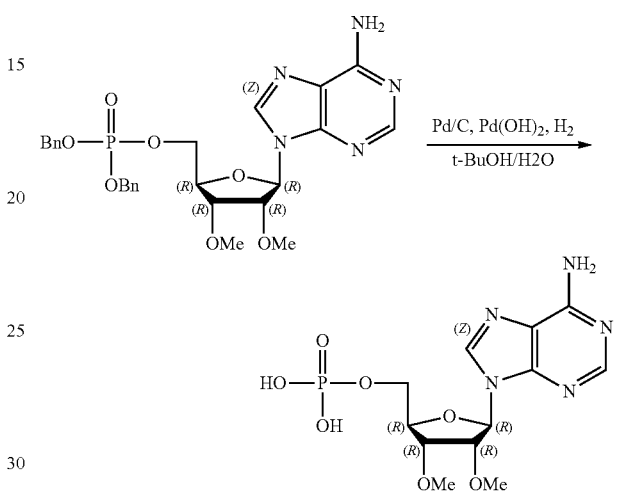

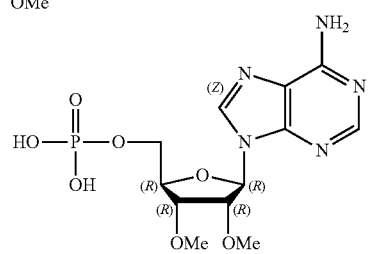

The mixture of the product of Step 4 above (500 mg, 900.0 μmol) was dissolved in t-BuOH (20 mL) and H$_2$O (20 mL), Pd/C (100 mg, 10% purity) and Pd(OH)$_2$ (126 mg, 89.72 p.mol, 10% purity) was added and the mixture was stirred at 25° C. for 16 h under H$_2$ atmosphere (50 psi). Filtered and the filtrate was concentrated to give the desired compound (400 mg, crude) as a colorless oil. $^1$H NMR (400 MHz, CD$_3$OD) δ 8.56 (s, 1H), 8.18 (s, 1H), 6.14 (d, J=6.4 Hz, 1H), 4.60-4.50 (m, 1H), 4.35-4.25 (m, 1H), 4.20-4.10 (m, 1H), 4.09-3.95 (m, 2H), 3.49 (s, 3H), 3.39 (s, 3H).

Step 6. Preparation of((2R,3R,4R,5R)-5-(6-amino-9H-purin-9-yl)-3,4-dimethoxytetrahydrofuran-2-v1)methyl hydrogen morpholinophosphonate

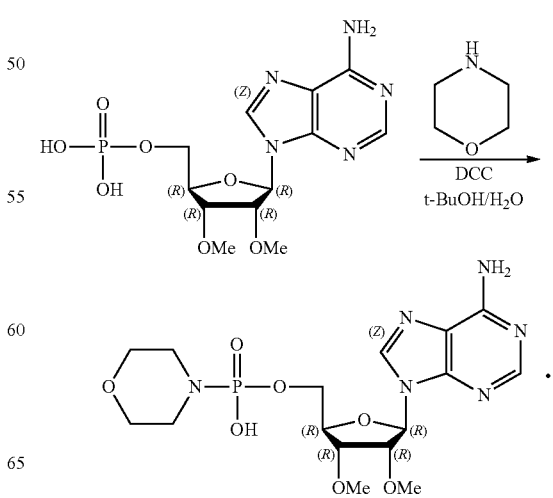

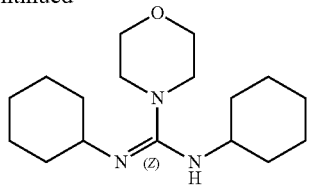

DCC (836 mg, 4.05 mmol) in t-BuOH (12 mL) was added dropwise to a reflux solution (110° C.) of the product of Step 5 above (380 mg, 1.01 mmol) and morpholine (353 mg, 4.05 mmol) in H$_2$O (12 mL) and t-BuOH (12 mL). The mixture was stirred at 110° C. for 12 h. The solution was cooled to room temperature. The solid was filtered off. The filtrate was collected and the organic solvent was removed in vacuo. The remaining aqueous phase was collected, and washed with MTBE (10 mL×3). The aqueous phase was collected and concentrated in vacuo to afford the desired compound (440 mg, crude) as light yellow sticky oil, which was used directly for the next step without further purification.

Step 7. Preparation of (2S,3S,4S,5R,6R)-2-((((((2R,3R,4R,5R)-5-(6-amino-9H-purin-9-yl)-3,4-dimethoxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

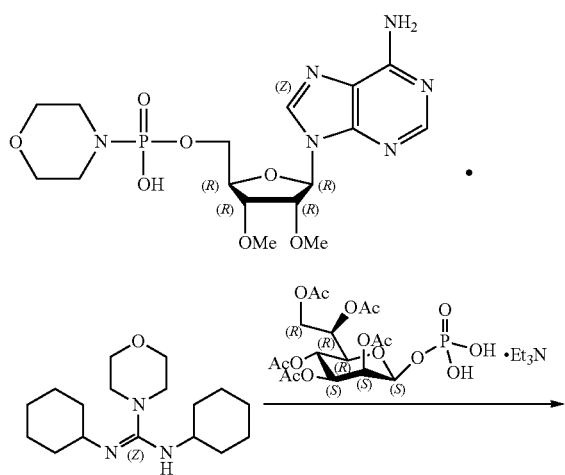

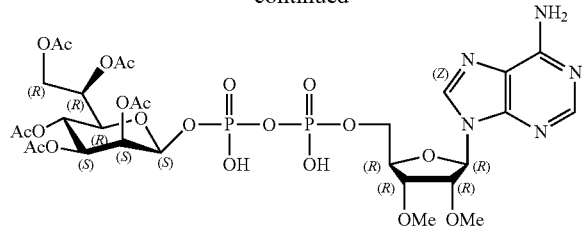

The product of Step 14 in the preparation of Compound 1 above (130 mg, 309.3 μmol) and the product of Step 6 above (390 mg, 878.3 μmol) were dried separately with pyridine (4 mL×3). The residue was re-dissolved in pyridine (4 mL) and 1H-Tetrazole (108 mg, 1.55 mmol) was added. The solution was stirred at 30° C. for 12 h. The solvent was removed in vacuo. The residue was re-dissolved in MeOH (10 mL). The solution was filtered. The filtrate was collected and concentrated. The residue was purified by column (DCM:(MeOH:NH$_3$.H$_2$O=50:1)=1:1) to afford crude product (80 mg), which was re-purified by prep-HPLC (column: Waters Xbridge 150*25 5 u; mobile phase: [water (10 mM NH$_4$HCO$_3$)-ACN]; B %: 0%-30%, 10 min) to afford the desired compound (30 mg, yield 11.21%) as a white solid. MS (ESI) m/z (M+H)$^+$: 858.4. $^1$H NMR (400 MHz, CD$_3$OD) δ 8.65 (s, 1H), 8.24 (s, 1H), 6.15-6.12 (m, 1H), 5.60-5.56 (m, 2H), 5.22-5.17 (m, 3H), 4.55-4.12 (m, 7H), 3.92-3.89 (m, 1H), 3.49 (s, 3H), 3.44 (s, 3H), 2.10 (s, 3H), 2.04 (s, 3H), 2.03 (s, 3H), 1.98 (s, 3H), 1.88 (s, 3H).

Compound 14

Adenosine-2'3'-dimethoxy-5'-(D-glycero-β-D-mannoheptopyranosyl) diphosphate

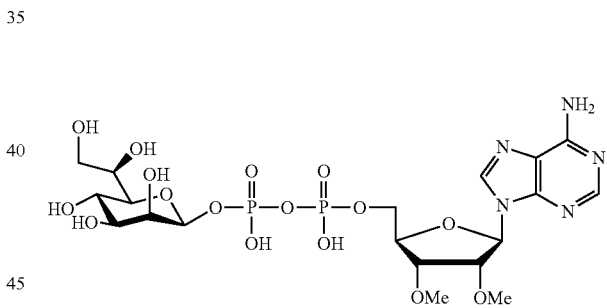

Step 1. Preparation of Adenosine-2'3'-dimethoxy-5'-(D-glycero-β-D-mannoheptopyranosyl) diphosphate

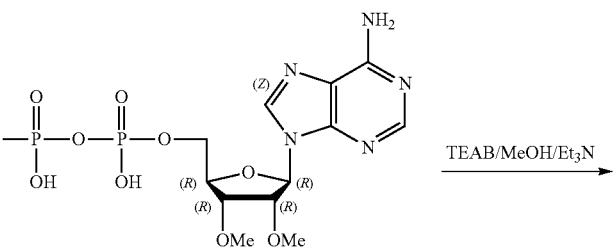

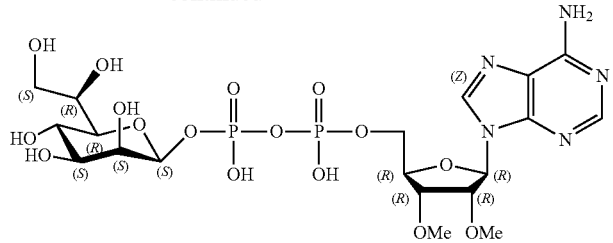

The solution of the product of Step 7 in the preparation of Compound 13 above (8.4 mg, 9.79 μmol) in 4 mL of buffer (TEAB (12 mL): MeOH (9 mL): TEA (0.15 mL)) was kept at −20° C. for 24 h. The solution was dried under lyophilization to give the desired compound (8 mg, yield: 65.85%) as white sticky solid. MS (ESI) m/z (M−H)+: 645.9.

Compound 15

(2S,3S,4S,5R,6R)-2-((((((2R,3S,4R,5R)-5-(6-amino-9H-purin-9-yl)-3,4-dihydroxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate

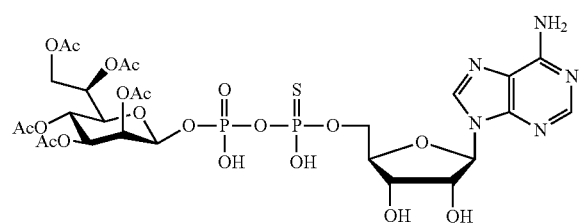

Step 1. Preparation of Compound ((3aR,4R,6R,6aR)-2,2-dimethyl-6-(6-(tritylamino)-9H-purin-9-yl)tetrahydrofuro[3,4-d][1,3]dioxol-4-yl)methanol

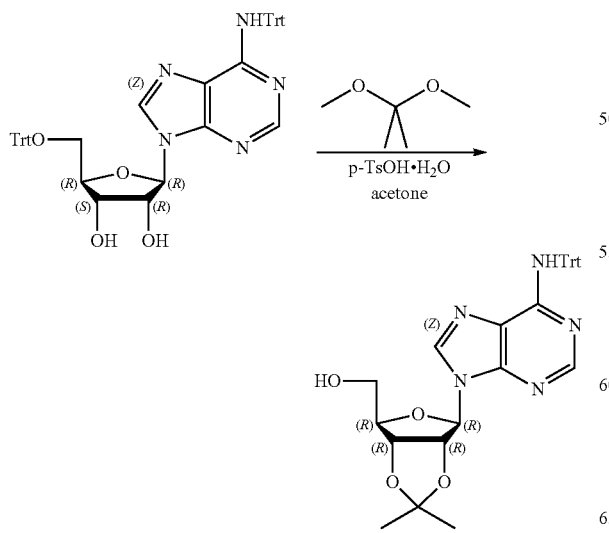

To a solution of product of Step 5 in the preparation of Compound 7 above (37.4 g, 49.8 mmol) and 2,2-dimethoxypropane (51.8 g, 497 mmol, 61.0 mL) in acetone (100 mL) was added p-TsOH.H₂O (11.4 g, 59.7 mmol). The mixture was stirred at 25° C. for 16 h. After completion of the reaction, the mixture was cooled to 0° C. and quenched with sat. NaHCO₃ (300 mL). The reaction mixture was extracted with EA (200 mL×3), the combined organic layers were washed with brine (200 mL), dried over Na₂SO₄, filtered and concentrated to give a residue, which was purified by silica gel column (PE:EA=1:0 to 2:3) to give the desired compound (9.96 g, yield: 35.57%) as a white solid. MS (ESI) m/z (M+H)+=550.1. ¹H NMR (400 MHz, DMSO-d6) δ 8.44 (s, 1H), 7.92 (s, 1H), 7.52 (s, 1H), 7.34-7.18 (m, 15H), 6.12 (d, J=2.9 Hz, 1H), 5.34 (dd, J=2.8, 6.2 Hz, 1H), 5.14 (t, J=5.5 Hz, 1H), 4.93 (dd, J=2.7, 6.1 Hz, 1H), 4.25-4.15 (m, 1H), 3.60-3.42 (m, 2H), 1.52 (s, 3H), 1.30 (s, 3H).

Step 2. Preparation of Compound ((3aR,4R,6R,6aR)-2,2-dimethyl-6-(6-(tritylamino)-9H-purin-9-yl)tetrahydrofuro[3,4-d][1,3]dioxol-4-yl)methyl hydrogen phosphonate triethylamine salt

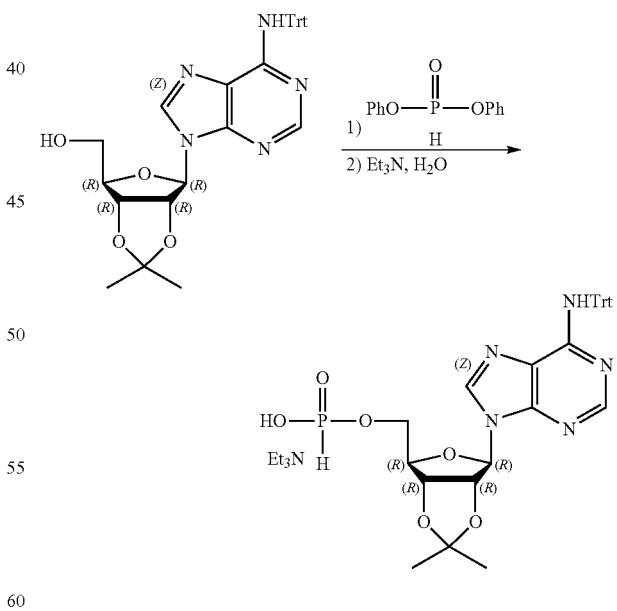

Phenoxyphosphonoyloxybenzene (3.41 g, 14.6 mmol) was added to a solution of product of Step 1 above (2 g, 3.64 mmol) in pyridine (20 mL). The resulting mixture was stirred at 25° C. for 2 h. Then Et₃N (2.21 g, 21.8 mmol, 3.04 mL) and H₂O (786.9 mg, 43.7 mmol) was added. The resulting mixture was stirred at 25° C. for 0.5 h. After completion of the reaction, the mixture was directly concentrated under reduced pressure to give crude product, which was purified by silica gel column (DCM:MeOH=1:0 to 10:1, adding 0.5% Et₃N) to give the desired compound (2 g, 2.55 mmol, 70.0% yield, 78% purity) as a yellow syrup. MS (ESI) m/z (M+H)⁺: 614.1

Step 3. Preparation of O—(((3aR,4R,6R,6aR)-2,2-dimethyl-6-(6-(tritylamino)-9H-purin-9-yl)tetrahydrofuro[3,4-d][1,3]dioxol-4-yl)methyl) phosphorothioate triethylamine salt

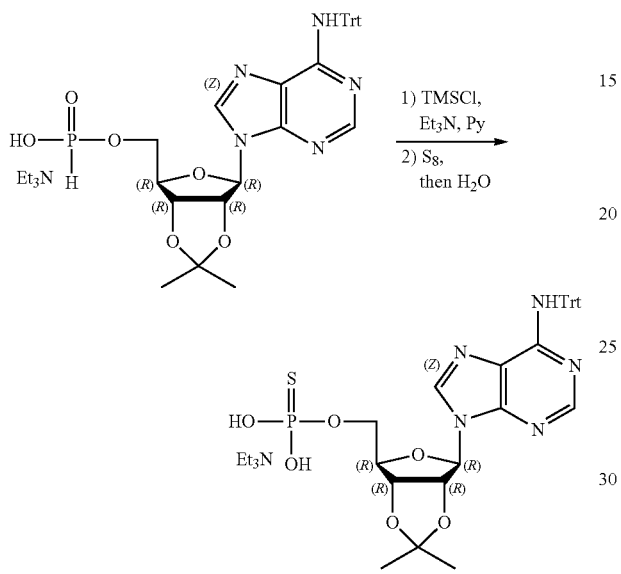

To a solution of product of Step 2 above (1.5 g, 2.40 mmol) in pyridine (6 mL) and Et₃N (6 mL) was added TMSCl (2.4 mL, 19.1 mmol) dropwise over 15 min under N₂ atmosphere. The mixture was stirred at 0° C. for 1 h, and then S (730 mg, 22.7 mmol) was added. The mixture was stirred at 0° C. for another 45 min. After completion of the reaction, the reaction was quenched with H₂O (10 mL) and the mixture was concentrated under reduced pressure to give the crude product, which was purified by silica gel chromatography (DCM:MeOH=20:1 to 10:1) and pre-HPLC (column: Boston Prime C18 150*30 mm 5 um; mobile phase: [water (0.05% ammonia hydroxide v/v)-ACN]; B %: 15%-45%, 9 min) to afford the desired compound (700 mg, yield 44.4%, 86% purity) as a white solid. MS (ESI) m/z (M+H)⁺: 646.1. ¹H NMR (400 MHz, DMSO) δ 8.71 (s, 1H), 7.91 (s, 1H), 7.48 (s, 1H), 7.39-7.12 (m, 15H), 6.12 (d, J=3.3 Hz, 1H), 5.28 (dd, J=3.3, 5.8 Hz, 1H), 5.07 (d, J=5.8 Hz, 1H), 4.39 (br s, 1H), 3.95-3.84 (m, 1H), 3.73 (td, J=5.6, 10.9 Hz, 1H), 1.56-1.48 (s, 3H), 1.31 (s, 3H)

Step 4. Preparation of (2R,3R,4S,5S,6S)-2-((R)-1,2-diacetoxyethyl)-6-((hydroxy(1H-imidazol-1-yl)phosphoryl)oxy)tetrahydro-2H-pyran-3,4,5-triyl triacetate

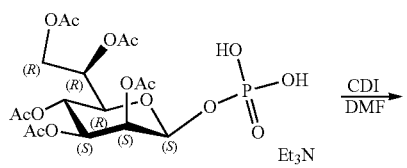

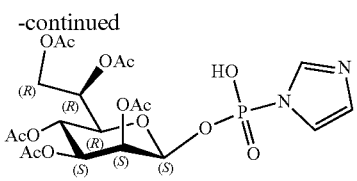

CDI (945 mg, 5.83 mmol) was added to a solution of the compound of the product of Step 14 in the preparation of Compound 1 above (350 mg, 0.58 mmol,) in anhydrous DMF (15 mL) under N₂ atmosphere. The resulting mixture was stirred at 25° C. for 3 h. After completion of the reaction, MeOH (0.2 mL) was added to quench the reaction, the mixture was concentrated under reduced pressure to give crude desired product (1 g, crude), which was used directly in next step.

Step 5. Preparation of Compound (2R,3R,4S,5S, 6S)-2-((R)-1,2-diacetoxyethyl)-6-(((((((3 aR,4R,6R, 6aR)-2,2-dimethyl-6-(6-(tritylamino)-9H-purin-9-yl) tetrahydrofuro[3,4-d][1,3]dioxol-4-yl)methoxy) (hydroxy)phosphorothioyl)oxy)(hydroxy) phosphoryl)oxy)tetrahydro-2H-pyran-3,4,5-triyl triacetate

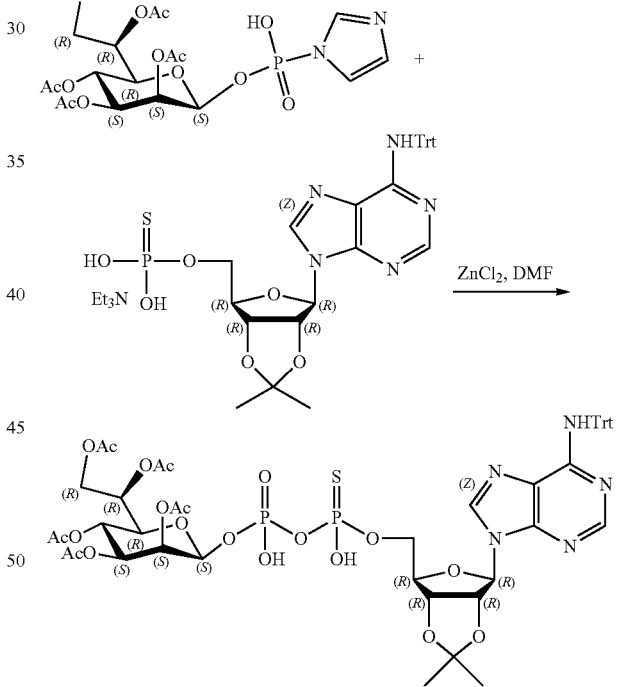

ZnCl₂ (1 g, 7.34 mmol) was added to a solution of product from step 4 above (320 mg, 0.58 mmol) and the product from step 3 above (500 mg, 0.67 mmol) in anhydrous DMF (15 mL) under N₂ atmosphere. The resulting mixture was stirred at 25° C. for 16 h. After completion of the reaction, the mixture was concentrated under reduced pressure to give the crude product, which was purified by silica gel column (DCM:MeOH=10:1, adding 0.5% Et₃N) to give the desired compound (600 mg, crude) as a light yellow solid, which was used directly in the next step without further purification. MS (ESI) m/z (M+H)⁺: 1128.6.

Step 6. Preparation of Compound (2S,3S,4S,5R, 6R)-2-(((((((2R,3S,4R,5R)-5-(6-amino-9H-purin-9-yl)-3,4-dihydroxytetrahydrofuran-2-yl)methoxy) (hydroxy)phosphorothioyl)oxy)(hydroxy) phosphoryl)oxy)-6-((R)-1,2-diacetoxyethyl) tetrahydro-2H-pyran-3,4,5-triyl triacetate

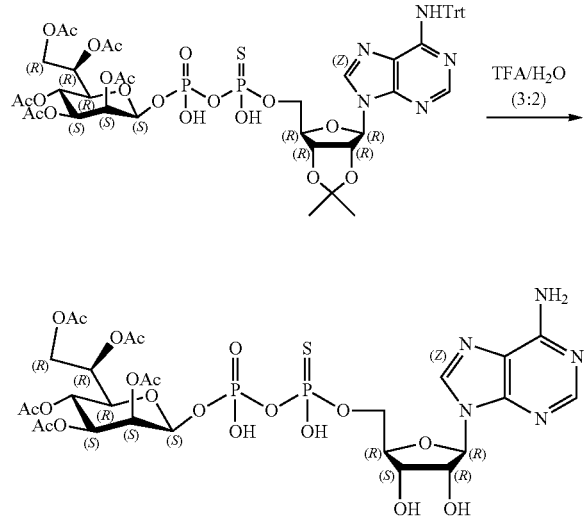

TFA (0.3 mL, 4.05 mmol) was added to a solution of the compound of the product of Step 5 above (200 mg, crude) in H₂O (2 mL). The mixture was stirred at 25° C. for 0.5 h. After completion of the reaction, the reaction was adjusted to pH=7 by adding Et₃N. The mixture was concentrated under reduced pressure to give crude product, which was purified by pre-HPLC (column: Waters Xbridge 150*25 5 u; mobile phase: [water (10 mM NH₄HCO₃)-ACN]; B %: 0%-30%, 10 min) to give the desired compound (18.6 mg, 99% purity) as a white solid. MS (ESI) m/z (M+H)⁺: 846.3. ¹H NMR (400 MHz, Methanol-d4) δ=8.78 (s, 0.5H), 8.71 (s, 0.5H), 8.21 (s, 1H), 6.13 (dd, J=2.0, 6.0 Hz, 1H), 5.76-5.60 (m, 2H), 5.26-5.16 (m, 3H), 4.74-4.68 (m, 1H), 4.53-4.42 (m, 2H), 4.37-4.21 (m, 4H), 4.01-3.89 (m, 1H), 2.17 (s, 3H), 2.10-2.06 (m, 6H), 2.04 (s, 1.5H), 2.02 (s, 1.5H), 1.96 (s, 3H)

Compound 16

Adenosine-5'-(D-glycero-β-D-manno-6-fluoro-heptopyranosyl) phosphorothioyloxyphosphate

Step 1. Preparation of Adenosine-5'-(D-glycero-β-D-manno-6-fluoro-heptopyranosyl) (hydroxyl)phosphorothioyloxyphosphate

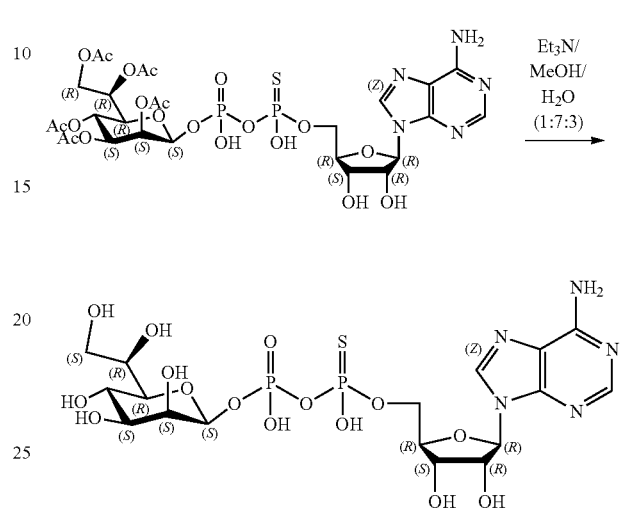

A solution of the compound of the product of Step 6 in the preparation of Compound 15 described above (4 mg, 4.73 μmol) in 7:3:1 ratio of MeOH/water/Et₃N (2 mL) was stirred at 25° C. for 5 h. After completion of the reaction, the mixture was concentrated and lyophilized from water to give the desired compound (3.2 mg, yield: 80.6%, 2Et₃N salt) as a white solid. MS (ESI) m/z (M–H)⁺: 634.1. ¹H NMR (400 MHz, D₂O) δ 8.46 (s, 0.5H), 8.43 (s, 0.5H), 8.08 (s, 0.5H), 8.06 (s, 0.5H), 5.96 (dd, J=5.9, 10.0 Hz, 1H), 5.38-5.28 (m, 0.5H), 5.13-5.03 (m, 0.5H), 4.45-4.31 (m, 2H), 4.23 (d, J=11.0 Hz, 1H), 4.14-4.03 (m, 1H), 3.96-3.87 (m, 2H), 3.85-3.76 (m, 1H), 3.66-3.47 (m, 4H), 3.34-3.24 (m, 1H), 3.02 (q, J=7.3 Hz, 12H), 1.09 (t, J=7.3 Hz, 18H)

Compound 17

(2S,3S,4S,5R,6R)-2-(((((((2R,3R,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl) tetrahydro-2H-pyran-3,4,5-triyl triacetate

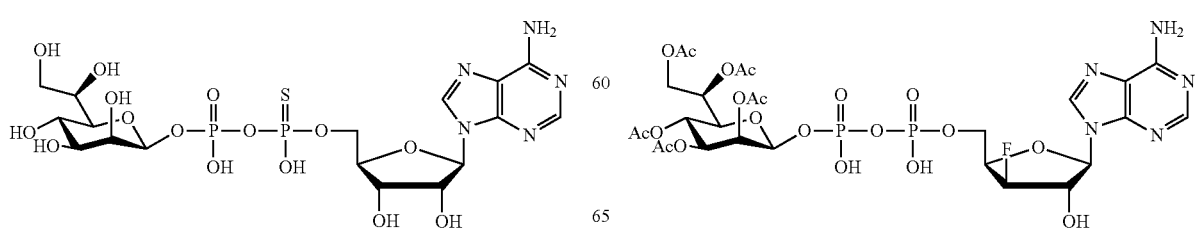

Step 1. Preparation of Compound (2R,3R,4R,5R)-5-(6-amino-9H-purin-9-yl)-2-(hydroxymethyl)-4-((4-methoxybenzyl)oxy)tetrahydrofuran-3-ol and (2R,3R,4S,5R)-2-(6-amino-9H-purin-9-yl)-5-(hydroxymethyl)-4-((4-methoxybenzyl)oxy)tetrahydrofuran-3-ol

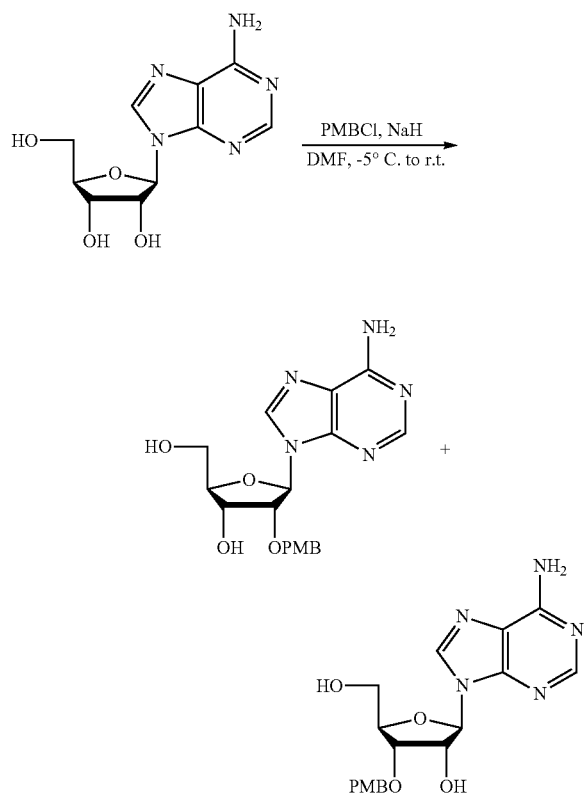

A suspension of adenosine (25 g, 93.55 mmol) in DMF (900 mL) was cooled down to −5° C. NaH (4.86 g, 121.61 mmol, 60% purity) was added to the solution. The mixture was stirred for further 1 h at −5° C. PMBCl (17.58 g, 112.26 mmol, 15.29 mL) was added dropwise to the suspension during 1 h. After the addition was completed, the reaction was let to reach 25° C., and stirred for 16 h. 40 mL of saturated NaHCO$_3$ solution was added into the mixture at 0° C. and stirred at room temperature for 10 min. Solid was filtered off and the filtrated was concentrated under reduced pressure to give the residue. The residue was purified by flesh chromatography column (eluted with 0-2% MeOH in DCM). Compound (2R,3R,4R,5R)-5-(6-amino-9H-purin-9-yl)-2-(hydroxymethyl)-4-((4-methoxybenzyl)oxy)tetrahydrofuran-3-ol (22 g, 59.70 mmol, 63.8% yield, 96.37% purity) was obtained as white solid. A mixture (12 g) of the desired two isomers was obtained as white solid. $^1$H NMR (400 MHz, DMSO-$d_6$) δ 8.29 (s, 1H), 8.06 (s, 1H), 7.35 (s, 2H), 7.04 (d, J=8.4 Hz, 2H), 6.70 (d, J=8.4 Hz, 2H), 6.01 (d, J=6.4 Hz, 1H), 5.47 (dd, J=4.4, 7.2 Hz, 1H), 5.29 (d, J=4.8 Hz, 1H), 4.65-4.42 (m, 2H), 4.39-4.20 (m, 2H), 4.00 (q, J=2.8 Hz, 1H), 3.72 (s, 3H), 3.71-3.61 (m, 1H), 3.58-3.47 (m, 1H).

Step 2. Preparation of Compound (2R,3R,4R,5R)-4-((4-methoxybenzyl)oxy)-5-(6-(tritylamino)-9H-purin-9-yl)-2-((trityloxy)methyl)tetrahydrofuran-3-ol

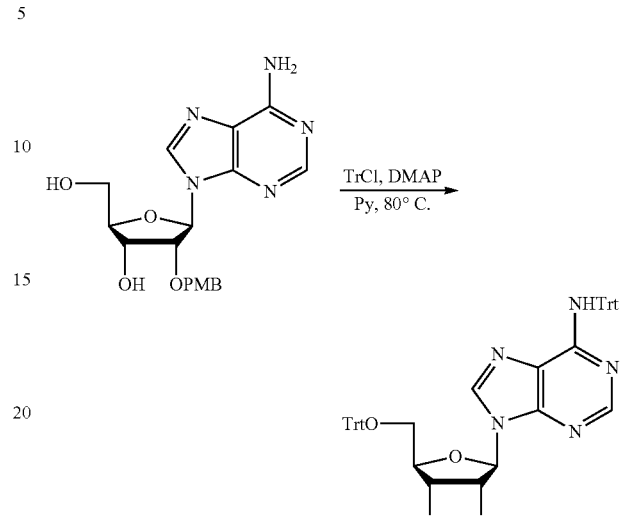

The compound of the product of Step 1 above (15.00 g, 38.72 mmol) was co-evaporated with pyridine (10 mL×2) twice and dissolved in pyridine (300 mL). TrtCl (26.99 g, 96.80 mmol) and DMAP (3.78 g, 30.98 mmol) were added. The mixture was stirred at 80° C. under N$_2$ for 15 h. The mixture was diluted with EA (800 mL) and was washed with saturated NaHCO$_3$ solution (200 mL×2) and brine (200 mL×2). The organic layer was dried over anhydrous Na$_2$SO$_4$, filtered and concentrated under reduced pressure to give the residue. The residue was purified by flash column chromatography (eluted with 0-40% EA in PE). The desired compound (22.6 g, 66.9% yield) was obtained as white solid. MS (ESI) m/z (M+H)$^+$=872.4

Step 3. Preparation of Compound 9-((2R,3S,4S,5R)-4-fluoro-3-((4-methoxybenzyl)oxy)-5-((trityloxy)methyl)tetrahydrofuran-2-yl)-N-trityl-9H-purin-6-amine

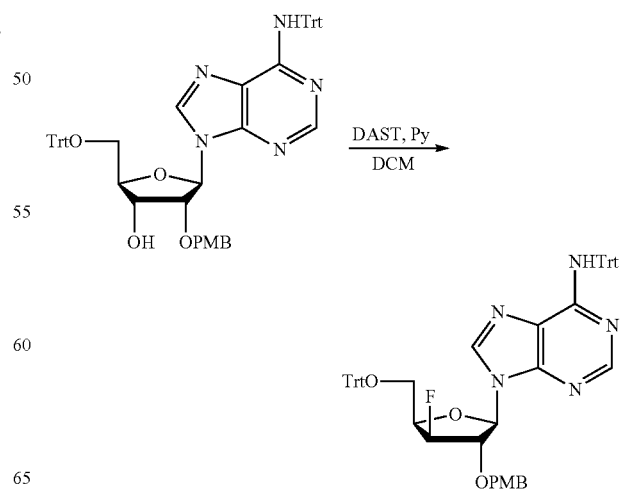

To a solution of the compound of the product of Step 2 above (5 g, 5.73 mmol) in DCM (50 mL) was added DAST (3.85 mL, 29.1 mmol) and pyridine (4.6 mL, 57.2 mmol). The mixture was stirred at 20° C. for 12 h. The reaction was quenched with sat.NaHCO$_3$ (30 mL) and the organic layer was separated. The aqueous layer was extracted with DCM (50 mL×2), the combined organic layers were washed with HCl (50 mL), brine (50 mL), dried over anhydrous Na$_2$SO$_4$, filtered and concentrated under reduced pressure. The residue was purified by silica gel column chromatography (PE/EA: 20/1 to 2/1) to afford the desired compound (2.1 g, yield 42.0%) as a yellow solid. MS (ESI) m/z (M+H)$^+$: 874.4 $^1$H NMR (400 MHz, DMSO-d$_6$) δ 7.99 (s, 1H), 7.91 (s, 1H), 7.56 (s, 1H), 7.44-7.18 (m, 32H), 6.84 (d, J=8.8 Hz, 2H), 6.16-6.10 (m, 1H), 5.50-5.28 (m, 1H), 4.81-4.70 (m, 1H), 4.62 (s, 2H), 4.57-4.43 (m, 1H), 3.71 (s, 3H), 3.42-3.37 (m, 1H), 3.31-3.24 (m, 1H).

Step 4. Preparation of Compound ((2R,3S,4S,5R)-3-fluoro-4-((4-methoxybenzyl)oxy)-5-(6-(tritylamino)-9H-purin-9-yl)tetrahydrofuran-2-yl)methanol

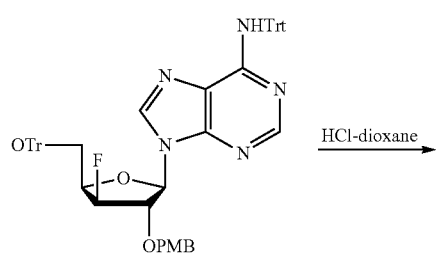

The solution of the compound of the product of Step 3 above (2.7 g, 3.09 mmol) in HCl/dioxane (20 mL) was stirred at 28° C. for 4 h. The reaction mixture was neutralized with sat.NaHCO$_3$ till pH=7, and then it was extracted with EtOAc (50 mL×3). The combined organic layers were washed with brine (50 mL), dried over anhydrous Na$_2$SO$_4$, filtered and concentrated under reduced pressure to give the residue which was purified by silica gel column chromatography (PE:EA=20:1 to 3:1). The desired compound (3 g, yield: 76.9%) was obtained as a yellow solid. MS (ESI) m/z (M+H)$^+$=631.2, 632.2. $^1$H NMR (400 MHz, DMSO-d$_6$) δ 8.20 (s, 1H), 7.94 (s, 1H), 7.52 (s, 1H), 7.37-7.18 (m, 17H), 6.90-6.83 (m, 2H), 6.12-6.05 (m, 1H), 5.41-5.25 (m, 1H), 5.10-5.05 (m, 1H), 4.81-4.74 (m, 1H), 4.70-4.62 (m, 2H), 4.34-4.22 (m, 1H) 3.81-3.73 (m, 1H) 3.72 (s, 3H).

Step 5. Preparation of Compound dibenzyl (((2R,3S,4S,5R)-3-fluoro-4-((4-methoxybenzyl)oxy)-5-(6-(tritylamino)-9H-purin-9-yl)tetrahydrofuran-2-yl)methyl) phosphate

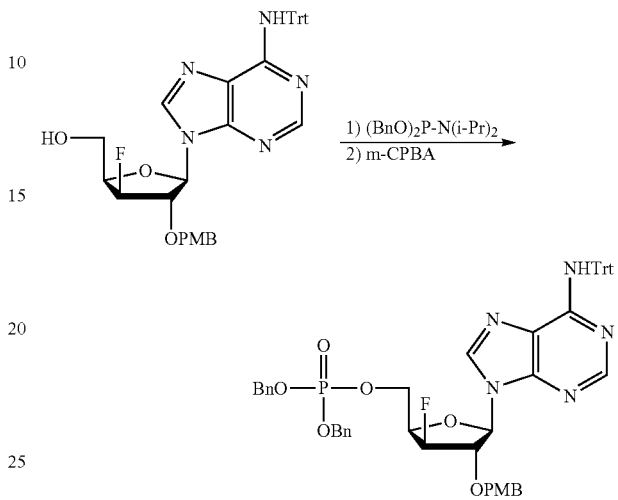

To a solution of the compound of the product of Step 4 above (1.5 g, 2.37 mmol) and 1H-imidazole-4, 5-dicarbonitrile (560 mg, 4.75 mmol,) in CH$_2$Cl$_2$ (20 mL) and CH$_3$CN (4 mL) was added (BnO)$_2$P—N(i-Pr)$_2$ (1.64 g, 4.75 mmol) at 0° C. The mixture was stirred at 0° C. for 10 min and then warmed to 25° C. The resultant mixture was stirred for another 1 h and cooled to 0° C. again. m-CPBA (1.02 g, 4.75 mmol, 80% purity) was added directly, then the reaction was warm to 25° C. and stirred at 25° C. for 16 h. The reaction was diluted with DCM (20 mL), washed with sat.NaHCO$_3$ (30 mL×2) and brine (30 mL). The organic phase was concentrated to give crude product. The crude product was purified by silica gel column chromatography (PE:EA=1:0 to 1:1). The desired compound (2.2 g, yield: 81.0% yield, 78% purity) was obtained as yellow oil. MS (ESI) m/z (M+H)$^+$: 892.3.

Step 6. Preparation of Compound ((2R,3R,4S,5R)-5-(6-amino-9H-purin-9-yl)-3-fluoro-4-hydroxytetrahydrofuran-2-yl)methyl dibenzyl phosphate and ((2R,3S,4S,5R)-5-(6-amino-9H-purin-9-yl)-3-fluoro-4-((4-methoxybenzyl)oxy)tetrahydrofuran-2-yl)methyl dibenzyl phosphate

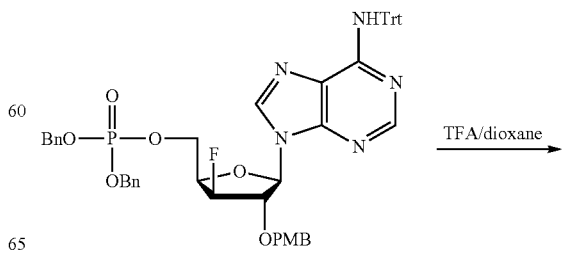

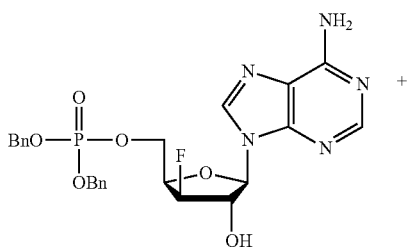

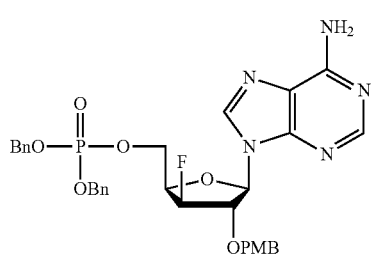

The solution of the compound of the product of Step 5 above (2.2 g, 2.47 mmol) and TFA (562 mg, 4.93 mmol, 365 µL) in DCM (18 mL) was stirred at 25-30° C. for 4 h. The reaction was adjusted to pH ~8-9 with saturated NaHCO₃ (40 mL) and extracted with DCM (50 mL×2). The combined organic phase was washed with brine (50 mL) and concentrated to give a crude product. The crude product was purified by silica gel column chromatography (PE:EA=1:0 to 0:1). The mixture of two compounds (1.1 g, yield: 76.7%) was obtained as yellow oil which was used for the further step without purification. MS (ESI) m/z (M+H)⁺=530.1, 650.1.

Step 7. Preparation of Compound ((2R,3R,4S,5R)-5-(6-amino-9H-purin-9-yl)-3-fluoro-4-hydroxytetrahydrofuran-2-yl)methyl dihydrogen phosphate

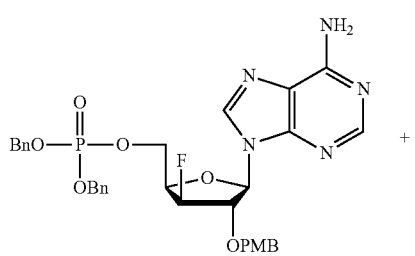

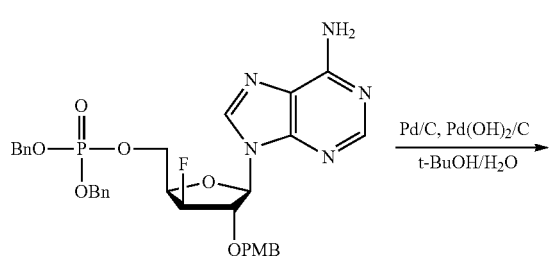

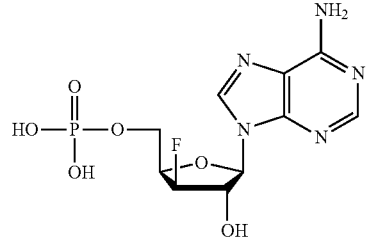

To a mixture of the compound of the product of Step 6 above (1.1 g, 1.69 mmol) in t-BuOH (15 mL) and H₂O (15 mL) were added Pd/C (0.2 g) and Pd(OH)₂ (0.2 g). The mixture was stirred at 25° C. under hydrogen atmosphere (50 psi) for 36 h. The mixture was filtered and the filtrated was concentrated under reduced pressure to give the crude. The crude was used for next step without further purification. The desired compound (0.45 g, crude) was obtained as grey solid. ¹H NMR (400 MHz, DMSO-d₆) δ 8.17 (s, 1H), 8.12 (s, 1H), 7.34 (br s, 2H), 5.96 (d, J=2.4 Hz, 1H), 5.34-4.95 (m, 1H), 4.76 (br d, J=15.6 Hz, 1H), 4.63-4.42 (m, 1H), 4.20-3.93 (m, 2H).

Step 8. ((2R,3R,4S,5R)-5-(6-amino-9H-purin-9-yl)-3-fluoro-4-hydroxytetrahydrofuran-2-yl)methyl hydrogen morpholinophosphonate (4'-morpholine-N,N'-dicyclohexylcarboxamidinium salt)

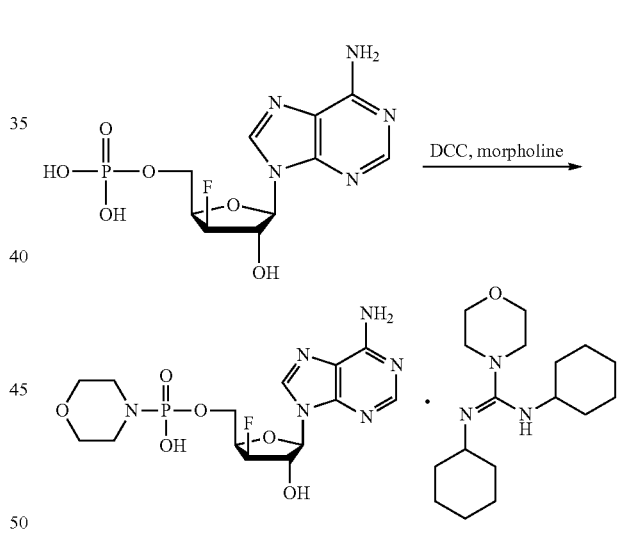

DCC (354.50 mg, 1.72 mmol, 347.5 µL) in t-BuOH (4 mL) was added dropwise to a refluxed (110° C.) solution of the compound of the product of Step 7 above (150 mg, 430 µmol) and morpholine (150 mg, 1.72 mmol) in H₂O (4 mL) and t-BuOH (4 mL) over a period of 15 min. The mixture was stirred at 100° C. under N₂ for 12 h. The solution was filtered. The filtrate was collected and concentrated. The residue was diluted with H₂O (30 mL), washed with TBME (20 mL×2). The aqueous phase was collected and concentrated in vacuo. The desired compound (290 mg, crude) was obtained as yellow oil, which was used directly for the next step without further purification. ¹H NMR (400 MHz, D₂O) δ 8.11 (s, 1H), 8.05 (s, 1H), 6.01-5.98 (m, 1H), 5.22-5.07 (m, 1H), 4.80-4.73 (m, 1H), 4.55-4.48 (m, 1H), 4.09-4.02 (m, 1H), 4.00-3.92 (m, 1H), 3.44-3.39 (m, 4H), 2.85-2.80 (m, 4H). ³¹P NMR δ 7.5.

Step 9. Preparation of Compound (2S,3S,4S,5R,6R)-2-((((((2R,3R,4S,5R)-5-(6-amino-9H-purin-9-yl)-3-fluoro-4-hydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

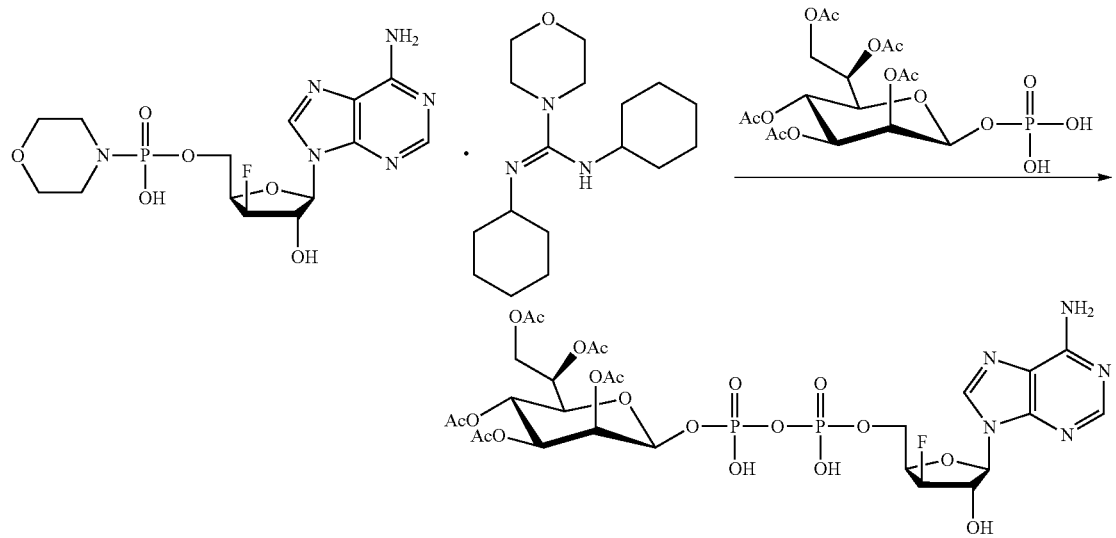

Compound 18

3'-(s)-fluoro-adenosine-5'-(D-glycero-β-D-manno-heptopyranosyl) diphosphate

The compound of the product of Step 8 above (150 mg, 299.79 μmol) and the compound of the product of Step 14 in the preparation of Compound 1 above (290 mg, 693.25 μmol) was dried with pyridine (3 mL×3). The residue was re-dissolved in pyridine (5 mL), and 1H-tetrazole (105.01 mg, 1.50 mmol, 132.92 μL) was added. The solution was stirred at 30° C. for 20 h. The volatile was removed in vacuo. The residue was dissolved in MeOH (5 mL) and filtered. The filtrate was collected. The solution was purified by column (DCM:(MeOH:NH$_3$.H$_2$O=50:1)=1.2:1) to give the crude product (120 mg). The crude product was purified by prep-HPLC (column: Waters Xbridge 150*25 5 u; mobile phase: [water (10 mM NH$_4$HCO$_3$)-ACN]; B %: 0%-30%, 12 min) to afford the desired compound (46.9 mg, purity: 90.6%, 18% yield) as white solid. MS (ESI) m/z (M+H)$^+$: 832.2. $^1$H NMR (400 MHz, CD$_3$OD) δ 8.25 (s, 1H), 8.19 (s, 1H), 6.12 (s, 1H), 5.60-5.50 (m, 2H), 5.25-5.09 (m, 4H), 4.80-4.71 (m, 1H), 4.69-4.62 (m, 1H), 4.47-4.31 (m, 3H), 4.27-4.18 (m, 1H), 3.92-3.88 (m, 1H), 2.12 (s, 3H), 2.03 (s, 3H), 2.02 (s, 3H), 1.98 (s, 3H), 1.92 (s, 3H). MS (ESI) m/z (M+H)$^+$=832.2.

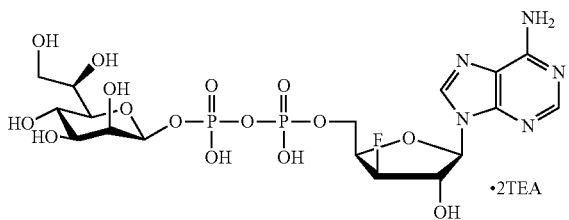

•2TEA

Step 1. Preparation of Compound 3'-(s)-fluoro-adenosine-5'-(D-glycero-β-D-manno-heptopyranosyl) diphosphate

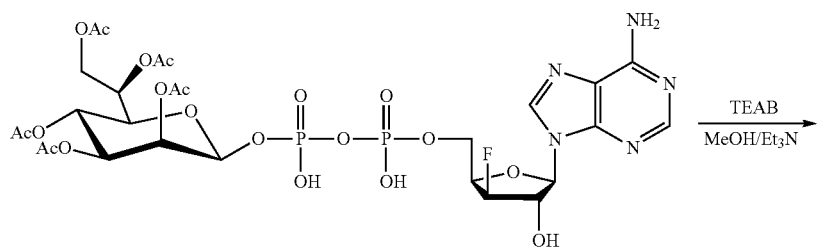

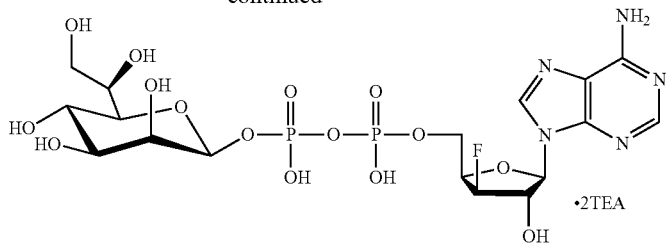

·2TEA

The solution of compound of the product of Step 9 of the preparation of Compound 17 above (6 mg, 7.22 µmol) in 4 mL of a solution consisting of (MeOH (9 mL), TEA (0.15 mL) and TEAB (12 mL)) was kept at −20° C. for 36 h. The solution was freeze dried. The desired compound (4 mg, 6.44 µmol) was obtained as white solid. MS (ESI) m/z (M−H)+: 620.2. $^1$H NMR (400 MHz, D$_2$O) δ 8.13 (s, 1H), 8.05 (s, 1H), 6.03-5.99 (m, 1H), 5.22-5.21 (m, 1H), 5.08-4.96 (m, 3H), 4.27-4.10 (m, 2H), 4.00-3.95 (m, 1H), 3.90-3.85 (m, 1H), 3.82-3.75 (m, 1H), 3.56-3.38 (m, 3H), 3.26-3.17 (m, 1H), 2.97-2.86 (m, 15H), 1.12-0.97 (m, 23H).

Compound 19

(2S,3S,4S,5R,6R)-2-(((((((3aS,4S,6R,6aR)-6-(6-amino-9H-purin-9-yl)-4-fluoro-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

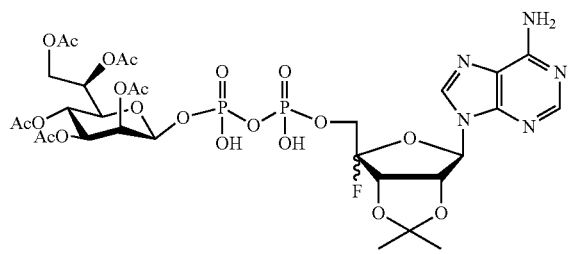

Step 1. Preparation of N-(9-((3aR,4R,6R,6aR)-6-(hydroxymethyl)-2,2-dimethyltetrahydrofuro[3,4-d][1,3]dioxol-4-yl)-9H-purin-6-yl)benzamide

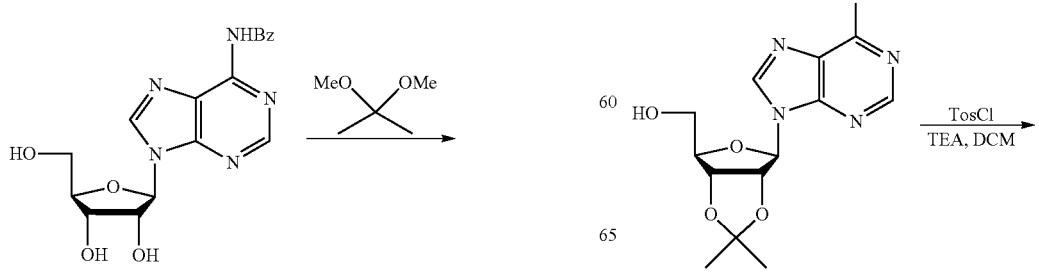

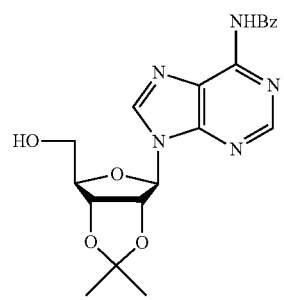

N-(9-((2R,3R,4S,5R)-3,4-dihydroxy-5-(hydroxymethyl)tetrahydrofuran-2-yl)-9H-purin-6-yl)benzamide (23.0 g, 61.9 mmol) and 2,2-dimethoxypropane (64.5 g, 619.3 mmol) were dissolved in acetone (400 mL). Then p-TsOH.H$_2$O (12.8 g, 74.3 mmol) was added. The reaction mixture was stirred at 25° C. for 4 h. After completion of the reaction, the reaction mixture was cooled to 0° C. and quenched with a saturated NaHCO$_3$ solution (200 mL). The reaction mixture was diluted with ethyl acetate (250 mL) and the milky aqueous layer was extracted with ethyl acetate (250 mL×2). The combined organic layers were washed with brine (250 mL), dried, concentrated in vacuum to give the desired compound (25.0 g, crude) as light yellow solid. $^1$H NMR (400 MHz, DMSO-d$_6$) δ 11.19 (br, 1H), 8.74 (s, 1H), 8.65 (s, 1H), 8.03-7.99 (m, 2H), 7.64-7.60 (m, 1H), 7.54-7.50 (m, 2H), 6.25-6.24 (m, 1H), 5.41 (dd, J=6.4 Hz, 2.4 Hz, 1H), 5.11 (t, J=5.2 Hz, 1H), 4.99-4.97 (m, 1H), 4.26-4.23 (m, 1H), 3.56-3.50 (m, 2H), 1.54 (s, 3H), 1.32 (s, 3H).

Step 2. Preparation of ((3aR,4R,6R,6aR)-6-(6-benzamido-9H-purin-9-yl)-2,2-dimethyltetrahydrofuro[3,4-d][1,3]dioxol-4-yl)methyl 4-methylbenzenesulfonate

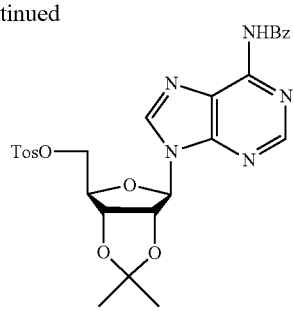

TosCl (15.0 g, 79.0 mmol) in CH$_2$Cl$_2$ (50 mL) was added to a solution of compound obtained in the step 1 above (25.0 g, 60.7 mmol), DMAP (1.4 g, 12.1 mmol) and TEA (12.3 g, 121.5 mmol) in CH$_2$Cl$_2$ (250 mL) at 0° C. The reaction mixture was stirred at 25° C. for 6 h. After completion of the reaction, the reaction mixture was cooled to 0° C. and quenched with a saturated NaHCO$_3$ solution (200 mL). The reaction mixture was diluted with ethyl acetate (200 mL) and the milky aqueous layer was extracted with ethyl acetate (200 mL×2). The combined organic layers were washed with brine (200 mL), dried, concentrated in vacuum to give the crude product which was purified by silica gel column (petroleum ether:ethyl acetate=1:0 to 0:1) to give the desired compound (35.0 g, yield: 76.7%, 75.3% purity) as a white solid. MS (ESI) m/z (M+H)$^+$: 566.0

Step 3. Preparation of N-(9-((3aR,4R,6aS)-2,2-dimethyl-6-methylenetetrahydrofuro[3,4-d][1,3]dioxol-4-yl)-9H-purin-6-yl)benzamide

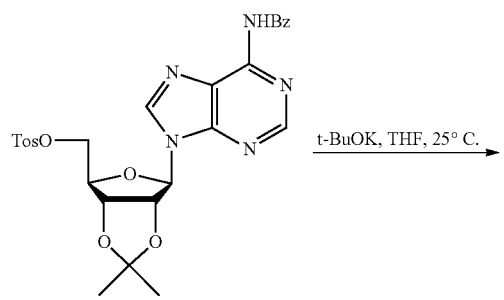

t-BuOK (15.7 g, 139 mmol) was added to a solution of compound of the product of Step 2 above (35.0 g, 46.6 mmol) in THF (400 mL). The resultant mixture was stirred at 25° C. for 2 h. The reaction mixture was added aq. NH$_4$Cl (200 mL) and extracted with ethyl acetate (200 mL×2). The organic phase was dried (Na$_2$SO$_4$) and concentrated under vacuum to give crude product. The crude product was purified by silica gel column (petroleum ether:ethyl acetate=1:0 to 0:1) to give the desired compound (9.7 g, 52.9% yield) as a light yellow solid. $^1$H NMR (400 MHz, DMSO-d$_6$) δ11.24 (s, 1H), 8.72 (s, 1H), 8.58 (s, 1H), 8.02-8.00 (m, 2H), 7.64-7.60 (m, 1H), 7.54-7.50 (m, 2H), 6.58 (s, 1H), 5.63-5.61 (m, 1H), 5.43-5.41 (m, 1H), 4.46 (s, 1H), 4.38-4.37 (m, 1H), 1.47 (s, 3H), 1.35 (s, 3H).

Step 4. Preparation of two isomers of compound N-(9-((3aR,4R,6R,6aS)-6-fluoro-6-(iodomethyl)-2,2-dimethyltetrahydrofuro[3,4-d][1,3]dioxol-4-yl)-9H-purin-6-yl)benzamide

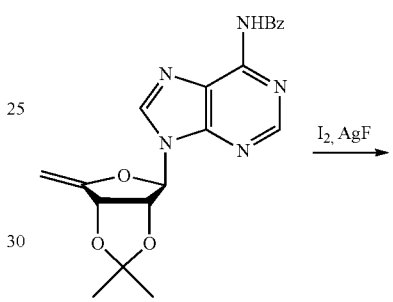

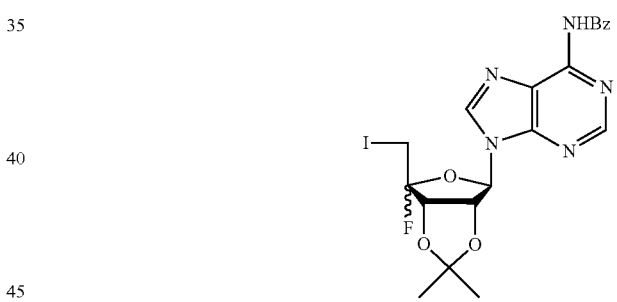

12 (18.0 g, 71.1 mmol) were sequentially added to a solution of the compound of the product of Step 3 above (7 g, 17.7 mmol) in CH$_3$CN (300 mL) at −20° C. Then the solution of AgF (2.26 g, 17.7 mmol) in CH$_3$CN (300 mL) was added. The mixture was stirred at −20° C. to −25° C. for 16 h. The reaction mixture was filtered and concentrated under reduced pressure, then ethyl acetate (300 mL) was added and washed with aqueous sodium hydrogen carbonate (100 mL), the organic phase was washed with brine (100 mL), dried with anhydrous Na$_2$SO$_4$, filtered and concentrated in vacuum. The crude product was purified by silica gel column (petroleum ether:ethyl acetate=1:0 to 0:1) to give the mixture of two isomers of the desired compound (4.00 g, yield: 40.4% yield, 97.1% purity) as light yellow solid. MS (ESI) m/z (M+H)$^+$: 540.0. $^1$H NMR (400 MHz, DMSO-d6) δ11.25 (br, 1H), 8.78-8.75 (m, 1H), 8.64-8.52 (m, 1H), 8.03-8.01 (m, 2H), 7.66-7.61 (m, 1H), 7.55-7.51 (m, 2H), 6.66-6.53 (m, 1H), 5.88-5.86 (m, 0.5H), 5.44-5.37 (m, 1H), 5.29-5.26 (m, 0.5H), 3.65-3.48 (m, 2H), 1.55 (s, 1.5H), 1.52 (s, 1.5H), 1.37 (s, 1.5H), 1.32 (s, 1.5H).

Step 5. Preparation of two isomers of N-(9-((3aR, 4R,6S,6aS)-6-fluoro-6-(hydroxymethyl)-2,2-dimethyltetrahydrofuro[3,4-d][1,3]dioxol-4-yl)-9H-purin-6-yl)benzamide

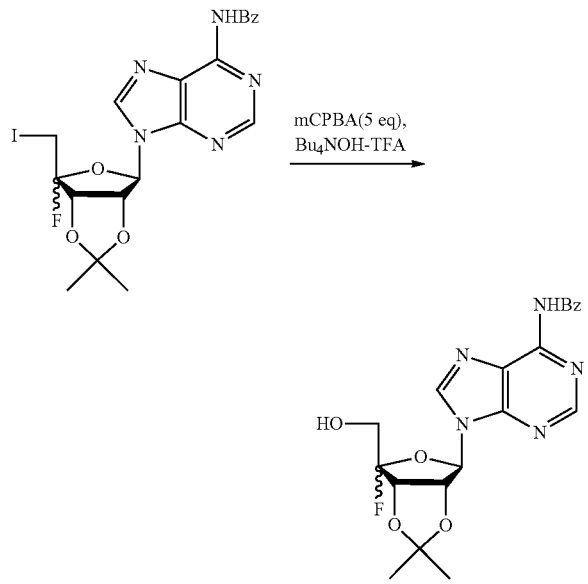

TFA (3.80 g, 33.3 mmol) and tetra(n-butyl)ammonium hydroxide (5.19 g, 19.9 mmol) were added to a solution of the mixture of the two isomers obtained from step 4 above (3.70 g, 6.66 mmol) in CH$_2$Cl$_2$ (80 mL), followed by addition of m-CPBA (6.76 g, 33.3 mmol, 85% purity) at 25° C. The mixture was stirred at 25° C. for 16 h. The reaction mixture was washed with sat. Na$_2$SO$_3$ solution (20 mL) and aq. NaHCO$_3$ solution (20 mL). The organic layer was dried over anhydrous Na$_2$SO$_4$, and concentrated at low pressure. The crude product was purified by silica gel column (petroleum ether:ethyl acetate=1:0 to 0:1) to give the mixture of the desired two isomers (1.20 g, yield: 39.8%, 94.9% purity) as light yellow solid. MS (ESI) m/z (M+H)$^+$: 430.0. $^1$H NMR (400 MHz, DMSO-d6) δ 11.23 (br. s, 1H), 8.79-8.73 (m, 1H), 8.62 (s, 0.3H), 8.54-8.48 (m, 0.7H), 8.05-7.98 (m, 2H), 7.65-7.59 (m, 1H), 7.56-7.49 (m, 2H), 6.63 (s, 0.3H), 6.48 (s, 0.7H), 5.81-5.75 (m, 1H), 5.41-5.32 (m, 1H), 5.21-5.14 (m, 1H), 3.80-3.54 (m, 2H), 1.52 (s, 1H), 1.50 (s, 2H), 1.36 (s, 2H), 1.32 (s, 1H).

Step 6. Preparation of the two isomers of ((3aS,4S, 6R,6aR)-6-(6-benzamido-9H-purin-9-yl)-4-fluoro-2, 2-dimethyltetrahydrofuro[3,4-d][1,3]dioxol-4-yl) methyl dibenzyl phosphate

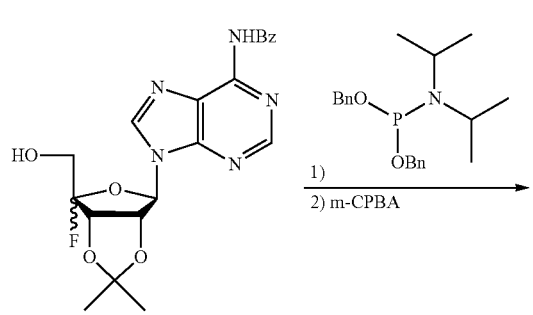

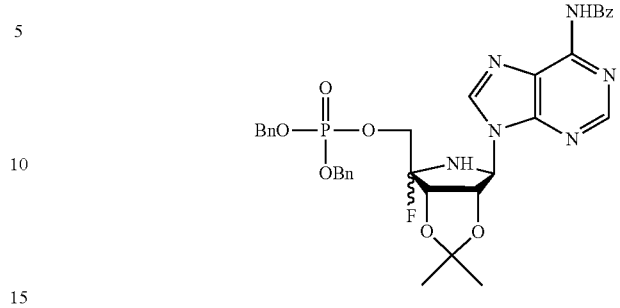

To a mixture of the two isomers obtained from step 5 above (850 mg, 1.98 mmol) and 1H-imidazole-4,5-dicarbonitrile (467 mg, 3.96 mmol) in CH$_2$Cl$_2$ (50 mL) and CH$_3$CN (17 mL) was added N-dibenzyloxyphosphanyl-N-isopropylpropan-2-amine (1.37 g, 3.96 mmol) at 0° C. The reaction mixture was stirred for 10 min and then warmed to 25° C. The resultant mixture was stirred for another 2 h and cooled to 0° C. again. m-CPBA (803 mg, 3.96 mmol, 85% purity) was added directly, and the reaction was slowly warmed to 25° C. and stirred for 2 h. The reaction was quenched with saturated NaHCO$_3$ (50 mL) and the organic phase was separated. The water phase was extracted with CH$_2$Cl$_2$ (50 mL×2). The combined organic phases were dried over anhydrous Na$_2$SO$_4$, filtered and concentrated under reduced pressure. The crude product was purified by silica gel column (petroleum ether:ethyl acetate=1:0 to 0:1) to give the desired two isomers (1.10 g, yield: 73.2%, 90.8% purity) as light yellow solid. MS (ESI) m/z (M+H)$^+$: 690.1. $^1$H NMR (400 MHz, DMSO-d6) δ 11.25 (br. s, 1H), 8.75 (s, 0.7H), 8.64 (s, 0.3H), 8.61 (s, 0.3H), 8.54 (s, 0.7H), 8.01 (d, J=8.4 Hz, 2H), 7.66-7.58 (m, 1H), 7.56-7.48 (m, 2H), 7.36-7.24 (m, 10H), 6.73 (s, 0.3H), 6.57 (s, 0.7H), 5.85 (d, J=5.6 Hz, 0.7H), 5.51-5.42 (m, 0.3H), 5.41-5.37 (m, 0.3H), 5.30 (t, J=6.0 Hz, 0.7H), 5.05-4.94 (m, 4H), 4.37-4.14 (m, 2H), 1.51 (s, 1H), 1.46 (s, 2H), 1.34 (s, 2H), 1.32 (s, 1H).

Step 7. Preparation of two isomers of ((3aS,4S,6R, 6aR)-6-(6-amino-9H-purin-9-yl)-4-fluoro-2,2-dimethyltetrahydrofuro[3,4-d][1,3]dioxol-4-yl)methyl dibenzyl phosphate

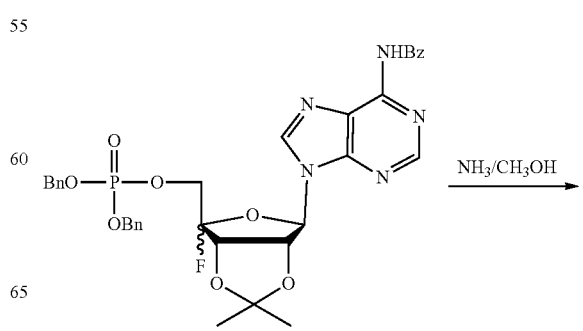

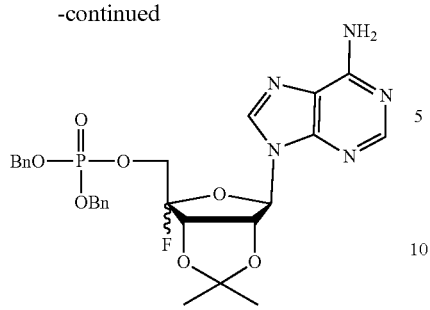

The two isomers obtained from step 6 above (1.10 g, 1.45 mmol) were dissolved in NH₃/MeOH (20 mL, 7M). The reaction mixture was stirred at 25° C. for 16 h. The reaction mixture was concentrated under reduced pressure to afford the crude product which was purified by silica gel column (petroleum ether:ethyl acetate=1:0 to 0:1 then CH$_2$Cl$_2$: MeOH=10:2) to give the desired isomers (710 mg, yield: 77.5%, 92.7% purity) as light yellow solid. MS (ESI) m/z (M+H)⁺=586.1.

Step 8. Preparation of the two isomers of ((3aS,4S, 6R,6aR)-6-(6-amino-9H-purin-9-yl)-4-fluoro-2,2-dimethyltetrahydrofuro[3,4-d][1,3]dioxol-4-yl) methyl dihydrogen phosphate

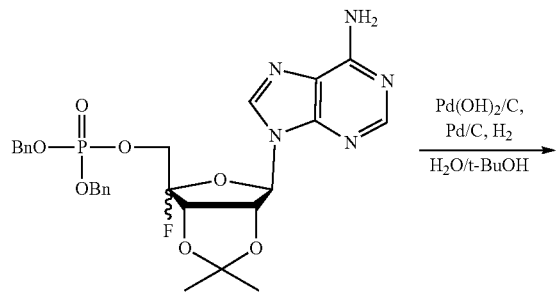

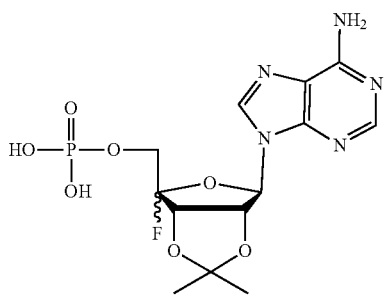

The mixture of two isomers obtained from step 7 above (600 mg, 1.02 mmol) in t-BuOH (20 mL) and H₂O (20 mL) was mixed with Pd(OH)₂ (300 mg, 427.23 μmol, 20%) and Pd/C (50 mg, 1.02 mmol, 10%), then the reaction mixture was stirred at 25° C. for 16 h under N₂ atmosphere (45 psi). Filtered and the filtrate was concentrated to give the desired isomers (200 mg, crude) as light yellow solid. ¹H NMR (400 MHz, DMSO-d₆) δ 8.26-8.17 (m, 2H), 6.59-6.46 (m, 1H), 5.68 (d, J=8.0 Hz, 1H), 5.57-5.45 (m, J=11.7 Hz, 1H), 5.37-5.30 (m, 1H), 4.21-4.06 (m, 2H), 1.80-1.52 (m, 3H), 1.49-1.35 (m, 3H).

Step 9. Preparation of ((3aS,4S,6R,6aR)-6-(6-amino-9H-purin-9-yl)-4-fluoro-2,2-dimethyltetrahydrofuro[3,4-d][1,3]dioxol-4-yl)methyl hydrogen morpholinophosphonate DCC morpholine salt

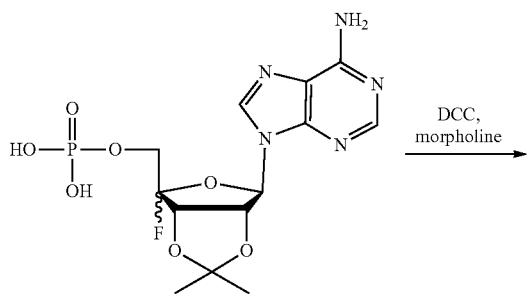

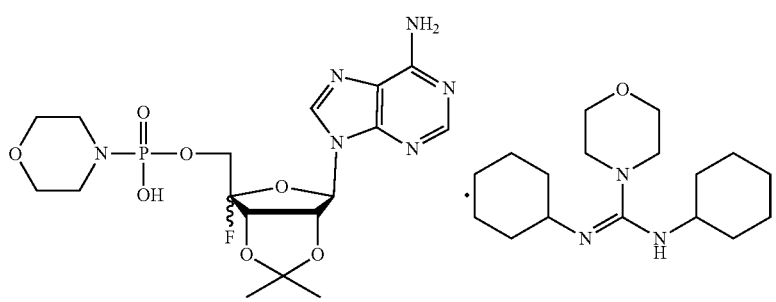

The solution of DCC (407 mg, 1.97 mmol) in t-BuOH (10 mL) was added dropwise to the solution of two isomers obtained from step 8 above (200 mg, 493 µmol) and morpholine (171 mg, 1.97 mmol) in $H_2O$ (10 mL) and t-BuOH (10 mL) under 80-90° C. The solution was stirred at 80-90° C. for 16 h under $N_2$. The reaction was cooled to room temperature and the solvent was removed to give the residue. The residue was dissolved in $H_2O$ (10 mL) and extracted with TBME (10 mL×2), the aqueous phase was concentrated under reduced pressure to give the desired isomers (310 mg, crude) as light yellow solid. $^1$H NMR (400 MHz, $D_2O$) δ 8.41-8.17 (m, 2H), 6.70-6.50 (m, 1H), 5.81-5.68 (m, 1H), 5.62-5.46 (m, 1H), 5.42-5.28 (m, 1H), 4.34-4.09 (m, 1H), 4.07-4.00 (m, 1H), 3.88-3.74 (m, 5H), 3.73-3.55 (m, 2H), 3.51-3.22 (m, 8H), 3.07-3.02 (m, 1H), 2.96-2.91 (m, 1H), 2.87-2.78 (m, 2H), 1.90 (br s, 4H), 1.81-1.70 (m, 4H), 1.68-1.57 (m, 5H), 1.51-1.44 (m, 3H), 1.39-1.26 (m, 8H), 1.19-1.08 (m, 2H).

Step 10. Preparation of two isomers of (2S,3S,4S,5R,6R)-2-(((((((3aS,6R,6aR)-6-(6-amino-9H-purin-9-yl)-4-fluoro-2,2-dimethyltetrahydrofuro[3,4-d][1,3]dioxol-4-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate The two isomers obtained from step 9 above (310 mg, 403 µmol) and the product from step 14 of in the preparation of Compound 1 above (226 mg, 322 µmol) was dried over dry pyridine (10 mL×3). The mixture was dissolved with pyridine (15 mL). 1H-tetrazole (94.2 mg, 1.35 mmol) was added and stirred at 25° C. for 72 h. The solvent was removed to give a residue. The residue was purified by silica gel column chromatography (DCM:MeOH (including 2% $NH_3 \cdot H_2O$)=1:0 to 1:1) to give crude desired product (170 mg, crude) as white solid. The crude product (60 mg) was purified by Pre-HPLC (column: Waters Xbridge 150*25 5 u; mobile phase: [water (10 mM $NH_4HCO_3$)-ACN]; B %: 0%-35%,10 min) to give isomer 1 (17 mg) and isomer 2 (7 mg).

Isomer 1: $^1$H NMR (400 MHz, $D_2O$) δ 8.24-8.11 (m, 2H), 6.46 (s, 1H), 5.41 (dd, J=11.7, 6.6 Hz, 1H), 5.35-5.23 (m, 2H), 5.19 (d, J=6.4 Hz, 1H), 5.09-4.85 (m, 3H), 4.26-3.97 (m, 3H), 3.91 (dd, J=12.1, 7.2 Hz, 1H), 3.77 (br d, J=9.8 Hz, 1H), 1.98 (s, 3H), 1.91 (s, 3H), 1.89 (s, 3H), 1.82 (s, 3H), 1.78 (s, 3H), 1.47 (s, 3H), 1.25 (s, 3H)

Isomer 2: $^1$H NMR (400 MHz, $D_2O$) δ 8.24-8.07 (m, 2H), 6.50-6.36 (m, 1H), 5.57 (d, J=5.6 Hz, 1H), 5.47-5.24 (m, 2H), 5.23-5.13 (m, 1H), 5.09-4.85 (m, 4H), 4.24-4.10 (m, 2H), 4.03 (dd, J=12.0, 7.1 Hz, 1H), 3.80 (dd, J=10.0, 2.7 Hz, 1H), 1.98 (s, 3H), 1.95 (s, 3H), 1.93 (s, 3H), 1.84 (s, 3H), 1.77 (s, 3H), 1.44 (s, 3H), 1.27 (s, 3H)

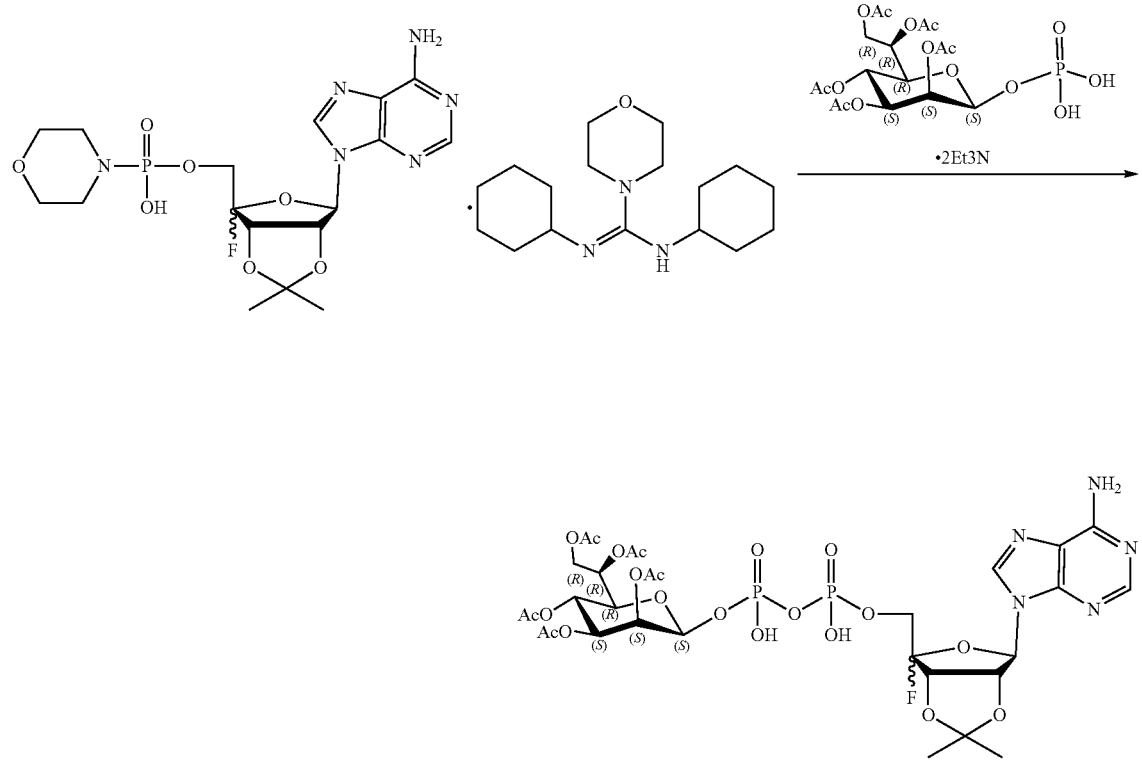

Compound 20

(2S,3S,4S,5R,6R)-2-(((((((2S,3S,4R,5R)-5-(6-amino-9H-purin-9-yl)-2-fluoro-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate The solution of two isomers obtained from step 10 of in the preparation of Compound 19 above (80.0 mg, 90.1 μmol) in TFA (0.6 mL) and H₂O (0.4 mL) was stirred at 25° C. for 0.5 h. The mixture was adjusted to pH=7 with Et₃N and concentrated to give crude product. The crude product was purified by Pre-HPLC (column: Waters Xbridge 150*25 5 u; mobile phase: [water (10 mM NH₄HCO₃)-ACN]; B %: 0%-35%, 9 min) to give one isomer (10 mg, 11.8 μmol, 13.1% yield) MS (ESI) m/z (M+H)⁺: 848.2 ¹H NMR (400 MHz, METHANOL-d₄) δ 8.37 (s, 1H), 8.13 (s, 1H), 6.26 (br s, 1H), 5.55-5.37 (m, 2H), 5.08 (br s, 3H), 4.86-4.70 (m, 1H), 4.44 (d, J=5.8 Hz, 1H), 4.32 (br d, J=12.0 Hz, 1H), 4.23-4.04 (m, 3H), 3.84 (br s, 1H), 3.22-3.16 (m, 7H), 2.01 (s, 3H), 1.93 (s, 3H), 1.88 (s, 3H), 1.80 (s, 3H), 1.72 (s, 3H). ¹⁹F δ -123.7, ³¹P δ -13.22 and -15.21.

Compound 21

(2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((S)-1,2-diacetoxyethyl)tetrahydro-2H-pyran-3,4,5-triyl triacetate

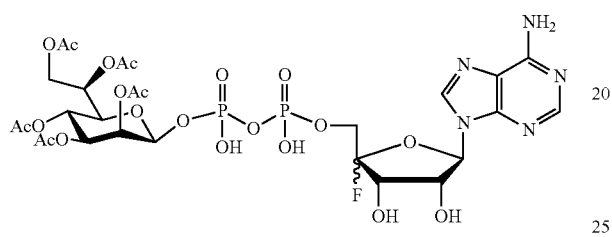

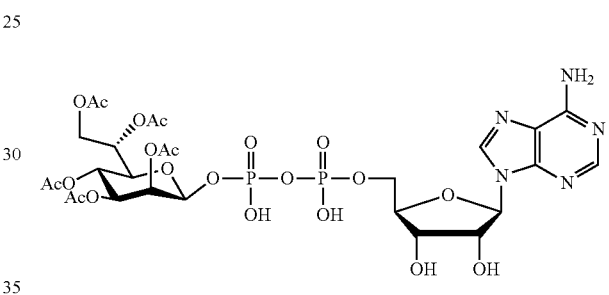

Step 1. Preparation of Compound (2S,3S,4S,5R,6R)-2-(((((((3S,4R,5R)-5-(6-amino-9H-purin-9-yl)-2-fluoro-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

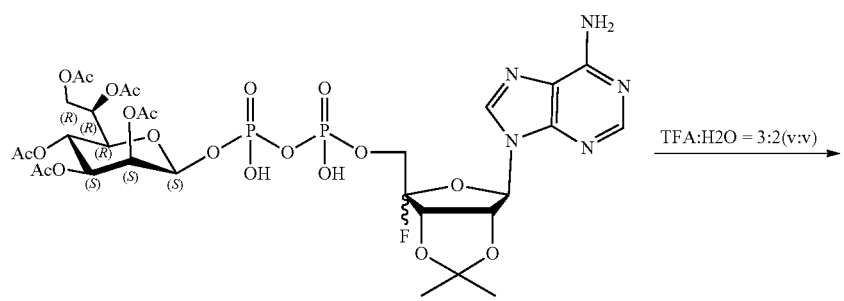

TFA:H2O = 3:2(v:v)

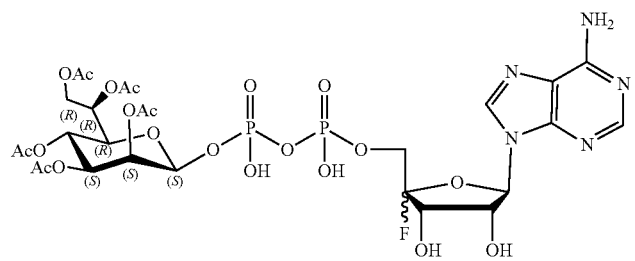

Step 1. Preparation of (2S,3S,4S,5R,6R)-2-((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((S)-1,2-diacetoxyethyl)tetrahydro-2H-pyran-3,4,5-triyl triacetate

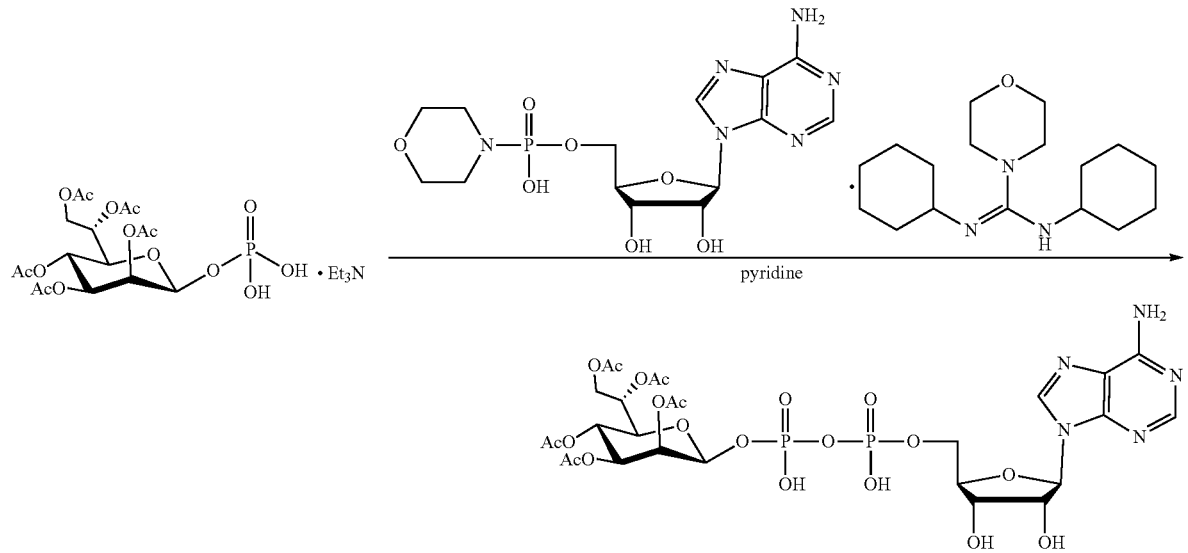

The mixture of compound (2R,3R,4S,5S,6S)-2-((S)-1,2-diacetoxyethyl)-6-(phosphonooxy)tetrahydro-2H-pyran-3,4,5-triyl triacetate trimethylamine salt (200 mg, 399.72 μmol; Inuki et al. *Org. Lett.* 2017, 19, 3079-3082; Zamyatina et al. *Carbohydrate Research* (2003), 338: 2571-2589) and compound AMP-morpholidate (4'-morpholine-N,N'-dicyclohexylcarboxamidinium salt) (360 mg, 864.71 μmol) was dried in pyridine (5 mL×3). Then the residue was redissolved in pyridine (5 mL). 1H-Tetrazole (100 mg, 1.43 mmol) was added. The solution was stirred at 30° C. for 24 h. The solvent was removed in vacuo. The residue was dissolved in MeOH (5 mL). The solid was filtered off. The filtrate was collected and concentrated. The residue was purified by column (DCM:(MeOH:NH$_3$.H$_2$O 50:1)=1:0~1:1.2) to give crude product which was repurified by prep-HPLC (column: Waters Xbridge 150*25 5 u; mobile phase: [water (10 mM NH$_4$HCO$_3$)-ACN]; B %: 0%-35%, 10 min) to give the desired compound (68 mg, yield: 20.24%) as white solid. MS (ESI) m/z (M+H)$^+$: 830.2. $^1$H NMR (400 MHz, CD$_3$OD) δ 8.59 (s, 1H), 8.19 (s, 1H), 6.08 (d, J=5.2 Hz, 1H), 5.62-5.57 (m, 1H), 5.55-5.47 (m, 1H), 5.28-5.22 (m, 1H), 5.19-5.12 (m, 2H), 4.65-4.57 (m, 1H), 4.49-4.39 (m, 2H), 4.33-4.15 (m, 4H), 3.94-3.84 (m, 1H), 2.14 (s, 3H), 2.05 (s, 3H), 1.96 (s, 3H), 1.93 (s, 3H), 1.89 (s, 3H).

Compound 22

Adenosine-5'-(L-glycero-β-D-mannoheptopyranosyl) diphosphate

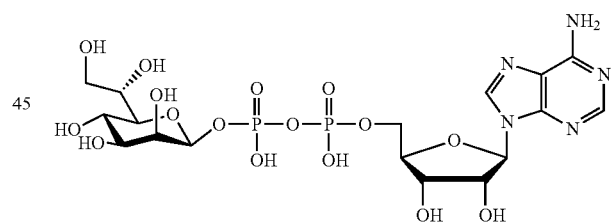

Step 1. Preparation of Adenosine-5'-(L-glycero-β-D-mannoheptopyranosyl) diphosphate

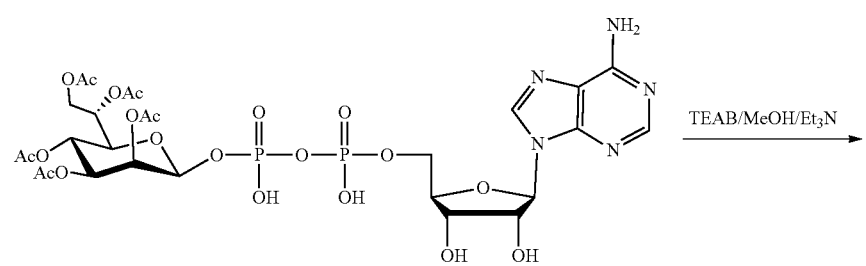

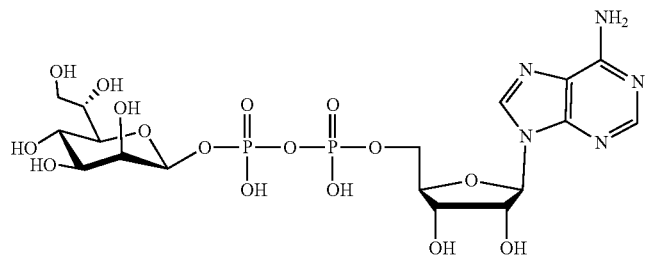

The compound of the product of Step 1 in the preparation of Compound 21 above (14.4 mg, 17.36 μmol) in 2 mL of (0.1 M TEAB (8 mL), MeOH (6 mL) and TEA (0.1 mL) was stirred at −20° C. for 56 h. The solution was freeze dried in vacuo to give the desired compound as trimethylamine salt (8 mg, yield: 30.51%), as a white sticky solid. MS (ESI) m/z (M−H)$^+$: 617.9. $^1$H NMR (400 MHz, D$_2$O) δ 8.30 (s, 1H), 8.04 (s, 1H), 6.00-5.92 (m, 1H), 5.04-4.99 (m, 1H), 4.58-4.54 (m, 1H), 4.25-4.33 (m, 1H), 4.23-4.15 (m, 1H), 4.09-3.97 (m, 3H), 3.91-3.85 (m, 1H), 3.76-3.67 (m, 1H), 3.55-3.42 (m, 3H), 3.17-3.10 (m, 1H), 3.00-2.94 (m, 14H), 1.08-1.03 (m, 22H).

Compound 23

(2R,3R,4S,5S,6S)-2-(acetoxymethyl)-6-(((((((2R,3R,4R,5R)-3,4-diacetoxy-5-(6-amino-9H-purin-9-yl)tetrahydrofuran-2-yl)methoxy)(hydroxy)phosphorothioyl)oxy)(hydroxy)phosphoryl)oxy)tetrahydro-2H-pyran-3,4,5-triyl triacetate

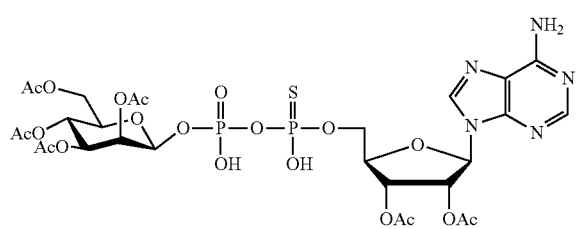

Step 1. Preparation of ((2-cyanoethoxy)(((2R,3R,4R,5R)-3,4-diacetoxy-5-(6-(tritylamino)-9H-purin-9-yl)tetrahydrofuran-2-yl)methoxy)phosphanyl)dipropylamine

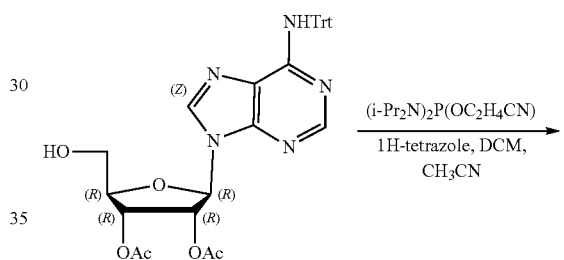

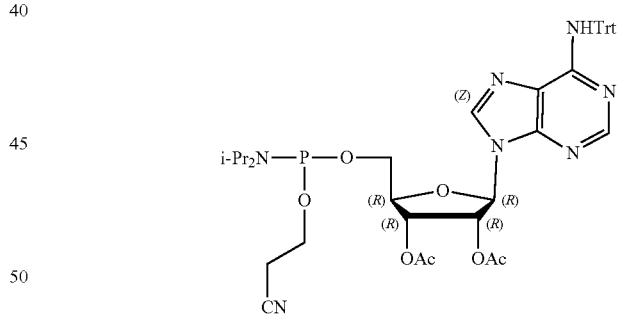

1H-tetrazole (71 mg, 1.01 mmol) in CH$_3$CN (1.5 mL) was added dropwise to a solution of compound of Step 7 in the preparation of Compound 7 above (300 mg, 0.51 mmol) and 3-bis(diisopropylamino)phosphanyloxypropanenitrile (304 mg, 1.01 mmol, 320 μL) in DCM (7.5 mL) under N$_2$ atmosphere at 0° C. The resulting mixture was stirred at 25° C. for 2 h. After completion of the reaction, the mixture was filtered and concentrated under reduced pressure to give crude product, which was purified by silica gel column (PE:EA=1:0 to 1:1) to give the desired compound (80 mg, yield: 19.0%, 89% purity) as colorless oil. MS (ESI) m/z (M+H)$^+$: 711.1 (hydrolyzed mass).

Step 2. Preparation of (2R,3R,4S,5S,6S)-2-(acetoxymethyl)-6-(((((2-cyanoethoxy)(((2R,3R,4R,5R)-3,4-diacetoxy-5-(6-(tritylamino)-9H-purin-9-yl)tetrahydrofuran-2-yl)methoxy)phosphorothioyl)oxy)(hydroxy)phosphoryl)oxy)tetrahydro-2H-pyran-3,4,5-triyl triacetate

5

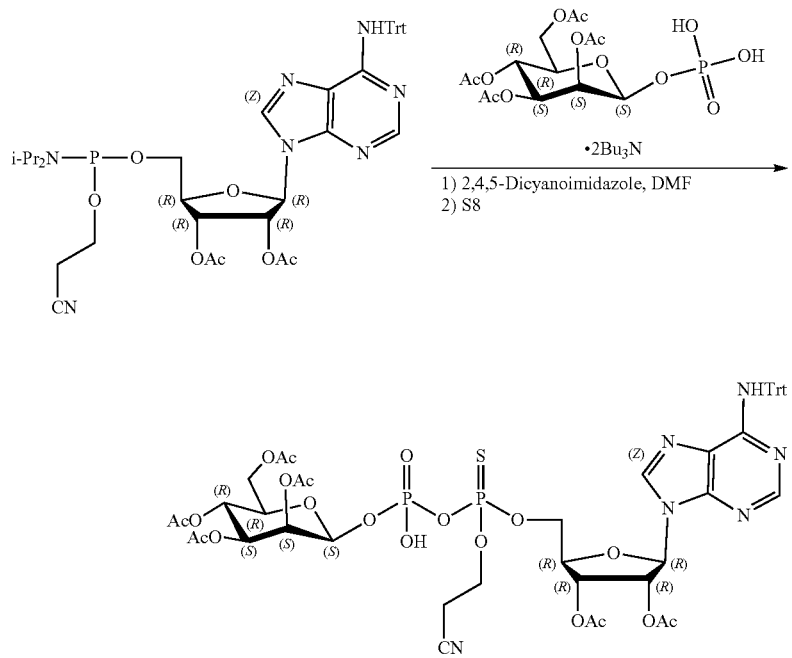

4,5-Dicyanoimidazole (24 mg, 203 µmol) was added to a solution of compound of product of Step 1 above (80 mg, 0.10 mmol) and compound of product of Step 4 in the preparation of Compound 5 (121 mg, 151 µmol) in DMF (3 mL) under N₂ atmosphere. The resulting mixture was stirred at 25° C. for 1 h. Then sulfur (5 mg, 151 µmol) was added. The resultant mixture was stirred at 25° C. for another 0.5 h. After completion of the reaction, the mixture was directly purified by pre-HPLC (column: Waters Xbridge 150*25 5 u; mobile phase: [water (10 mM NH4HCO3)-ACN]; B %: 38%-64.25%, 7 min) to afford the desired compound (23 mg, yield: 15.8%, 80% purity) as a white solid. MS (ESI) m/z (M+H)⁺: 1153.5.

Step 3. Preparation of Compound (2R,3R,4S,5S,6S)-2-(acetoxymethyl)-6-(((((2-cyanoethoxy)(((2R,3R,4R,5R)-3,4-diacetoxy-5-(6-amino-9H-purin-9-yl)tetrahydrofuran-2-yl)methoxy)phosphorothioyl)oxy)(hydroxy)phosphoryl)oxy)tetrahydro-2H-pyran-3,4,5-triyl triacetate

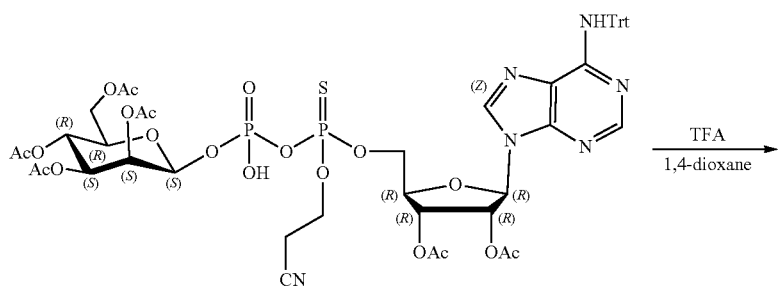

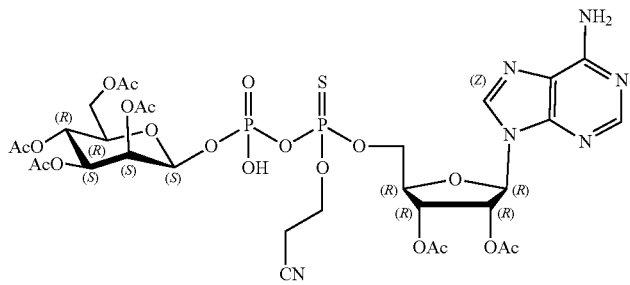

TFA (616 mg, 5.40 mmol, 0.4 mL) was added to a solution of compound of product of Step 2 above (5 mg, 4.34 µmol) in dioxane (0.6 mL). The resulting mixture was stirred at 40° C. for 2 h. After completion of the reaction, the mixture was diluted with ethyl acetate (10 mL), and washed with saturated NaHCO$_3$ (10 mL). The organic phase was dried over anhydrous Na$_2$SO$_4$, filtered and concentrated under reduced pressure to give compound G-3 (6 mg, crude) as light yellow syrup, which was used directly in next step. MS (ESI) m/z (M+H)$^+$: 909.9.

Step 4. Preparation of Compound (2R,3R,4S,5S,6S)-2-(acetoxymethyl)-6-((((((2R,3R,4R,5R)-3,4-diacetoxy-5-(6-amino-9H-purin-9-yl)tetrahydrofuran-2-yl)methoxy)(hydroxy)phosphorothioyl)oxy)(hydroxy)phosphoryl)oxy)tetrahydro-2H-pyran-3,4,5-triyl triacetate DBU (3.30 mg, 21.7 µmol, 3.3 µL) was added to a solution of compound of Step 3 above (5 mg, 4.34 µmol) in CH$_3$CN (0.5 mL). The reluting mixture was stirred at 25° C. for 0.5 h. After completion of the reaction, the mixture was diluted with ethyl acetate (10 mL), and washed with 1N HCl (10 mL). The organic phase was dried over anhydrous Na$_2$SO$_4$, filtered and concentrated under reduced pressure to give the desired cude compound (7 mg) as light yellow syrup, which was purified by pre-HPLC (column: Boston Green ODS 150*30 5 u; mobile phase: [water (0.075% TFA)-ACN]; B %: 30%-50%,7.5 min) to afford the desired compound. MS (ESI) m/z (M+H)$^+$: 858.5.

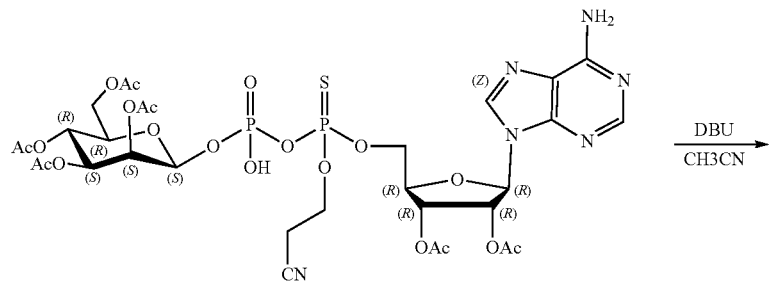

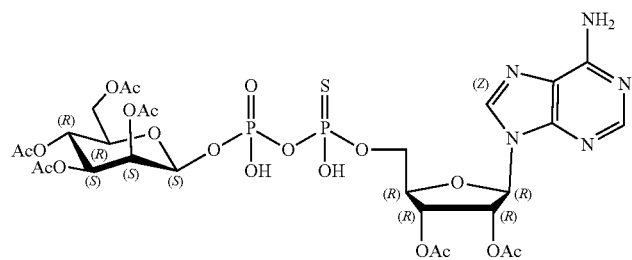

153

Compound 24

Adenosine-(5'-(Mannose-pyranosyl)(hydroxy)phosphorothioyloxyphosphate

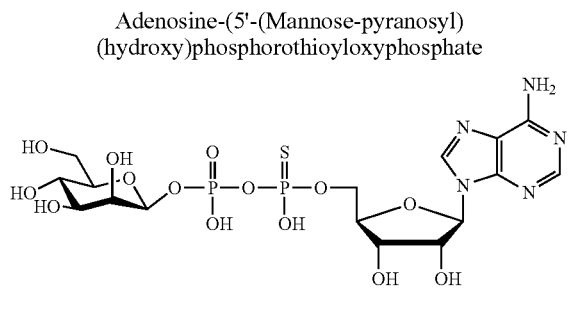

Step 1. Preparation of Adenosine-(5'-(Mannose-pyranosyl)(hydroxy)phosphorothioyloxyphosphate

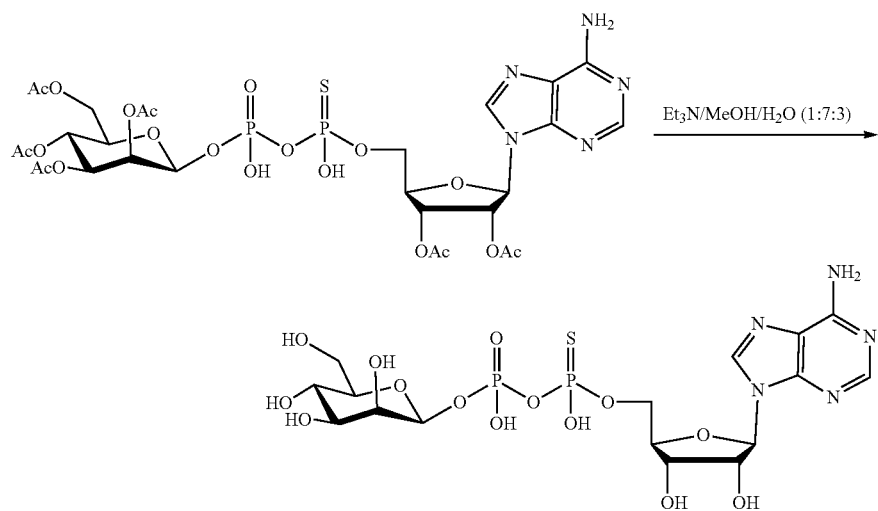

A solution of compound of the product of Step 4 in the preparation of Compound 23 above is dissolved in 7:3:1 ratio of MeOH/water/Et₃N solution was stirred at 25° C. for 10 h. After completion of the reaction, the mixture is concentrated and lyophilised from water to give the desired compound.

154

Compound 25

(2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

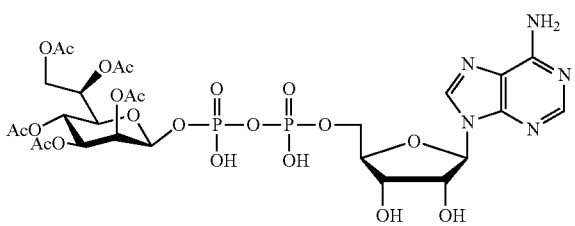

Step 1. The preparation of (2S,3S,4S,5R,6R)-2-(((((((2R,3S,4R,5R)-5-(6-amino-9H-purin-9-yl)-3,4-dihydroxytetrahydrofuran-2-yl)methoxy)(hydroxy)phosphoryl)oxy)(hydroxy)phosphoryl)oxy)-6-((R)-1,2-diacetoxyethyl)tetrahydro-2H-pyran-3,4,5-triyl triacetate

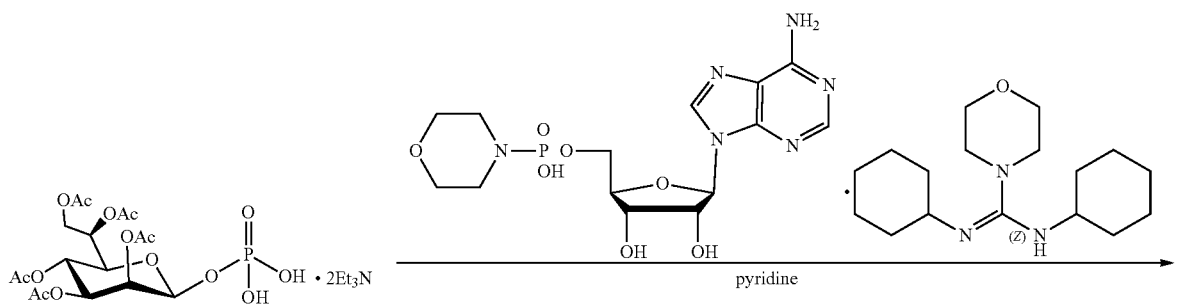

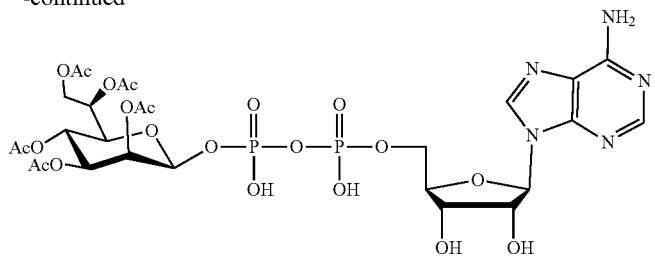

The mixture of compound of the product of Step 14 in the preparation of Compound 1 above (220 mg, 439.70 μmol) and AMP-morpholidate (4'-morpholine-N,N'-dicyclohexyl-carboxamidinium salt) (549.2 mg, 1.32 mmol) was dried in pyridine (5 mL×3). Then the residue was re-dissolved in pyridine (5 mL), and 1H-tetrazole (154.01 mg, 2.20 mmol) was added. The solution was stirred at 30° C. for 48 h. The solvent was removed in vacuo. The residue was dissolved in MeOH (10 mL). The solid was filtered off. The filtrate was collected and concentrated. The residue was purified by column (DCM: (MeOH: $NH_3.H_2O=50:1$)=1:0~1.2:1) to give the crude product (140 mg), which was re-purified by prep-HPLC column: Waters Xbridge 150*25 5 u; mobile phase: [water (10 mM $NH_4HCO_3$)-ACN]; B %: 0%-35%, 10 min) to afford the desired compound (50 mg, yield 13.6%) as white solid. $^1$H NMR (400 MHz, methanol-d4) δ 8.58 (s, 1H), 8.18 (s, 1H), 6.07 (d, J=5.2 Hz, 1H), 5.53-5.56 (br. s, 2H), 5.16-5.22 (m, 3H), 4.60-4.63 (m, 1H), 4.40-4.46 (m, 2H), 4.19-4.24 (m, 4H), 3.87-3.89 (m, 1H), 2.13 (s, 3H), 2.04-2.03 (s, 3H), 2.03 (s, 3H), 1.99 (s, 3H), 1.92 (s, 3H). MS (ESI) m/z (M+H)$^+$: 830.4.

Compound 26

(2S,3S,4S,5R,6R)-2-(((((((2R,3S,4S,5R)-5-(6-amino-9H-purin-9-yl)-3-fluoro-4-hydroxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate

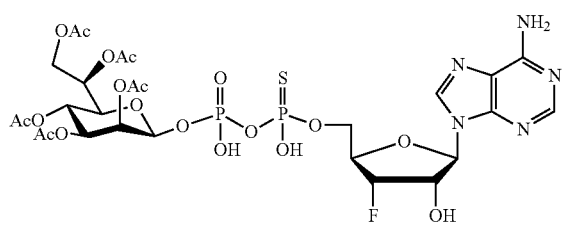

Step 1. Preparation of Compound ((2R,3R,4S,5R)-3-fluoro-4-((4-methoxybenzyl)oxy)-5-(6-(tritylamino)-9H-purin-9-yl)tetrahydrofuran-2-yl)methanol

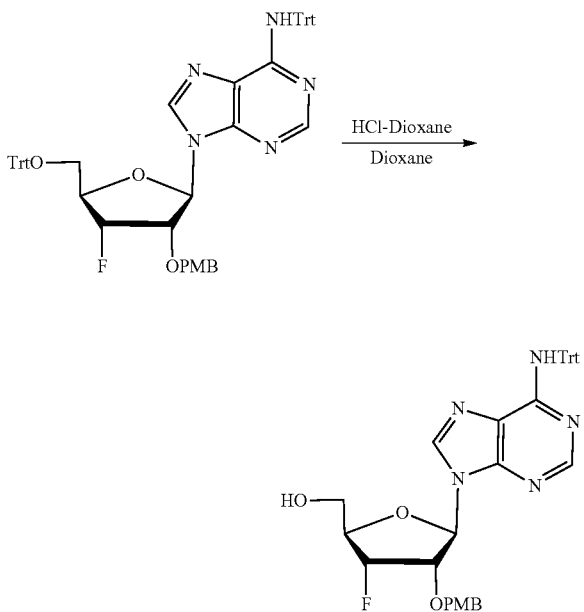

To a mixture of compound of product of Step 5 in Example 1 (4.1 g, 4.6 mmol) in dioxane (100 mL) was added HCl-dioxane (4 M, 10 mL) dropwise. The mixture was stirred at 26° C. for 30 min. After completion of the reaction, the mixture was diluted with EA (500 mL) and washed with saturated $NaHCO_3$ (100 mL×3) and brine (100 mL×3). The organic layer was dried over anhydrous $Na_2SO_4$, filtered and concentrated under reduced pressure to give the residue. The residue was purified by column chromatography (PE: EA=1:0 to 1:1) to afford the desired compound (1.8 g, yield: 60.7%) as a white solid. MS (ESI) m/z (M+H)$^+$: 646.1. $^1$H NMR (400 MHz, DMSO-d$_6$) δ 8.42 (s, 1H), 7.86 (s, 1H), 7.34-7.19 (m, 15H), 7.03 (d, J=8.6 Hz, 2H), 6.74 (d, J=8.8 Hz, 2H), 6.06 (d, J=8.1 Hz, 1H), 5.58-5.52 (m, 1H), 5.46-5.22 (m, 1H), 4.98-4.89 (m, 1H), 4.57-4.26 (m, 4H), 3.70 (s, 3H), 3.63-3.60 (m, 2H).

Step 2. Preparation of Compound ((2R,3R,4S,5R)-3-fluoro-4-((4-methoxybenzyl)oxy)-5-(6-(tritylamino)-9H-purin-9-yl)tetrahydrofuran-2-yl)methyl hydrogen phosphonate

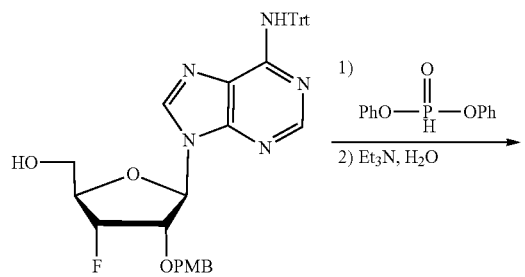

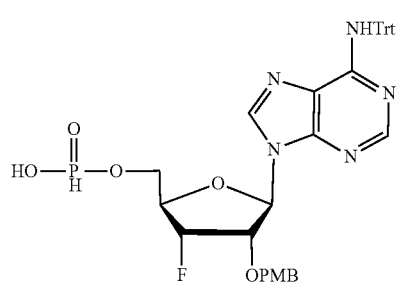

To a solution of compound of product of Step 1 above (1.8 g, 2.8 mmol) in pyridine (6 mL) was added phenoxyphosphonoyloxybenzene (1.65 mL, 8.6 mmol). The mixture was stirred at 25° C. for 2 h. Then TEA (1.45 g, 14.37 mmol, 2 mL) and H₂O (515 μL, 28.5 mmol) were added to the mixture. The mixture was stirred at 25° C. for another 0.5 h. After completion of the reaction, the mixture was concentrated under reduced pressure. The crude product was purified by silica gel column chromatography (DCM:MeOH=20:1 to 10:1, adding 0.5% Et₃N) to afford the desired compound (2 g, yield: 90%) as light yellow oil. MS (ESI) m/z (M+H)⁺: 696.2.

Step 3. Preparation of Compound O-(((2R,3R,4S,5R)-3-fluoro-4-((4-methoxybenzyl)oxy)-5-(6-(tritylamino)-9H-purin-9-yl)tetrahydrofuran-2-yl)methyl) O,O-dihydrogen phosphorothioate triethyl amine salt

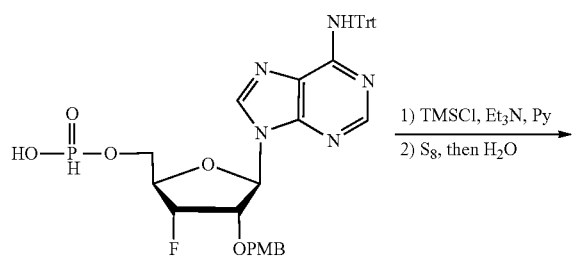

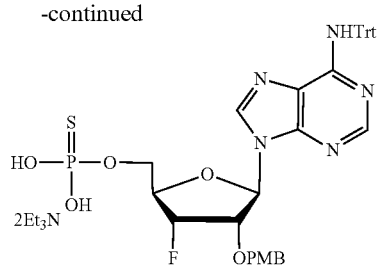

To a solution of compound of product of Step 2 above (2 g, 2.8 mmol) in pyridine (5 mL) and Et₃N (5 mL) was added TMSCl (1.82 mL, 14.3 mmol) dropwise over 15 min under N₂ atmosphere. The mixture was stirred at 0° C. for 1 h, and then sulfur (555 mg, 17.3 mmol) was added. The mixture was stirred at 0° C. for another 45 min. After completion of the reaction, the reaction was quenched with H₂O (10 mL) and the mixture was concentrated under reduced pressure to give crude product, which was purified by silica gel chromatography (DCM:MeOH=20:1 to 10:1, adding 0.5% Et₃N) to afford the desired compound (900 mg, yield 43%) as a yellow syrup. MS (ESI) m/z (M+H)⁺: 728.3. $^1$H NMR (400 MHz, DMSO-d₆) δ 8.60 (s, 1H), 7.87 (s, 1H), 7.45 (s, 1H), 7.37-7.23 (m, 15H), 7.08 (d, J=8.5 Hz, 2H), 6.75 (d, J=8.8 Hz, 2H), 6.05 (d, J=8.0 Hz, 1H), 5.60-5.35 (m, 1H), 5.14-4.96 (m, 1H), 4.63-4.34 (m, 3H), 4.11-3.82 (m, 2H), 3.69 (s, 3H), 3.12-2.89 (m, 12H), 1.19 (t, J=7.3 Hz, 18H).

Step 4. Preparation of Compound (2R,3R,4S,5S,6S)-2-((R)-1,2-diacetoxyethyl)-6-((hydroxy(1H-imidazol-1-yl)phosphoryl)oxy)tetrahydro-2H-pyran-3,4,5-triyl triacetate

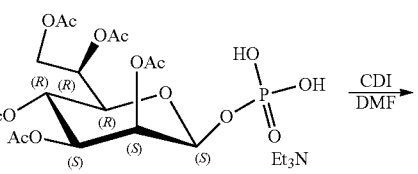

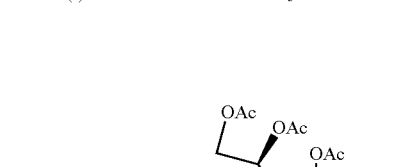

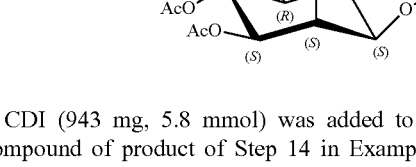

CDI (943 mg, 5.8 mmol) was added to a solution of compound of product of Step 14 in Example 1 (350 mg, 581.8 μmol, Et₃N) in anhydrous DMF (15 mL) under N₂ atmosphere. The resulting mixture was stirred at 25° C. for 3 h. After completion of the reaction, MeOH (0.28 mL) was added to quench the reaction, the mixture was concentrated under reduced pressure to give the desired compound (1 g, crude), which was used directly in next step.

Step 5. Preparation of Compound (2R,3R,4S,5S, 6S)-2-((R)-1,2-diacetoxyethyl)-6-(((((((2R,3R,4S, 5R)-3-fluoro-4-((4-methyloxybenzyl)oxy)-5-(6-(tritylamino)-9H-purin-9-yl)tetrahydrofuran-2-yl) methoxy)(hydroxy)phosphorothioyl)oxy)(hydroxy) phosphoryl)oxy)tetrahydro-2H-ptran-3,4,5-triyltriacetate

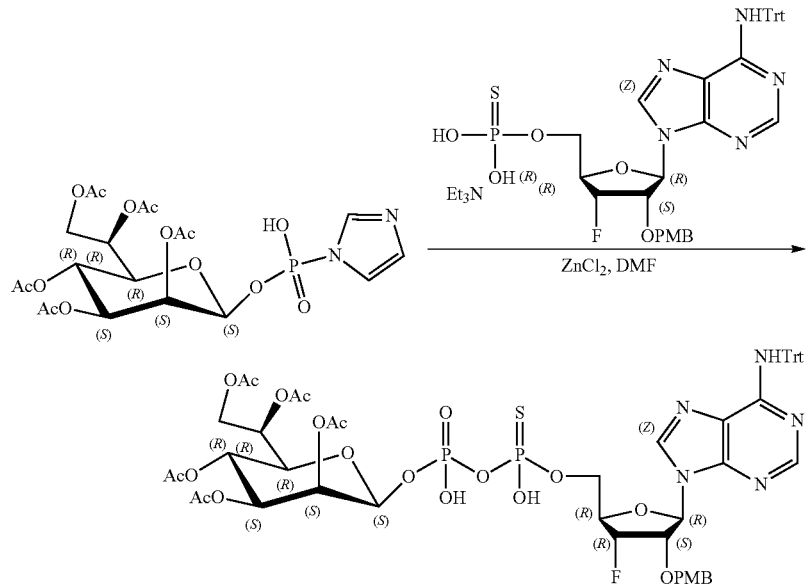

ZnCl$_2$ (1.1 g, 8.2 mmol) was added to a solution of compound of product of Step 4 above (380 mg, 690.4 μmol) and compound of product of Step 3 above (580 mg, 699.7 μmol) in anhydrous DMF (10 mL) under N$_2$ atmosphere. The resulting mixture was stirred at 25° C. for 16 h. After completion of the reaction, the mixture was concentrated under reduced pressure to give crude product, which was purified by silica gel column (DCM:MeOH=10:1, adding 0.5% Et$_3$N) to give the desired compound (350 mg, yield: 40%) as a white solid. MS (ESI) m/z (M+H)$^+$: 1210.5

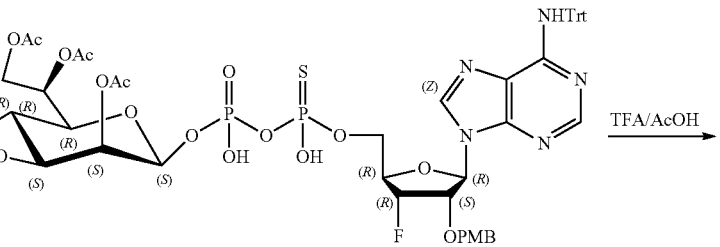

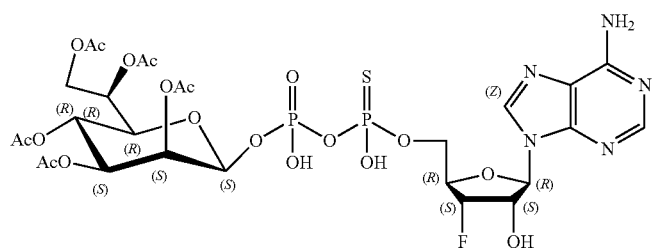

The solution of compound of product of Step 5 above (350 mg, 289 μmol) in DCM (1 mL) and TFA (0.2 mL, 2.7 mmol) was stirred at 25° C. for 3 h. After completion of the reaction, the mixture was adjusted to pH=7 by adding Et$_3$N. The reaction was concentrated under reduced pressure. The product was purified by Pre-HPLC (water (10 mM NH$_4$HCO$_3$)-ACN]; B %: 0%-30%,10 min) to afford the desired compound (70 mg, yield 39.9%) as white solid. MS (ESI) m/z (M+H)$^+$: 848.2 $^1$H NMR (400 MHz, MeOD) δ 8.83 (s, 0.5H), 8.75 (s, 0.5H), 8.20 (s, 1H), 6.27-6.06 (m, 1H), 5.76-5.61 (m, 2H), 5.30-5.16 (m, 3H), 5.09-4.93 (m, 2H), 4.60-4.12 (m, 5H), 3.97-3.95 (m, 1H), 2.15 (s, 1.5H), 2.14 (s, 1.5H), 2.08-2.04 (m, 6H), 2.02 (s, 1.5H), 2.00 (s, 1.5H), 1.95 (s, 1.5H), 1.94 (s, 1.5H).

Compound 27

Adenosine-3'-fluoro-5'-(D-glycero-β-D-manno-heptopyranosyl) (hydroxy)phosphorothioyloxyphosphate

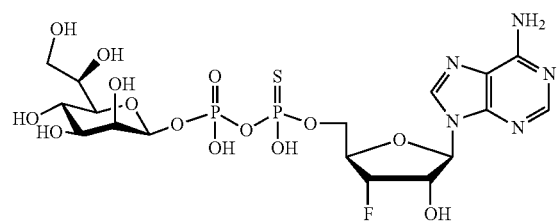

Step 1. Adenosine-3'-fluoro-5'-(D-glycero-β-D-manno-heptopyranosyl) (hydroxy)phosphorothioyloxyphosphate Compound of product of Step 6 in Example 26 (10 mg, 11.8 μmol) in the solution of MeOH/water/Et$_3$N (7:3:1, 1.1 mL) was stirred at 20° C. for 5 h. After completion of the reaction, the mixture was concentrated and lyophilized from water to give the desired compound as trimethylamine salt (8 mg, yield 91.8%) as white solid.

MS (ESI) m/z (M−H)$^-$: 636.0. $^1$H NMR (400 MHz, D$_2$O) δ 8.67-8.49 (m, 1H), 8.15 (s, 1H), 6.16-6.02 (m, 1H), 5.45-5.18 (m, 1H), 4.97-4.82 (m, 1H), 4.32-4.18 (m, 1H), 4.15-3.87 (m, 4H), 3.75-3.53 (m, 5H), 3.44-3.35 (m, 1H), 2.97 (q, J=7.2 Hz, 12H), 1.12 (t, J=7.2 Hz, 18H).

Compound 28

(2S,3S,4S,5S,6S)-2-((S)-2-acetoxy-1-fluoroethyl)-6-((((((2R,3S,4R,5R)-5-(6-amino-9H-purin-9-yl)-3,4-dihydroxytetrahydrofuran-2-yl)methoxy)(hydroxy)phosphorothioyl)oxy)(hydroxy)phosphoryl)oxy) tetrahydro-2H-pyran-3,4,5-triyl triacetate

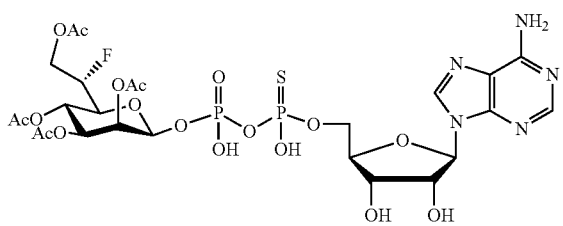

Step 1. Preparation of Compound (2S,3S,4S,5S,6S)-2-((S)-2-acetoxy-1-fluoroethyl)-6-((hydroxy (1H-imidazol-1-yl)phosphoryl)oxy)tetrahydro-2H-pyran-3,4,5-triyl triacetate

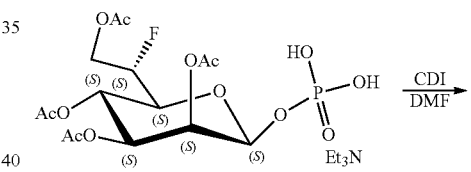

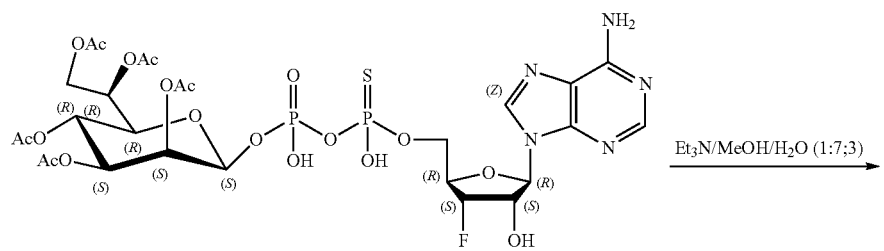

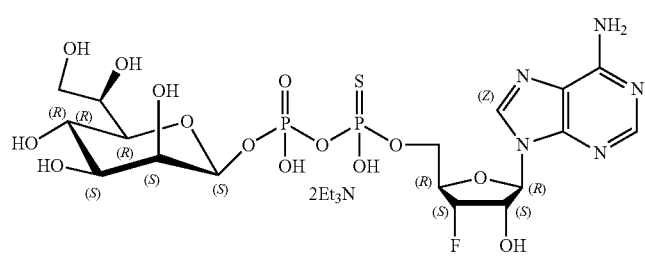

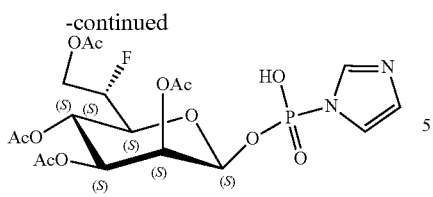

To the mixture of compound of product of Step 12 in Example 3 (420 mg, 748.01 μmol, Et₃N) in DMF (8 mL) was added CDI (1.2 g, 7.5 mmol). The mixture was stirred at 25° C. for 4 h. After completion of the reaction, MeOH (0.3 mL) was added to quench the reaction, the mixture was concentrated under reduced pressure to give the desired compound (1.3 g, crude), which was used directly in next step.

Step 2. Preparation of Compound (2S,3S,4S,5S, 6S)-2-((S)-2-acetoxy-1-fluoroethyl)-6-(((((((3aR,4R, 6R,6aR)-2,2-dimethyl-6-(6-(tritylamino)-9H-purin-9-yl)tetrahydrofuro[3,4-d][1,3]dioxol-4-yl)methoxy) (hydroxy)phosphorothioyl)oxy)(hydroxy) phosphoryl)oxy)tetrahydro-2H-pyran-3,4,5-triyl triacetate

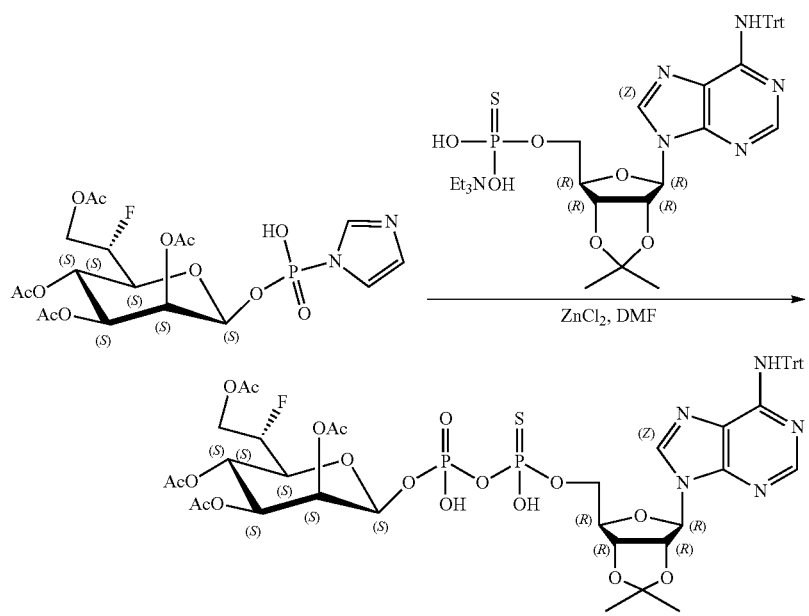

ZnCl₂ (1.2 g, 8.5 mmol) was added to a solution of compound of product of Step 1 above (1.3 g, 2.6 mmol) and compound of product of Step 3 in Example 15 (530 mg, 709 μmol, Et₃N) in anhydrous DMF (10 mL) under N₂ atmosphere. The resulting mixture was stirred at 25° C. for 16 h. After completion of the reaction, the mixture was concentrated under reduced pressure to give crude product, which was purified by silica gel column (DCM:MeOH=20:1, adding 1% Et₃N) to give the desired compound (380 mg, yield: 47.5%) as a white solid.

MS (ESI) m/z (M+H)⁺: 1088.7.

Step 3. Preparation of Compound (2S,3S,4S,5S, 6S)-2-((S)-2-acetoxy-1-fluoroethyl)-6-(((((((2R,3S, 4R,5R)-5-(6-amino-9H-purin-9-yl)-3,4-dihydroxytetrahydrofuran-2-yl)methoxy)(hydroxy) phosphorothioyl)oxy)(hydroxy)phosphoryl)oxy) tetrahydro-2H-pyran-3,4,5-triyl triacetate

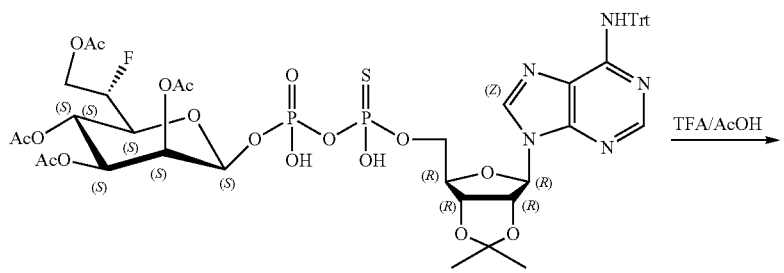

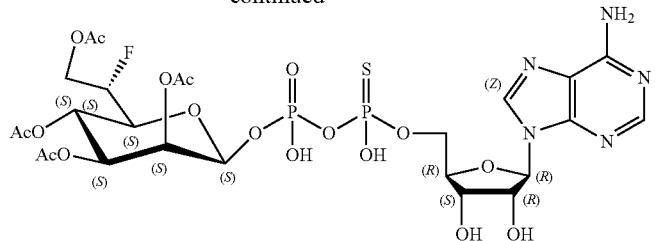

TFA (0.6 mL, 8.10 mmol) was added to a solution of compound obtained in Step 2 above (370 mg, 340.1 µmol) in H$_2$O (0.4 mL). The mixture was stirred at 25° C. for 1.5 h. After completion of the reaction, the reaction was adjusted to pH=7 by adding Et$_3$N. The mixture was concentrated under reduced pressure to give the crude product, which was purified by pre-HPLC (column: Waters Xbridge 150*25 5 u; mobile phase: [water (10 mM NH$_4$HCO$_3$)-ACN]; B %: 0%-30%,10 min) to give the desired compound (44.5 mg, yield: 16.0%, 98.5% purity) as a white solid. MS (ESI) m/z (M+H)$^+$: 806.1. $^1$H NMR (400 MHz, CD$_3$OD) δ 8.68 (s, 1H), 8.19 (s, 1H), 6.11-6.09 (m, 1H), 5.72-5.57 (m, 2H), 5.37-5.32 (m, 1H), 5.22-5.20 (m, 1H), 4.77-4.73 (m, 1H), 4.69-4.60 (m, 2H), 4.52-4.45 (m, 2H), 4.26-4.24 (m, 3H), 3.91-3.83 (m, 1H), 2.13 (s, 3H), 2.03 (s, 3H), 2.02 (s, 3H), 1.92 (s, 3H).

Compound 29

Adenosine-5'-(L-glycero-β-D-manno-6-fluoro-heptopyranosyl) (hydroxy)phosphorothioyloxyphosphate

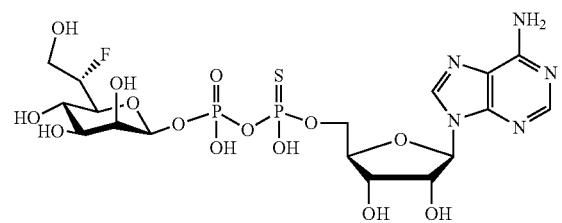

Step 1. Preparation of Compound Adenosine-5'-(L-glycero-β-D-manno-6-fluoro-heptopyranosyl) (hydroxy)phosphorothioyloxyphosphate

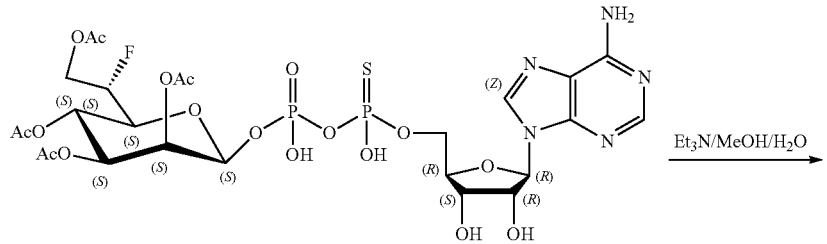

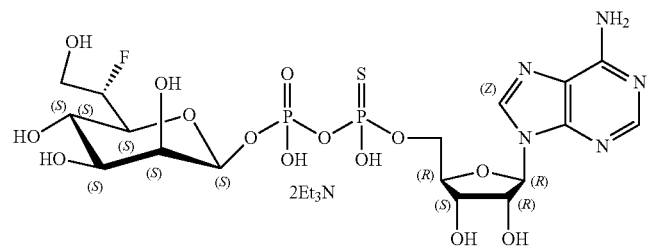

A solution of compound of product of Step 3 in Example 28 (16.1 mg, 10.0 μmol) in the solution of MeOH/water/Et₃N (7:3:1, 2 mL) was stirred at 25° C. for 3.5 h. After completion of the reaction, the mixture was concentrated and lyophilized from water to give the desired compound (14.3 mg, yield: 85.2%, 2Et₃N) as a white amorphous solid. MS (ESI) m/z (M−H)⁺: 636.1. ¹H NMR (400 MHz, D₂O) δ 8.47 (s, 0.3H), 8.43 (s, 0.7H), 8.07 (s, 0.7H), 8.06 (s, 0.3H), 5.98-5.95 (m, 1H), 5.41-5.11 (m, 1H), 4.86-4.73 (m, 1H), 4.39-4.37 (m, 1H), 4.26-4.24 (m, 1H), 4.12-4.10 (m, 2H), 4.00-3.94 (m, 1H), 3.83-3.64 (m, 4H), 3.54-3.51 (m, 1H), 3.33-3.21 (m, 1H), 3.02 (q, J=7.2 Hz, 12H), 1.10 (t, J=7.2 Hz, 18H).

Compound 30

(2S,3S,4S,5R,6R)-2-(((((((2R,3R,4R,5R)-5-(6-amino-9H-purin-9-yl)-3,4-dimethoxytetrahydrofuran-2-yl)methoxy)(hydroxy)phosphorothioyl)oxy)(hydroxy)phosphoryl)oxy)-6-((R)-1,2-diacetoxyethyl)tetrahydro-2H-pyran-3,4,5-triyl triacetate

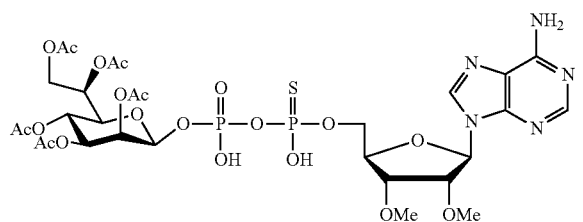

Step 1. Preparation of Compound ((2R,3R,4R,5R)-3,4-dimethoxy-5-(6-(tritylamino)-9H-purin-9-yl)tetrahydrofuran-2-yl)methyl hydrogen phosphonate

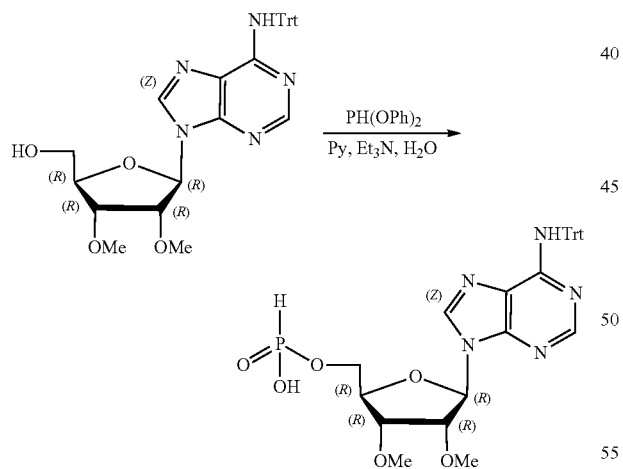

PH(OPh)₂ (1.35 g, 5.75 mmol) was added to a solution of compound of product of Step 2 in Example 13 (1 g, 1.86 mmol) in pyridine (10 mL). The resulting mixture was stirred at 25° C. for 2 h. Then Et₃N (1.33 mL, 9.52 mmol) and H₂O (0.37 mL, 20.42 mmol) was added. The resulting mixture was stirred at 25° C. for 0.5 h. The solvent was removed to give the crude product, which was purified by silica gel chromatography (DCM:MeOH=1:0 to 10:1, adding 0.5% Et₃N) to give the desired compound (1.5 g, yield: 94.7%, Et₃N) as light yellow oil. MS (ESI) m/z (M+H)⁺: 602.1.

Step 2. Preparation of Compound O-(((2R,3R,4R,5R)-3,4-dimethoxy-5-(6-(tritylamino)-9H-purin-9-yl)tetrahydrofuran-2-yl)methyl) O,S-dihydrogen phosphorothioate

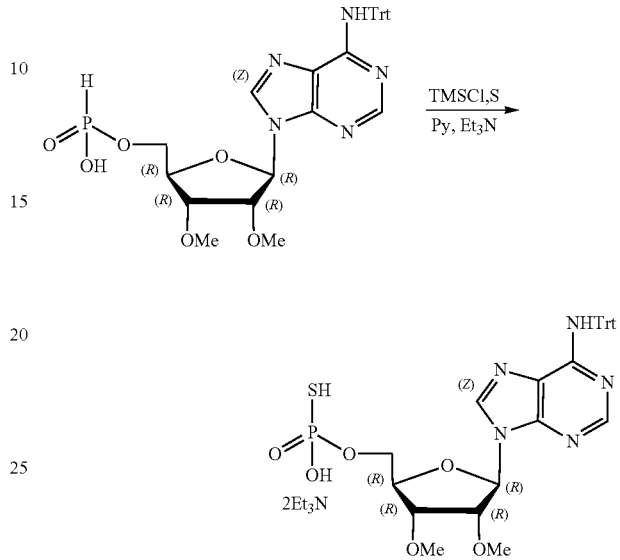

TMSCl (2.00 mL, 15.7 mmol) was added to a solution of compound of product of Step 1 above (1.3 g, 1.85 mmol, Et₃N) in pyridine (15 mL) and Et₃N (15 mL). The mixture was stirred at 25° C. for 0.5 h and then sulfur (758 mg, 23.6 mmol) was added. The resulting mixture was stirred for another 1 h. And then H₂O (3.79 mL, 210 mmol) was added. The mixture was stirred for another 0.5 h. The reaction was filtered and the filtrate was concentrated to give crude product, which was purified by silica gel chromatography column (DCM:MeOH=1:0 to 10:1, adding 0.5% Et₃N). The desired compound (400 mg, yield: 33.1%, 2Et₃N) was obtained as yellow oil. MS (ESI) m/z (M+H)⁺: 634.1. ¹H NMR (400 MHz, CDCl₃) δ 8.37 (s, 1H), 8.00 (s, 1H), 7.40-7.35 (m, 2H), 7.34-7.27 (m, 8H), 7.23-7.15 (m, 5H), 6.14-6.05 (m, 1H), 4.49-4.42 (m, 1H), 4.37-4.28 (m, 2H), 4.24-4.10 (m, 2H), 3.45-3.41 (m, 6H), 3.03 (q, J=7.2 Hz, 12H), 1.27 (t, J=7.2 Hz, 18H).

Step 3. Preparation of Compound (2R,3R,4S,5S,6S)-2-((R)-1,2-diacetoxyethyl)-6-(((((((2R,3R,4R,5R)-3,4-dimethoxy-5-(6-(tritylamino)-9H-purin-9-yl)tetrahydrofuran-2-yl)methoxy)(hydroxy)phosphorothioyl)oxy)(hydroxy)phosphoryl)oxy)tetrahydro-2H-pyran-3,4,5-triyl triacetate

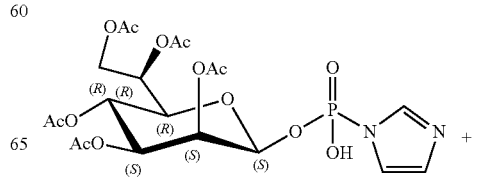

-continued

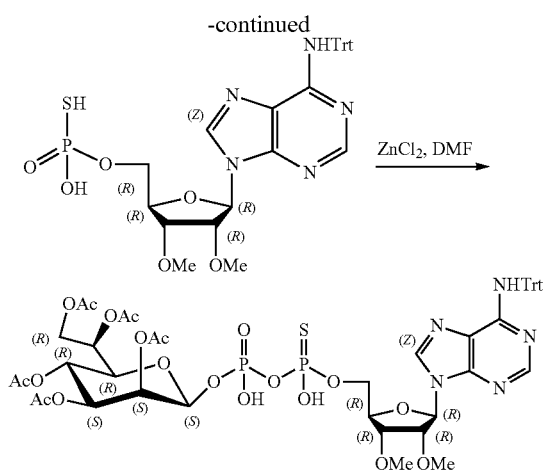

ZnCl$_2$ (516 mg, 3.79 mmol) was added to the solution of compound of product of Step 4 in Example 26 (191 mg, 293 umol, Et$_3$N) and compound of product of Step 2 above (400 mg, 315 μmol) in DMF (10 mL). The mixture was stirred at 25° C. for 24 h under Ar atmosphere. The solvent was removed to give the crude product. The residue was purified by silica gel chromatography column (DCM:MeOH=1:0 to 10:1, adding 1% Et$_3$N). The desired compound (400 mg, yield: 95.4%) was obtained as colorless oil. MS (ESI) m/z (M+H)$^+$: 1116.5.

Step 4. Preparation of Compound (2S,3S,4S,5R, 6R)-2-((((((2R,3R,4R,5R)-5-(6-amino-9H-purin-9-yl)-3,4-dimethoxytetrahydrofuran-2-yl)methoxy) (hydroxy)phosphorothioyl)oxy)(hydroxy) phosphoryl)oxy)-6-((R)-1,2-diacetoxyethyl) tetrahydro-2H-pyran-3,4,5-triyl triacetate The mixture of compound of product of Step 3 above (400 mg, 358 μmol) with TFA (1 mL) in DCM (5 mL) was stirred at 25° C. for 1 h. After completion of the reaction, the mixture was adjusted to pH=7 with Et$_3$N, the solvent was removed and the residue was purified by Pre-HPLC (Waters Xbridge 150*25 5 u, water (10 mM NH$_4$HCO$_3$)—CH$_3$CN, 0~30%) to give the desired compound (20 mg, yield: 6.4%) as white solid. MS (ESI) m/z (M+H)$^+$: 874.2. $^1$H NMR (400 MHz, CD$_3$OD) δ 8.77 (s, 0.4H), 8.71 (s, 0.6H), 8.17 (s, 1H), 6.18-6.12 (m, 1H), 5.76-5.59 (m, 2H), 5.21-5.13 (m, 3H), 4.61-4.53 (m, 2H), 4.45-4.32 (m, 3H), 4.27-4.20 (m, 2H), 3.95-3.90 (m, 1H), 3.51 (s, 3H), 3.42 (s, 1.4H), 3.41 (s, 1.6H), 2.11 (s, 3H), 2.06-2.02 (m, 6H), 1.99 (s, 1.6H), 1.97 (s, 1.4H), 1.91 (s, 3H).

Compound 31

Adenosine-2'3'-dimethoxy-5'-(D-glycero-β-D-mannoheptopyranosyl) (hydroxy)phosphorothioyloxyphosphate

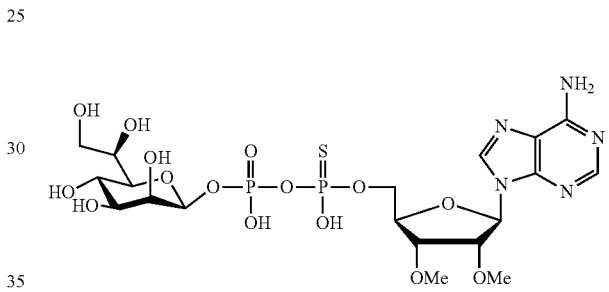

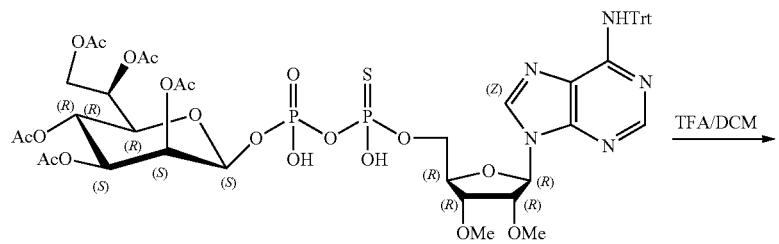

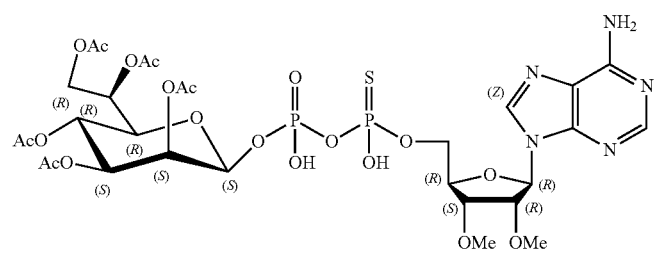

Step 1. Preparation of Compound Adenosine-2'3'-dimethoxy-5'-(D-glycero-β-D-mannoheptopyranosyl) (hydroxy)phosphorothioyloxyphosphate

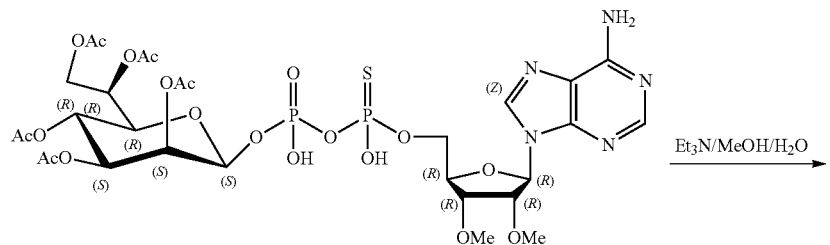

The mixture of compound of product of Step 4 in Example 30 (8 mg, 9.16 µmol) in MeOH (0.7 mL), H₂O (0.3 mL) and Et₃N (0.1 mL) was stirred at 15-20° C. for 3 h. Then the solution was lyophilized on a freeze drier. The desired compound (6 mg, yield: 76%, 2Et₃N) was obtained as white solid. MS (ESI) m/z (M−H)⁻=662.1. ¹H NMR (400 MHz, D₂O) δ 8.47 (s, 0.4H), 8.45 (s, 0.6H), 8.10 (s, 1H), 6.02 (d, J=6.0 Hz, 1H), 5.13-5.05 (m, 1H), 4.50-4.42 (m, 2H), 4.40-4.36 (m, 1H), 4.28-4.19 (m, 1H), 4.20-4.10 (m, 2H), 4.00-3.92 (m, 1H), 3.85-3.80 (m, 1H), 3.59-3.55 (m, 2H), 3.52-3.41 (m, 2H), 3.36 (s, 3H), 3.27 (s, 3H), 3.02 (q, J=7.3 Hz, 12H), 1.10 (t, J=7.3 Hz, 18H).

Compound 32

(2R,3R,4S,5S,6S)-2-((R)-1,2-diacetoxyethyl)-6-(((((((2R,3S,4R,5R)-3,4-dihydroxy-5-(6-hydroxy-9H-purin-9-yl)tetrahydrofuran-2-yl)methoxy)(hydroxy)phosphoryl)oxy)(hydroxy)phosphoryl)oxy) tetrahydro-2H-pyran-3,4,5-triyl triacetate

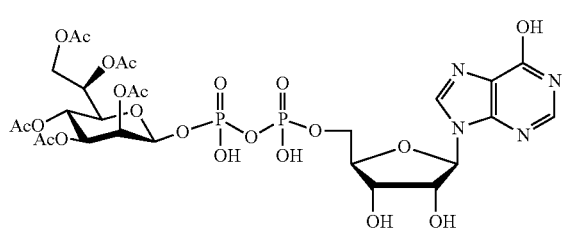

Step 1. Preparation of Compound ((2R,3S,4R,5R)-3,4-dihydroxy-5-(6-hydroxy-9H-purin-9-yl)tetrahydrofuran-2-yl)methyl hydrogen morpholinophosphonate

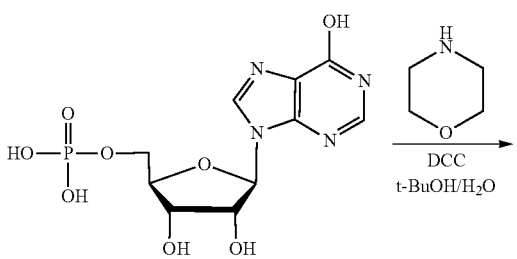

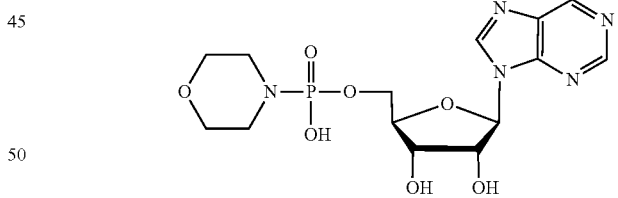

DCC (1.19 g, 5.74 mmol) in t-BuOH (6 mL) was added to a refluxed solution (110° C.) of compound ((2R,3S,4R,5R)-3,4-dihydroxy-5-(6-hydroxy-9H-purin-9-yl)tetrahydrofuran-2-yl)methyl dihydrogen phosphate (500 mg, 1.44 mmol) and morpholine (500 mg, 5.74 mmol) in t-BuOH (6 mL) and H₂O (6 mL) under N₂. The solution was stirred at 110° C. under N₂ for 12 h. After completion of the mixture, the solution was cooled to 20° C., and the solid was filtered off. The filtrate was collected, and the organic solvent was removed in vacuo. The residue was diluted with H₂O (10 mL), washed with TBME (20 mL×3). The aqueous phase was collected and concentrated in vacuo to give the desired compound as DCC salt (810 mg, crude) and as light yellow oil, which was used directly for the next step without further purification.

Step 2. Preparation of Compound (2R,3R,4S,5S, 6S)-2-((R)-1,2-diacetoxyethyl)-6-(((((((2R,3S,4R, 5R)-3,4-dihydroxy-5-(6-hydroxy-9H-purin-9-yl) tetrahydrofuran-2-yl)methoxy)(hydroxy)phosphoryl) oxy)(hydroxy)phosphoryl)oxy)tetrahydro-2H-pyran-3,4,5-triyl triacetate

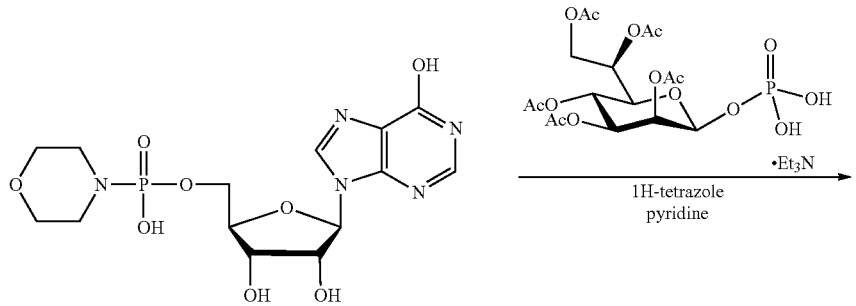

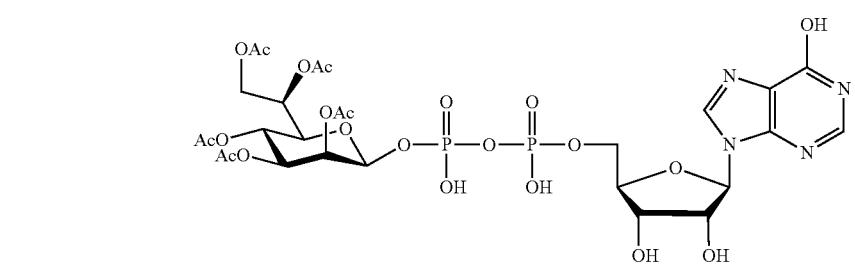

Compound of product of Step 1 above (250 mg, 500 umol) and the compound of product of Step 14 in Example 14 (810 mg, 1.94 mmol) was dried with pyridine (5 mL×3). The residue was dissolved in anhydrous pyridine (5 mL), and 1H-tetrazole (175 mg, 2.50 mmol) was added. The solution was stirred at 20° C. for 12 h. Then the solution was warmed up to 30° C. and continued stirring for 12 h. The solvent was removed in vacuo. The residue was dissolved in EtOH (20 mL). The solid was filtered off. The filtrate was collected and concentrated in vacuo. The residue was purified by silica gel column (DCM: (MeOH: $NH_3.H_2O$=50:1) =1:0 to 1:1.2) to give crude product (80 mg), which was repurified by prep-HPLC (column: Waters Xbridge 150*25 5 u; mobile phase: [water (10 mM $NH_4HCO3$)-ACN]; B %: 0%-30%,10 min) to give the desired compound (20 mg, yield: 4.82%) as white solid. MS (ESI) m/z (M+H)$^+$: 831.4. $^1$H NMR (400 MHz, $CD_3OD$) δ 8.53 (s, 1H), 8.06 (s, 1H), 6.07 (d, J=5.4 Hz, 1H), 5.48-5.47 (m, 1H), 5.34-5.32 (m, 1H), 5.22-5.19 (m, 3H), 4.66-4.58 (m, 1H), 4.47-4.43 (m, 2H), 4.25-4.19 (m, 4H), 3.89-3.88 (m, 1H), 2.12 (s, 3H), 2.06 (s, 3H), 2.04 (s, 3H), 2.00 (s, 3H), 1.92-1.90 (m, 3H).

Compound 33

Inosine-5'-(D-glycero-β-D-mannoheptopyranosyl) diphosphate

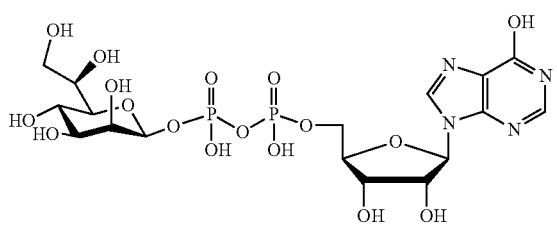

Step 1. Preparation of Compound Inosine-5'-(D-glycero-β-D-mannoheptopyranosyl) diphosphate The compound of product of Step 2 in Example 32 above in 2 mL of (0.1 M TEAB (8 mL), MeOH (6 mL) and TEA (0.1 mL) was stirred at −20° C. for 2 days. The solution was freeze dried in vacuo to give the desired compound as trimethylamine salt.

Prodrugs of HBP

HBP, shown below in Formula 1b, is very hydrophilic, making it difficult for the molecule to penetrate cell membranes to reach ALPK1, which is a cytosolic protein.

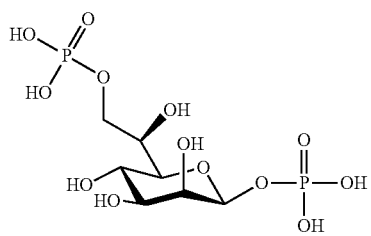

(1b)

Accordingly, the disclosure provides various prodrugs of HBP adapted to enable penetration of the plasma membrane. In embodiments, the prodrug comprises one or more biolabile protecting groups at one or more of the phosphate moieties of HBP. In embodiments, the one or more biolabile protecting groups is linked via an ester linkage to the one or more phosphate moieties of HBP. Exemplary protecting groups that may be attached in this manner include, for example, a carbonyloxymethyl (e.g., POM, POC), a cyclosaligenyl (e.g., cycloSal), a cyclic 1-aryl-1,3-propanyl ester (e.g., HepDirect), an aryloxy amino acid phosphoramidate or phosphonamidate (e.g., ProTide), and a methylaryl haloalkylamidate. Further examples include S-acyl-2-thioethyl (SATE), S-[(2-hydroxyethyl)sulfidyl]-2-thioethyl (DTE), alkyloxyalkyl (e.g., HDP, ODE), an amino acid phosphoramidate or phosphonamidate monoester, a bis(amino acid) phosphoramidate or phosphonamidate, and a di- or tri-phosphonate.

Type I: Carbonyloxymethyl

Carbonyloxymethyl is a class of phosphate protecting groups. In some embodiments, carbonyloxymethyl protecting groups have the generic Formula 2a

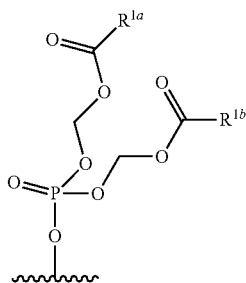

(2a)

wherein $R^{1a}$ and $R^{1b}$ are each independently $C_{1-12}$ alkyl or $C_{1-12}$ alkoxy, and the wavy line indicates the point of attachment to the rest of the molecule. In some embodiments, $R^{1a}$ and $R^{1b}$ are each independently $C_{1-8}$ alkyl or $C_{1-8}$ alkoxy.

Without being bound to any particular theory, it is believed that phosphate groups protected by Carbonyloxymethyl moieties are deprotected in vivo through a series of chemical conversion described in Scheme I, below.

Scheme I

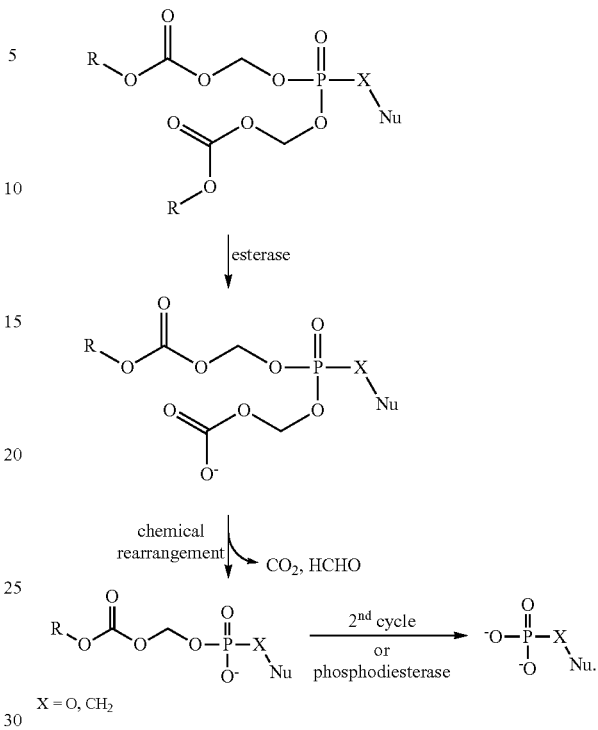

$X = O, CH_2$

In some embodiments, the prodrug of HBP has a Formula 3a

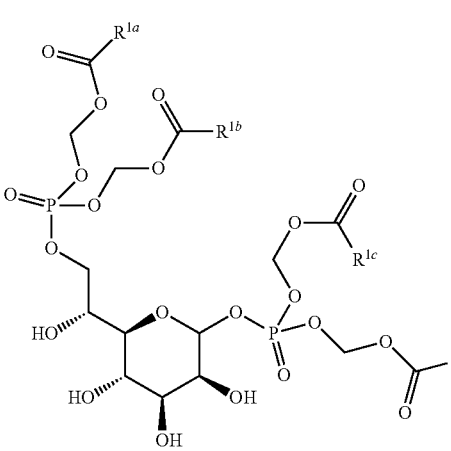

(3a)

wherein $R^{1a}$, $R^{1b}$, $R^{1c}$, and $R^{1d}$ are each independently $C_{1-12}$ alkyl or $C_{1-12}$ alkoxy. In some embodiments, $R^{1a}$, $R^{1b}$, $R^{1c}$, and $R^{1d}$ are each independently $C_{1-8}$ alkyl or $C_{1-8}$ alkoxy.

Carbonyloxymethyl prodrugs of HBP can be prepared using the methods described in Hwang, Y. and Cole, P. A. *Organic Letters* 2004, 6, 1555; Inuki, S. et al., Fujimoto, Y. *Organic Letters* 2017, 19, 3079, or similar.

Type II: Cyclosaligenyl (cycloSal)

Cyclosaligenyl (cycloSal) are a class of phosphate protecting groups. In some embodiments, cycloSal protecting groups have the generic Formula 2b

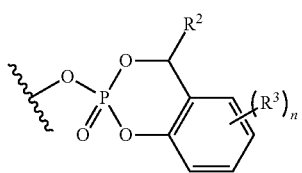

wherein $R^2$ is H, $C_{1-8}$ alkyl, or halogen; $R^3$ is H, $C_{1-8}$ alkyl, or halogen; the subscript n is an integer from 1 to 3; and the wavy line indicates the point of attachment to the rest of the molecule. In some embodiments, $R^2$ is H or $C_{1-8}$ alkyl. In some embodiments, $R^3$ is $C_{1-8}$ alkyl. In some embodiments, the subscript n is 1.

Without being bound to any particular theory, it is believed that phosphate groups protected by one or more cycloSal moieties are deprotected in vivo via 1 or more pathways described in Scheme II, below.

wherein $R^{2a}$ and $R^{2b}$ are each independently H, $C_{1-8}$ alkyl, or halogen; $R^{3a}$ and $R^{3b}$ are each independently is H, $C_{1-8}$ alkyl, or halogen; and the subscripts n1 and n2 are each independently an integer from 1 to 3. In some embodiments, $R^{2a}$ and $R^{2b}$ are each independently H or $C_{1-8}$ alkyl. In some embodiments, $R^{3a}$ and $R^{3b}$ are each independently $C_{1-8}$ alkyl. In some embodiments, the subscripts n1 and n2 are each 1.

CycloSal prodrugs of HBP can be prepared using the methods described in Spaiilovi, P. et al., *Chem Med Chem* 2010, 5, 1386; Inuki, S. et al., *Organic Letters* 2017, 19, 3079, or similar.

Type III: Cyclic 1-Aryl-1,3-Propanyl Ester (HepDirect)

Cyclic 1-aryl-1,3-propanyl esters (HepDirects) are a class of phosphate protecting groups. In some embodiments, HepDirect protecting groups have the generic Formula 2c

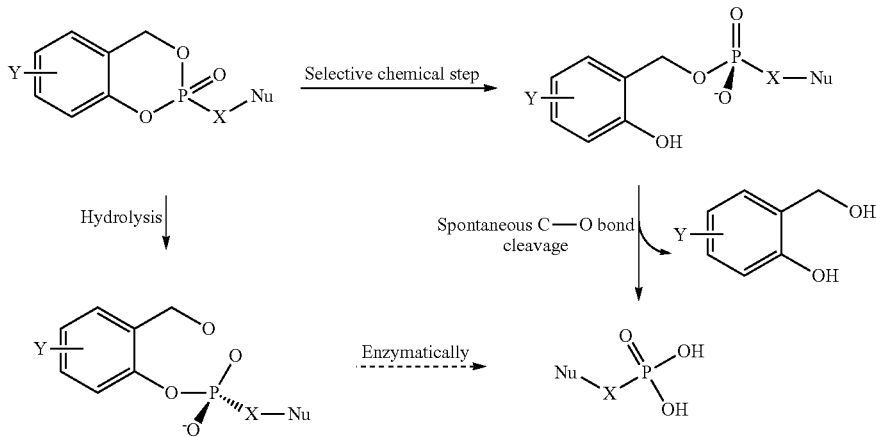

Scheme II

In some embodiments, the prodrug of HBP has a Formula 3b

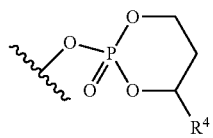

wherein $R^4$ is aryl or 5- or 6-membered heteroaryl, wherein the heteroaryl group has 1-3 heteroatom ring vertices selected from the group consisting of O, N, and S; and the wavy line indicates the point of attachment to the rest of the molecule. In some embodiments, $R^4$ is aryl or 6-membered heteroaryl. In some embodiments $R^4$ is phenyl or pyridyl.

Figure 34:
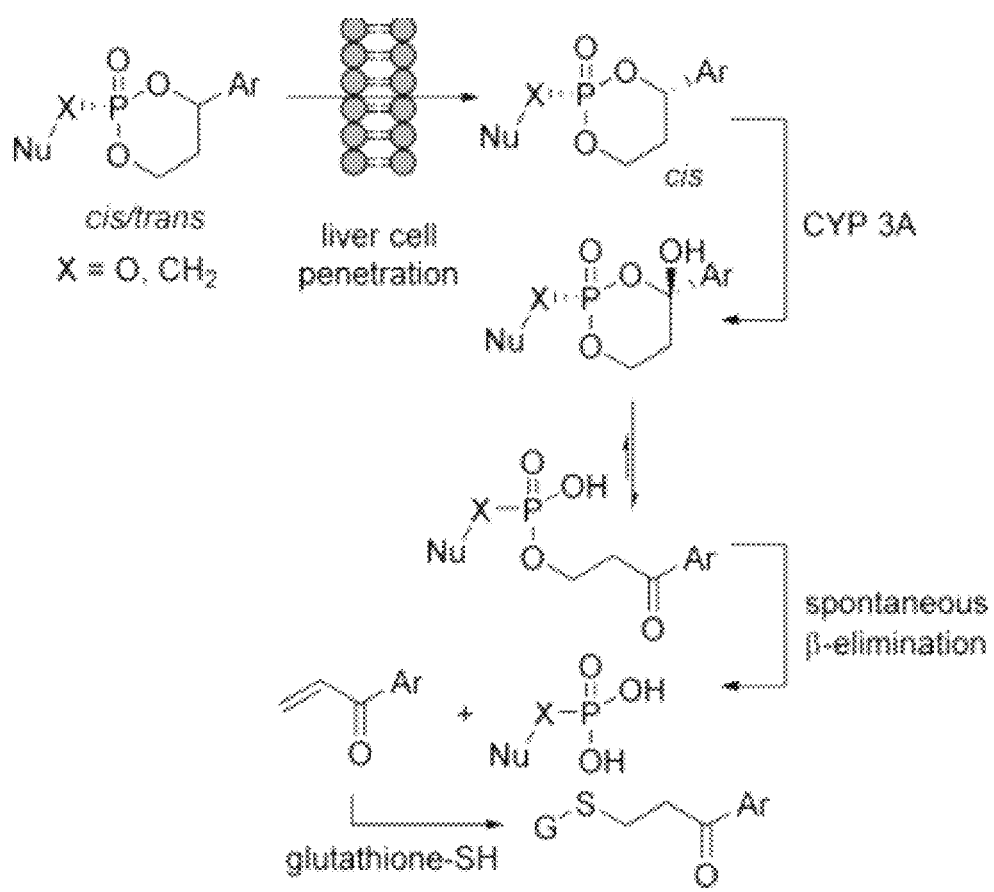
FIG. 34: Schematic of a Scheme III pathway.

Without being bound to any particular theory, it is believed that phosphate groups protected by HepDirect moieties are deprotected in vivo via the pathway described in Scheme (FIG. 34).

In some embodiments, the prodrug of HBP has a Formula 3c

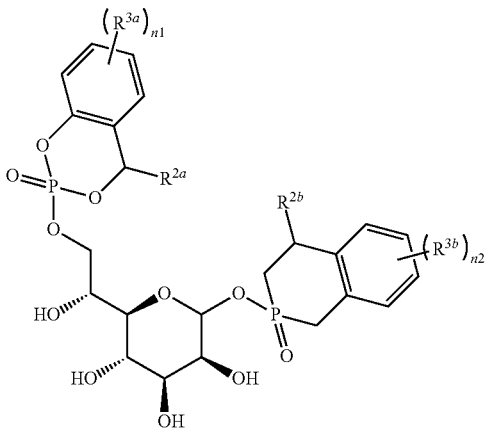

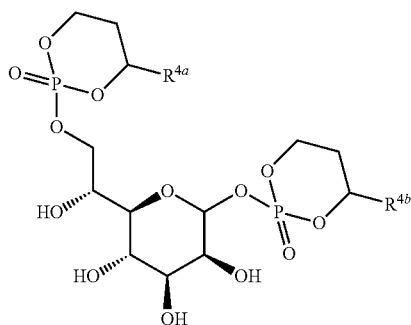

(3c)

wherein $R^{4a}$ and $R^{4b}$ are each independently aryl or 5- or 6-membered heteroaryl, the heteroaryl group having 1-3 heteroatom ring vertices selected from the group consisting of O, N, and S. In some embodiments, $R^{4a}$ and $R^{4b}$ are each independently aryl or 6-membered heteroaryl. In some embodiments $R^{4a}$ and $R^{4b}$ are each independently phenyl or pyridyl.

HepDirect prodrugs of HBP can be prepared using the methods described in Reddy, K. R. et al., *Tetrahedron Letters* 2005, 46, 4321; Inuki, S. et al., *Organic Letters* 2017, 19, 3079, or similar.

Type IV: Aryloxy Amino Acid Amidate (Protide)

Aryloxy amino acid amidates (Protides) are a class of phosphate protecting group. In some embodiments protide protecting groups have the generic Formula 2d

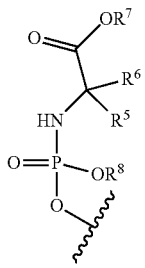

(2d)

wherein $R^5$ and $R^6$ are each independently H or $C_{1-8}$ alkyl; $R^7$ is $C_{1-8}$ alkyl; $R^8$ is aryl; and the wavy line indicates the point of attachment to the rest of the molecule. In some embodiments, $R^7$ is methyl or isopropyl. In some embodiments, $R^8$ is phenyl.

Figure 35:
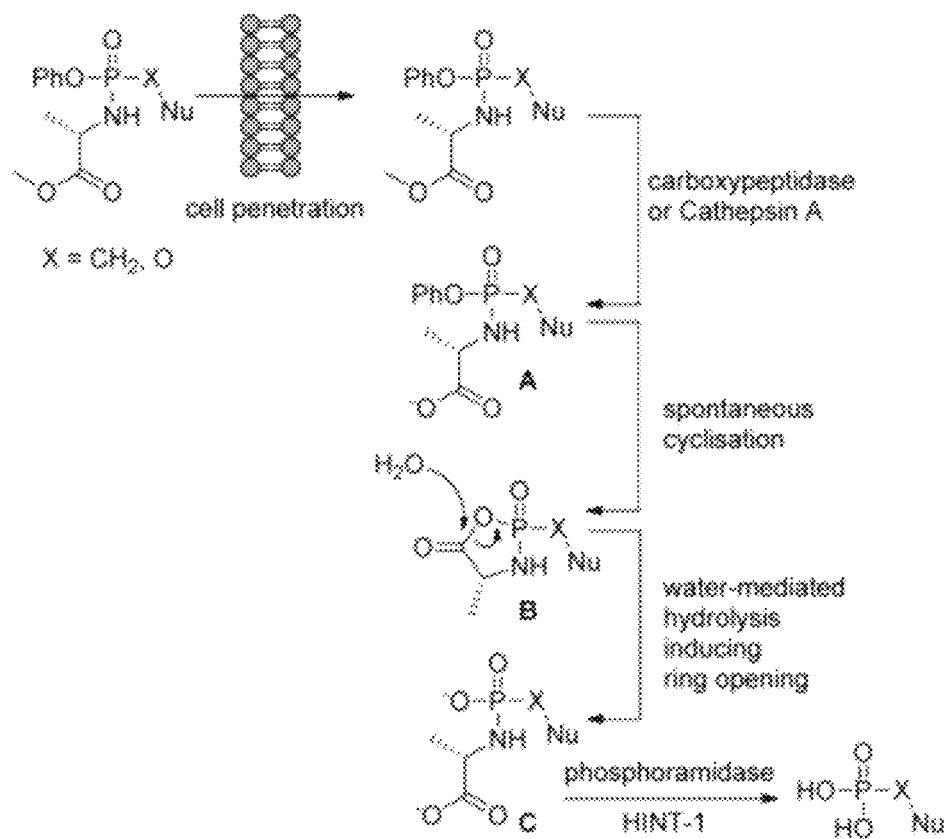
FIG. 35: Schematic of a Scheme IV pathway.

Without being bound to any particular theory, it is believed that phosphate groups protected by Protide moieties are deprotected in vivo via the pathway described in Scheme IV (FIG. 35).

In some embodiments, the prodrug of HBP has a Formula 3d

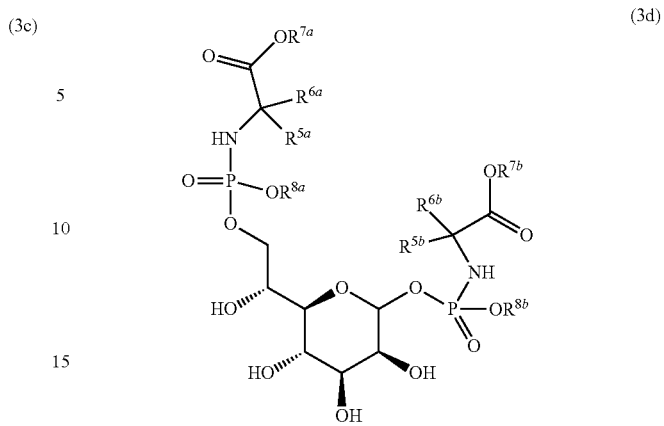

(3d)

wherein $R^{5a}$, $R^{5b}$, $R^{6a}$, and $R^{6}$ are each independently H or $C_{1-8}$ alkyl; $R^{7a}$ and $R^{7b}$ are each independently $C_{1-8}$ alkyl; $R^{8a}$ and $R^{8b}$ are each independently aryl. In some embodiments, $R^{7a}$ and $R^{7b}$ are each independently is methyl or isopropyl. In some embodiments, $R^{8a}$ and $R^{8b}$ are each phenyl.

Protide prodrugs of HBP can be prepared using the methods described in van Boom, J. H. et al., *Tetrahedron* 1975, 31, 2953; Inoue, J.-i. and Fujimoto, Y. *Organic Letters* 2017, 19, 3079, or similar.

Type V: Methylaryl haloalkylamidate

Methylaryl haloalkylamidates are a class of phosphate protecting groups. In some embodiments methylaryl haloalkylamdiate protecting groups have the generic Formula 2e

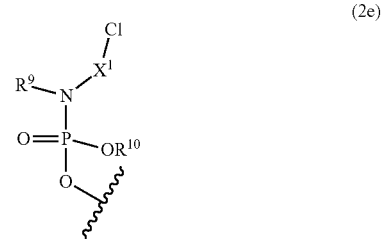

(2e)

wherein $R^9$ is $C_{1-8}$ alkyl; $X^1$ is $C_{3-5}$ alkylene; and $R^{10}$ is aryl, heteroaryl, aryl$C_{1-4}$alkylene, or heteroarylC1.4alkylene, the heteroaryl group is a 5 or 6 membered ring having 1-3 heteroatom ring vertices selected from the group consisting of 0, N, and S. In some embodiments, $R^9$ is $C_{1-4}$ alkyl. In some embodiments, $X^1$ is C4 alkylene. In some embodiments, $R^{10}$ is aryl or aryl$C_{1-4}$alkylene. In some embodiments, $R^{10}$ is phenyl. In some embodiments, $R^{10}$ is benzyl.

Without being bound to any particular theory it is believed that phosphate groups protected by methylaryl haloalkylamdiate moieties are deprotected in vivo through a series of chemical conversion described in Scheme V, below. It is understood that the groups defined for $R^9$ and $R^{10}$ are exemplary and are not intended to be limiting.

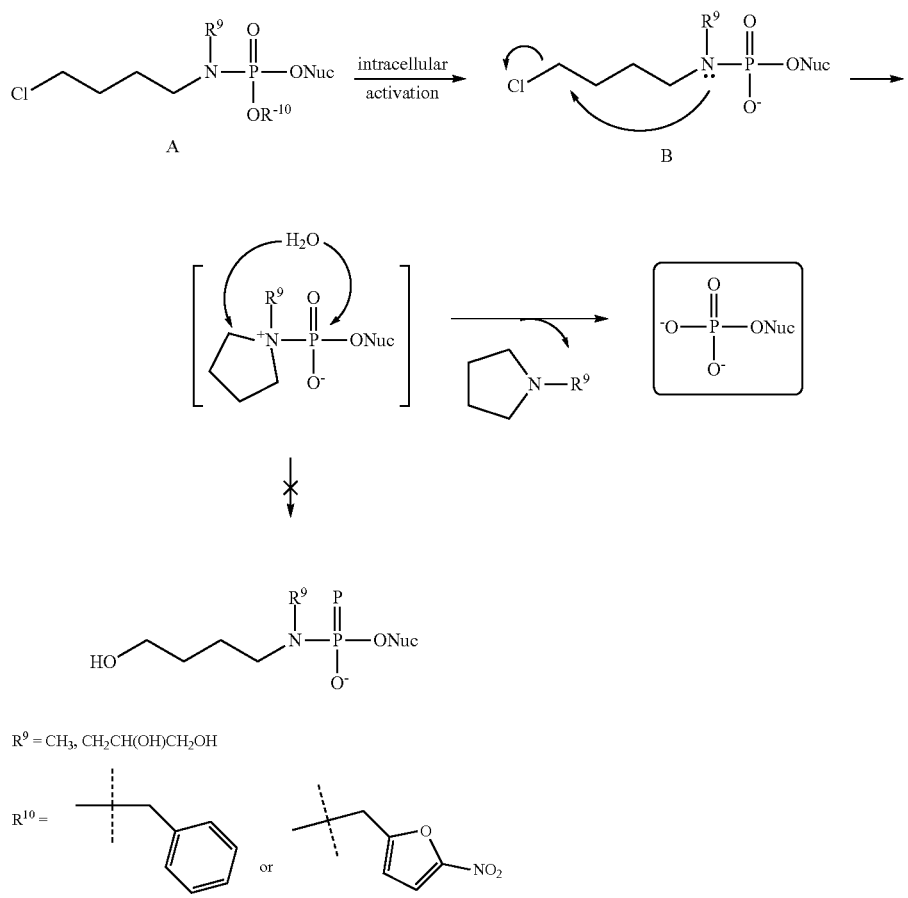

In some embodiments, the prodrug of HBP has a Formula 3e

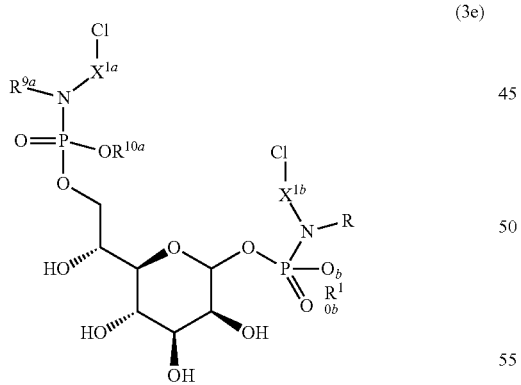

(3e)

wherein $R^{9a}$ and $R^{9b}$ are each independently $C_{1-8}$ alkyl; $X^{1a}$ and $X^{1b}$ are each independently $C_{3-5}$ alkylene; and $R^{10a}$ and $R^{10b}$ are each independently aryl, heteroaryl, aryl$C_{1-4}$alkylene, or heteroaryl$C_{1-4}$alkylene, the heteroaryl group is a 5 or 6 membered ring having 1-3 heteroatom ring vertices selected from the group consisting of O, N, and S. In some embodiments, $R^{9a}$ and $R^{9b}$ are each independently $C_{1-4}$ alkyl. In some embodiments, $X^{1a}$ and $X^{1b}$ are each independently $C_4$ alkylene. In some embodiments, $R^{10a}$ and $R^{10b}$ are each independently aryl or aryl$C_{1-4}$alkylene. In some embodiments, $R^{10a}$ and $R^{10b}$ are each independently is phenyl. In some embodiments, $R^{10a}$ and $R^{10b}$ are each independently are benzyl.

Methylaryl haloalkylamdiate prodrugs of HBP can be prepared using the methods described in Wu, W. et al., Journal of Medicinal Chemistry 2007, 50, 3743; Inoue, J.-i. and Fujimoto, Y. Organic Letters 2017, 19, 3079, or similar.

A person of skill in the art will recognize that each of the two phosphate moieties of HBP can be independently protected with any of Type I to Type V protecting groups using the methods described above. Accordingly, in some embodiments, the prodrug of HBP is represented by Formula 3

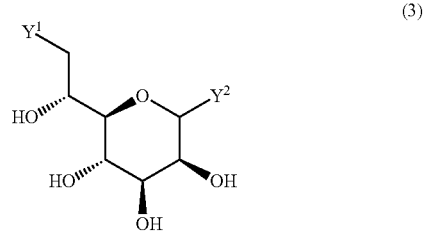

(3)

wherein $Y^1$ and $Y^2$ are independently each a phosphate, Formula 2a, Formula 2b, Formula 2c, Formula 2d, or Formula 2e, provided that $Y^1$ and $Y^2$ are not both phosphate.

In some embodiments the prodrug of HBP is a compound of Table 1

TABLE 1
| Compound | Chemical Name |
|---|---|
| 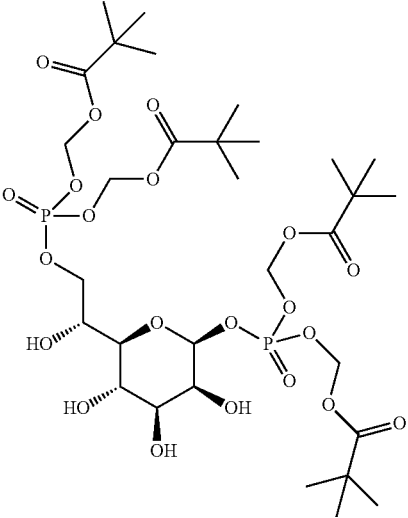<br>1.001 | (R)-2-((2R,3S,4S,5S,6S)-6-((bis(pivaloxymethoxy)phosphoryl)oxy)-3,4,5-trihydroxytetrahydro-2H-pyran-2-yl)-2-hydroxyethyl bis(pivaloxymethyl) phosphate |
| 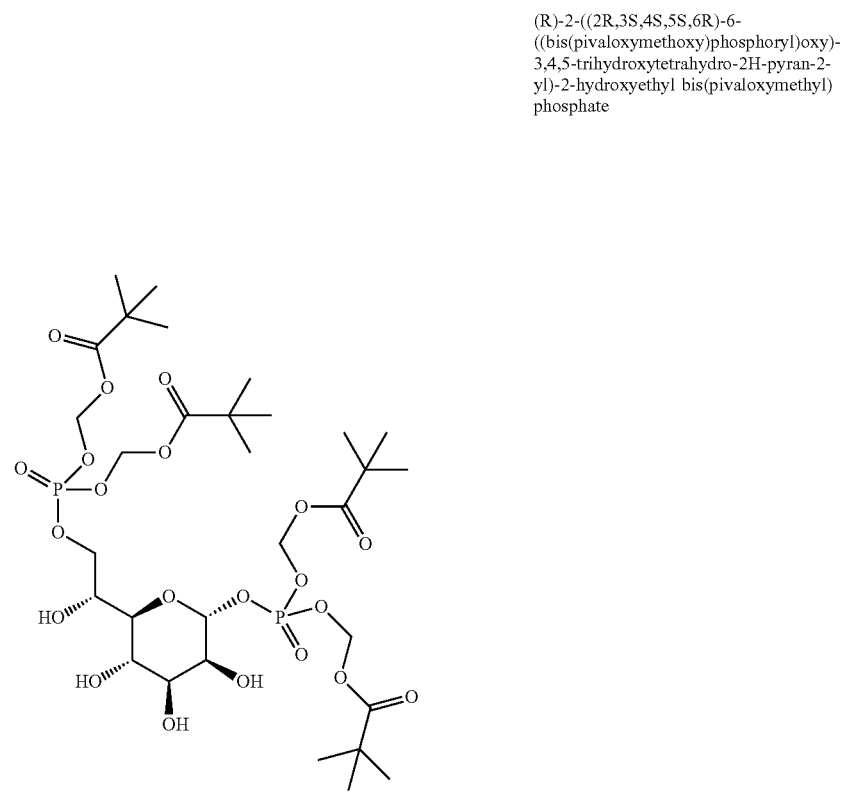<br>1.002 | (R)-2-((2R,3S,4S,5S,6R)-6-((bis(pivaloxymethoxy)phosphoryl)oxy)-3,4,5-trihydroxytetrahydro-2H-pyran-2-yl)-2-hydroxyethyl bis(pivaloxymethyl) phosphate |

TABLE 1-continued

| Compound | Chemical Name |
|---|---|
| 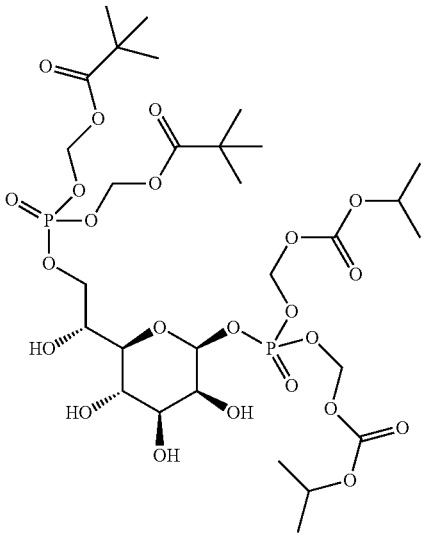<br>1.003 | (R)-2-((2R,3S,4S,5S,6S)-6-((bis(methylisopropylcarbonate)methyl-phosphoryl)oxy)-3,4,5-trihydroxytetrahydro-2H-pyran-2-yl)-2-hydroxyethyl bis(pivaloxymethyl) phosphate |
| 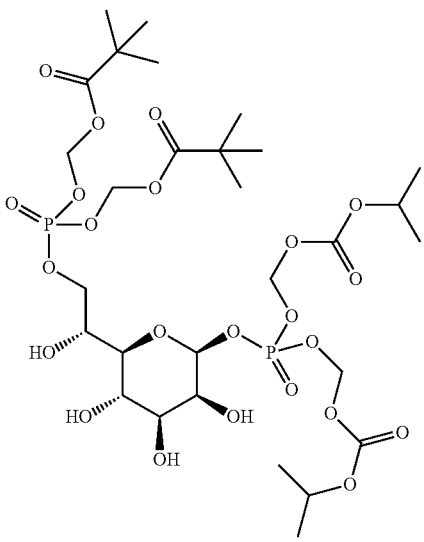<br>1.004 | (R)-2-((2R,3S,4S,5S,6R)-6-((bis(methylisopropylcarbonate)methyl-phosphoryl)oxy)-3,4,5-trihydroxytetrahydro-2H-pyran-2-yl)-2-hydroxyethyl bis(pivaloxymethyl) phosphate |
| 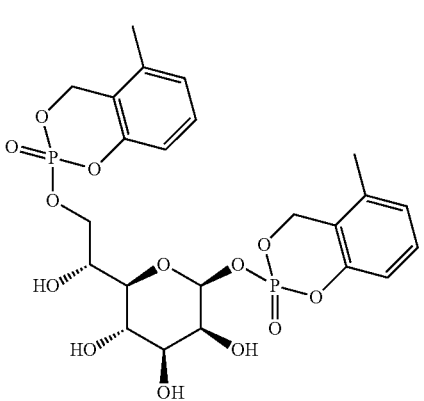<br>1.005 | 2-((2R)-2-hydroxy-2-((2R,3S,4S,5S,6S)-3,4,5-trihydroxy-6-((5-methyl-2-oxido-4H-benzo[d][1,3,2]dioxaphosphinin-2-yl)oxy)tetrahydro-2H-pyran-2-yl)ethoxy)-5-methyl-4H-benzo[d][1,3,2]dioxaphosphinine 2-oxide |

TABLE 1-continued

| Compound | Chemical Name |
|---|---|
| 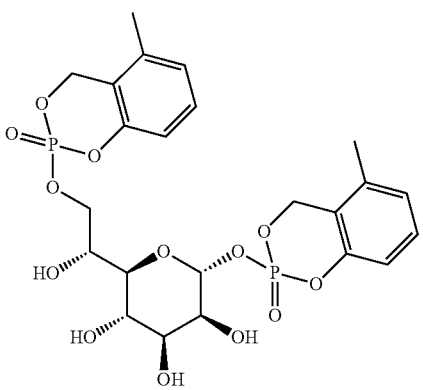<br>1.006 | 2-((2R)-2-hydroxy-2-((2R,3S,4S,5S,6R)-3,4,5-trihydroxy-6-((5-methyl-2-oxido-4H-benzo[d][1,3,2]dioxaphosphinin-2-yl)oxy)tetrahydro-2H-pyran-2-yl)ethoxy)-5-methyl-4H-benzo[d][1,3,2]dioxaphosphinine 2-oxide |
| 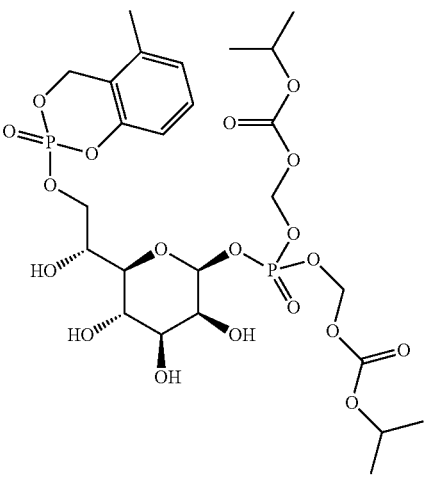<br>1.007 | 2-((2R)-2-hydroxy-2-((2R,3S,4S,5S,6S)3,4,5-trihydroxy-6-((bis(methyliso-propylcarbonate)methylphosphoryl)oxy)tetrahydro-2H-pyran-2-yl)ethoxy)-5-methyl-4H-benzo[d][1,3,2]dioxaphosphinine 2-oxide |
| 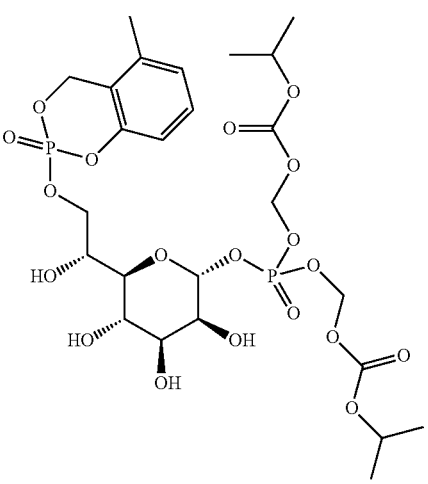<br>1.008 | 2-((2R)-2-hydroxy-2-((2R,3S,4S,5S,6R)3,4,5-trihydroxy-6-((bis(methylisopropyl-carbonate)methylphosphoryl)oxy)tetrahydro-2H-pyran-2-yl)ethoxy)-5-methyl-4H-benzo[d][1,3,2]dioxaphosphinine 2-oxide |

TABLE 1-continued

| Compound | Chemical Name |
|---|---|
| 1.009 | (2R,4S)-2-((R)-2-hydroxy-2-((2R,3S,4S,5S,6S)-3,4,5-trihydroxy-6-(((2R,4R)-2-oxido-4-(pyridin-4-yl)-1,3,2-dioxaphosphinan-2-yl)oxy)tetrahydro-2H-pyran-2-yl)ethoxy)-4-(pyridin-4-yl)-1,3,2-dioxaphosphinane 2-oxide |
| 1.010 | (2R,4S)-2-((R)-2-hydroxy-2-((2R,3S,4S,5S,6R)-3,4,5-trihydroxy-6-(((2R,4R)-2-oxido-4-(pyridin-4-yl)-1,3,2-dioxaphosphinan-2-yl)oxy)tetrahydro-2H-pyran-2-yl)ethoxy)-4-(pyridin-4-yl)-1,3,2-dioxaphosphinane 2-oxide |
| 1.011 | (2R,4R)-4-(3-chlorophenyl)-2-((((2S,3S,4S,5S,6R)-6-((R)-2-(((2R,4S)-4-(3-chlorophenyl)-2-oxido-1,3,2-dioxaphosphinan-2-yl)oxy)-1-hydroxyethyl)-3,4,5-trihydroxytetrahydro-2H-pyran-2-yl)oxy)-1,3,2-dioxaphosphinane 2-oxide |
| 1.012 | (2R,4R)-4-(3-chlorophenyl)-2-(((2R,3S,4S,5S,6R)-6-((R)-2-(((2R,4S)-4-(3-chlorophenyl)-2-oxido-1,3,2-dioxaphosphinan-2-yl)oxy)-1-hydroxyethyl)-3,4,5-trihydroxytetrahydro-2H-pyran-2-yl)oxy)-1,3,2-dioxaphosphinan 2-oxide |

TABLE 1-continued

| Compound | Chemical Name |
|---|---|
| 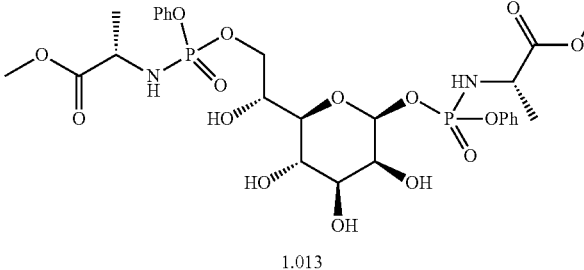<br>1.013 | methyl (((2R)-2-hydroxy-2-((2R,3S,4S,5S,6S)-3,4,5-trihydroxy-6-(((((S)-1-methoxy-1-oxopropan-2-yl)amino)(phenoxy)phosphoryl)oxy)tetrahydro-2H-pyran-2-yl)ethoxy)(phenoxy)phosphoryl)-L-alaninate |
| 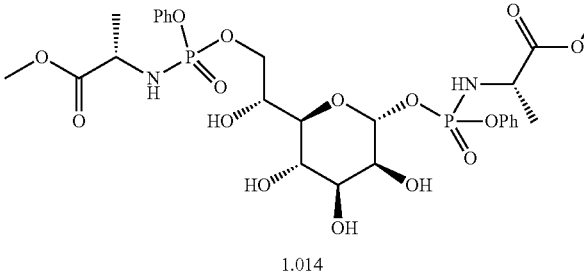<br>1.014 | methyl ((2R)-2-hydroxy-2-((2R,3S,4S,5S,6R)-3,4,5-trihydroxy-6-(((((S)-1-methoxy-1-oxopropan-2-yl)amino)(phenoxy)phosphoryl)oxy)tetrahydro-2H-pyran-2-yl)ethoxy)(phenoxy)phosphoryl)-L-alaninate |
| 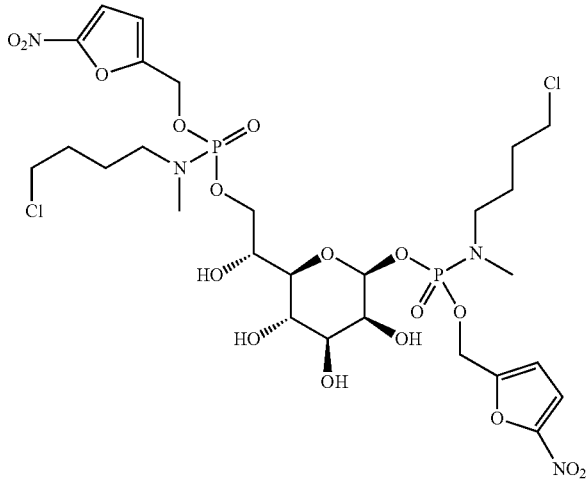<br>1.015 | (2R)-2-((2R,3S,4S,5S,6S)-6-((((4-chlorobutyl)(methyl)amino)((5-nitrofuran-2-yl)methoxy)phosphoryl)oxy)-3,4,5-trihydroxytetrahydro-2H-pyran-2-yl)-2-hydroxyethyl((5-nitrofuran-2-yl)methyl)(4-chlorobutyl)(methyl)phosphoramidate |

| Compound | Chemical Name |
|---|---|
| 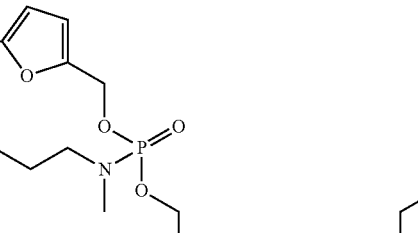<br>1.016 | (2R)-2-((2R,3S,4S,5S,6R)-6-((((4-chlorobutyl)(methyl)amino)((5-nitrofuran-2-yl)methoxy)phosphoryl)oxy)-3,4,5-trihydroxytetrahydro-2H-pyran-2-yl)-2-hydroxyethyl((5-nitrofuran-2-yl)methyl)(4-chlorobutyl)(methyl)phosphoramidate |

Synthesis of H1b-ADP and HMP-1bP

D-glycero-D-manno-heptose-1β-ADP ("H1b-ADP", Compound IX) and D-glycero-D-manno-heptose-1β-P (HMP-1bP, Compound VIII)

The synthesis of H1b-ADP proceeded from Compound I, which was synthesized according to Inuki, et al., *Organic Letters* (2017), 19: 3079-3082. Compound IX below was synthesized according to Zamyatina et al., *Angewandte Chemie*, Int'l Ed. (2000), 39(22): 4150-4153.

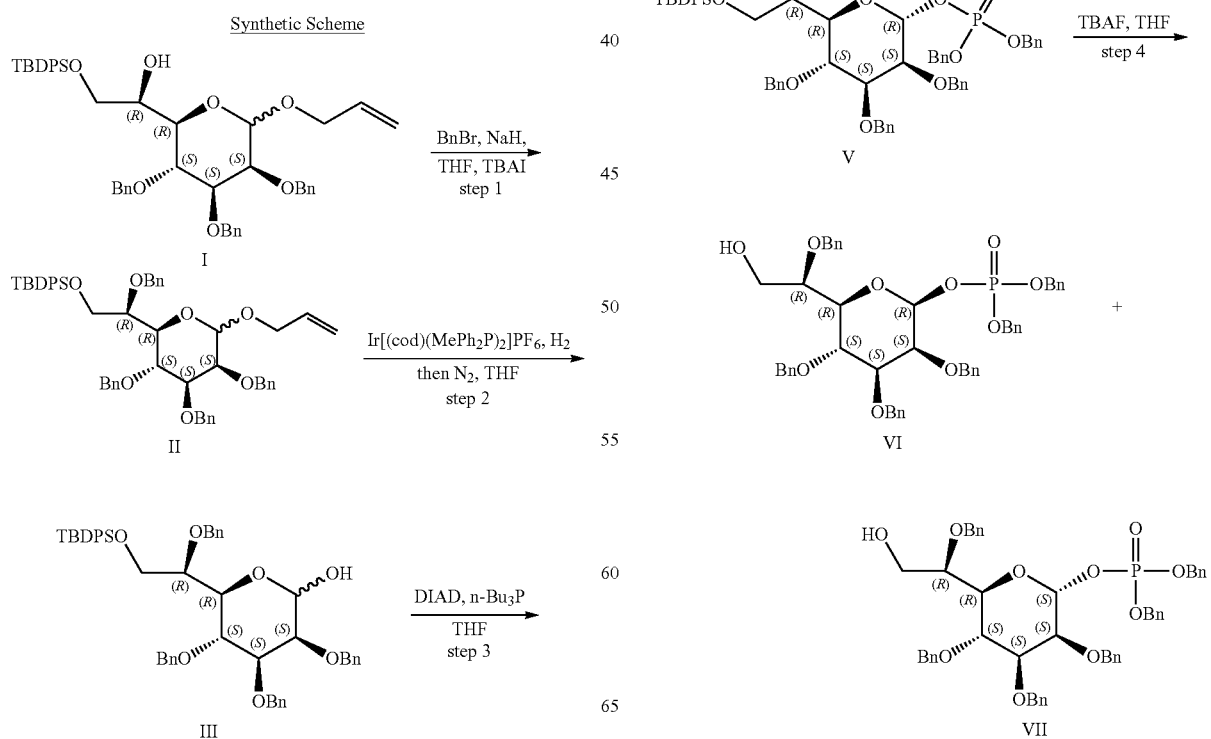

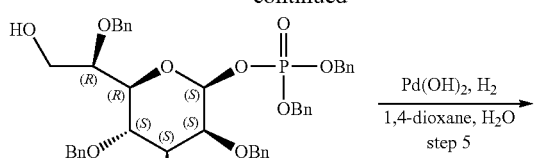

VI

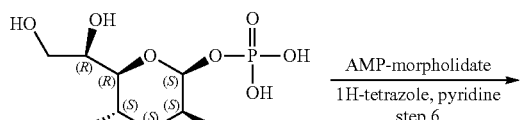

VIII

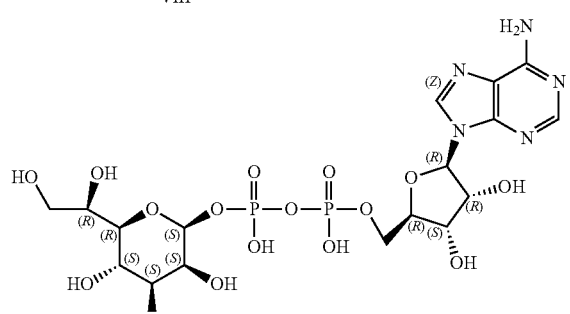

IX

All moisture-sensitive reactions were performed using syringe-septum cap techniques under Ar. Analytical thin layer chromatography (TLC) was performed on Silica gel 60 F 254 Plates (Qindao, 0.25 mm thickness). 1 H-NMR spectra were recorded with a Varian-400 spectrometer, and chemical shifts were reported as (ppm) values relative to internal tetramethylsilane or the residual proton of the deuterated solvent. 13 C-NMR spectra were recorded with a Varian-400 spectrometer, and chemical shifts were reported as δ (ppm) values relative to internal tetramethylsilane or the residual proton of the deuterated solvent. 31 P-NMR spectra were recorded with a Varian-400 spectrometer, and chemical shifts were reported as δ (ppm) values relative to external 85% phosphoric acid. 1 H-NMR spectra are tabulated as follows: chemical shift, multiplicity (br=broad, s=singlet, d=doublet, t=triplet, q=quartet, m=multiplet), number of protons, and coupling constant(s).

Step 1. Synthesis of Compound II

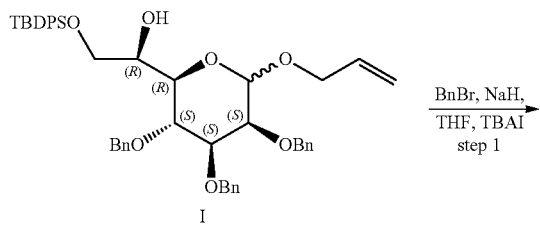

I

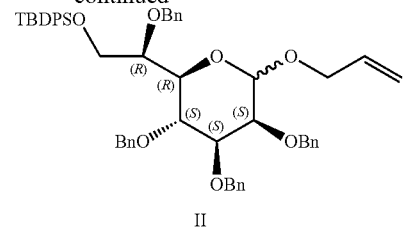

II

To a stirred mixture of compound I (17.93 g, 23.65 mmol), TBAI (0.9 g, 2.365 mmol) and BnBr (7.1 mL, 59.14 mmol) in DMF (270 mL) was added NaH (60% oil dispersion, 2.4 g, 59.14 mmol) at 0° C. After stirring overnight, the reaction was quenched with H$_2$O. The whole mixture was extracted with PE/EtOAc (1:9). The extract was washed with H$_2$O and brine, and dried over MgSO$_4$. The filtrate was concentrated under reduced pressure to give an oily residue, which was purified by flash chromatography over silica gel with PE-EtOAc (5:1) to give compound II (6.3407 g, 32% yield) as a colorless oil $^1$H NMR (CDCl$_3$, 400 MHz) δ (ppm): $^1$H NMR (CDCl$_3$, 400 MHz) 1.04 (s, 9H); 3.75-3.77 (m, 1H); 3.84-3.96 (m, 5H); 2.44-2.47 (d, 1H); 4.05-4.14 (m, 3H); 4.56-4.86 (m, 8H); 5.10-5.21 (m, 2H); 5.79-5.84 (m, 1H); 7.02-7.05 (m, 2H), 7.16-7.38 (m, 24H); 7.60-7.67 (m, 4H)

Step 2. Synthesis of Compound III

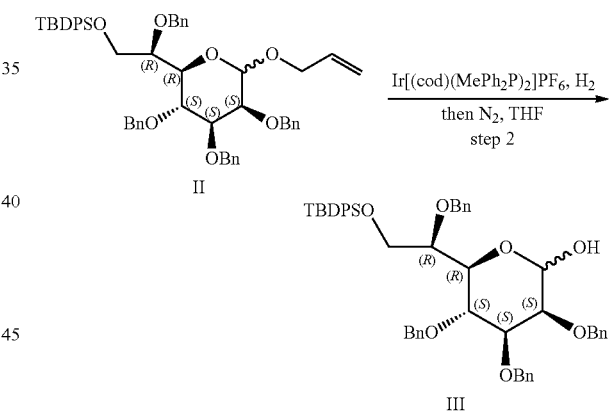

A solution of Ir[(cod)(MePh$_2$P)$_2$]PF$_6$ (210 mg, 253 mmol) in THF (35 mL) was stirred at room temperature under 1 atm H$_2$ atmosphere until a light yellow solution was generated, then N$_2$ was bubbled through the solution to remove any residual hydrogen gas. The resulting solution of Ir catalyst was added to a stirred solution of compound II (1.0741 g, 1.27 mmol) in THF (35 mL) at room temperature. After stirring for 6 h at this temperature, H$_2$O (22 mL) and I2 (650 mg, 2.56 mmol) was added to the stirred mixture at room temperature. After stirring for 1 h at this temperature, the reaction was quenched with saturated Na$_2$S$_2$O$_3$. The whole mixture was extracted with EtOAc. The extract was washed with saturated NaHCO$_3$ and dried over with MgSO$_4$. The filtrate was concentrated under reduced pressure to give an oily residue, which was purified by flash chromatography over silica gel with PE-EtOAc (1:1) to give compound III (0.68 g, 66.3% yield) as a colorless oil. $^1$H NMR (CDCl$_3$, 400 MHz) δ (ppm): 1.03 (s, 9H), 3.72 (s, 1H); 3.93~4.05 (m, 6H); 4.23~4.45 (m, 1H); 4.55~4.80 (m, 7H); 5.13 (br, 1H); 7.02~7.07 (m, 2H); 7.21~7.37 (m, 24H); 7.62~7.68 (m, 4H).

Step 3. Synthesis of Compound IV and V

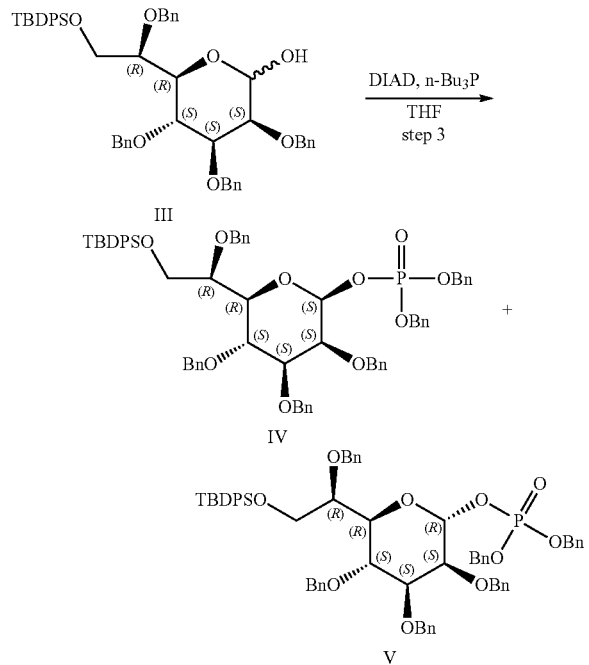

To a stirred mixture of compound III (680 mg, 0.842 mmol), dibenzyl phosphate (702 mg, 2.53 mmol), n-Bu₃P (0.51 g, 2.53 mmol) and MS 5 Å (500 mg) in CH₂Cl₂ (20 mL) was added Et₃N (0.71 mL, 5.06 mmol) at room temperature. After stirring for 30 min at this temperature, DIAD (0.51 g, 2.53 mmol) was added at room temperature. After stirring overnight, the mixture was concentrated under reduced pressure to give an oily residue. The crude product was purified by flash chromatography over silica gel with PE-EtOAc (7:3) to give a mixture of compound IV and V (0.966 g, 100%) which was used in next step directly.

Step 4. Synthesis of Compound VI and VII

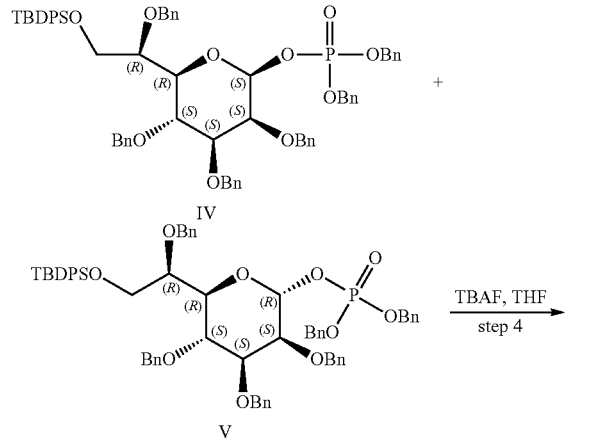

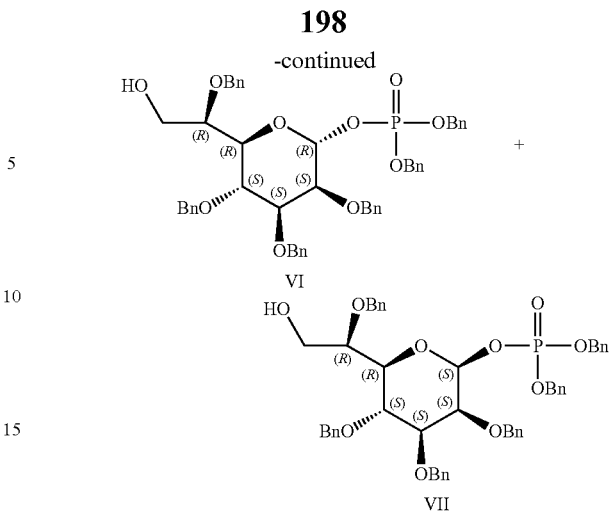

To a stirred solution of a mixture of compounds IV and V (0.966 g, 0.904 mmol) in THF (20 mL) was added TBAF (1 M in THF, 1.4 mL, 1.4 mmol) at room temperature. After stirring overnight, the reaction was quenched with saturated NH₄Cl. The whole mixture was extracted with EtOAc. The extract was washed with saturated NaHCO₃ and dried over MgSO₄. The filtrate was concentrated under reduced pressure to give an oily residue, which was purified by flash chromatography with petroleum/EtOAc (3:1) to give compound VI (169.7 mg, 22.6%) and compound VII (225 mg, 30%) as a colorless oil. Compound VI: ¹H NMR (CDCl₃, 400 MHz) δ (ppm): 3.52~3.54 (m, 1H); 3.67~3.73 (m, 2H), 3.84~3.87 (dd, 1H); 3.97~3.99 (m, 1H); 4.04~4.07 (m, 1H); 4.47~4.50 (m, 1H); 4.58~4.60 (m, 1H); 4.71~4.74 (m, 1H); 4.87~4.89 (m, 1H); 4.93~5.03 (m, 9H); 5.70~5.72 (dd, 1H); 7.19~7.33 (m, 30H). ³¹P NMR (CDCl₃, 400 MHz) δ −2.60. Compound VII: 1H NMR (CDCl₃, 400 MHz) δ3.56-3.59 (dd, 1H); 3.65~3.68 (m, 2H); 3.81~3.84 (m, 2H); 4.02~4.07 (m, 1H); 4.52~4.56 (m, 1H); 4.59~4.61 (m, 1H); 4.68~4.78 (m, 3H); 4.86~4.88 (m, 1H); 4.95~5.11 (m, 7H); 5.24~5.26 (d, 1H); 7.18~7.39 (m, 30H). ³¹P NMR (CDCl₃, 400 MHz) δ −2.50

Step 5. Synthesis of Compound VIII
(D-glycero-D-manno-heptose-1β-P)

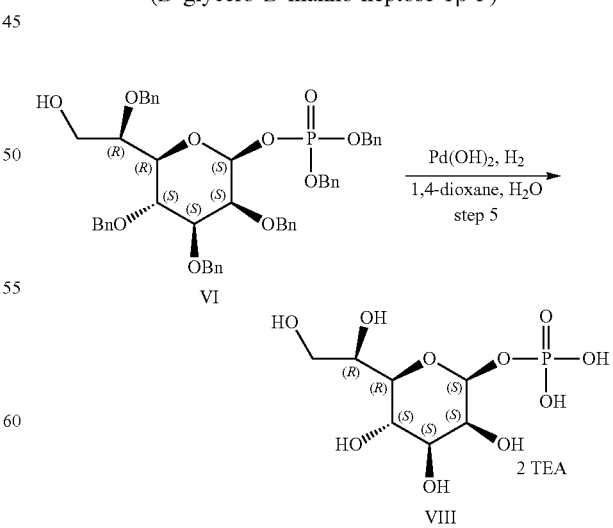

A mixture of compound VI (105 mg, 0.126 mmol) and 20% w/w Pd(OH)₂/C (21 mg, 0.03 mmol) in 1,4-dioxane/

$H_2O$ (5 mL, 4:1) was stirred at room temperature under $H_2$ (1 atm) for 2 days. The mixture was filtrated through an Advantech PTFE membrane filter with a pore size of 0.5 m with $H_2O$. The filtrate was cooled to 0° C. and was added TEA (53 uL, 0.378 mmol) and stirred at this temperature for 3 h. The resulting mixture was lyophilized to give compound VIII-2Et$_3$N as a white solid (74.3 mg, quant.).

Step 6. Synthesis of Compound IX
(D-Glycero-D-Manno-Heptose-1-ADP)

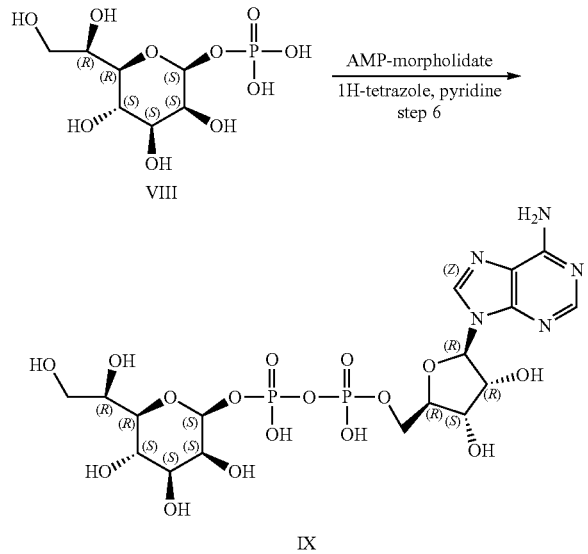

The compound VIII (28.6 mg, 0.058 mmol) was dissolved in anhydrous pyridine and concentrated under vacuum. This azeotropic was repeated three times to remove of residual water. AMP-morpholidate (97 mg, 0.233 mmol) and 1H-tetrazole (32 mg, 0.453 mmol) was added to the dried compound VIII. Anhydrous pyridine (2 mL) was added, and the mixture was stirred under $N_2$ atmosphere for 78 h. After concentration, the residue was precipitated and washed with ethyl acetate. The resulting solid was purified by preparative HPLC (RP-C18) using as the mobile phase 10 Mm $NH_4COOCH_3$ in water (solvent A) and acetonitrile (solvent B), and as an elution gradient 5%-85% (solvent B) over 3 minutes followed by 85%-95% (solvent B) over 0.5 minutes and holding at 95% for 1 minute at a flow rate of 0.4 ml/min.; Column: HSS T3 1.8 um, 2.1*100 mm, Column 40 C) to give a mixture of compound IX and compound VIII. The mixture was purified again on a Sephadex G-15 column to give compound IX as a white solid (3.5 mg, 10%). The $^1H$ NMR and $^{31}P$ NMR data were consistent with that reported in the literature.

The invention is further described and exemplified by the following non-limiting examples.

HBP is a metabolic intermediate in the bacterial ADP heptose biosynthetic pathway. HBP is generated from D-glycero-D-manno-heptose-7-phosphate by either the HldA enzyme or the kinase domain of the HldE enzyme, depending on bacterial strain, and converted into D-glycero-β-D-manno-heptose-1-phosphate (HMP-1bP) by the bacterial enzyme GmhB. HMP-1bP is in turn converted into D-glycero-D-manno-heptose-1β-ADP (H1b-ADP) by the bacterial enzyme HldC or in some bacterial cells by the ADP transferase domain of HldE. H1b-ADP is then converted to L-glycero-D-manno-heptose-1β-ADP (H1b-ADP-6L) by HldD (GmhD). See FIG. 16 for a schematic of the pathway and associated enzymes.

Others have used genetic approaches to knock out various enzymes both up and downstream of HBP in this biosynthetic pathway to clarify the role of HBP in inducing an innate immune response, particularly as it pertains to infection-induced NFKiB activation via ALPK1-TIFA-TRAF6. See e.g., Gaudet et al., Science 348:1251 2015; Milivojevic et al., PLOS Pathogens 13(2) e1006224 2017; and Zimmermann et al., Cell Reports 20:2384 2017. Guadet concludes that NFkB activation "was directly attributable to the presence of HBP" because "disruption of the ADP-heptose pathway upstream of HBP in Escherichia coli or N. meningitidis abrogated NF-kB activation." Guadet at p. 1252. Milivojevic utilized S. typhimurium cells deleted for the HldE gene and showed that these cells, which are unable to synthesize HBP, failed to induce IL-8 production in both infected and bystander cells, while cells deficient for enzymes acting downstream of HBP, GmhB or WaaC, induced strong IL-8 expression. Milivojevic at p. 12.

In view of this prior work pointing to HBP as the key molecule for inducing innate immunity, we were surprised to find that molecules in addition to HBP, such as HMP-1bP and H1b-ADP were also able to induce IL-8 and TNFα mRNA expression in cells in an ALPK1-dependent manner using chemically synthesized HBP, HMP-1bP, and H1b-ADP (Example 1). Moreover, and even more surprisingly, we found H1b-ADP to be much more potent than either HBP or HMP-1bP at inducing cytokine expression in this assay. We also found, unexpectedly, that chemically synthesized HBP was unable to bind to ALPK1 in a thermal shift assay (Example 2), and was further unable to induce ALPK1 autophosphorylation (Example 3). Instead, we unexpectedly found that only H1b-ADP was able to bind ALPK1 and induce its autophosphorylation in these assays. In further experiments, we found that H1b-ADP was able to activate ALPK1-dependent NFkB pathway signaling via phosphoporylation of IkB (Example 4). In addition, we found H1b-ADP-6L is also able to activate ALPK1-dependent phosphoporylation of its downstream substrate, TIFA (Example 5). Finally, in a murine tumor model, we found that H1b-ADP, but not HBP or HMP-1bP, had potent anti-tumor activity (Example 7 and Example 8) and that this activity synergistically enhanced the anti-tumor activity of both a checkpoint inhibitor (anti-PD-1 antibody) and an agonist of an immune co-stimulatory molecule (anti-OX40 agonist antibody).

Together, the data provided here indicates that bacterial metabolites in addition to HBP, namely HMP-1bP, H1b-ADP, and H1b-ADP-6L, can induce ALPK1-dependent signaling relevant to the induction of innate immunity and that at least one of these molecules, H1b-ADP, further has surprising and unexpected anti-tumor activity both alone and in combination with other immune modulators. Although this molecule had been recognized as a TLR-9 agonist (US 20100016250 by Nagata et al., Kyowa Hakko Kirin Co.), and on that basis proposed to be useful generally for treating allergy, tumors, infectious diseases, and as an immunostimulatory agent, the present results are the first to demonstrate its activity in ALPK1-dependent signaling and the first to demonstrate anti-tumor activity in an animal model.

EXAMPLES

Figure 2B:
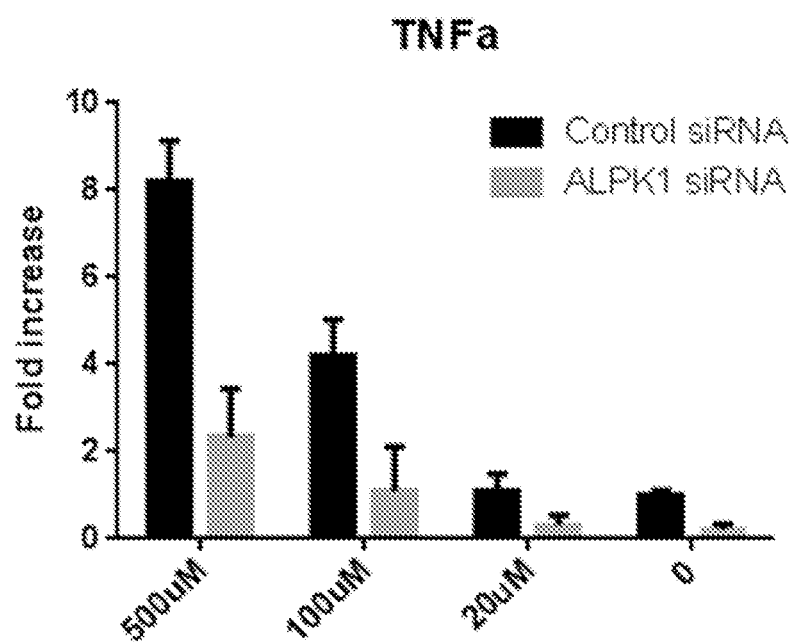
Figure 3A:
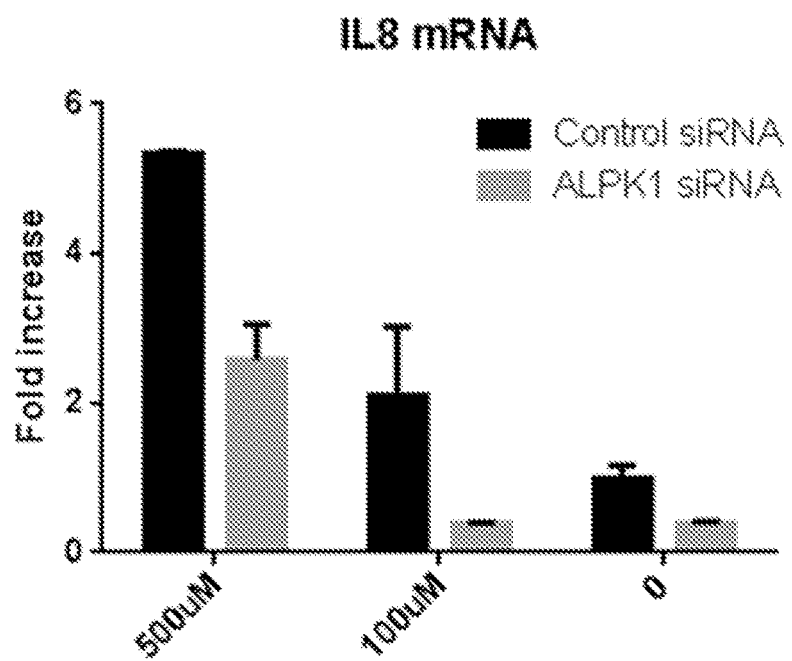
FIG. 3A-B: IL-8 (A) and TNFα (B) mRNA expression were both increased by HMP-1bP (chemically-synthesized) in an ALPK1-dependent manner.
Figure 3B:
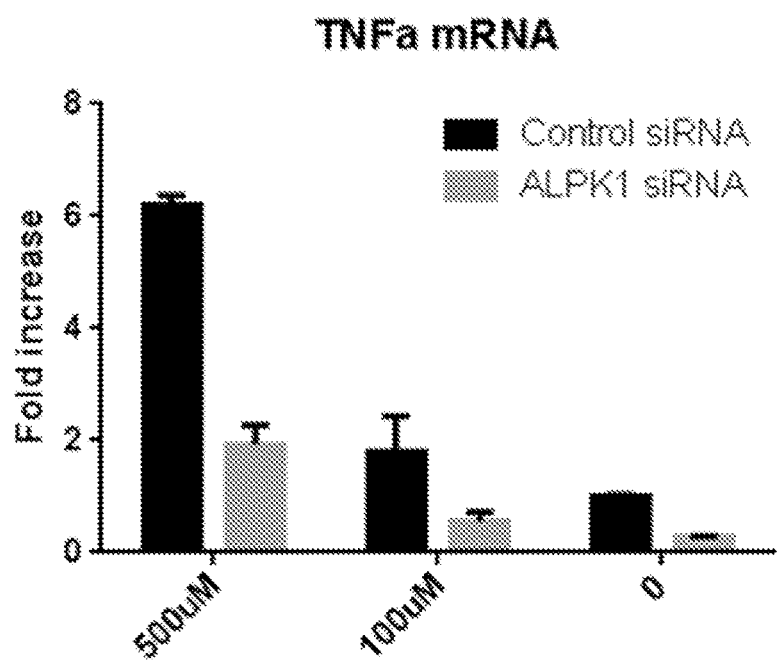
Figure 4A:
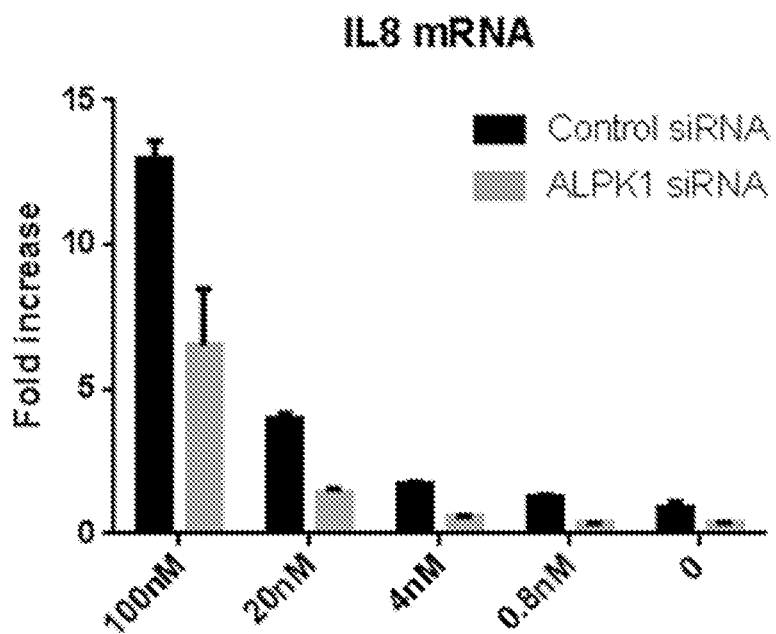
FIG. 4A-B: IL-8 (A) and TNFα (B) mRNA expression were both increased by H1b-ADP (chemically-synthesized) in an ALPK1-dependent manner.
Figure 4B:
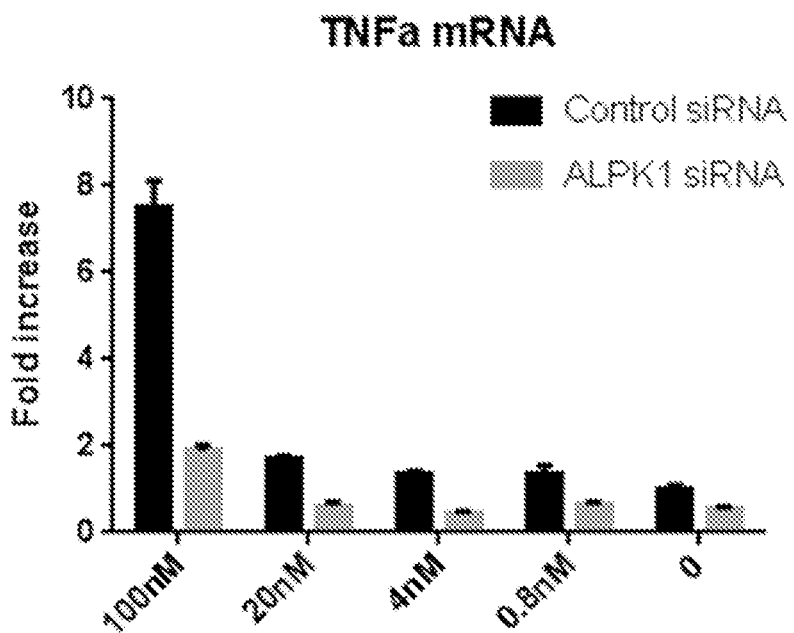

Example 1: Chemically Synthesized HBP, HMP-1bP, and H1b-ADP Each Induce IL-8 and TNFα mRNA Expression in 293HEK Cells in an ALPK1 Dependent Manner To test whether HBP, HMP-1bP, and H1b-ADP were able to induce cytokine expression in an ALPK1 dependent manner, we used an ALPK1-directed small interfering RNA (siRNA) to silence ALPK1 expression in HEK293 cells. Cells were plated ($1 \times 10^4$ cells/well) into 96-well plates and transfected with either control siRNA or ALPK1-directed siRNA according to the manufacturer's protocols (Lipofectamine™ RNAiMax™, Invitrogen 13778075). Following 2 days of culture, either (1) HBP (500 uM, 100 uM, 20 uM, FIG. 2A-2B) (2) HMP-1bP (500 uM, 100 uM, FIG. 3A-3B), (3) H1b-ADP (100 nM, 20 nM, 4 nM, 0.8 nM, FIG. 4A-4B) was added to culture medium and cells were harvested 4 hours later. Total RNA was isolated (TRIzol™, ThermoFisher) and cDNA was synthesized (PrimeScript™ RT reagent Kit (Takara) and amplified (AceQ™ qPCR SYBR™ Green Master Mix, Vazyme Biotech using a QuantStudio™ 7 Flex Real-Time PCR Systems (ThermoFisher) according to manufacturers' protocols. IL-8 and TNFα mRNA expression were both increased in an ALPK1-dependent manner, as evidenced by the decrease in expression of both cytokines in the presence of ALPK1-directed siRNA. These results suggest that each of HBP, HMP-1bP, and H1b-ADP activates IL-8 and TNFα gene expression through ALPK1.

Figure 5A:
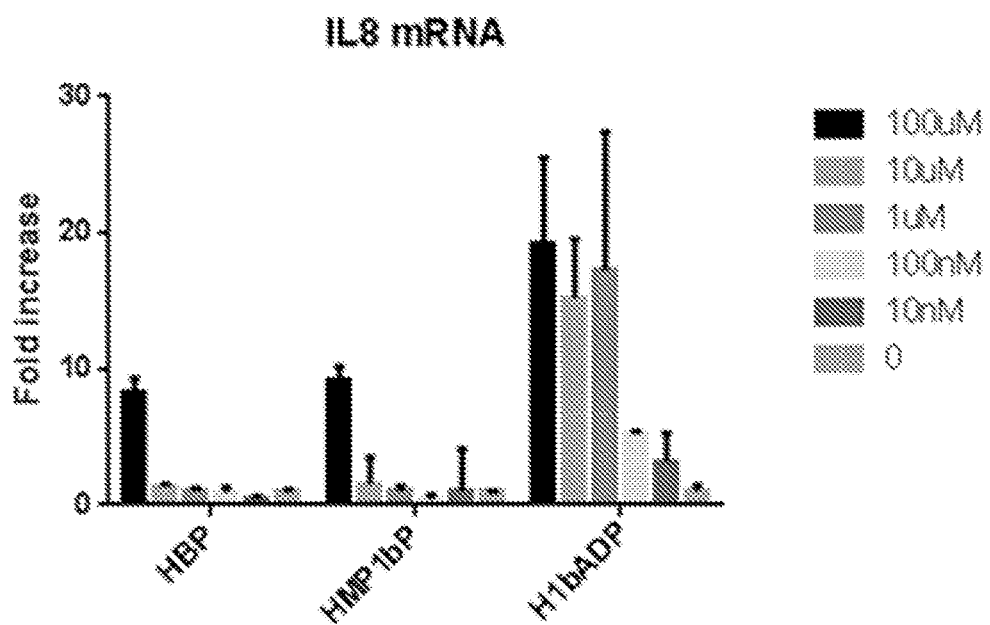
FIG. 5A-B: IL-8 (A) and TNFα (B) mRNA expression induced by each of HBP, HMP-1bP, and H1b-ADP.
Figure 5B:
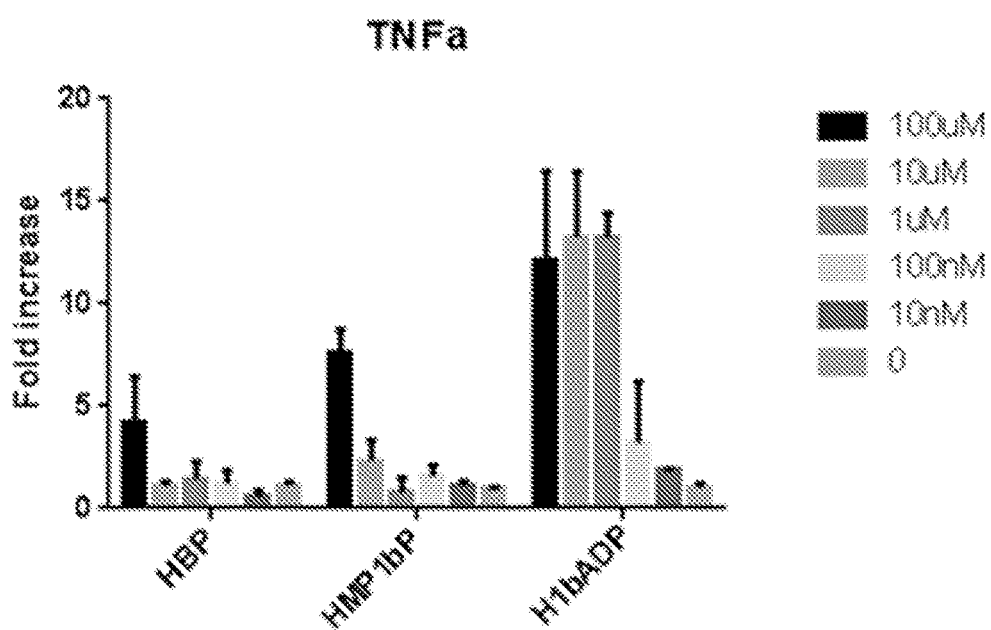

Surprisingly, H1b-ADP was significantly more potent than the other molecules in this assay. As shown in FIG. 5, both IL-8 and TNFα mRNA expression were induced by H1b-ADP at nanomolar concentrations (10 nM) while 100 uM of either HBP or HMP-1bP was required. This was surprising because, as discussed above, previous reports by two groups showed that HBP, and not its downstream metabolites including HMP-1bP and H1b-ADP, is responsible for IL-8 induction through the ALPK1-TIFA pathway (Gaudet et al., *Science* 348:1251 2015; Milivojevic et al., *PLOS Pathogens* 13(2) e1006224 2017).

Example 2: H1b-ADP, but not HBP or HMP-1bP, Binds to ALPK1

The thermal shift assay is widely used to determine the binding of a molecule to a protein of interest. The assay is based on the increase in thermal energy required for denaturation of a protein where another molecule is bound to the protein. SYPRO Orange is a fluorescent compound used in the detection of thermal shift. SYPRO Orange binds to hydrophobic surfaces of the protein, and water strongly quenches its fluorescence. When the protein unfolds, the exposed hydrophobic surfaces bind the dye, resulting in an increase in fluorescence. When another molecule is bound to the protein, an increase in the temperature required for unfolding of the protein is observed.

Figure 6:
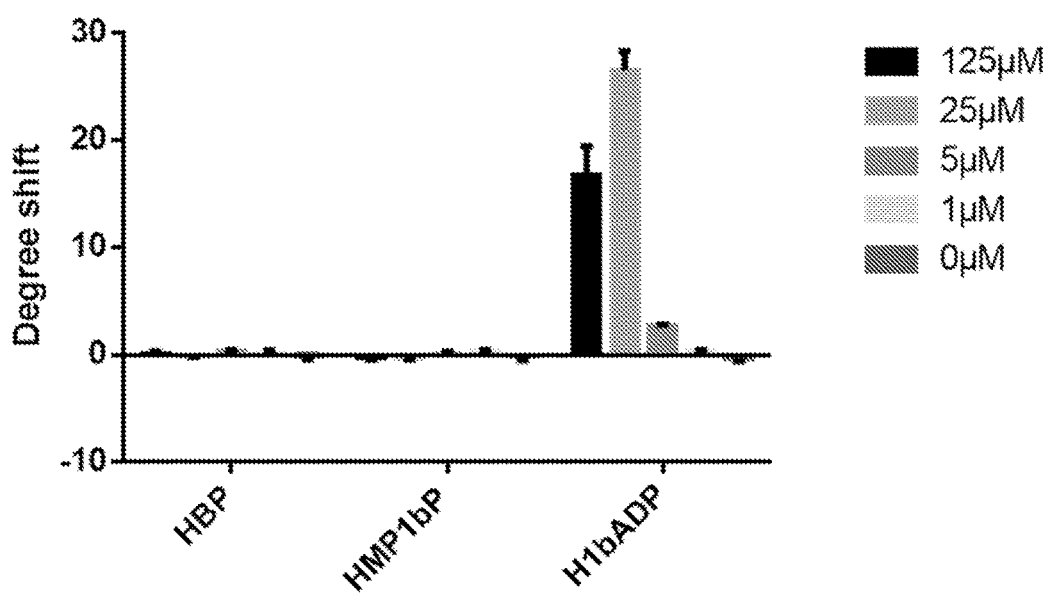
FIG. 6: Thermal-shift assay showing binding to ALPK1 in the presence of chemically-synthesized HBP, HMP-1bP, and H1b-ADP (only H1b-ADP binds).

This assay system was used to determine whether or not chemically synthesized HBP, HMP-1bP, and H1b-ADP directly bind to ALPK1. FIG. 6 shows the thermal shift of ALPK1 (7 uM mixed with 1000×SYPRO Orange) incubated in the absence or presence of 1 uM, 5 uM, 25 uM, or 125 uM of each of HBP, HMP-1bP, and H1b-ADP. Neither HBP nor HMP-1bP were able to induce a thermal shift. Only H1b-ADP induced a shift of more than 1 degree, at each of the three highest concentrations tested, 5 uM, 25 uM, and 125 uM. These results indicate that H1b-ADP, but not HBP or HMP-1bP, are able to directly bind to ALPK1.

We previously found HBP bound ALPK1 in this assay using HBP produced in vitro by enzymatic catalysis from its precursor, D-glycero-D-manno-heptose-7-P (HMP). In those studies, the enzyme used for in vitro production of HBP was the sugar kinase HIda, which was purified from wild-type *E. coli* cells. As discussed below in Example 9 below, we now believe that the purified HIda enzyme was contaminated with additional enzymes, presumably Gmhb and H1dE, that converted at least some of the HBP to H1b-ADP in those earlier assays.

Figure 7:
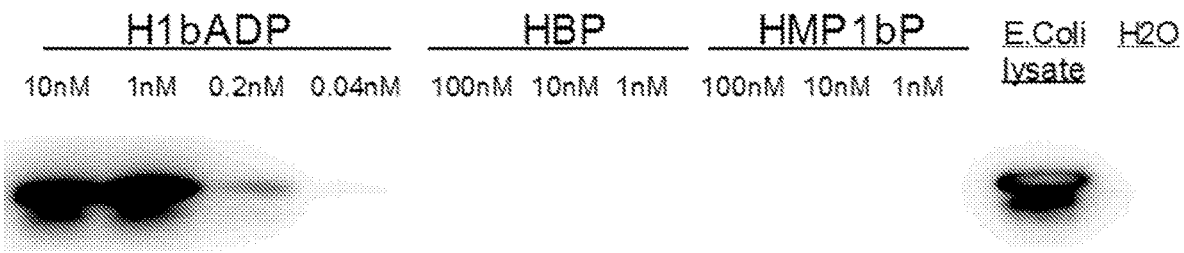
FIG. 7: Cell-free kinase assay showing phosphorylation of the ALPK1 substrate TIFA in the presence of chemically-synthesized HBP, HMP-1bP and H1b-ADP (TIFA is phosphorylated only in the presence of H1b-ADP).
Figure 8:
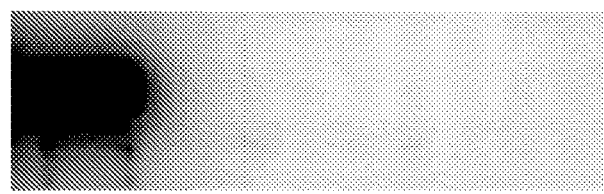
FIG. 8: Cell-free kinase assay of auto-phosphorylation of ALPK1 in the presence of H1b-ADP (chemically-synthesized).

Example 3: H1b-ADP, but not HBP or HMP-1bP, Induces ALPK1 Autophosphorylation ALPK1 activation results in its autophosphorylation. Accordingly, we next asked whether the binding of H1b-ADP to ALPK1 was sufficient to induce ALPK1 autophosphorylation. Phosphorylation assays were performed according to standard protocols. Briefly, ALPK1 was incubated (2 nM, 25° C., 1 h) in assay buffer (20 al, 25 mM HEPES pH 7.5, 50 mM KCl, 0.1 mM EDTA, 0.1 mM EGTA, 2 mM DTT, 1.5 mM $CaCl_2$, 10 mM $MgCl_2$) with ATP and chemically synthesized HBP, HMP-1bP, or H1b-ADP followed by denaturing gel electrophoresis and Western analysis with an anti-phospho-threonine antibody (CST) to detect autophosphorylation of ALPK1. As shown in FIG. 7, phosphorylation of ALPK1 was detected only in the presence of H1b-ADP (10 nM, 1 nM, and 0.2 nM), indicating that H1b-ADP, but not HBP or HMP-1bP induces ATP-dependent autophosphorylation and activation of ALPK1. The range of concentrations of HBP and HMP-1bP used in this assay (1 nM, 10 nM, 100 nM) was 10-fold higher than that used for H1b-ADP.

We previously found HBP was able to induce ALPK1 autophosphorylation in this assay using HBP produced in vitro by enzymatic catalysis from its precursor, D-glycero-D-manno-heptose-7-P (HMP). In those studies, the enzyme used for in vitro production of HBP was the sugar kinase HIda, which was purified from wild-type *E. coli* cells. As discussed below in Example 9, we now believe that the purified HIda enzyme was contaminated with additional enzymes that converted at least some of the HBP to H1b-ADP in those earlier assays.

Example 4: H1b-ADP Induces ALPK1 Dependent Phosphorylation of IκB

NFκB RelA (p65) is a transcription factor which must translocate from the cytoplasm to the nucleus where it interacts with the promoter region of numerous target genes to regulate their transcription. Target genes of NFκB RelA include, for example, inflammatory cytokines such as IL-8, TNFα, CXCL1, and CXCL3. For nuclear translocation of p65 to occur, the cytoplasmic complex in which it resides must first be degraded. This process is initiated by the phosphorylation and consequent activation of IκB. IκB phosphorylation can therefore be used as a marker for NFκB activation.

We next tested whether H1b-ADP-induced autophosphorylation of ALPK1 was effective to activate NFκB using phosphorylation of IκB as a marker for this activity. Phosphorylation assays were performed according to standard protocols and phosphorylated protein was detected by gel electrophoresis and Western blotting using an antibody that detects phosphorylated IκB. Briefly, assays were performed in a 20 µl volume at 25° C. in assay buffer (25 mM HEPES pH 7.5, 50 mM KCl, 0.1 mM EDTA, 0.1 mM EGTA, 2 mM DTT, 1.5 mM $CaCl_2$, 10 mM $MgCl_2$) containing 2 nM ALPK1 and H1b-ADP (how much) with or without ATP, or either ALPK1 alone or H1b-ADP alone, both in the presence of ATP. After 1 hour of incubation, the reaction was loaded to denaturing gel for protein electrophoresis and Western was performed to detect phosphorylation of IkB using p-IkB antibody (Abcam).

Figure 9:
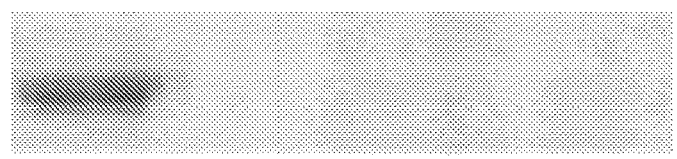
FIG. 9: Cell-free kinase assay of ALPK1-dependent phosphorylation of IκB in the presence of H1b-ADP (chemically-synthesized).

As shown in FIG. 9, IkB phosphorylation was detected only in the presence of both ALPK1 and H1b-ADP in the presence of ATP. These results indicate that HBP-induced autophosphorylation of ALPK1 activates the NFkB pathway.

Example 5: H1b-ADP-6L Induces ALPK1 Dependent Phosphorylation of TIFA

L-glycero-D-manno-heptose-1β-ADP (H1b-ADP-6L) is another bacterial metabolite in the same biosynthetic pathway as HBP, HMP-1bP, and H1b-ADP. It is formed from H1b-ADP by the action of the bacterial HldD (GmhD) enzyme. We asked whether this molecule, which is structurally very similar to H1b-ADP, has ALPK1 biological activity.

Figure 10:
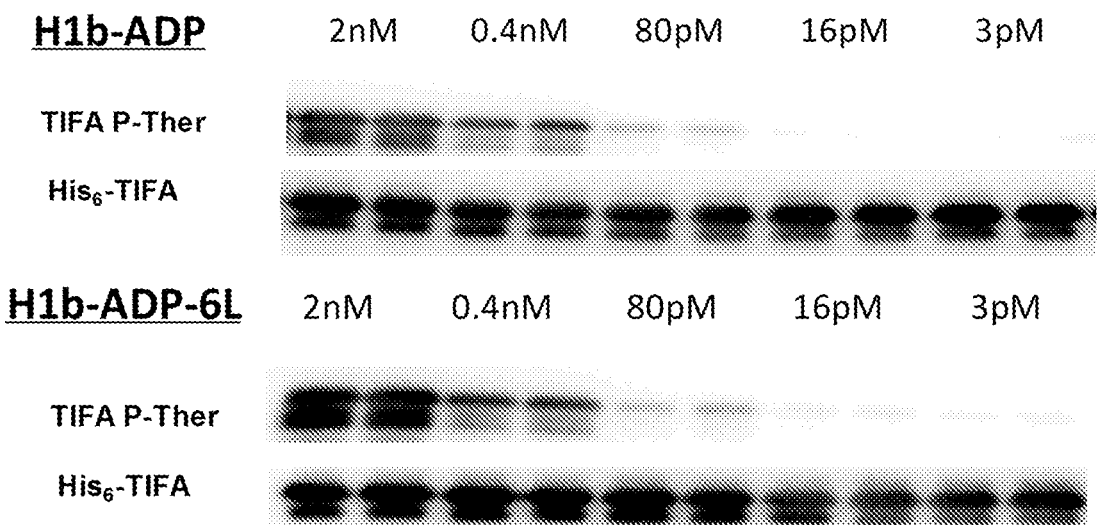
FIG. 10: Cell-free kinase assay showing phosphorylation of the ALPK1 substrate TIFA in the presence of chemically-synthesized H1b-ADP and H1b-ADP-6L.

We performed an in vitro kinase assay with H1b-ADP and H1b-ADP-6L along with ALPK1 protein (2 nM), and TIFA protein (1.6 uM) in kinase buffer containing 50 uM ATP. TIFA phosphorylation was analyzed by denaturing gel electrophoresis followed by western blotting using an anti-phosphothreonine antibody. H1b-ADP or H1b-ADP-6L was added at 2 nM, 0.4 nM, 80 pM, 16 pM, and 3 pM. As shown in FIG. 10, H1b-ADP-6L activated ALPK1-dependent signaling in a manner similar to H1b-ADP.

Figure 11:
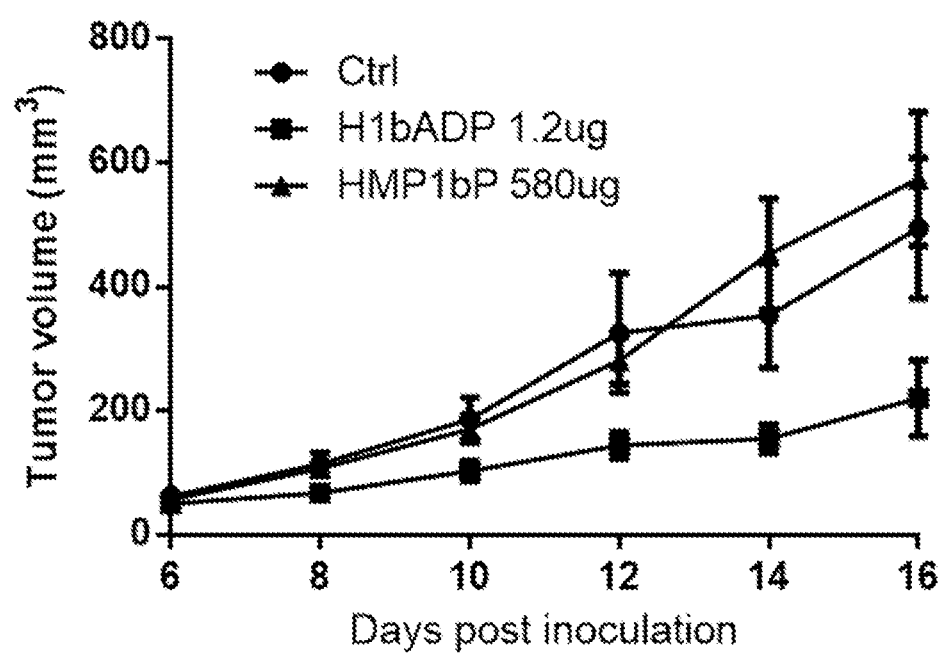
FIG. 11: Intratumoral injection of H1b-ADP, but not HMP-1bP, inhibits tumor growth in mouse CT26 xenograft model.

Example 6: H1b-ADP, but not HMP-1bP, Intratumoral Injection Slows Tumor Growth and Induces Inflammatory Gene Overexpression in Tumor Tissues We used a CT26 tumor xenograft model to test the anti-cancer activity of H1b-ADP. Tumor cells ($2\times10^5$ per 100 uL CT26 cells) were inoculated subcutaneously into the right flank of BALB/c mice. At day 6, mice whose tumors had reached 3-5 mm in diameter were randomized and grouped into three groups (n=8 each group), control, HMP-1bP (580 ug), and H1b-ADP (1.2 ug). Injections were performed using a total volume of 20 uL at days 6, 8, 10, 12, and 14 post inoculation. Tumor volumes were calculated every 2 days from caliper measurements of tumor dimension using the formula $(L\times W^2)/2$, where L is the longer measurement. As shown in FIG. 11, H1b-ADP, but not HMP-1bP, reduced tumor growth in this model system, indicating that H1b-ADP was able to elicit an anti-tumor immune response effective to suppress tumor growth.

We next asked whether H1b-ADP caused an increase in pro-inflammatory cytokines within the tumor. Tumor cells ($2\times10^5$ per 100 µL CT26 cells) were inoculated subcutaneously into the right flank of BALB/c mice. 2.5 µg (n=2), 250 ng (n=2), 50 ng (n=2) of H1b-ADP or control (n=2) was intratumorally injected (20 uL) at day 7 post inoculation. 4 hours post-injection, tumor issues were dissected and harvested. Total RNA was isolated (TRIzol™, ThermoFisher) and cDNA was synthesized (PrimeScript™ RT reagent Kit, Takara) and amplified (AceQ™ qPCR SYBR™ Green Master Mix, Vazyme Biotech using a QuantStudio™ 7 Flex Real-Time PCR Systems (ThermoFisher) according to manufacturers' protocols.

Figure 12:
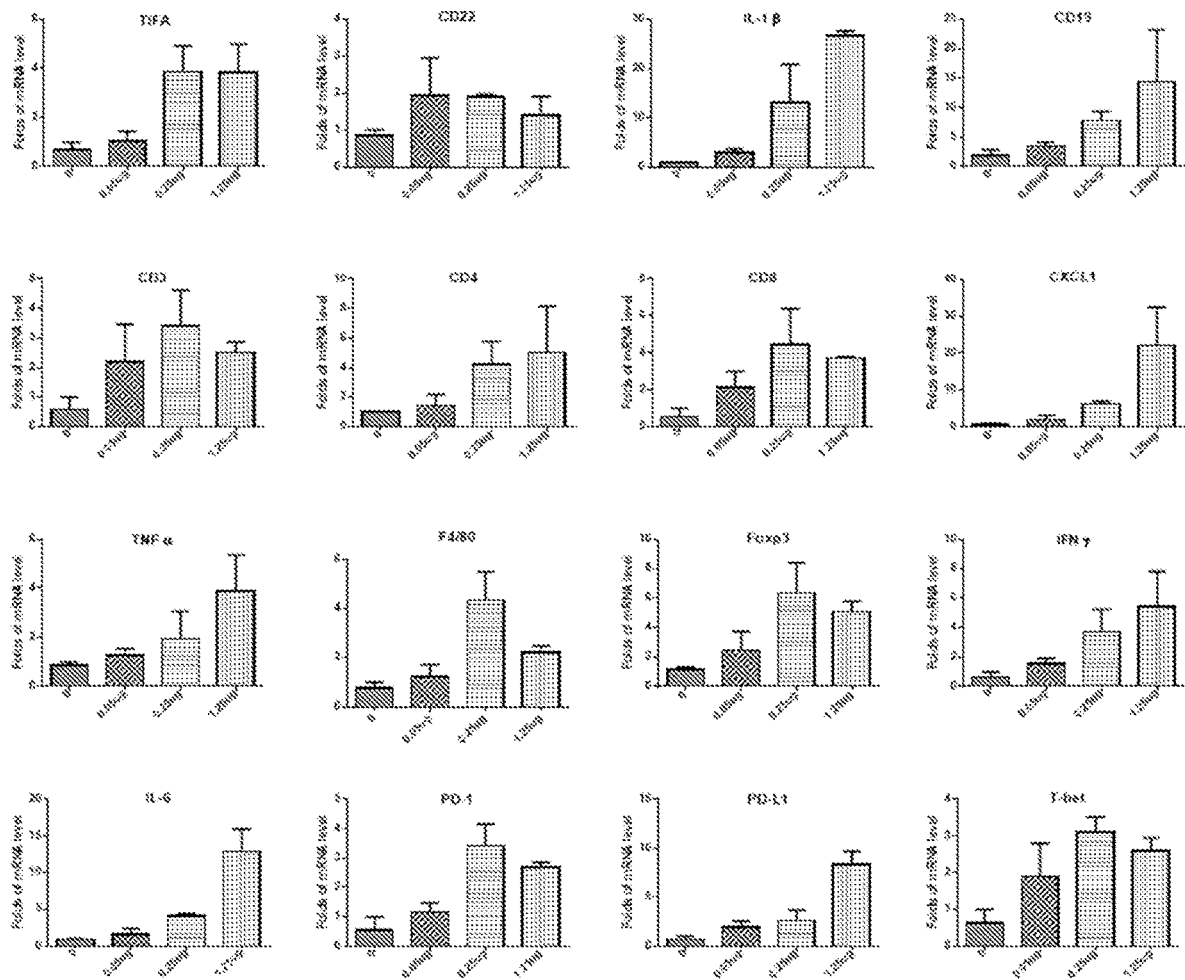
FIG. 12: Intratumoral injection of H1b-ADP results in increased expression of cytokines and PD-1, PD-L1.

The results are shown in FIG. 12. In this experiment, mRNA expression of inflammatory cytokine IL-1b, Tnfa, Ifn gamma, and IL-6, and chemokine Cxcl1 was increased upon H1b-ADP injection, indicating inflammation was activated in the tumor. mRNA expression of cytotoxic T cell marker CD8, T-helper cell marker CD4, regulatory T cell marker Foxp3 and Th1 cell marker T-bet was increased upon H1b-ADP injection, indicating increase number of cytotoxic T, T-helper cell, regulatory T cell and Th1 cell in the H1b-ADP injected tumor. PD-1 and PD-L1 expression was increased in H1b-ADP injected tumor, suggesting combining anti-PD-1 or anti-PD-L1 therapy with H1b-ADP injection may have synergistic effect in slowing tumor growth.

Example 7: H1b-ADP and an Anti-PD-1 Antibody Act Synergistically to Inhibit Tumor Growth Antagonistic antibodies targeting B7 immunoglobulin superfamily molecules (CTLA-4, PD-1, and PD-L1) represent an immune checkpoint inhibition approach that has generated anti-tumor immunity and clinical responses in various types of cancers. However, many patients do not respond to monotherapy based on these antibodies and many others relapse after therapy. Accordingly, there is a need for co-therapies to address primary and secondary resistance to immune checkpoint inhibitor therapy.

Figure 13A:
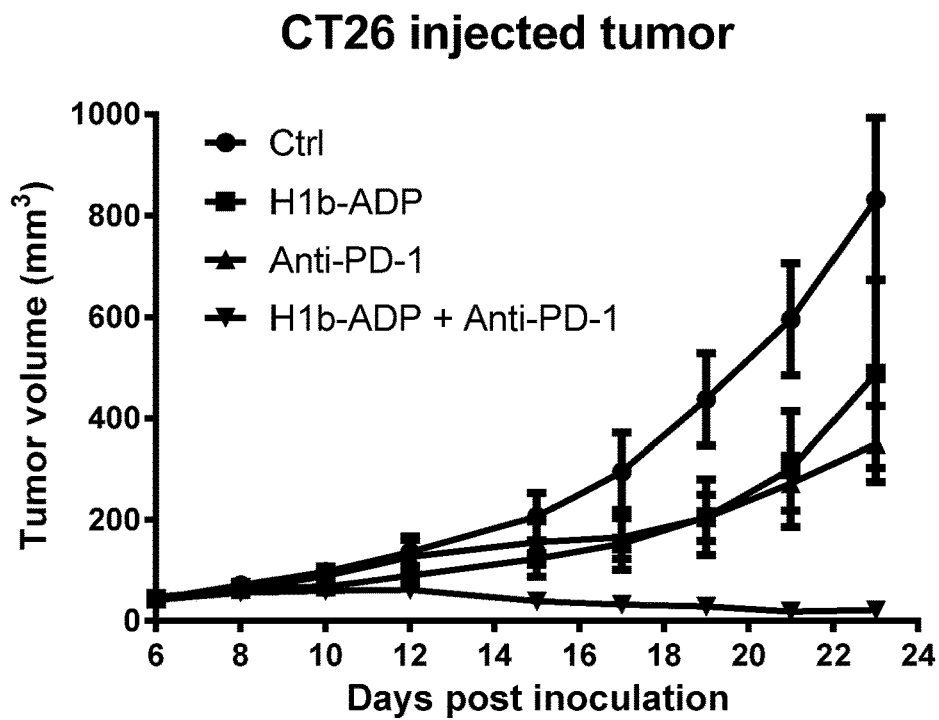
FIG. 13A-B: Intratumoral injection of H1b-ADP and anti-PD-1 antibody (RMP1-14) synergistically inhibit tumor growth in the injected tumor (A) and the distant tumor (B) in mouse CT26 xenograft model.
Figure 13B:
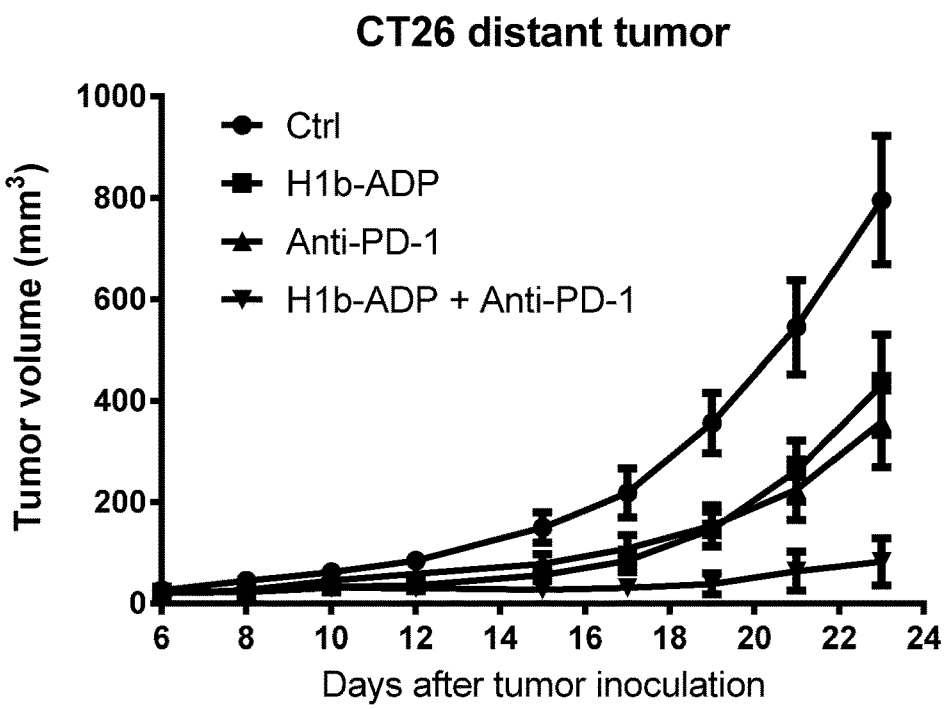

To test whether H1b-ADP could augment an anti-tumor response by a checkpoint inhibitor, we tested the effects of co-administration with an anti-PD1 antibody. Tumor cells ($2\times10^5$ per 100 µL CT26 cells) were inoculated subcutaneously into the left and right flanks of BALB/c mice. At day 7, mice whose tumors had reached 5 mm in diameter were randomized and grouped (n=8 each group) into the following four groups: anti-PD1 antibody; rat IgG; H1b-ADP+rat IgG; H1b-ADP+anti-PD1 antibody. We utilized RMP1-14 as the anti-PD1 antibody (10 mg/kg) and a rat IgG 2a (2A3) as the control IgG. Each of the anti-PD-1 antibody and the control IgG was administered intraperitoneally in a 200 µL volume on days 6, 10, 12, and 17 post-inoculation. H1b-ADP (6.2 µg) was intratumorally injected in a 20 µL volume at day 6, 8, 10, 12, and 15. Tumor volumes were calculated every 2 days from caliper measurements of tumor dimensions using the formula $(L\times W^2)/2$, where L is the longer measurement. The results are shown in FIG. 13A for injected tumors and FIG. 13B for distant tumors. In this experiment, administration of either H1b-ADP or anti-PD1 antibody alone markedly suppressed tumor growth, and to a similar degree. The combination of H1b-ADP and anti-PD1 antibody not only inhibited tumor growth but led to the disappearance of several tumors. These results indicate that the combination of H1b-ADP and a checkpoint-inhibitor such as an anti-PD1 antibody is effective to suppress growth and even inhibit the viability of tumor cells in vivo.

Example 8: H1b-ADP and an Anti-OX40 Agonist Antibody Act Synergistically to Inhibit Tumor Growth We next conducted a similar experiment using an anti-OX40 (CD134) agonist antibody. OX40 (CD134) is a tumor necrosis factor receptor superfamily co-stimulatory receptor molecule expressed by activated immune cells. As noted above, there is a need for co-therapies to address primary and secondary resistance to checkpoint inhibitor therapy and one approach is to administer an immune co-stimulator such as an anti-OX40 agonist antibody.

Figure 14:
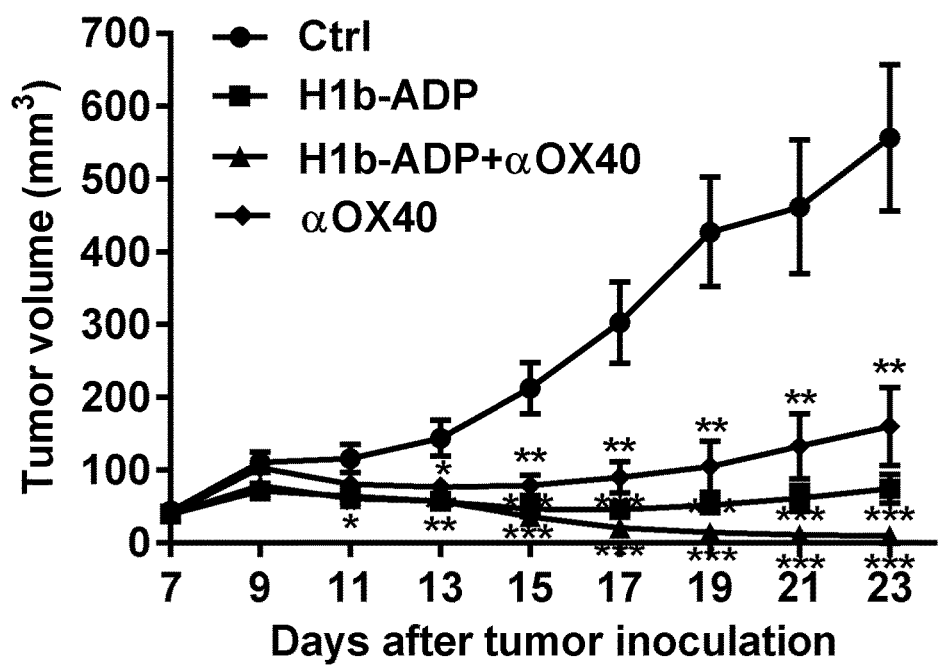
FIG. 14: Intratumoral injection of H1b-ADP and anti-PD-1 antibody (OX40) synergistically inhibit tumor growth in mouse CT26 xenograft model.

The experiment was carried out as above except for the following variations. At day 7, mice whose tumors had reached 5 mm in diameter were randomized and grouped into the following four groups: anti-OX40 antibody; rat IgG; H1b-ADP+rat IgG; H1b-ADP+anti-OX40 antibody. We utilized BE0031 as the anti-OX40 antibody and a rat IgG 2a (2A3) as the control IgG. BE0031 (2 ug), rat IgG (2 ug), and/or H1b-ADP (6.2 µg) was administered intratumorally in a 20 µL volume on days 7, 9, and 11 post-inoculation. The results are shown in FIG. 14.

Example 9: HIda Enzyme Purified from Wild-Type *E. coli* was Apparently Contaminated with Other Bacterial Enzymes We previously found that HBP was able to bind to ALPK1 in a thermal shift assay using HBP produced in vitro by enzymatic catalysis from its precursor, D-glycero-D-manno-heptose-7-phosphate. In those studies, the enzyme used for in vitro production of HBP was the sugar kinase HIdA which was purified from wild-type *E. coli* cells transfected with an HIdA expression plasmid. *E. coli* cells do not express the HIdA or HIdC enzymes, and instead express HIdE, which is a fusion protein containing a kinase domain and an ADP transferase domain. These two domains of HIdE are homologous to the kinase domain of HIdA and the ADP transferase domain of HIdC, respectively. In related studies using the same in vitro produced HBP, we showed HBP activation of ALPK1 autophosphorylation and phosphorylation of IkB downstream of ALPK1.

We now believe that the purified HIdA enzyme used in those experiments was contaminated with *E. coli* enzymes, such as HIdE, that converted at least some of the HBP to H1b-ADP. A previous report on the structure-function activity of the HIdA enzyme suggested that the kinase domains of the HIdA and HIdE enzymes can dimerize resulting in their co-purification. Lee T. W. et al, *J. Med. Chem.* 2013 56:1405-17. Thus, it is likely that some *E. coli* HIdE was co-purified with the recombinant HIdA used in our previous studies. We further speculate that GmhB and HIdA may also form a complex such that GmhB was also co-purified with the recombinant HIdA. Such contamination with *E. coli* GmhB and HIdE would have resulted in at least some conversion of the in vitro produced HBP into H1b-ADP in those prior studies.

Figure 15:
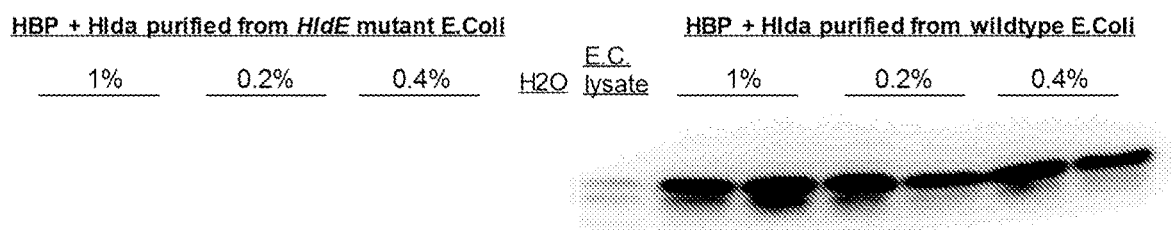
FIG. 15: Western analysis of phospho-TIFA following in vitro kinase reaction for ALPK1-dependent TIFA phosphorylation in the presence of either HBP+HIda purified from HIdE mutant *E. coli* (left) or HBP+HIda purified from wild-type *E. coli* (right).

To test this, we performed an in vitro kinase reaction for ALPK1-dependent TIFA phosphorylation in the presence of either HBP or HIdA purified from *E. coli* containing inactivated HIdE, or in the presence of HBP and HIdA purified from the same HIdE wild-type *E. coli* used in the previous experiments. The results are shown in FIG. 15. Phosphorylated TIFA (three concentrations, 1%, 0.2% and 0.4%) was detected as described above by denaturing gel electrophoresis followed by Western analysis. Phosphorylated TIFA was detected only in assays using the HIdA purified from wildtype *E. coli*, and not in those using HIdA purified from the HIdE mutant *E. coli* cells.

In order to avoid aberrant results obtained with in vitro produced HBP due to contaminating bacterial enzymes, we utilized chemically-synthesized sugar molecules in Examples 1-8 above and in Examples 10-18 below.

Figure 16A:
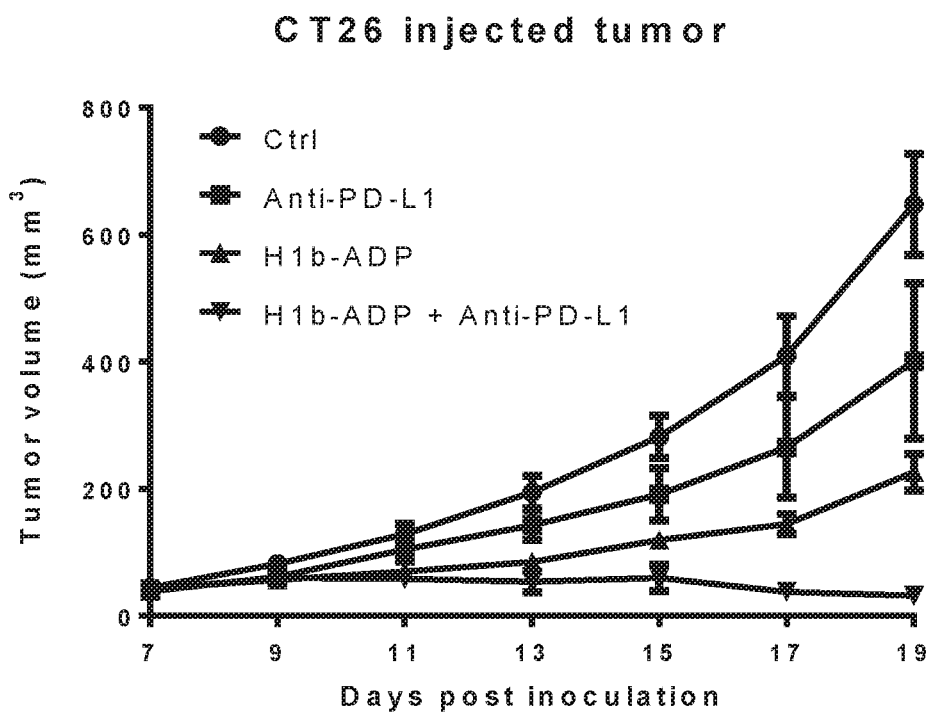
FIG. 16A-B: Intratumoral injection of H1b-ADP and anti-PD-L1 antibody synergistically inhibit tumor growth in the injected tumor (A) and the distant tumor (B) in mouse CT26 xenograft model.
Figure 16B:
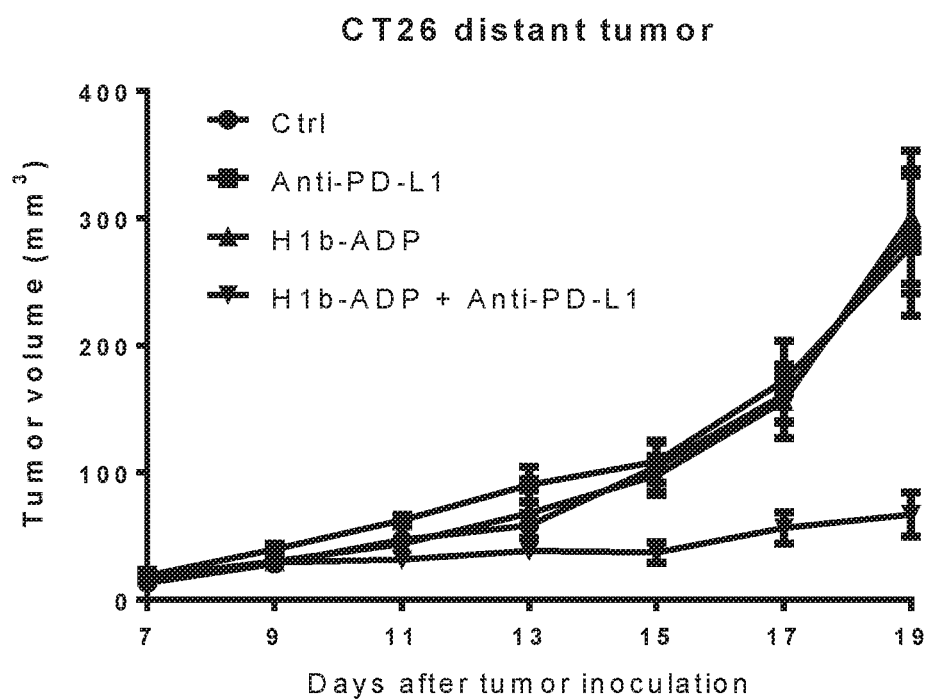

Example 10: H1b-ADP and an Anti-PD-L1 Antibody Act Synergistically to Inhibit Tumor Growth The experiment was carried out as combo experiments of anti-PD-1 except for the following variations. At day 7, mice whose tumors had reached 5 mm in diameter were randomized and grouped into the following four groups: anti-PD-L1 antibody; rat IgG; H1b-ADP+rat IgG; H1b-ADP+anti-PD-L1 antibody. We utilized BP0101 (BioxCell) as the anti-PD-L1 antibody and a rat IgG 2a (2A3) as the control IgG. Each of the anti-PD-L1 antibody (200 µg) and the control IgG (200 µg) was administered intraperitoneally in a 200 µL volume on days 7, 9, 11, and 15 post-inoculation. H1b-ADP (6.2 µg) was administered intratumorally in a 20 µL volume on days 7, 9, 11, 13, 15 post-inoculation. The results are shown in FIG. 16A for injected tumors and FIG. 16B for distant tumors. These results indicate that the combination of H1b-ADP and a checkpoint-inhibitor such as an anti-PD-L1 antibody is effective to suppress growth and even inhibit the viability of tumor cells in vivo.

Example 11: H1b-ADP and IFNα Act Synergistically to Inhibit Tumor Growth

Figure 17A:
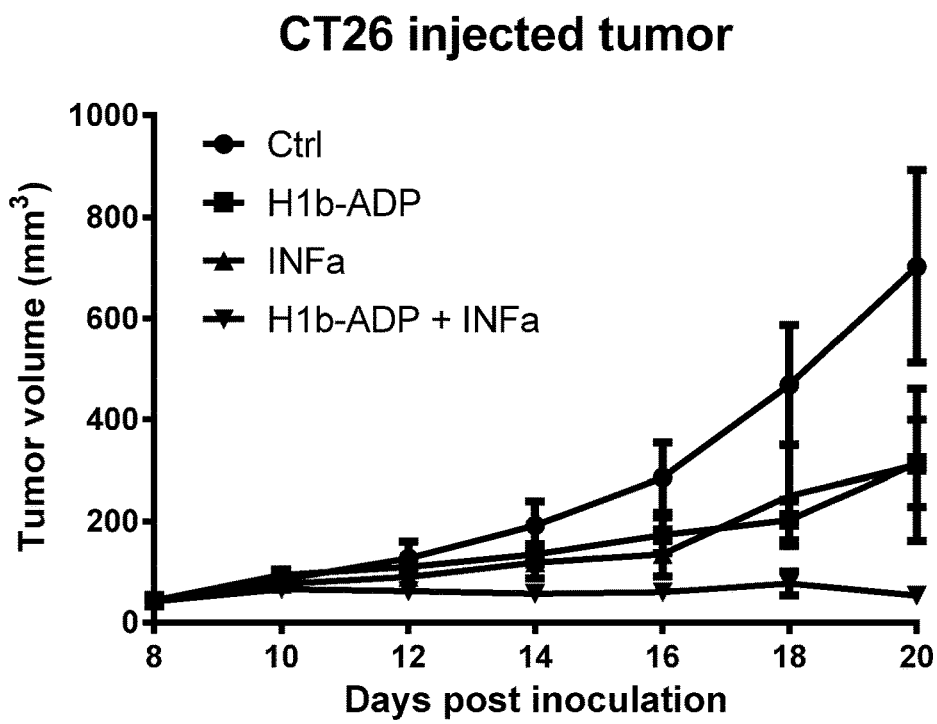
FIG. 17A-B: Intratumoral injection of H1b-ADP and IFN-a synergistically inhibit tumor growth in the injected tumor (A) and the distant tumor (B) in mouse CT26 xenograft model.
Figure 17B:
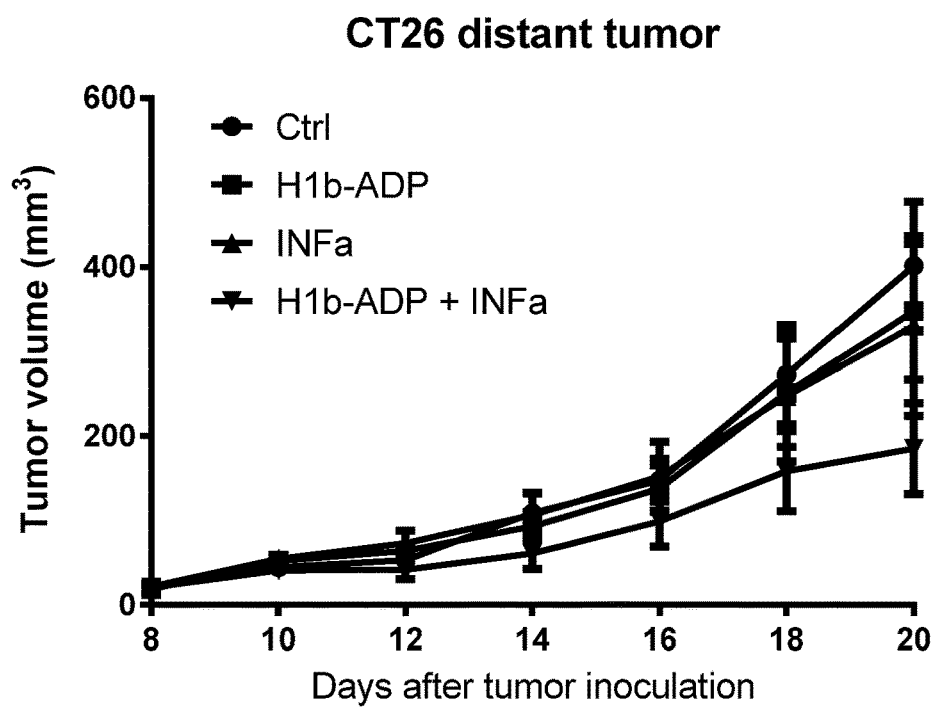

The experiment was carried out as combo experiments of anti-PD-1 except for the following variations. At day 8, mice whose tumors had reached 5 mm in diameter were randomized and grouped into the following four groups: INFα (752803, BioLegend); PBS; H1b-ADP; H1b-ADP+INFα. Each of the IFNα (0.1 µg) and H1b-ADP (6.2 µg) was administered intratumorally in a 20 µL volume on days 8, 10, and 12 post-inoculation. The results are shown in FIG. 17A for injected tumors and FIG. 17B for distant tumors. These results indicate that the combination of H1b-ADP and interferon pathway or JAK-STAT pathway activators such as IFNα is effective to suppress growth and even inhibit the viability of tumor cells in vivo.

Figure 18:
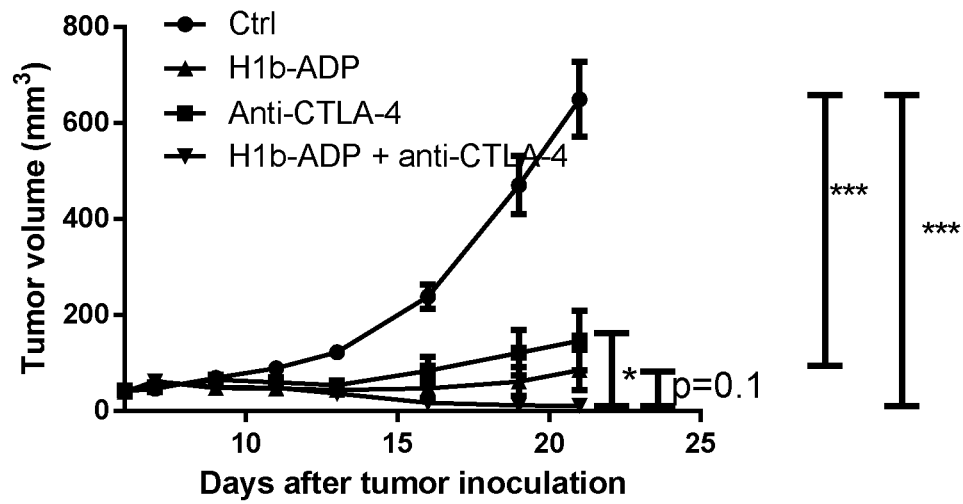
FIG. 18: Intratumoral injection of H1b-ADP and anti-CTLA-4 antibody synergistically inhibit tumor growth in mouse CT26 xenograft model. Pair-wise p values were determined by T test and are shown by bars on the right, *$p<0.05$,  $p<0.01$, * $p<0.001$.

Example 12: H1b-ADP and an Anti-CTLA-4 Antibody Act Synergistically to Inhibit Tumor Growth The experiment was carried out as combo experiments of anti-PD1 except for the following variations. At day 6, mice whose tumors had reached 5 mm in diameter were randomized and grouped into the following four groups: anti-CTLA-4 antibody; rat IgG; H1b-ADP+rat IgG; H1b-ADP+anti-CTLA-4 antibody. We utilized 9D9 (BioxCell) as the anti-CTLA-4 antibody and a rat IgG 2b isotype (MPC-11 clone, BE0086, BioXCell) as the control IgG. Each of the anti-CTLA-4 antibody (25 µg) and the control IgG (25 µg) was administered intraperitoneally in a 200 µL volume on days 6 and 9 post-inoculation. H1b-ADP (6.2 µg) was administered intratumorally in a 20 µL volume on days 6, 7, 9, 11 post-inoculation. The results are shown in FIG. 18. These results indicate that the combination of H1b-ADP and a checkpoint-inhibitor or deleting T-reg cells such as an anti-CTLA-4 antibody is effective to suppress growth and even inhibit the viability of tumor cells in vivo.

Figure 19:
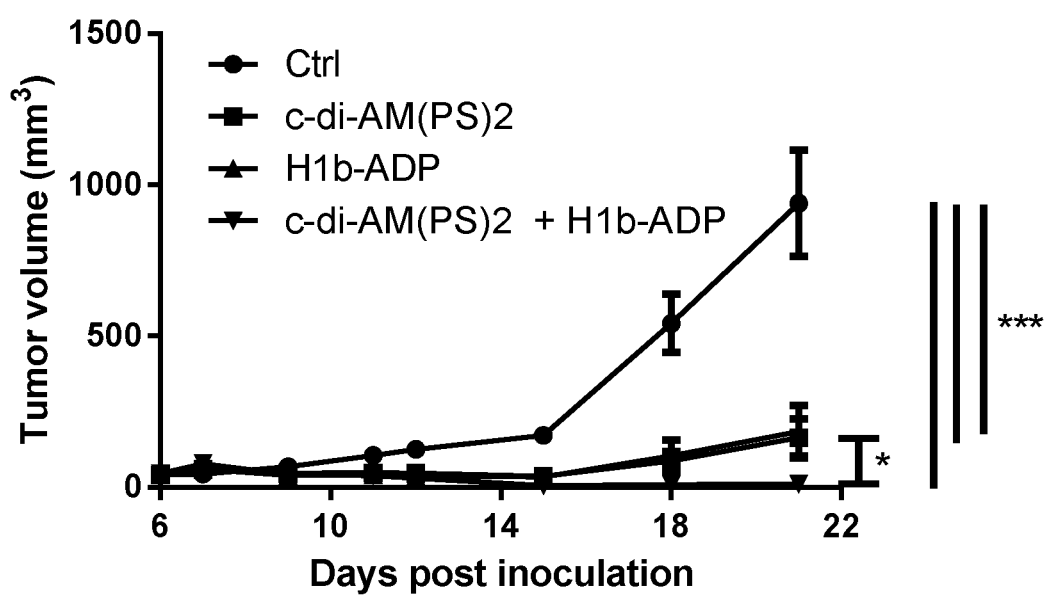
FIG. 19: Intratumoral injection of H1b-ADP and STING agonist c-di-AM(PS)2 synergistically inhibit tumor growth in mouse CT26 xenograft model. Pair-wise p values were determined by T test and are shown by bars on the right, *$p<0.05$,  $p<0.01$, * $p<0.001$.

Example 13: H1b-ADP and an STING Agonist Act Synergistically to Inhibit Tumor Growth The experiment was carried out as combo experiments of anti-PD1 except for the following variations. At day 6, mice whose tumors had reached 5 mm in diameter were randomized and grouped into the following four groups: c-di-AM(PS)2; PBS; H1b-ADP; H1b-ADP+c-di-AM(PS)2. We utilized c-di-AM(PS)2 as the STING agonist. Each of the c-di-AM(PS)2 (1 µg) and H1b-ADP (6.2 µg) was administered intratumorally in a 20 µL volume on days 6, 7, and 9 post-inoculation. The results are shown in FIG. 19. These results indicate that the combination of H1b-ADP and a STING agonist and innate immunity agonist such as c-di-AM(PS)2 is effective to suppress growth and even inhibit the viability of tumor cells in vivo.

Figure 20:
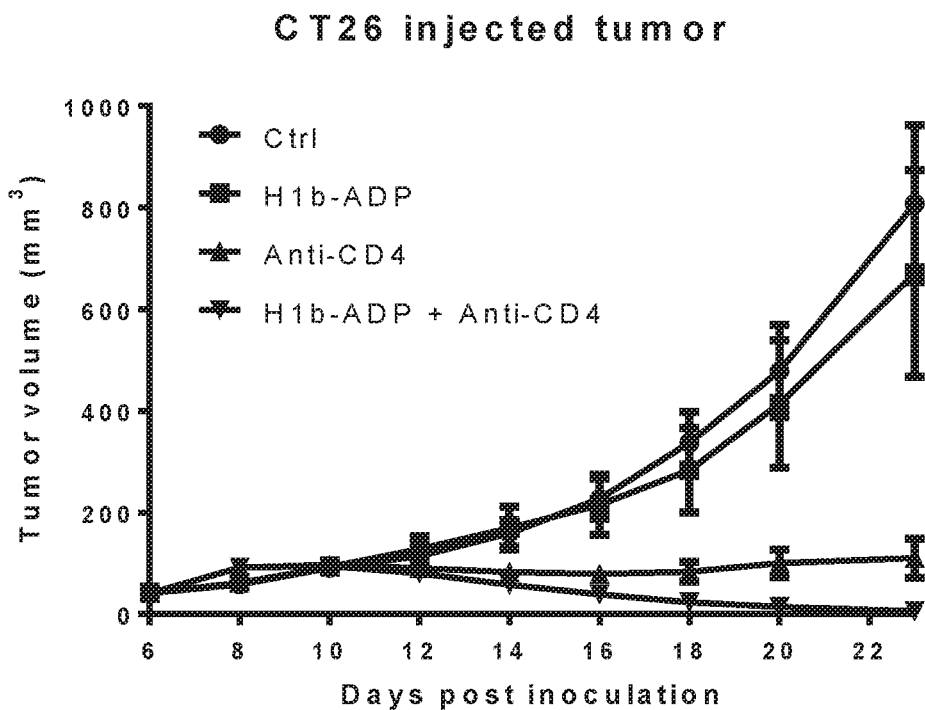
FIG. 20: Intratumoral injection of H1b-ADP and anti-CD4 antibody synergistically inhibit tumor growth in mouse CT26 xenograft model.

Example 14: H1b-ADP and an Anti-CD4 Antibody Act Synergistically to Inhibit Tumor Growth The experiment was carried out as combo experiments of anti-PD-1 except for the following variations. At day 6, mice whose tumors had reached 5 mm in diameter were randomized and grouped into the following four groups: anti-CD4 antibody (GK1.5 clone, BE0003-1, BioXcell); rat IgG; H1b-ADP+rat IgG; H1b-ADP+anti-CD4 antibody. Each of the anti-CD4 antibody (200 μg) and the control IgG (200 μg) was administered intraperitoneally in a 200 μL volume on days 3, 4, 8 post-inoculation. H1b-ADP (6.2 μg) was administered intratumorally in a 20 μL volume on days 6, 8, 10, 12, 14 post-inoculation. The results are shown in FIG. 20. These results indicate that the combination of H1b-ADP and a CD4 or T-reg depleting antibody is effective to suppress growth and even inhibit the viability of tumor cells in vivo.

Figure 21:
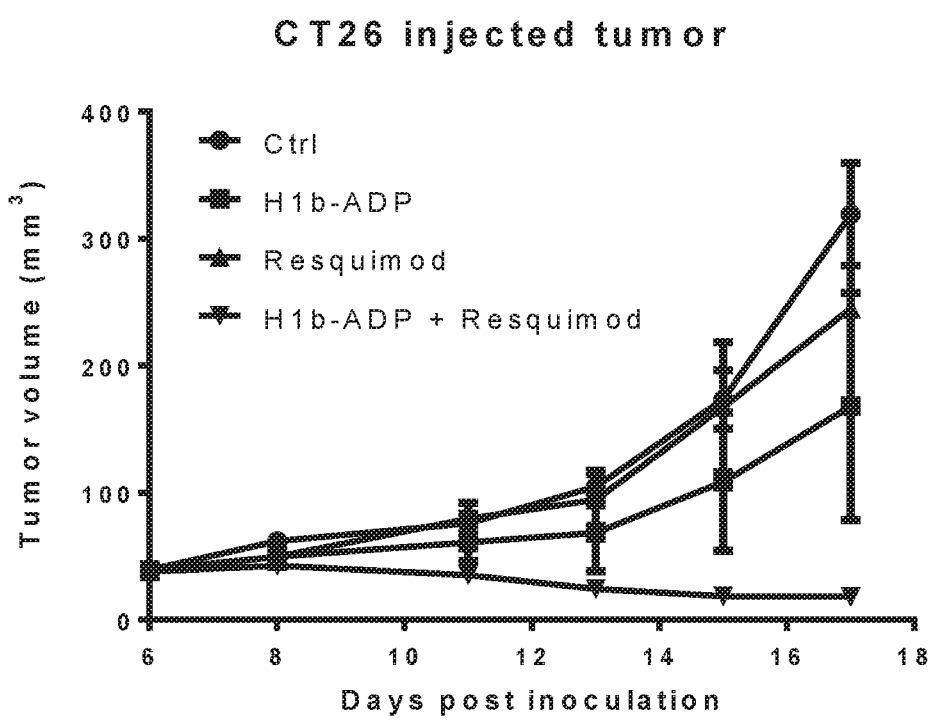
FIG. 21: Intratumoral injection of H1b-ADP and TLR agonist resquimod synergistically inhibit tumor growth in mouse CT26 xenograft model.

Example 15: H1b-ADP and a TLR Agonist Act Synergistically to Inhibit Tumor Growth The experiment was carried out as combo experiments of anti-PD-1 except for the following variations. At day 6, mice whose tumors had reached 5 mm in diameter were randomized and grouped into the following four groups: Resquimod; PBS; H1b-ADP; H1b-ADP+Resquimod. Resquimod (10 μg) and H1b-ADP (6.2 μg) were administered intratumorally in a 20 μL volume on days 6, 8, 11 post-inoculation. The results are shown in FIG. 21. These results indicate that the combination of H1b-ADP and a TLR agonist is effective to suppress growth and even inhibit the viability of tumor cells in vivo. The results are shown in FIG. 21.

Figure 22:
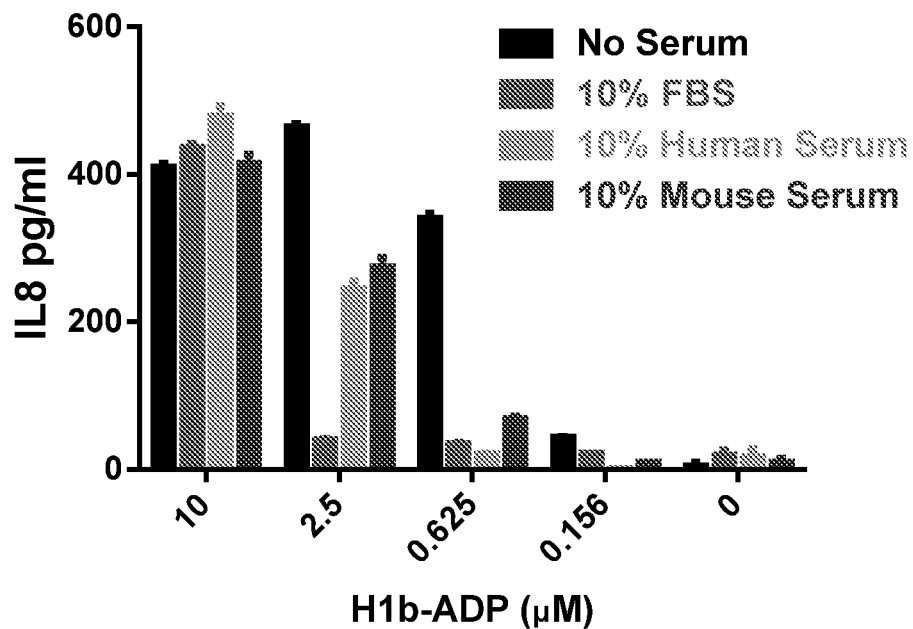
FIG. 22: Fetal bovine, human, and mouse serum decrease H1b-ADP's activity in inducing IL8 secretion in HEK293 cells.
Figure 23:
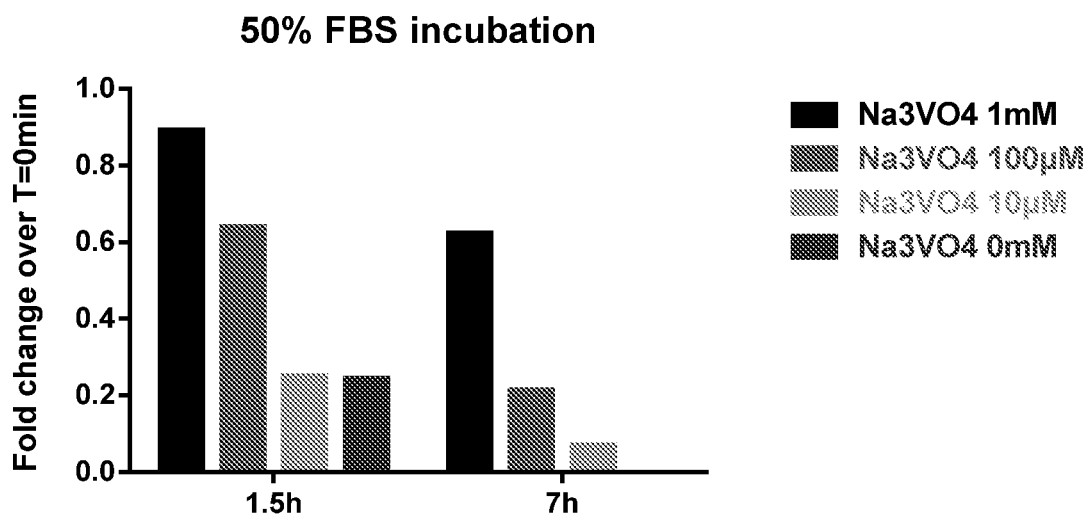
FIG. 23: $Na_3VO_4$ protects H1b-ADP from degradation by fetal bovine serum.
Figure 24:
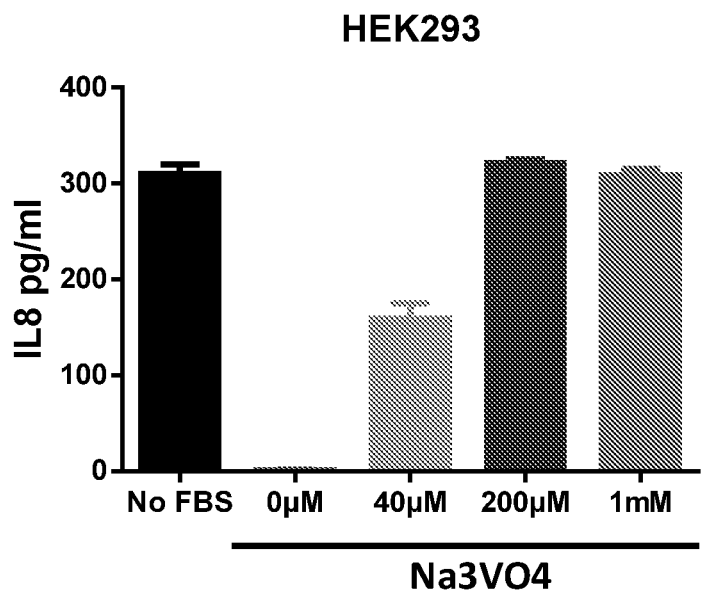
FIG. 24: $Na_3VO_4$ protects H1b-ADP from degradation by fetal bovine serum and retains its activity of inducing IL8 secretion in HEK293 cells.
Figure 25:
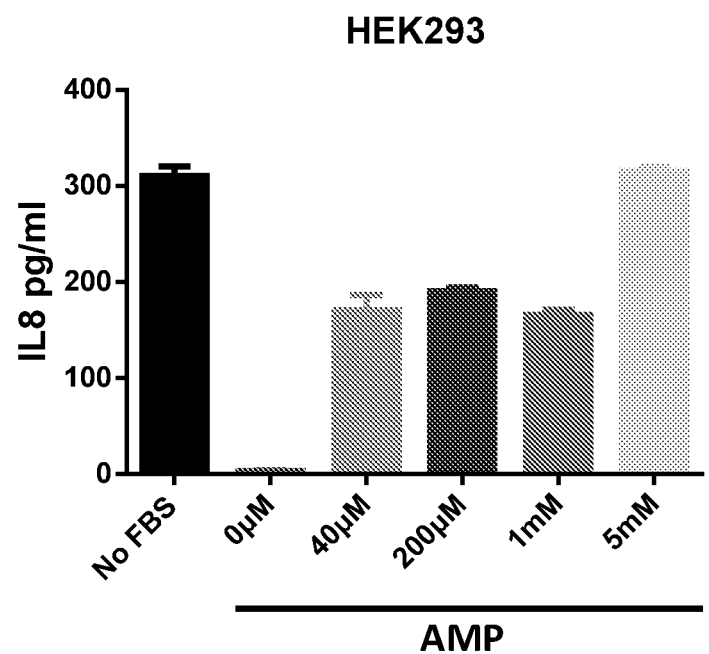
FIG. 25: AMP protects H1b-ADP from degradation by fetal bovine serum and retains its activity of inducing IL8 secretion in HEK293 cells.
Figure 26:
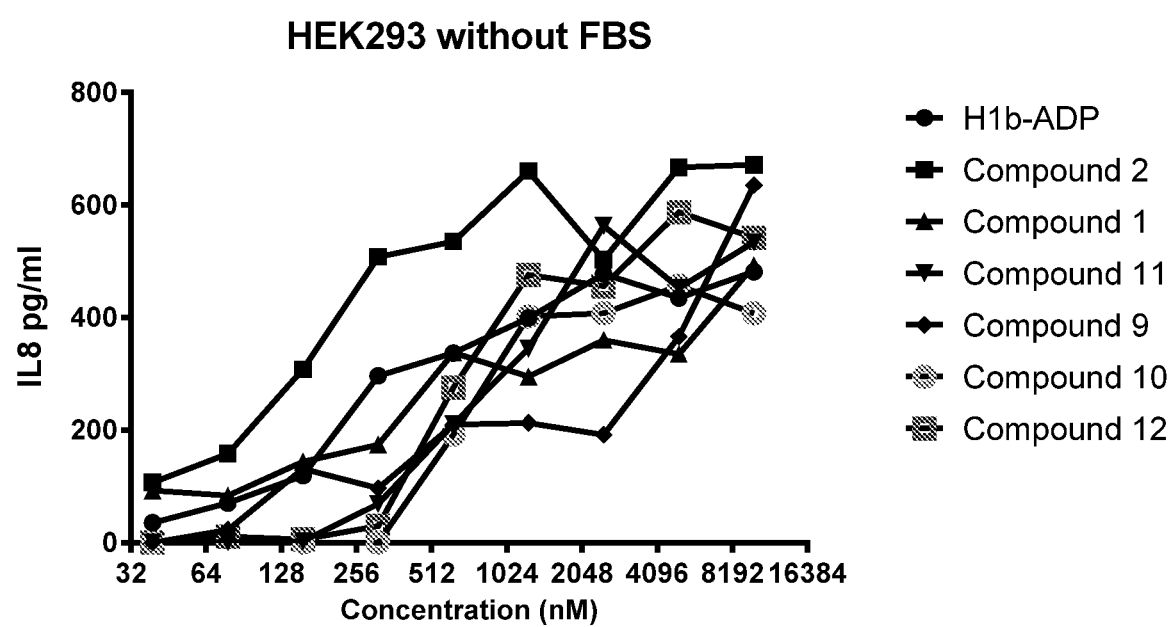
FIG. 26: Compounds of Formula I (1, 2, 9-12) activate IL8 secretion in HEK293 cells through activating ALPK1. HEK293 cells were cultured without FBS.

Example 16: H1b-ADP is Degraded by Phosphatases in Serum and can be Protected by Phosphatase Inhibitors and AMP H1b-ADP's activity to activate ALPK1 in HEK293 cells greatly declined when cells were cultured with fetal bovine, human or mouse serum (FIG. 22), suggesting that components in animal serum can neutralize H1b-ADP's activity. To examine if H1b-ADP is chemically converted to an inactive form, we incubated H1b-ADP with FBS and analyzed the product using LC-MS. We found that along with increasing incubation time, the H1b-ADP amount declined and a new material with similar absorption intensity at UV 254 nm increased. The material is determined to be AMP using standard substance, suggesting that the P—O—P phosphate anhydride bond in H1b-ADP is hydrolyzed by enzyme in serum. FBS contains 110-352 U/ml alkaline phosphatase. Alkaline phosphatase is a widely used dephosphorylating reagent able to hydrolyze phosphate esters in a variety of molecules including alcohols, amine, pyrophosphate, and phenols. Phosphatase such as the alkaline phosphatase may be responsible for H1b-ADP hydrolysis. We pre-mixed H1b-ADP with phosphatase inhibitor sodium orthovanadate ($Na_3VO_4$) before incubation with FBS. 1 mM $Na_3VO_4$ treatment effectively inhibited H1b-ADP hydrolysis (FIG. 23), indicating phosphatase activity in the serum is required for its degradation. To determine if phosphatase alone is sufficient to hydrolyze H1b-ADP, we incubated H1b-ADP with bovine alkaline phosphatase and found that the phosphatase activity was blocked by increasing amount of $Na_3VO_4$. We noticed that the H1b-ADP hydrolysis in the serum slowed down as incubation time went by, indicating gradually down-regulated phosphatase activity. We hypothesized that the accumulation of hydrolysis product AMP can inhibit phosphatase activity. Pre-treatment of H1b-ADP with AMP before serum incubation inhibited phosphatase activity and the inhibition was AMP dose-dependent. Consequently, addition of $Na_3VO_4$ (FIG. 24) or AMP (FIG. 25) to the FBS-containing medium could restore H1b-ADP's activity in the cell based assay, confirming that the phosphatases in FBS is responsible for dampening H1b-ADP's activity.

Example 17: H1b-ADP Derivative Compounds Activate ALPK1 In Vitro

Figure 27A:
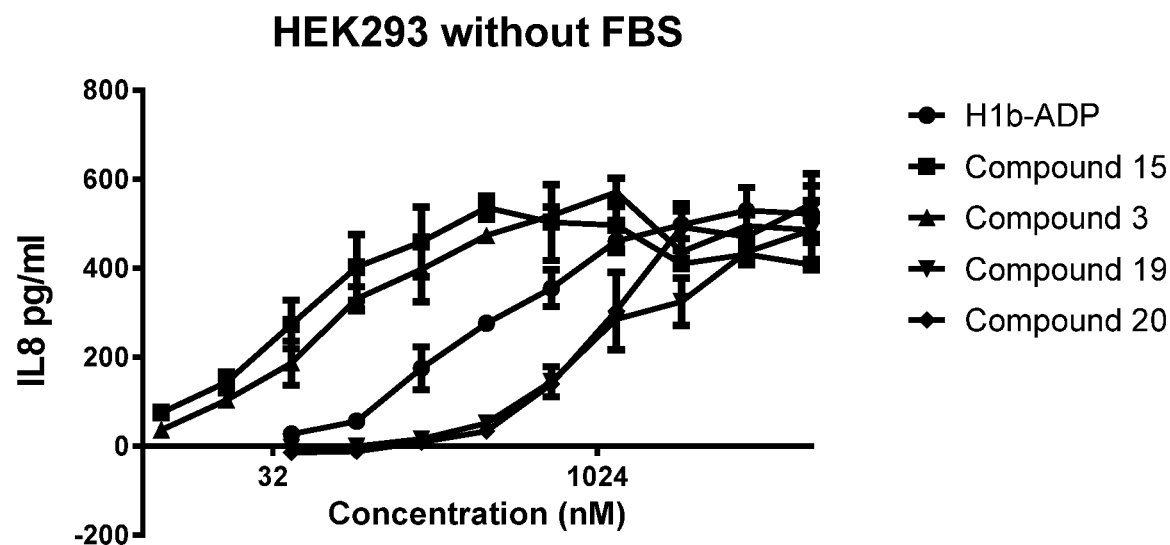
FIGS. 27A-B: Compounds of Formula I (3, 15, 19, 20) activate IL8 secretion in HEK293 without FBS (A) and with 10% FBS (B) cells through activating ALPK1. Compound 15 is resistant to FBS degradation.
Figure 27B:
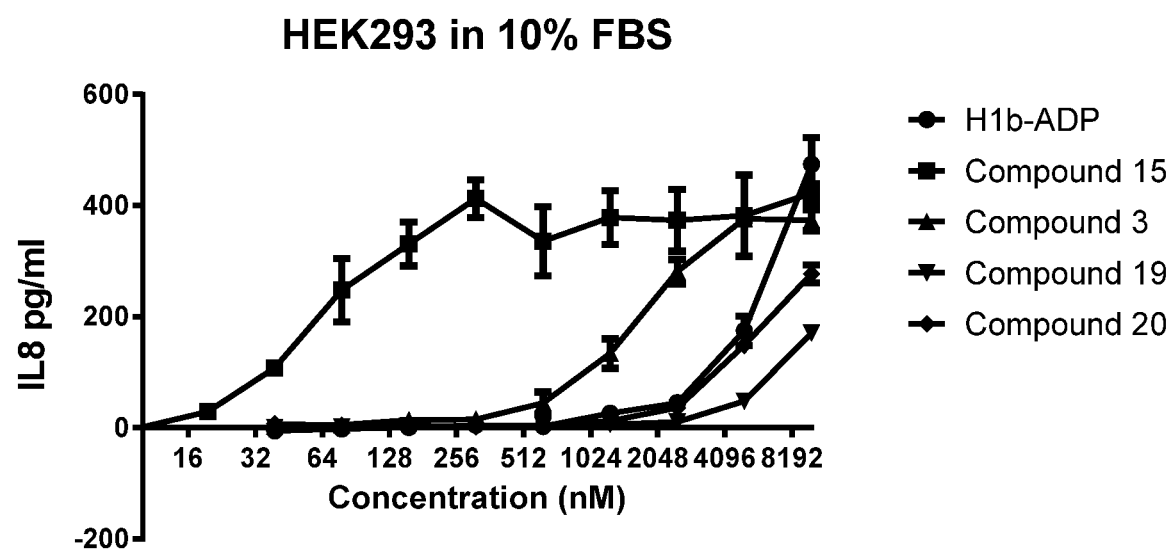
Figure 28A:
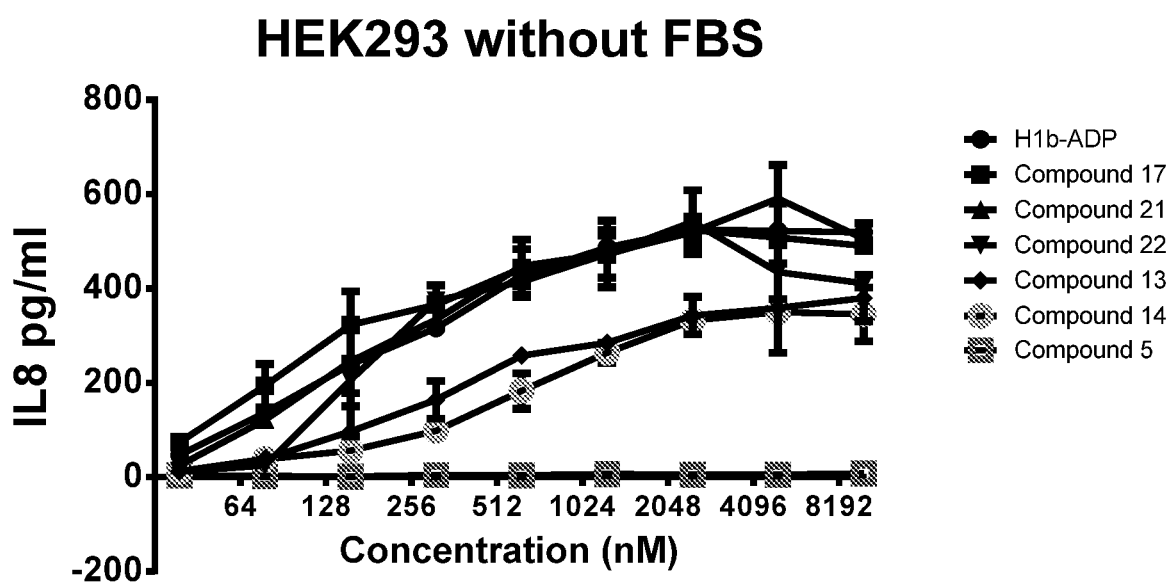
FIGS. 28A-B: Compounds of Formula I (5, 13, 14, 17, 21, 22) activate ALPK1 as demonstrated by increased IL8 secretion in HEK293 cells without FBS (A) and with 10% FBS (B).
Figure 28B:
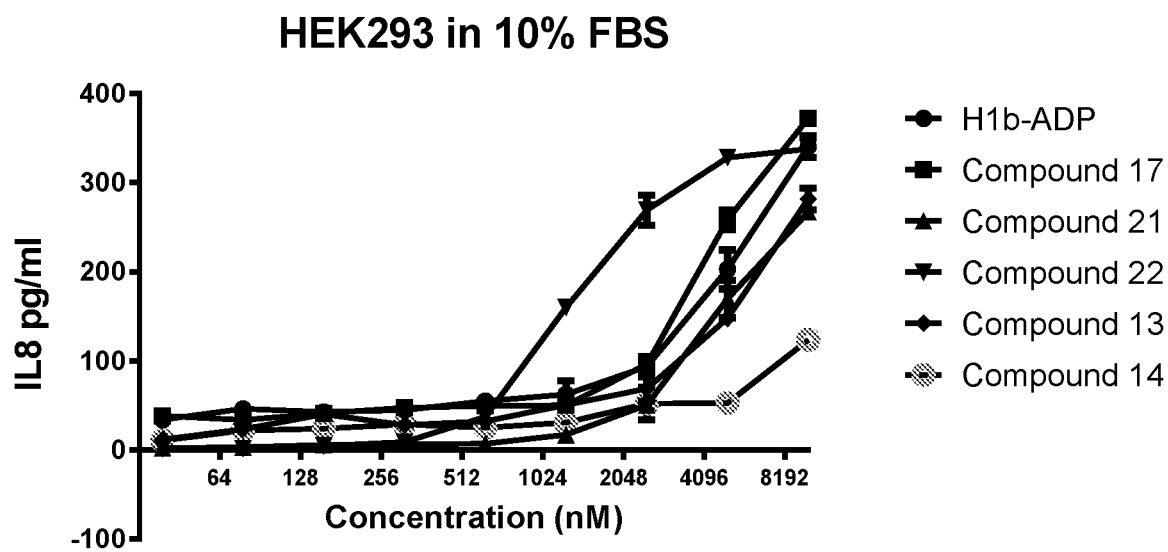
Figure 29A:
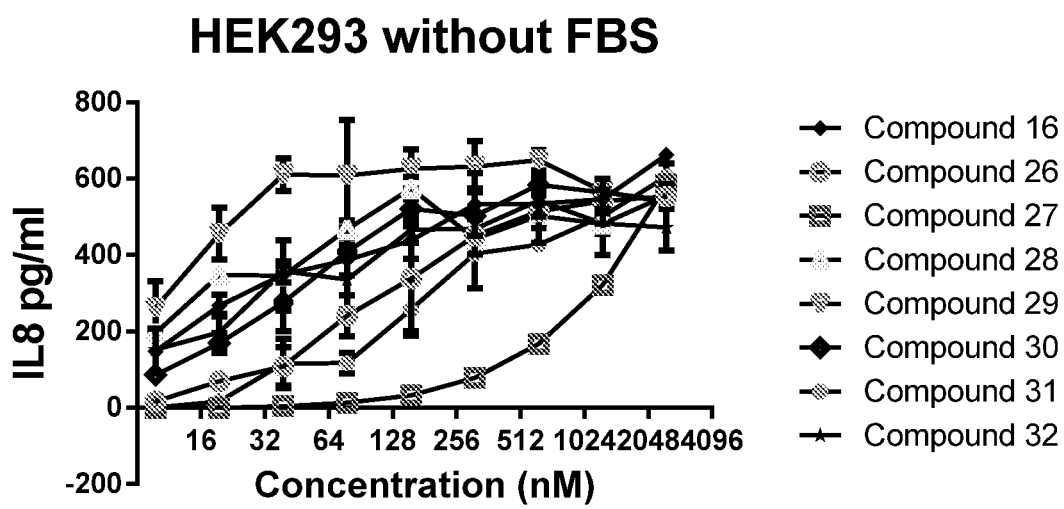
FIGS. 29A-B: Compounds of Formula I (16, 26-32) activate ALPK1 as demonstrated by increased IL8 secretion in HEK293 cells without FBS (A) and with 10% FBS (B).
Figure 29B:
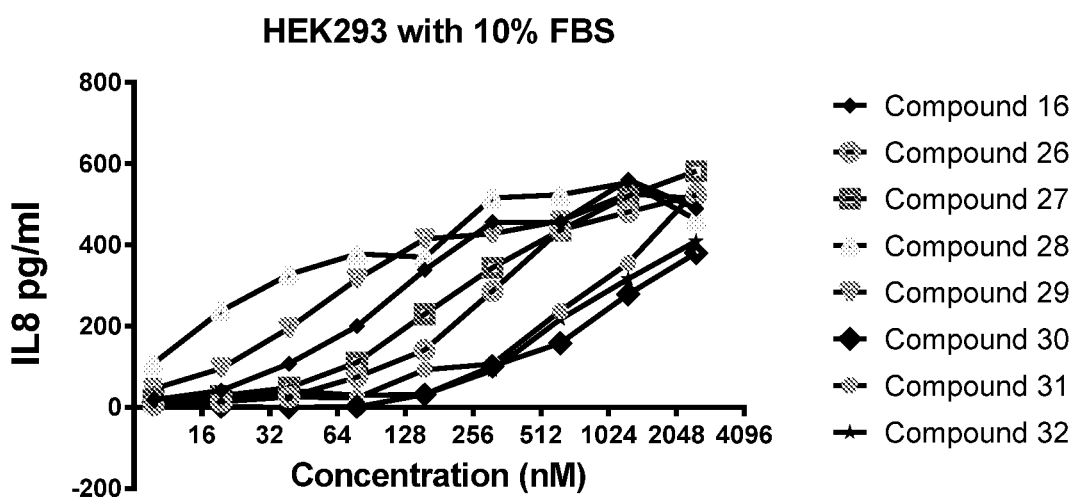

A number of H1b-ADP derivative compounds were made as described herein and tested for biological activity as agonists of ALPK1 in vitro. In these experiments, serial dilutions of the compounds were added to the tissue culture media of HEK293 cells with (FIG. 27B, FIG. 28B, FIG. 29B) or without (FIG. 26, FIG. 27A, FIG. 28A, FIG. 29A) 10% FBS, as indicated in the figures. After 4 hours, the cell supernatant was collected and analyzed for IL8 concentration using IL8 ELISA (BD) as an indicator of ALPK1 activation.

H1b-ADP derivative compounds 1-3, 9-17, 19, 20-22, 26-32 demonstrated ALPK1 activating activity. Among the tested compounds, Compound 15 also showed an unexpected resistance to serum degradation (compare FIG. 27A and FIG. 27B).

Example 18: H1b-ADP Derivative Compounds Inhibit Tumor Growth

Figure 30:
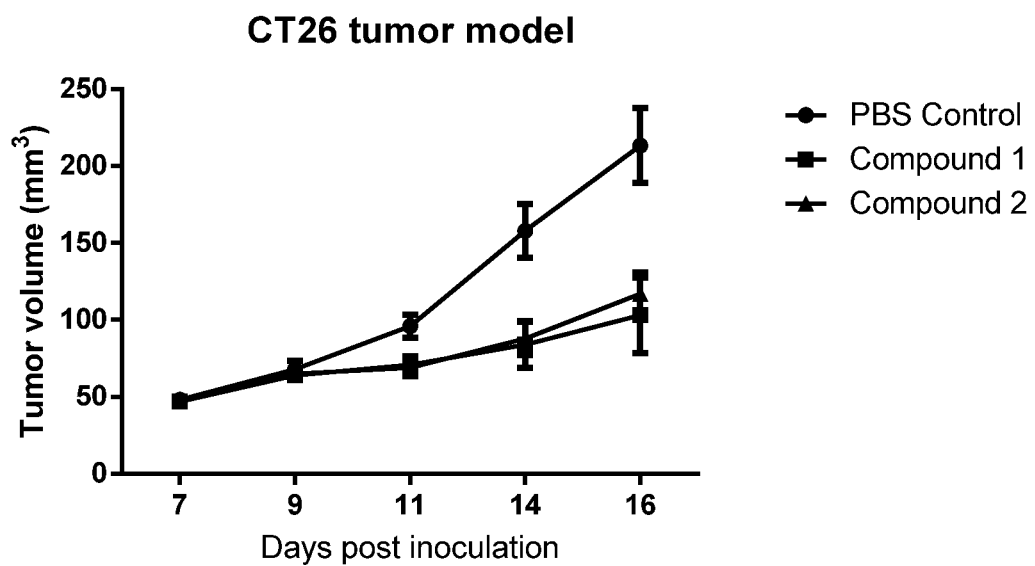
FIG. 30 Compounds of Formula I (1, 2) inhibit tumor growth in CT26 syngeneic mouse tumor model.

We used a CT26 tumor xenograft model to test the anti-cancer activity of H1b-ADP derivative Compounds 1 and 2. Tumor cells ($2\times10^5$ per 100 uL CT26 cells) were inoculated subcutaneously into the right flank of BALB/c mice. At day 7, mice whose tumors had reached 3-5 mm in diameter were randomized and grouped into three groups (n=9 each group), control, Compound 1 (50 nmol), and Compound 2 (50 nmol). Injections were performed using a total volume of 20 uL at days 7, 9, and 11 post inoculation. Tumor volumes were calculated every 2 days from caliper measurements of tumor dimension using the formula $(L\times W^2)/2$, where L is the longer measurement. As shown in FIG. 30, Compounds 1 and 2 reduced tumor growth in this model system, indicating that H1b-ADP's derivatives were able to elicit an anti-tumor immune response effective to suppress tumor growth.

Example 19: H1b-ADP can Activate Macrophage at an Extremely Low Concentration

Figure 31:
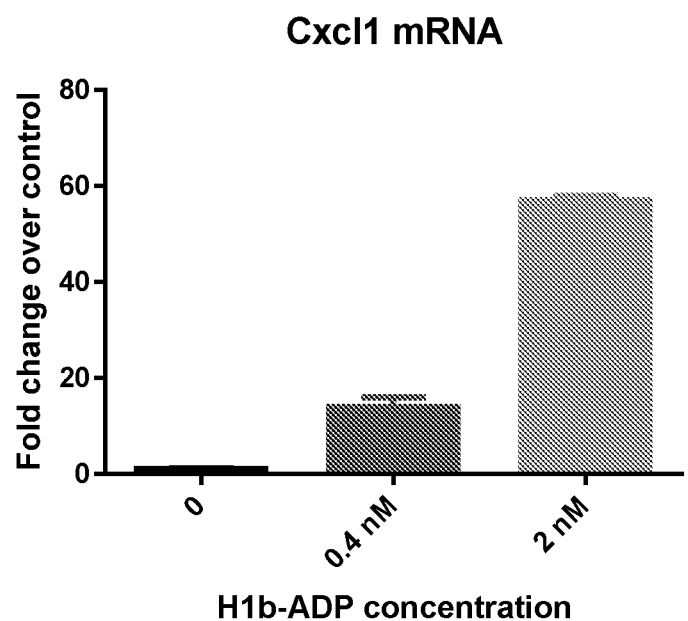
FIG. 31: Bone marrow-derived mouse macrophages can be activated by a very low concentration of H1b-ADP.

In these experiments, mouse bone marrow-derived macrophages were treated with 0.4 nM or 2 nM H1b-ADP for 2.5 hours and harvested for mRNA expression analysis of Cxcl1 by qPCR. Cxcl1 mRNA expression is presented as fold change over non-treated control and showed a dose-dependent response (FIG. 31). These results suggest that tissue residential macrophages may utilize extracellular H1b-ADP to monitor the local infection. Accordingly, very low doses of H1b-ADP, or an agonist thereof, may be used to enhance or potentiate an immune response in a local tissue.

Figure 32A:
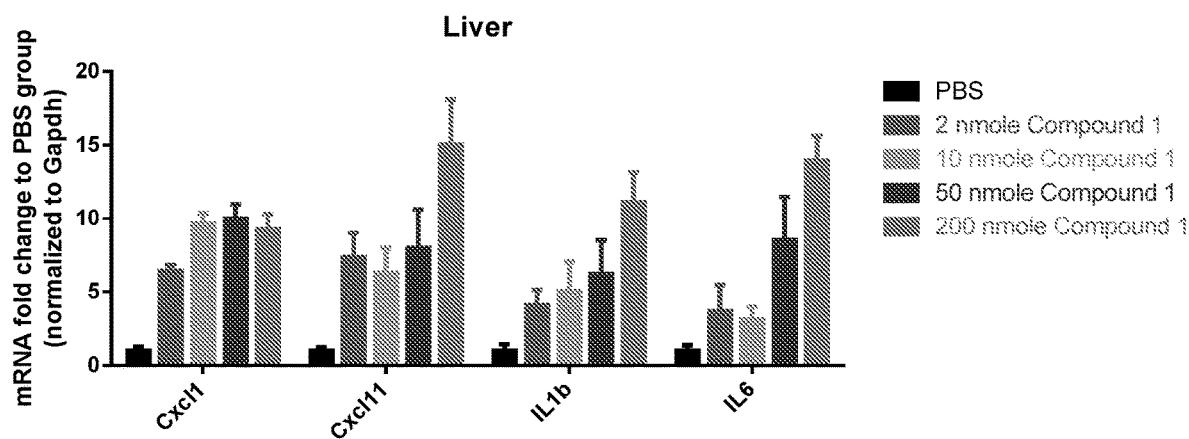
FIG. 32A-B: Compound 1 activates an inflammatory response in liver tissue (A) at a dose as low as 2 nmole (1.2 µg) and in lung tissue (B) at a dose of 200 nmole.
Figure 32B:
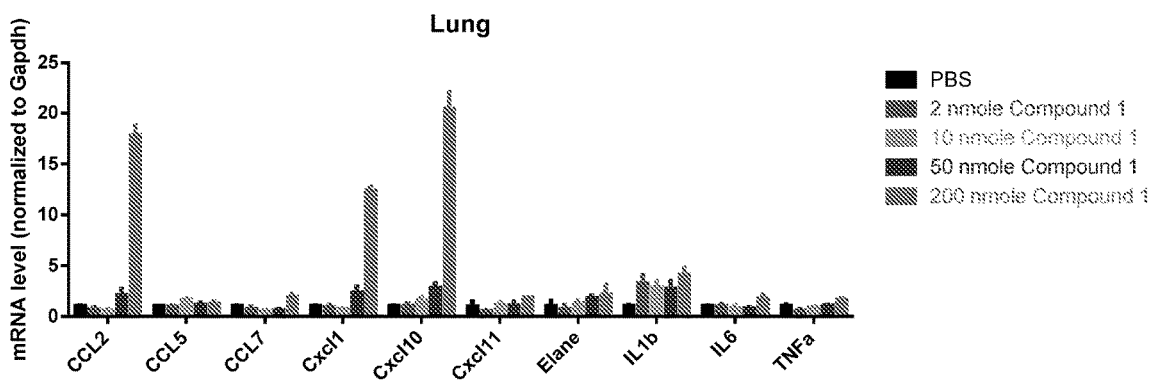

In additional experiments, Compound 1 was injected subcutaneously into 7 week old C57 mice at concentrations of 2, 10, 50, and 200 nmol. Tissue was harvested three hours later and RNA extracted. Quantitative PCR (qPCR) was performed to determine the tissue expression levels Cxcl1, Cxcl11, IL1b, and IL6 in mouse liver (FIG. 32A) and lung (FIG. 32B) tissue. Additional chemokines and cytokines were assayed in the lung tissue. The data show that liver tissue is very sensitive to activation of inflammatory chemokines and cytokines by this H1b-ADP derivative. These results further suggest that the treatment of liver diseases and disorders with ALPK1 agonists as described herein can be accomplished with a very low dose H1b-ADP and derivatives thereof, such as Compound 1. For example, it is expected from these data that doses in the range of 1 nanogram to 1 milligram per kilogram body weight (1 ng/kg to 1 mg/kg), preferably 1 microgram to 100 micrograms per kilogram body weight (1 ug/kg to 100 ug/kg) could be used to treat liver diseases and disorders.

Figure 33:
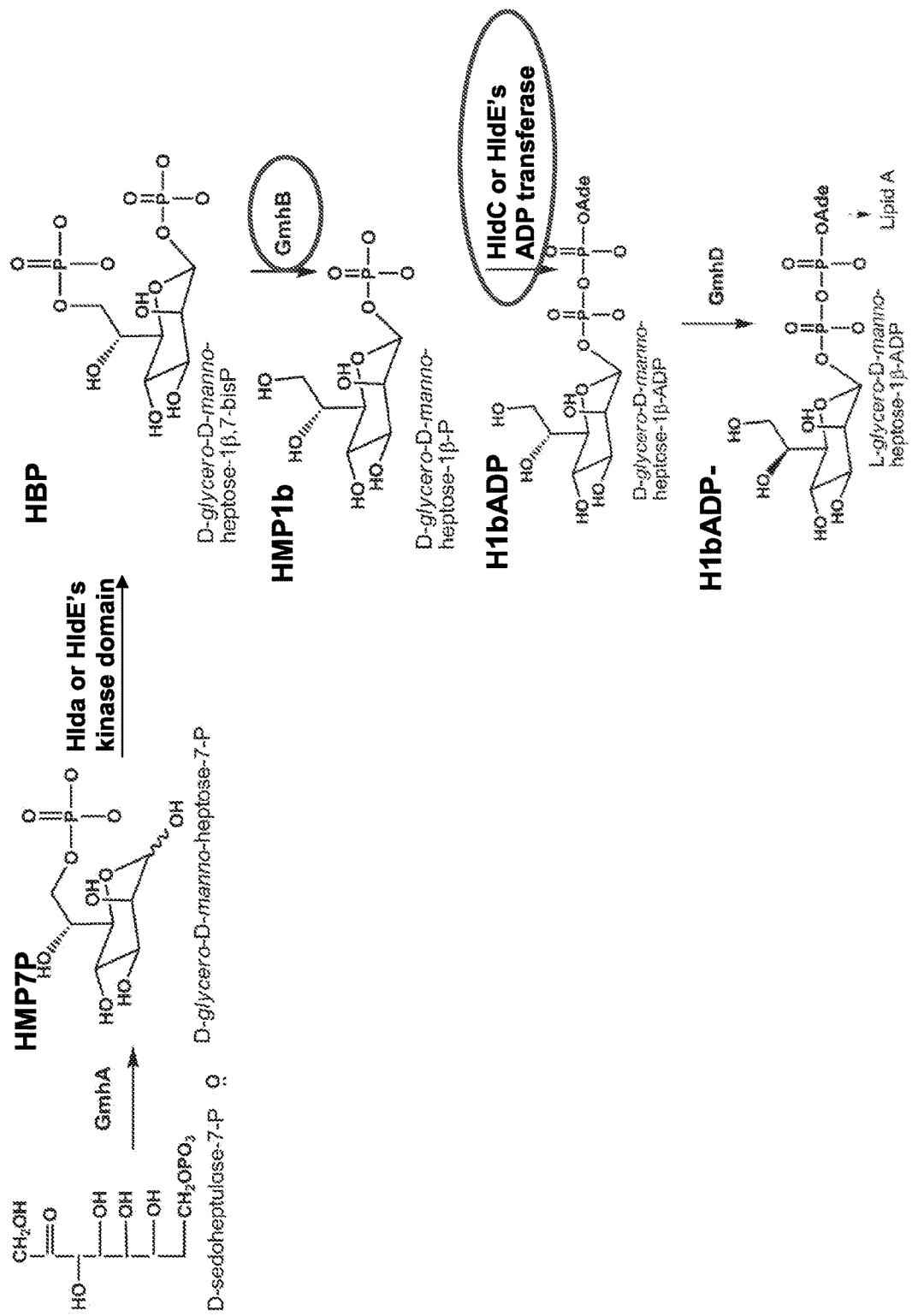
FIG. 33: Schematic of bacterial H1b-ADP-biosynthetic pathway.

The *E. coli* H1b-ADP biosynthetic pathway is shown in FIG. 33.

Those skilled in the art will recognize or be able to ascertain using no more than routine experimentation, many equivalents to the specific embodiments of the invention as described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING

```
<160> NUMBER OF SEQ ID NOS: 2

<210> SEQ ID NO 1
<211> LENGTH: 1244
<212> TYPE: PRT
<213> ORGANISM: Homo sapiens
<220> FEATURE:
<221> NAME/KEY: PEPTIDE
<222> LOCATION: (1)..(1244)
<223> OTHER INFORMATION: ALPK1 Isoform 1

<400> SEQUENCE: 1

Met Asn Asn Gln Lys Val Val Ala Val Leu Leu Gln Glu Cys Lys Gln
1               5                   10                  15

Val Leu Asp Gln Leu Leu Leu Glu Ala Pro Asp Val Ser Glu Glu Asp
                20                  25                  30

Lys Ser Glu Asp Gln Arg Cys Arg Ala Leu Leu Pro Ser Glu Leu Arg
            35                  40                  45

Thr Leu Ile Gln Glu Ala Lys Glu Met Lys Trp Pro Phe Val Pro Glu
        50                  55                  60

Lys Trp Gln Tyr Lys Gln Ala Val Gly Pro Glu Asp Lys Thr Asn Leu
65                  70                  75                  80

Lys Asp Val Ile Gly Ala Gly Leu Gln Gln Leu Leu Ala Ser Leu Arg
                85                  90                  95

Ala Ser Ile Leu Ala Arg Asp Cys Ala Ala Ala Ala Ile Val Phe
                100                 105                 110

Leu Val Asp Arg Phe Leu Tyr Gly Leu Asp Val Ser Gly Lys Leu Leu
            115                 120                 125

Gln Val Ala Lys Gly Leu His Lys Leu Gln Pro Ala Thr Pro Ile Ala
        130                 135                 140

Pro Gln Val Val Ile Arg Gln Ala Arg Ile Ser Val Asn Ser Gly Lys
145                 150                 155                 160

Leu Leu Lys Ala Glu Tyr Ile Leu Ser Ser Leu Ile Ser Asn Asn Gly
                165                 170                 175

Ala Thr Gly Thr Trp Leu Tyr Arg Asn Glu Ser Asp Lys Val Leu Val
                180                 185                 190

Gln Ser Val Cys Ile Gln Ile Arg Gly Gln Ile Leu Gln Lys Leu Gly
            195                 200                 205

Met Trp Tyr Glu Ala Ala Glu Leu Ile Trp Ala Ser Ile Val Gly Tyr
```

-continued

```
            210                 215                 220
Leu Ala Leu Pro Gln Pro Asp Lys Lys Gly Leu Ser Thr Ser Leu Gly
225                 230                 235                 240

Ile Leu Ala Asp Ile Phe Val Ser Met Ser Lys Asn Asp Tyr Glu Lys
                    245                 250                 255

Phe Lys Asn Asn Pro Gln Ile Asn Leu Ser Leu Leu Lys Glu Phe Asp
                260                 265                 270

His His Leu Leu Ser Ala Ala Glu Ala Cys Lys Leu Ala Ala Ala Phe
            275                 280                 285

Ser Ala Tyr Thr Pro Leu Phe Val Leu Thr Ala Val Asn Ile Arg Gly
        290                 295                 300

Thr Cys Leu Leu Ser Tyr Ser Ser Ser Asn Asp Cys Pro Pro Glu Leu
305                 310                 315                 320

Lys Asn Leu His Leu Cys Glu Ala Lys Glu Ala Phe Glu Ile Gly Leu
                    325                 330                 335

Leu Thr Lys Arg Asp Asp Glu Pro Val Thr Gly Lys Gln Glu Leu His
                340                 345                 350

Ser Phe Val Lys Ala Ala Phe Gly Leu Thr Thr Val His Arg Arg Leu
            355                 360                 365

His Gly Glu Thr Gly Thr Val His Ala Ala Ser Gln Leu Cys Lys Glu
        370                 375                 380

Ala Met Gly Lys Leu Tyr Asn Phe Ser Thr Ser Ser Arg Ser Gln Asp
385                 390                 395                 400

Arg Glu Ala Leu Ser Gln Glu Val Met Ser Val Ile Ala Gln Val Lys
                    405                 410                 415

Glu His Leu Gln Val Gln Ser Phe Ser Asn Val Asp Asp Arg Ser Tyr
                420                 425                 430

Val Pro Glu Ser Phe Glu Cys Arg Leu Asp Lys Leu Ile Leu His Gly
            435                 440                 445

Gln Gly Asp Phe Gln Lys Ile Leu Asp Thr Tyr Ser Gln His His Thr
        450                 455                 460

Ser Val Cys Glu Val Phe Glu Ser Asp Cys Gly Asn Asn Lys Asn Glu
465                 470                 475                 480

Gln Lys Asp Ala Lys Thr Gly Val Cys Ile Thr Ala Leu Lys Thr Glu
                    485                 490                 495

Ile Lys Asn Ile Asp Thr Val Ser Thr Thr Gln Glu Lys Pro His Cys
                500                 505                 510

Gln Arg Asp Thr Gly Ile Ser Ser Leu Met Gly Lys Asn Val Gln
            515                 520                 525

Arg Glu Leu Arg Arg Gly Gly Arg Asn Trp Thr His Ser Asp Ala
        530                 535                 540

Phe Arg Val Ser Leu Asp Gln Asp Val Glu Thr Glu Thr Glu Pro Ser
545                 550                 555                 560

Asp Tyr Ser Asn Gly Glu Gly Ala Val Phe Asn Lys Ser Leu Ser Gly
                    565                 570                 575

Ser Gln Thr Ser Ser Ala Trp Ser Asn Leu Ser Gly Phe Ser Ser Ser
                580                 585                 590

Ala Ser Trp Glu Glu Val Asn Tyr His Val Asp Asp Arg Ser Ala Arg
            595                 600                 605

Lys Glu Pro Gly Lys Glu His Leu Val Asp Thr Gln Cys Ser Thr Ala
        610                 615                 620

Leu Ser Glu Glu Leu Glu Asn Asp Arg Glu Gly Arg Ala Met His Ser
625                 630                 635                 640
```

```
Leu His Ser Gln Leu His Asp Leu Ser Leu Gln Glu Pro Asn Asn Asp
                645                 650                 655

Asn Leu Glu Pro Ser Gln Asn Gln Pro Gln Gln Gln Met Pro Leu Thr
                660                 665                 670

Pro Phe Ser Pro His Asn Thr Pro Gly Ile Phe Leu Ala Pro Gly Ala
                675                 680                 685

Gly Leu Leu Glu Gly Ala Pro Glu Gly Ile Gln Glu Val Arg Asn Met
            690                 695                 700

Gly Pro Arg Asn Thr Ser Ala His Ser Arg Pro Ser Tyr Arg Ser Ala
705                 710                 715                 720

Ser Trp Ser Ser Asp Ser Gly Arg Pro Lys Asn Met Gly Thr His Pro
                725                 730                 735

Ser Val Gln Lys Glu Glu Ala Phe Glu Ile Ile Val Glu Phe Pro Glu
                740                 745                 750

Thr Asn Cys Asp Val Lys Asp Arg Gln Gly Lys Glu Gln Gly Glu Glu
                755                 760                 765

Ile Ser Glu Arg Gly Ala Gly Pro Thr Phe Lys Ala Ser Pro Ser Trp
            770                 775                 780

Val Asp Pro Glu Gly Glu Thr Ala Glu Ser Thr Glu Asp Ala Pro Leu
785                 790                 795                 800

Asp Phe His Arg Val Leu His Asn Ser Leu Gly Asn Ile Ser Met Leu
                805                 810                 815

Pro Cys Ser Ser Phe Thr Pro Asn Trp Pro Val Gln Asn Pro Asp Ser
                820                 825                 830

Arg Lys Ser Gly Gly Pro Val Ala Glu Gln Gly Ile Asp Pro Asp Ala
                835                 840                 845

Ser Thr Val Asp Glu Glu Gly Gln Leu Leu Asp Ser Met Asp Val Pro
            850                 855                 860

Cys Thr Asn Gly His Gly Ser His Arg Leu Cys Ile Leu Arg Gln Pro
865                 870                 875                 880

Pro Gly Gln Arg Ala Glu Thr Pro Asn Ser Ser Val Ser Gly Asn Ile
                885                 890                 895

Leu Phe Pro Val Leu Ser Glu Asp Cys Thr Thr Thr Glu Glu Gly Asn
                900                 905                 910

Gln Pro Gly Asn Met Leu Asn Cys Ser Gln Asn Ser Ser Ser Ser Ser
                915                 920                 925

Val Trp Trp Leu Lys Ser Pro Ala Phe Ser Ser Gly Ser Ser Glu Gly
            930                 935                 940

Asp Ser Pro Trp Ser Tyr Leu Asn Ser Ser Gly Ser Ser Trp Val Ser
945                 950                 955                 960

Leu Pro Gly Lys Met Arg Lys Glu Ile Leu Glu Ala Arg Thr Leu Gln
                965                 970                 975

Pro Asp Asp Phe Glu Lys Leu Leu Ala Gly Val Arg His Asp Trp Leu
                980                 985                 990

Phe Gln Arg Leu Glu Asn Thr Gly Val Phe Lys Pro Ser Gln Leu His
            995                1000                1005

Arg Ala His Ser Ala Leu Leu Leu Lys Tyr Ser Lys Lys Ser Glu
        1010                1015                1020

Leu Trp Thr Ala Gln Glu Thr Ile Val Tyr Leu Gly Asp Tyr Leu
        1025                1030                1035

Thr Val Lys Lys Lys Gly Arg Gln Arg Asn Ala Phe Trp Val His
        1040                1045                1050
```

His Leu His Gln Glu Glu Ile Leu Gly Arg Tyr Val Gly Lys Asp
    1055                1060                1065

Tyr Lys Glu Gln Lys Gly Leu Trp His His Phe Thr Asp Val Glu
    1070                1075                1080

Arg Gln Met Thr Ala Gln His Tyr Val Thr Glu Phe Asn Lys Arg
    1085                1090                1095

Leu Tyr Glu Gln Asn Ile Pro Thr Gln Ile Phe Tyr Ile Pro Ser
    1100                1105                1110

Thr Ile Leu Leu Ile Leu Glu Asp Lys Thr Ile Lys Gly Cys Ile
    1115                1120                1125

Ser Val Glu Pro Tyr Ile Leu Gly Glu Phe Val Lys Leu Ser Asn
    1130                1135                1140

Asn Thr Lys Val Val Lys Thr Glu Tyr Lys Ala Thr Glu Tyr Gly
    1145                1150                1155

Leu Ala Tyr Gly His Phe Ser Tyr Glu Phe Ser Asn His Arg Asp
    1160                1165                1170

Val Val Val Asp Leu Gln Gly Trp Val Thr Gly Asn Gly Lys Gly
    1175                1180                1185

Leu Ile Tyr Leu Thr Asp Pro Gln Ile His Ser Val Asp Gln Lys
    1190                1195                1200

Val Phe Thr Thr Asn Phe Gly Lys Arg Gly Ile Phe Tyr Phe Phe
    1205                1210                1215

Asn Asn Gln His Val Glu Cys Asn Glu Ile Cys His Arg Leu Ser
    1220                1225                1230

Leu Thr Arg Pro Ser Met Glu Lys Pro Cys Thr
    1235                1240

<210> SEQ ID NO 2
<211> LENGTH: 1166
<212> TYPE: PRT
<213> ORGANISM: Homo sapiens
<220> FEATURE:
<221> NAME/KEY: PEPTIDE
<222> LOCATION: (1)..(1166)
<223> OTHER INFORMATION: ALPK1 Isoform 2

<400> SEQUENCE: 2

Met Cys Arg Lys Arg Thr Arg Ala Arg Thr Ser Ala Ala Glu Ala Ser
1               5                   10                  15

Leu Arg Ala Ser Ile Leu Ala Arg Asp Cys Ala Ala Ala Ala Ile
                20                  25                  30

Val Phe Leu Val Asp Arg Phe Leu Tyr Gly Leu Asp Val Ser Gly Lys
                35                  40                  45

Leu Leu Gln Val Ala Lys Gly Leu His Lys Leu Gln Pro Ala Thr Pro
        50                  55                  60

Ile Ala Pro Gln Val Val Ile Arg Gln Ala Arg Ile Ser Val Asn Ser
65                  70                  75                  80

Gly Lys Leu Leu Lys Ala Glu Tyr Ile Leu Ser Ser Leu Ile Ser Asn
                85                  90                  95

Asn Gly Ala Thr Gly Thr Trp Leu Tyr Arg Asn Glu Ser Asp Lys Val
            100                 105                 110

Leu Val Gln Ser Val Cys Ile Gln Ile Arg Gly Gln Ile Leu Gln Lys
        115                 120                 125

Leu Gly Met Trp Tyr Glu Ala Ala Glu Leu Ile Trp Ala Ser Ile Val
    130                 135                 140

Gly Tyr Leu Ala Leu Pro Gln Pro Asp Lys Lys Gly Leu Ser Thr Ser

-continued

```
            145                 150                 155                 160
Leu Gly Ile Leu Ala Asp Ile Phe Val Ser Met Ser Lys Asn Asp Tyr
                    165                 170                 175
Glu Lys Phe Lys Asn Asn Pro Gln Ile Asn Leu Ser Leu Leu Lys Glu
                    180                 185                 190
Phe Asp His His Leu Leu Ser Ala Ala Glu Ala Cys Lys Leu Ala Ala
                    195                 200                 205
Ala Phe Ser Ala Tyr Thr Pro Leu Phe Val Leu Thr Ala Val Asn Ile
    210                 215                 220
Arg Gly Thr Cys Leu Leu Ser Tyr Ser Ser Asn Asp Cys Pro Pro
225                 230                 235                 240
Glu Leu Lys Asn Leu His Leu Cys Glu Ala Lys Glu Ala Phe Glu Ile
                    245                 250                 255
Gly Leu Leu Thr Lys Arg Asp Asp Pro Val Thr Gly Lys Gln Glu
                    260                 265                 270
Leu His Ser Phe Val Lys Ala Ala Phe Gly Leu Thr Thr Val His Arg
    275                 280                 285
Arg Leu His Gly Glu Thr Gly Thr Val His Ala Ala Ser Gln Leu Cys
    290                 295                 300
Lys Glu Ala Met Gly Lys Leu Tyr Asn Phe Ser Thr Ser Ser Arg Ser
305                 310                 315                 320
Gln Asp Arg Glu Ala Leu Ser Gln Glu Val Met Ser Val Ile Ala Gln
                    325                 330                 335
Val Lys Glu His Leu Gln Val Gln Ser Phe Ser Asn Val Asp Asp Arg
                    340                 345                 350
Ser Tyr Val Pro Glu Ser Phe Glu Cys Arg Leu Asp Lys Leu Ile Leu
                    355                 360                 365
His Gly Gln Gly Asp Phe Gln Lys Ile Leu Asp Thr Tyr Ser Gln His
    370                 375                 380
His Thr Ser Val Cys Glu Val Phe Glu Ser Asp Cys Gly Asn Asn Lys
385                 390                 395                 400
Asn Glu Gln Lys Asp Ala Lys Thr Gly Val Cys Ile Thr Ala Leu Lys
                    405                 410                 415
Thr Glu Ile Lys Asn Ile Asp Thr Val Ser Thr Thr Gln Glu Lys Pro
                    420                 425                 430
His Cys Gln Arg Asp Thr Gly Ile Ser Ser Ser Leu Met Gly Lys Asn
                    435                 440                 445
Val Gln Arg Glu Leu Arg Arg Gly Gly Arg Asn Trp Thr His Ser
    450                 455                 460
Asp Ala Phe Arg Val Ser Leu Asp Gln Asp Val Glu Thr Glu Thr Glu
465                 470                 475                 480
Pro Ser Asp Tyr Ser Asn Gly Glu Gly Ala Val Phe Asn Lys Ser Leu
                    485                 490                 495
Ser Gly Ser Gln Thr Ser Ser Ala Trp Ser Asn Leu Ser Gly Phe Ser
                    500                 505                 510
Ser Ser Ala Ser Trp Glu Glu Val Asn Tyr His Val Asp Asp Arg Ser
    515                 520                 525
Ala Arg Lys Glu Pro Gly Lys Glu His Leu Val Asp Thr Gln Cys Ser
    530                 535                 540
Thr Ala Leu Ser Glu Glu Leu Glu Asn Asp Arg Glu Gly Arg Ala Met
545                 550                 555                 560
His Ser Leu His Ser Gln Leu His Asp Leu Ser Leu Gln Glu Pro Asn
                    565                 570                 575
```

```
Asn Asp Asn Leu Glu Pro Ser Gln Asn Gln Pro Gln Gln Gln Met Pro
            580                 585                 590

Leu Thr Pro Phe Ser Pro His Asn Thr Pro Gly Ile Phe Leu Ala Pro
        595                 600                 605

Gly Ala Gly Leu Leu Glu Gly Ala Pro Glu Gly Ile Gln Glu Val Arg
610                 615                 620

Asn Met Gly Pro Arg Asn Thr Ser Ala His Ser Arg Pro Ser Tyr Arg
625                 630                 635                 640

Ser Ala Ser Trp Ser Ser Asp Ser Gly Arg Pro Lys Asn Met Gly Thr
                645                 650                 655

His Pro Ser Val Gln Lys Glu Ala Phe Glu Ile Val Glu Phe
                660                 665                 670

Pro Glu Thr Asn Cys Asp Val Lys Asp Arg Gln Gly Lys Glu Gln Gly
        675                 680                 685

Glu Glu Ile Ser Glu Arg Gly Ala Gly Pro Thr Phe Lys Ala Ser Pro
        690                 695                 700

Ser Trp Val Asp Pro Glu Gly Glu Thr Ala Glu Ser Thr Glu Asp Ala
705                 710                 715                 720

Pro Leu Asp Phe His Arg Val Leu His Asn Ser Leu Gly Asn Ile Ser
                725                 730                 735

Met Leu Pro Cys Ser Ser Phe Thr Pro Asn Trp Pro Val Gln Asn Pro
                740                 745                 750

Asp Ser Arg Lys Ser Gly Gly Pro Val Ala Glu Gln Gly Ile Asp Pro
            755                 760                 765

Asp Ala Ser Thr Val Asp Glu Gly Gln Leu Leu Asp Ser Met Asp
770                 775                 780

Val Pro Cys Thr Asn Gly His Gly Ser His Arg Leu Cys Ile Leu Arg
785                 790                 795                 800

Gln Pro Pro Gly Gln Arg Ala Glu Thr Pro Asn Ser Ser Val Ser Gly
                805                 810                 815

Asn Ile Leu Phe Pro Val Leu Ser Glu Asp Cys Thr Thr Thr Glu Glu
                820                 825                 830

Gly Asn Gln Pro Gly Asn Met Leu Asn Cys Ser Gln Asn Ser Ser Ser
            835                 840                 845

Ser Ser Val Trp Trp Leu Lys Ser Pro Ala Phe Ser Ser Gly Ser Ser
850                 855                 860

Glu Gly Asp Ser Pro Trp Ser Tyr Leu Asn Ser Ser Gly Ser Ser Trp
865                 870                 875                 880

Val Ser Leu Pro Gly Lys Met Arg Lys Glu Ile Leu Glu Ala Arg Thr
                885                 890                 895

Leu Gln Pro Asp Asp Phe Glu Lys Leu Leu Ala Gly Val Arg His Asp
            900                 905                 910

Trp Leu Phe Gln Arg Leu Glu Asn Thr Gly Val Phe Lys Pro Ser Gln
        915                 920                 925

Leu His Arg Ala His Ser Ala Leu Leu Lys Tyr Ser Lys Lys Ser
        930                 935                 940

Glu Leu Trp Thr Ala Gln Glu Thr Ile Val Tyr Leu Gly Asp Tyr Leu
945                 950                 955                 960

Thr Val Lys Lys Lys Gly Arg Gln Arg Asn Ala Phe Trp Val His His
                965                 970                 975

Leu His Gln Glu Glu Ile Leu Gly Arg Tyr Val Gly Lys Asp Tyr Lys
                980                 985                 990
```

```
Glu Gln Lys Gly Leu Trp His His Phe Thr Asp Val Glu Arg Gln Met
        995                 1000                1005

Thr Ala Gln His Tyr Val Thr Glu Phe Asn Lys Arg Leu Tyr Glu
    1010                1015                1020

Gln Asn Ile Pro Thr Gln Ile Phe Tyr Ile Pro Ser Thr Ile Leu
    1025                1030                1035

Leu Ile Leu Glu Asp Lys Thr Ile Lys Gly Cys Ile Ser Val Glu
    1040                1045                1050

Pro Tyr Ile Leu Gly Glu Phe Val Lys Leu Ser Asn Asn Thr Lys
    1055                1060                1065

Val Val Lys Thr Glu Tyr Lys Ala Thr Glu Tyr Gly Leu Ala Tyr
    1070                1075                1080

Gly His Phe Ser Tyr Glu Phe Ser Asn His Arg Asp Val Val Val
    1085                1090                1095

Asp Leu Gln Gly Trp Val Thr Gly Asn Gly Lys Gly Leu Ile Tyr
    1100                1105                1110

Leu Thr Asp Pro Gln Ile His Ser Val Asp Gln Lys Val Phe Thr
    1115                1120                1125

Thr Asn Phe Gly Lys Arg Gly Ile Phe Tyr Phe Asn Asn Gln
    1130                1135                1140

His Val Glu Cys Asn Glu Ile Cys His Arg Leu Ser Leu Thr Arg
    1145                1150                1155

Pro Ser Met Glu Lys Pro Cys Thr
    1160                1165
```

What is claimed is:

1. A compound represented by formula (I):

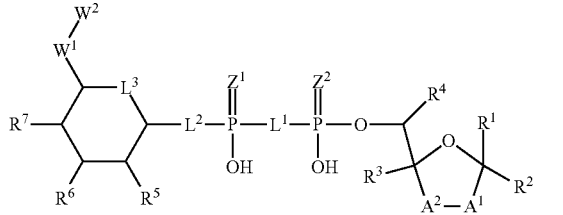

(I)

and/or a stereoisomer, tautomer, stable isotopes, prodrug or pharmaceutically acceptable salt thereof, wherein:

$A^1$ and $A^2$ are independently selected from 0, S and —$C(R^8R^9)$—, wherein $R^8$ and $R^9$ are independently selected from H, D, —OH, $N_3$, —CN, halogen, C1-C4 alkyl, C1-C4 alkoxyl, C1-C4 haloalkyl, C1-C4 haloalkoxyl, C1-C4 alkanoyloxyl, C1-C4 alkenyloxyl and substituted or unsubstituted aralkyloxyl, wherein the optional substituents are 1-3 substituents independently selected from D, halogen, —OH, =O, C1-C4 alkyl and C1-C4 alkoxy; at least one of $A^1$ or $A^2$ is —$C(R^8R^9)$; wherein $R^8$ or $R^9$ in $A^1$ can cyclize with $R^8$ or $R^9$ in $A^2$ to form C3-C6 cycloalkyl and cycloheteroalkyl containing 3 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy;

$L^1$ and $L^2$ are independently selected from O, CH2, CHF and CF2;

$L^3$ is O, S or $CH_2$;

$Z^1$ and $Z^2$ are independently selected from O and S;

$W^1$ is —$C(R^{10}R^{11})$—, wherein $R^{10}$ is halogen and $R^{11}$ is selected from H, D, —OH, halogen, and optionally substitued groups selected from C1-C4 alkyl, C1-C4 alkoxyl, C1-C4 haloalkyl, C1-C4- haloalkoxyl, C1-C4 alkenyloxyl, aralkyloxyl and $R^{12} CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members, wherein the optional substituents for $R^{11}$ are 1-3 substituents independently selected from D, halogen, —OH, =O, C1-C4 alkyl and C1-C4 alkoxy;

$W^2$ is C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein $R^{12}$ is C1-C4 alkyl, C1-C4 alkoxy, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^1$ is C6-C10 aryl or heteroaryl containing 5 to 10 ring atoms and having 1-4 heteroatoms selected from N, O and S as ring members, wherein R1 is optionally substituted with 1-3 substituents selected from of D, halogen, —OH, =O, CN, $NH_2$, C1-C4 alkyl, C1-C4 alkoxy, C1-C4 alkylamine, C1-C4 dialkyamine and $(R^{13}R^{14})NCO$—, wherein $R^{13}$ and $R^{14}$ are independently selected from H, C1-C4 alkyl, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^2$, $R^3$ and $R^4$ are independently selected from H, D, halogen, C1-C4 alkyl and C1-C4 haloalkyl;

$R^5$, $R^6$ and $R^7$ are selected from H, D, halogen and —OH, $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein any two of the adjacent groups of $R^5$, $R^6$ and $R^7$ can cyclize to form cycloheteroalkyl containing 5 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy.

2. The compound according to claim 1, which is a compound of Formula IA, and/or a stereoisomer, a stable isotope, prodrug or a pharmaceutically acceptable salt thereof Formula 1A

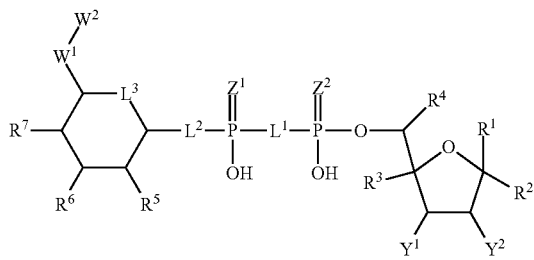

wherein:
$Y^1$ and $Y^2$ are independently selected from H, D, —OH, $N_3$, —CN, halogen and optionally substituted groups selected from C1-C4 alkyl, C1-C4 alkoxyl, C1-C4 haloalkyl, C1-C4 haloalkoxyl, C1-C4 alkanoyloxyl, C1-C4 alkenyloxyl and aralkyloxyl; wherein the optional substituents are 1-3 substituents independently selected from D, halogen, —OH, =O, C1-C4 alkyl and C1-C4 alkoxy;

$R^1$-$R^7$, $L^1$-$L^3$, $Z^1$, $Z^2$, $W^1$ and $W^2$ are defined in claim 1.

3. The compound according to claim 2, wherein
$Y^1$ and $Y^2$ are independently selected from H, D, —OH, halogen, C1-C4 alkyl, C1-C4 alkoxyl, C1-C4 haloalkyl, C1-C4 haloalkoxyl, C1-C4 alkanoyloxyl and C1-C4 alkenyloxyl;
$R^1$-$R^7$, $L^1$-$L^3$, $Z^1$, $Z^2$, $W^1$ and $W^2$ are defined in claim 1.

4. The compound according to claim 2, wherein
$Y^1$ and $Y^2$ are independently selected from —OH, halogen, C1-C4 alkyl and C1-C4 alkanoyloxyl;
$R^1$-$R^7$ $L^1$-$L^3$ $Z^1$, $Z^2$, $W^1$ and $W^2$ are defined in claim 1.

5. The compound according to claim 1, which is a compound of Formula IB, and/or a stereoisomer, a stable isotope, prodrug or a pharmaceutically acceptable salt thereof:

Formula 1B wherein:
$n^1$ and $n^2$ are each an integrer independently selected from the group consisting of 0-2;
$X^1$ and $X^2$ are independently selected from H, D, —OH, $N_3$, —CN, halogen and optionally substituted groups selected from C1-C4 alkyl, C1-C4 alkoxyl, C1-C4 haloalkyl, C1-C4 haloalkoxyl, C1-C4 alkanoyloxyl, C1-C4 alkenyloxyl and aralkyloxyl; wherein the optional substituents are 1-3 substituents independently selected from D, halogen, —OH, =O, C1-C4 alkyl and C1-C4 alkoxy;
$R^1$-$R^7$ $L^1$-$L^3$ $Z^1$, $Z^2$, $W^1$ and $W^2$ are defined in claim 1.

6. The compound according to claim 5, wherein $n^1$ and $n^2$ are each 0.

7. The compound according to claim 5, wherein
$X^1$ and $X^2$ are independently selected from H, D, and C1-C4 alkyl;
$R^1$-$R^7$ $L^1$-$L^3$ $Z^1$, $Z^2$, $W^1$ and $W^2$ are defined in claim 1.

8. The compound according to claim 1, wherein $R^2$, $R^3$, and $R^4$ are each H.

9. The compound according to claim 1, wherein $R^5$, $R^6$, and $R^7$ are each independently selected from the group consisting of —OH, and C1-C4 alkanoyloxyl.

10. The compound according to claim 1, wherein $L^3$ is O.
11. The compound according to claim 1, wherein $L^2$ is O.
12. The compound according to claim 1, wherein $L^1$ is O or S.

13. The compound according to claim 1, wherein $W^1$ is —$C(R^{10}R^{11})$—, wherein $R^{10}$ is halogen and $R^{11}$ is selected from H, D, —OH, halogen, C1-C4 alkyl, C1-C4 alkoxyl, C1-C4 haloalkyl, C1-C4- haloalkoxyl, C1-C4 alkanoyloxyl, C1-C4 alkenyloxyl and $R^{12}CO_2$—, wherein $R^{12}$ is selected from C1-C4 alkyl, C1-C4 alkoxyl, C1-C4 alkanoyloxyl and C1-C4 alkenyloxyl.

14. The compound according to claim 1, wherein $W^1$ is —$C(R^{10}R^{11})$—, wherein $R^{10}$ is halogen and $R^{11}$ is selected from H, D, —OH, halogen and C1-C4 alkanoyloxyl.

15. The compound according to claim 1, wherein $W^2$ is C1-C3 alkyl optionally substituted with 1-3 substituents independently selected from D, halogen, —OH, =O and C1-C3 alkoxyl, C1-C3 haloalkyl, C1-C3 haloalkoxyl, C1-C3 alkenyloxyl and $R^{12}CO_2$—, wherein $R^{12}$ is C1—C alkyl, C1-C4 alkoxy and C1-C4 alkylamino.

16. The compound according to claim 1, wherein $W^2$ is C1-C3 alkyl optionally substituted with 1-3 substituents independently selected from D, halogen, —OH and $R^{12}CO_2$—, wherein $R^{12}$ is C1-C3 alkyl.

17. The compound according to claim 1, wherein $W^2$ is C1 alkyl optionally substituted with 1 substituent selected from —OH and $R^{12}CO_2$—, wherein $R^{12}$ is C1-C3 alkyl.

18. The compound according to claim 1, wherein $R^1$ is selected from
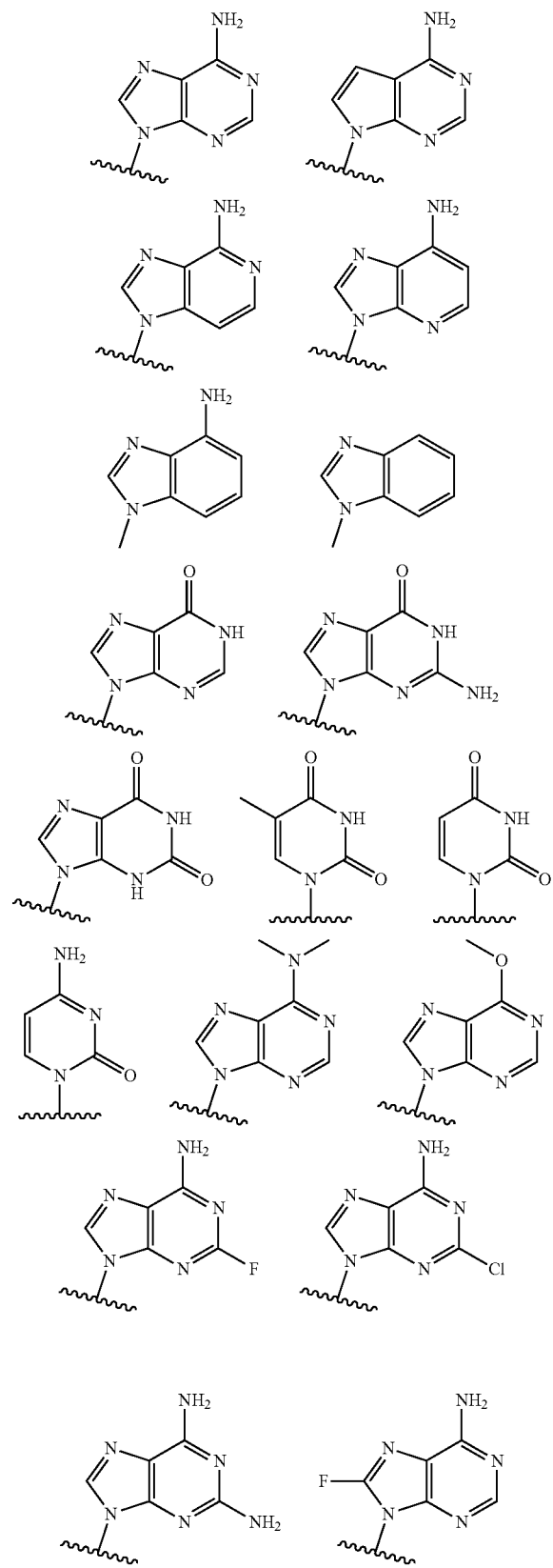
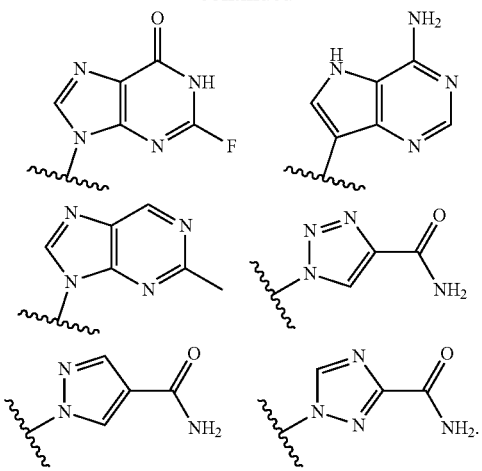
19. The compound according to claim 1, wherein $R^1$ is selected from
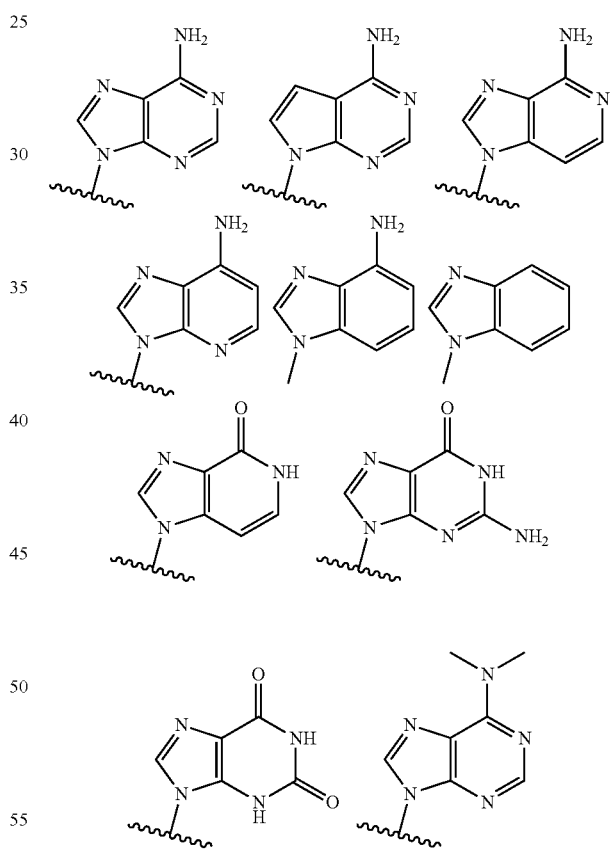
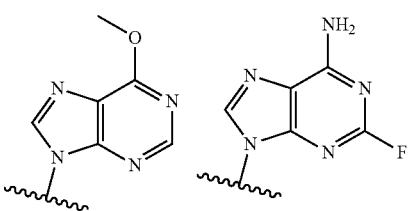

-continued

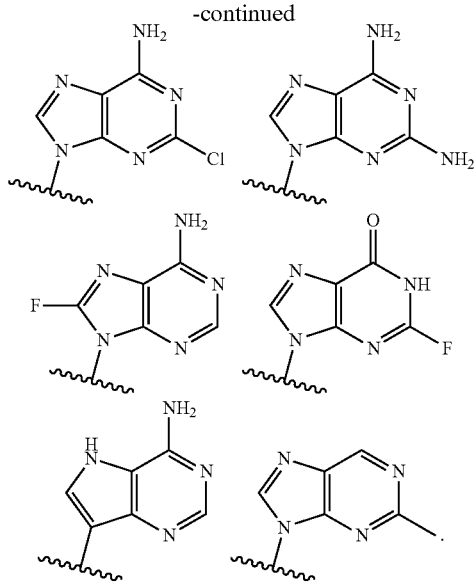

20. The compound according to claim 1, wherein $R^1$ is

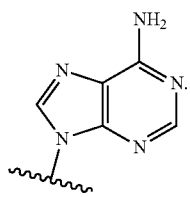 [SMILES: *n1cnc2c(N)ncnc21]

21. The compound according to claim 1, and/or a stereoisomer, a stable isotope, prodrug or a pharmaceutically acceptable salt thereof, wherein the compound is selected from:

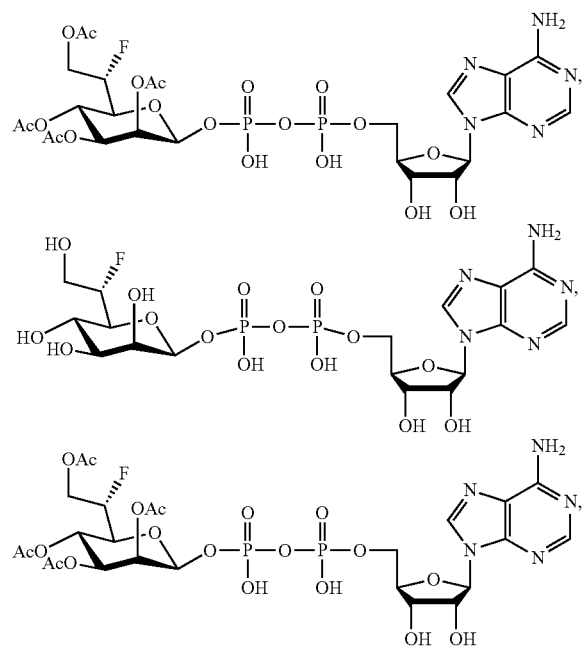

-continued
and

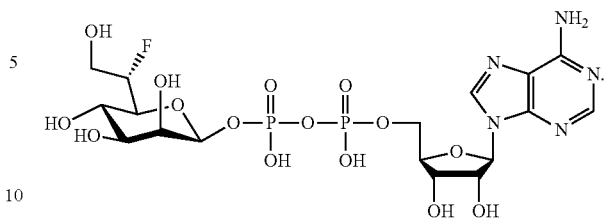

22. A pharmaceutical composition comprising a compound of claim 1, and a pharmaceutically acceptable carrier.

23. A method for activating ALPK1, the method comprising administering an effective amount of a compound or a pharmaceutically acceptable salt of a compound of claim 1.

24. A method for modulating an immune response in a subject in need of such treatment, the method comprising administering to the subject an effective amount of a compound or a pharmaceutically acceptable salt of a compound of claim 1.

25. A method for treating cancer in a subject in need of such treatment, the method comprising administering to the subject an effective amount of a compound or a pharmaceutically acceptable salt of a compound of claim 1.

26. A method for treating or preventing a disease or disorder caused by an infectious agent selected from a bacteria, virus, or parasite in a subject in need thereof, the comprising administering to the subject an effective amount of a compound or a pharmaceutically acceptable salt of a compound of claim 1.

27. The method of claim 24, wherein modulating an immune response is selected from activation of innate immunity and activation of adaptive immunity.

28. The method of claim 25, wherein the cancer is selected from soft tissue sarcoma, breast cancer, head and neck cancer, melanoma, cervical cancer, bladder cancer, hematologic malignancy, glioblastoma, pancreatic cancer, prostate cancer, colon cancer, breast cancer, renal cancer, lung cancer, merkel cell carcinoma, small intestine cancer, thyroid cancer, acute myelogenous leukemia (AML), acute lymphocytic leukemia (ALL), chronic lymphocytic leukemia (CLL), chronic myelogenous leukemia (CML), gastric cancer, gastrointestinal stromal tumors, non-Hodgkins lymphoma, Hodgkins lymphoma, liver cancer, leukemia, lymphoma, T-cell lymphoma, brain cancer, and multiple myeloma.

29. The method of claim 26, wherein the infectious agent is a virus.

30. The method of claim 29, wherein the virus is selected from the group consisting of ebolavirus, hepatitis B virus, hepatitis C virus, herpes simplex virus, human immunodeficiency virus (HIV), human papillomavirus (HPV-6, HPV-11), human SARS coronavirus, influenza A virus, influenza B virus, influenza C virus, measles virus, rabies virus, poliovirus, SARS corona virus, and yellow fever virus.

31. The method of claim 25, further comprising administering to the subject one or more additional therapeutic agents or immune modulators, and combinations thereof.

32. The method of claim 31, wherein the one or more additional therapeutic agents or immune modulators is selected from the group consisting of an inhibitor or antagonist of an immune checkpoint regulator, a vaccine, preferably a vaccine against an immune checkpoint regulator, an immune stimulatory molecule, an agonist of an immune co-stimulatory molecule, a recombinant protein, and a T cell, preferably a chimeric antigen receptor T (CAR-T) cell.

33. The method of claim 32, wherein the immune checkpoint regulator is selected from the programed cell death 1 (PD-1) receptor (CD279), a ligand of PD-1 (e.g., PD-L1), cytotoxic T-lymphocyte associated protein 4 (CTLA4), tumor necrosis factor receptor superfamily member 9 (alternatively TNFRSF9, 4-1BB) and 4-1BB ligands, tumor necrosis factor receptor superfamily member 4 (alternatively TNFRSF4, OX40) and OX40 ligands, glucocorticoid-induced TNFR-related protein (GITR), Tumor Necrosis Factor Receptor Superfamily Member 7 (alternatively TNFRSF7, cluster of differentiation 27, CD27), TNFRSF25 and TNF-like ligand 1A (TL1A), TNF Receptor Superfamily Member 5 (alternatively TNFRSF5, CD40) and CD40 ligand, Herpesvirus entry mediator (HVEM)-tumor necrosis factor ligand superfamily member 14 (alternatively TNFSF14, LIGHT)-lymphotoxin alpha (LTA), herpesvirus entry mediator- (HVEM)- B- and T-lymphocyte attenuator (BTLA)-CD160 (alternatively TNFSF14), lymphocyte activating gene 3 (LAG3), T-cell immunoglobulin and mucin-domain containing-3 (TIM3), sialic-acid-binding immunoglobulin-like lectins (SIGLECs), inducible T-cell costimulator (ICOS) and ICOS ligand, B7-H3 (B7 family, alternatively CD276), V-set domain-containing T-cell activation inhibitor 1 (VTCN1, alternatively B7-H4), V-Type immunoglobulin domain-containing suppressor of T-cell activation (VISTA), human endogenous retrovirus-H long terminal repeat-associating protein 2 (HHLA2)-transmembrane and Immunoglobulin domain containing 2 (TMIGD2), butyrophilins, natural killer cell receptor 2B4 (alternatively NKR2B4, CD244) and B-Cell Membrane Protein (CD48), T-Cell Immunoreceptor with Immunoglobulin (Ig) and immunoreceptor tyrosine-based inhibition motif domains (TIGIT) and Poliovirus receptor (PVR) family members, killer-cell immunoglobulin-like receptors (KIRs), Immunoglobulin-like transcripts (ILTs) and leukocyte immunoglobulin-like receptor (LIRs), natural killer group protein 2 member D (NKG2D) and natural killer group protein 2 member A (NKG2A), major histocompatibility complex (MEW) class I polypeptide-related sequence A (MICA) and MHC class I polypeptide-related sequence B (MICB), natural killer cell receptor 2B4 (CD244), colony stimulating factor 1 receptor (CSF1R), indoleamine 2,3-dioxygenase (IDO), transforming growth factor beta (TGF(3), Adenosine-ecto-nucleotidase triphosphate diphosphohydrolase 1 (CD39)- 5'-nucleotidase (CD73), C—X—C motif chemokine receptor 4 (CXCR4) and C—X-C motif chemokine ligand 12 (CXCL12), phosphatidylserine, signal regulatory protein alpha (SIRPA) and integrin associated protein (CD47), vascular endothelial growth factor (VEGF), and neuropilin.

34. The method of claim 33, wherein the one or more additional therapeutic agents or immune modulators is a PD-1/PD-L1 inhibitor.

35. The method of claim 34, wherein the PD-1/PD-L1 inhibitor is selected from the group consisting of nivolumab, pembrolizumab, pidilizumab, BMS-936559, atezolizumab, durvalumab, and avelumab.

36. The method of claim 31, wherein the immune modulator is selected from interferon alpha (INFa), a stimulator of interferon genes ("STING") agonist, a TLR agonist (e.g., resquimod), and an anti-0X40 (CD134) agonist antibody.

37. The method of claim 36, wherein immune modulator is an agonist of an immune co-stimulatory molecule.

38. The method of claim 37, wherein the agonist of an immune co-stimulatory molecule is an anti-OX40 (CD134) agonist antibody.

39. A method for treating a liver disease or disorder in a subject in need of such treatment, the method comprising administering to the subject a compound of claim 1.

40. The method of claim 39, wherein the liver disease or disorder is selected from liver cancer, non-alcoholic steatohepatitis (NASH), and a disease or disorder caused by infection with the hepatitis C virus (HCV) or the hepatitis B virus (HBV).

41. A vaccine composition or vaccine adjuvant composition comprising a compound or a pharmaceutically acceptable salt of claim 1.

42. A compound represented by formula (IB):

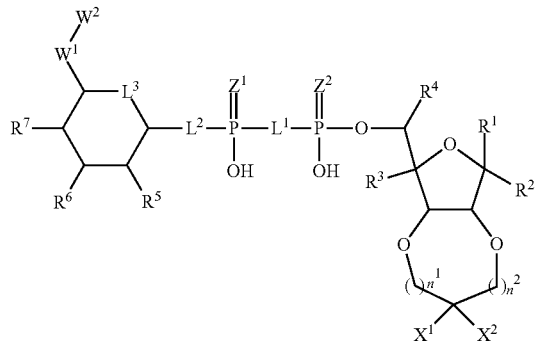

Formula IB and/or a stereoisomer, tautomer, stable isotope, prodrug or pharmaceutically acceptable salt thereof, wherein:

$n^1$ and $n^2$ are each an integrer independently selected from the group consisting of 0-2;

$X^1$ and $X^2$ are independently selected from H, D, —OH, $N_3$, —CN, halogen and optionally substituted groups selected from C1-C4 alkyl, C1-C4 alkoxyl, C1-C4 haloalkyl, C1-C4 haloalkoxyl, C1-C4 alkanoyloxyl, C1-C4 alkenyloxyl and aralkyloxyl; wherein the optional substituents are 1-3 substituents independently selected from D, halogen, —OH, =O, C1-C4 alkyl and C1-C4 alkoxy;

$L^1$ and $L^2$ are independently selected from O, $CH_2$, CHF and $CF_2$;

$L^3$ is O, S or $CH_2$;

$Z^1$ and $Z^2$ are independently selected from O and S;

$W^1$ is —$C(R^{10} R^{11})$—, wherein $R^{11}$ is halogen and $R^H$ is selected from H, D, —OH, halogen, and optionally substitued groups selected from C1-C4 alkyl, C1-C4 alkoxyl, C1-C4 haloalkyl, C1-C4- haloalkoxyl, C1-C4 alkenyloxyl, aralkyloxyl and $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members, wherein the optional substituents for $R^{11}$ are 1-3 substituents independently selected from D, halogen, —OH, =O, C1-C4 alkyl and C1-C4 alkoxy;

$W^2$ is H or C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein $R^{12}$ is C1-C4 alkyl, C1-C4 alkoxy, C1-C4 alkylamino, C3-C6 cycloalkyl, cyclohetereoalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^1$ is C6-C10 aryl or heteroaryl containing 5 to 10 ring atoms and having 1-4 heteroatoms selected from N, O and S as ring members, wherein R1 is optionally substituted with 1-3 substituents selected from of D, halogen, —OH, =O, CN, $NH_2$, C1-C4 alkyl, C1-C4 alkoxy, C1-C4 alkylamine, C1-C4 dialkylamine and $(R^{13}R^{14})NCO$—, wherein $R^{13}$ and $R^{14}$ are independently selected from H, C1-C4 alkyl, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^2$, $R^3$ and $R^4$ are independently selected from H, D, halogen, C1-C4 alkyl and C1-C4 haloalkyl;

$R^5$, $R^6$ and $R^7$ are selected from H, D, halogen and —OH, $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein any two of the adjacent groups of $R^5$, $R^6$ and $R^7$ can cyclize to form cycloheteroalkyl containing 5 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy.

43. The compound according to claim 42, wherein $n^1$ and $n^2$ are each 0.

44. The compound according to claim 42, wherein $X^1$ and $X^2$ are independently selected from H, D, and C1-C4 alkyl.

45. A method for activating ALPK1, the method comprising administering an effective amount of a compound or a pharmaceutically acceptable salt of a compound of claim 42.

46. A method for modulating an immune response in a subject in need of such treatment, the method comprising administering to the subject an effective amount of a compound or a pharmaceutically acceptable salt of a compound of claim 42.

47. A method for treating cancer in a subject in need of such treatment, the method comprising administering to the subject an effective amount of a compound or a pharmaceutically acceptable salt of a compound of claim 42.

48. A method for treating or preventing a disease or disorder caused by an infectious agent selected from a bacteria, virus, or parasite in a subject in need thereof, the comprising administering to the subject an effective amount of a compound or a pharmaceutically acceptable salt of a compound of claim 42.

49. A method for treating a liver disease or disorder in a subject in need of such treatment, the method comprising administering to the subject a compound of claim 42.

50. The method of claim 49, wherein the liver disease or disorder is selected from liver cancer, non-alcoholic steatohepatitis (NASH), and a disease or disorder caused by infection with the hepatitis C virus (HCV) or the hepatitis B virus (HBV).

51. A compound represented by formula (IC):

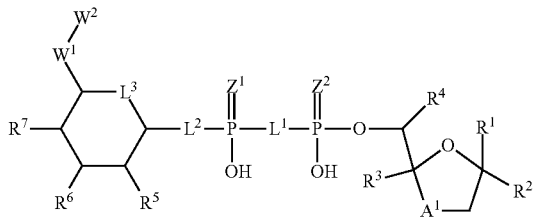

Formula 1C and/or a stereoisomer, tautomer, stable isotope, prodrug or pharmaceutically acceptable salt thereof, wherein:

$A^1$ is —$C(R^8R^9)$—, O or S, wherein $R^8$ and $R^9$ are independently selected from H, D, —OH, $N_3$, —CN, halogen, C1-C4 alkyl, C1-C4 alkoxyl, C1-C4 haloalkyl, C1-C4 haloalkoxyl, C1-C4 alkanoyloxyl, C1-C4 alkenyloxyl and substituted or unsubstituted aralkyloxyl, wherein the optional substituents are 1-3 substituents independently selected from D, halogen, —OH, =O, C1-C4 alkyl and C1-C4 alkoxy;

$L^1$ and $L^2$ are independently selected from O, $CH_2$, CHF and $CF_2$;

$L^3$ is O, S or $CH_2$;

$Z^1$ and $Z^2$ are independently selected from O and S;

$W^1$ is —$C(R^{10}R^{11})$—, wherein $R^{10}$ is halogen and $R^{11}$ is selected from H, D, —OH, halogen, and optionally substitued groups selected from C1-C4 alkyl, C1-C4 alkoxyl, C1-C4 haloalkyl, C1-C4- haloalkoxyl, C1-C4 alkenyloxyl, aralkyloxyl and $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein the optional substituents for $R^{11}$ are 1-3 substituents independently selected from D, halogen, —OH, =O, C1-C4 alkyl and C1-C4 alkoxy;

$W^2$ is C1-C3 alkyl optionally substituted with 1-3 substituents independently selected from D, halogen, —OH, =O, C1-C3 alkoxyl, C1-C3 haloalkyl, C1-C3 haloalkoxyl, C1-C3 alkenyloxyl and $R^{12}CO_2$—, wherein $R^{12}$ is C1-C4 alkyl, C1-C4 alkoxy, C1-C4 alkylamino, C3-C6 cycloalkyl, cyclohetereoalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^1$ is C6-C10 aryl or heteroaryl containing 5 to 10 ring atoms and having 1-4 heteroatoms selected from N, O and S as ring members, wherein R1 is optionally substituted with 1-3 substituents selected from of D, halogen, —OH, =O, CN, $NH_2$, C1-C4 alkyl, C1-C4 alkoxy, C1-C4 alkylamine, C1-C4 dialkylamine and (R13R14)NCO—, wherein $R^{13}$ and $R^{14}$ are independently selected from H, C1-C4 alkyl, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members;

$R^2$, $R^3$ and $R^4$ are independently selected from H, D, halogen, C1-C4 alkyl and C1-C4 haloalkyl;

$R^5$, $R^6$ and $R^7$ are selected from H, D, halogen and —OH, $R^{12}CO_2$—, wherein $R^{12}$ is selected from C1-C4 alkyl, C1-C4 alkoxyl, C1-C4 alkenyloxyl, C1-C4 alkylamino, C3-C6 cycloalkyl, cycloheteroalkyl containing 3 to 6 ring members and having 1-3 heteroatoms selected from N, O and S as ring members, C6-C10 aryl, and heteroaryl containing 5 to 10 ring atoms and having 1-3 heteroatoms selected from N, O and S as ring members; wherein any two of the adjacent groups of $R^5$, $R^6$ and $R^7$ can cyclize to form cycloheteroalkyl containing 5 to 9 ring members and having 1-3 heteroatoms selected from N, O and S as ring members, each optionally substituted by 1-3 substituents independently selected from D, halogen, —OH, =O, C1-C4 alkyl and C1-C4 alkoxy.

52. A method for activating ALPK1, the method comprising administering an effective amount of a compound or a pharmaceutically acceptable salt of a compound of claim 51.

53. A method for modulating an immune response in a subject in need of such treatment, the method comprising administering to the subject an effective amount of a compound or a pharmaceutically acceptable salt of a compound of claim 51.

54. A method for treating cancer in a subject in need of such treatment, the method comprising administering to the subject an effective amount of a compound or a pharmaceutically acceptable salt of a compound of claim 51.

55. A method for treating or preventing a disease or disorder caused by an infectious agent selected from a bacteria, virus, or parasite in a subject in need thereof, the comprising administering to the subject an effective amount of a compound or a pharmaceutically acceptable salt of a compound of claim 51.

56. A method for treating a liver disease or disorder in a subject in need of such treatment, the method comprising administering to the subject a compound of claim 51.

57. The method of claim 56, wherein the liver disease or disorder is selected from liver cancer, non-alcoholic steatohepatitis (NASH), and a disease or disorder caused by infection with the hepatitis C virus (HCV) or the hepatitis B virus (HBV).

* * * * *

UNITED STATES PATENT AND TRADEMARK OFFICE
CERTIFICATE OF CORRECTION

PATENT NO. : 11,186,606 B2
APPLICATION NO. : 16/759426
DATED : November 30, 2021
INVENTOR(S) : Tian Xu et al.

It is certified that error appears in the above-identified patent and that said Letters Patent is hereby corrected as shown below:

In the Claims

Column 227, Claim 21:
21. The compound according to claim 1, and/or a stereoisomer, a stable isotope, prodrug or a pharmaceutically acceptable salt thereof, wherein the compound is selected from:

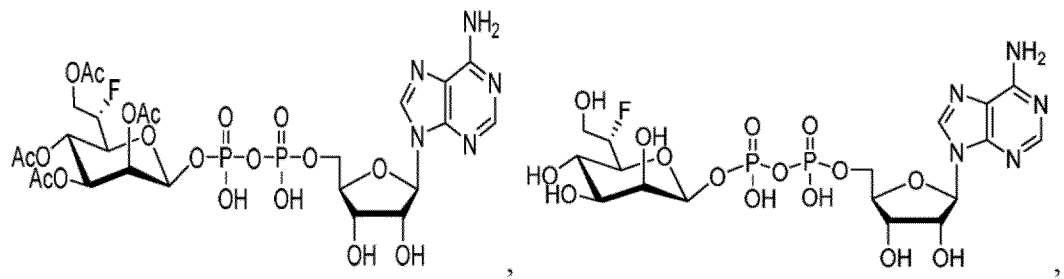

,

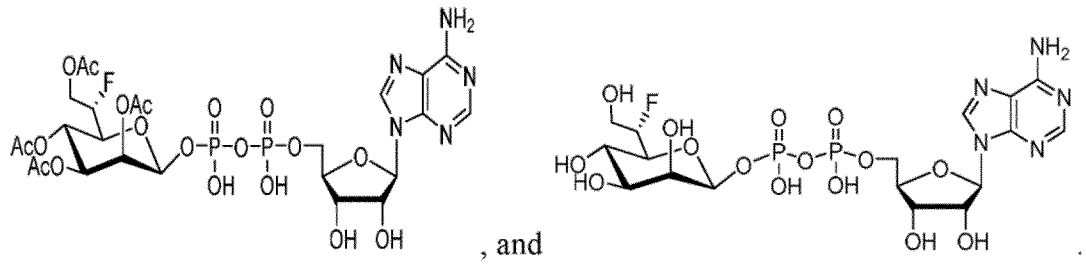

, and

Signed and Sealed this
Twentieth Day of June, 2023

Katherine Kelly Vidal
*Director of the United States Patent and Trademark Office*

CERTIFICATE OF CORRECTION (continued)
U.S. Pat. No. 11,186,606 B2

Should read:

21. The compound according to claim 1, and/or a stereoisomer, a stable isotope, prodrug or a pharmaceutically acceptable salt thereof, wherein the compound is selected from:

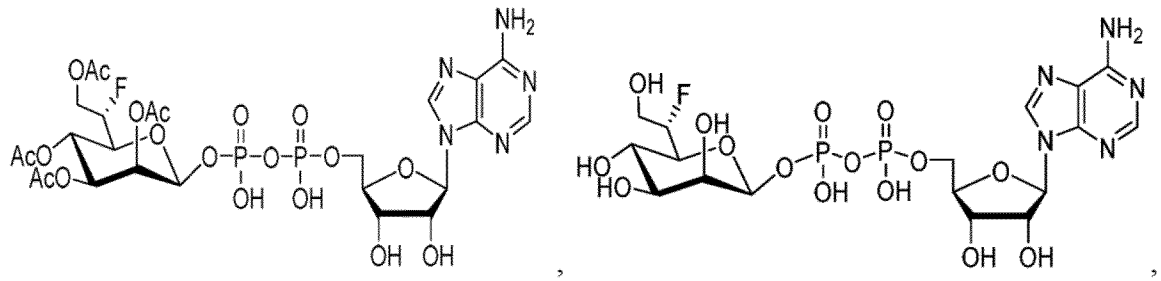

,

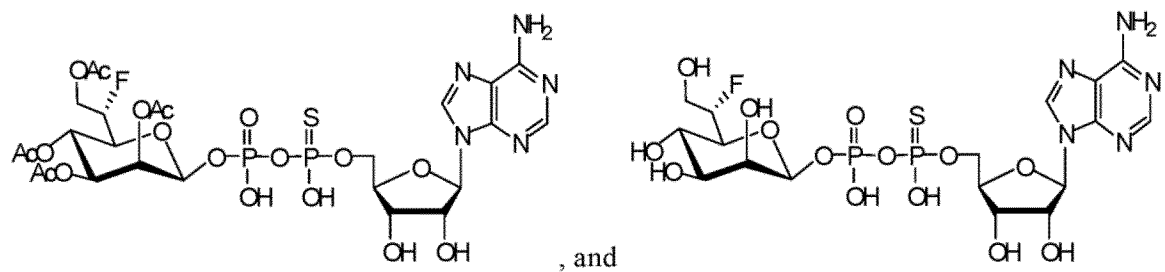

, and .